(12) United States Patent
Wang et al.

(10) Patent No.: US 11,858,964 B2
(45) Date of Patent: Jan. 2, 2024

(54) VIRUS-INSPIRED COMPOSITIONS AND METHODS OF REDIRECTING PREEXISTING IMMUNE RESPONSES USING THE SAME FOR TREATMENT OF CANCER

(71) Applicant: VerImmune Inc., Washington, DC (US)

(72) Inventors: Joshua Weiyuan Wang, Alexandria, VA (US); Ken Matsui, Frederick, MD (US); Philip Alan Storm, Redwood City, CA (US); Kristin Marie Peters, Reisterstown, MD (US)

(73) Assignee: VerImmune Inc., Washington, DC (US)

( * ) Notice: Subject to any disclaimer, the term of this patent is extended or adjusted under 35 U.S.C. 154(b) by 32 days.

(21) Appl. No.: 17/505,466

(22) Filed: Oct. 19, 2021

(65) Prior Publication Data

US 2022/0135624 A1 May 5, 2022

Related U.S. Application Data

(60) Provisional application No. 63/220,485, filed on Jul. 10, 2021, provisional application No. 63/093,525, filed on Oct. 19, 2020.

(51) Int. Cl.
| | | |
|---|---|---|
| *A61K 39/00* | (2006.01) | |
| *A61K 39/12* | (2006.01) | |
| *A61K 39/295* | (2006.01) | |
| *A61K 39/155* | (2006.01) | |
| *C07K 14/005* | (2006.01) | |
| *C12N 7/00* | (2006.01) | |
| *A61P 35/00* | (2006.01) | |

(52) U.S. Cl.
CPC ........ *C07K 14/005* (2013.01); *A61K 39/0011* (2013.01); *A61K 39/12* (2013.01); *A61K 39/295* (2013.01); *A61P 35/00* (2018.01); *C12N 7/00* (2013.01); *A61K 2039/585* (2013.01); *A61K 2039/6075* (2013.01); *A61K 2039/6081* (2013.01); *A61K 2039/70* (2013.01); *C07K 2319/50* (2013.01); *C12N 2710/20022* (2013.01); *C12N 2710/20034* (2013.01); *C12N 2710/20052* (2013.01)

(58) Field of Classification Search
CPC ............ A61K 2039/6075; A61K 39/12; A61K 39/295; C07K 14/005; C07K 14/025
See application file for complete search history.

(56) References Cited

U.S. PATENT DOCUMENTS

| | | |
|---|---|---|
| 7,521,209 B2 | 4/2009 | Brown |
| 8,062,642 B1 | 11/2011 | Rose et al. |
| 8,168,190 B2 | 5/2012 | Murray |
| 9,045,727 B2 | 6/2015 | Compans et al. |
| 9,149,503 B2 | 10/2015 | Roden et al. |
| 9,580,474 B2 | 2/2017 | Viscidi et al. |
| 9,855,347 B2 | 1/2018 | De Los Pinos et al. |
| 10,117,947 B2 | 11/2018 | De Los Pinos et al. |
| 10,688,172 B2 | 6/2020 | Coursaget et al. |
| 10,933,129 B2 | 3/2021 | Altreuter et al. |
| 2002/0039584 A1 | 4/2002 | Hallek et al. |
| 2004/0209295 A1 | 10/2004 | Schwabe et al. |
| 2004/0223976 A1 | 11/2004 | Bianchi et al. |
| 2007/0104689 A1 | 5/2007 | Gillies et al. |
| 2007/0160628 A1 | 7/2007 | Birkett et al. |
| 2007/0184473 A1 | 8/2007 | Shirwan et al. |
| 2010/0092504 A1 | 4/2010 | Rose et al. |
| 2010/0135902 A1 | 6/2010 | Roberts et al. |
| 2010/0172936 A1 | 7/2010 | Lowy et al. |
| 2010/0260792 A1 | 10/2010 | Murata et al. |
| 2013/0295125 A1 | 11/2013 | Sundberg et al. |
| 2014/0050753 A1 | 2/2014 | Viscidi et al. |
| 2014/0099337 A1 | 4/2014 | Davis et al. |
| 2015/0231239 A1 | 8/2015 | Hung et al. |

(Continued)

FOREIGN PATENT DOCUMENTS

| | | |
|---|---|---|
| EP | 2416798 B1 | 9/2017 |
| WO | 01/23422 A1 | 4/2001 |

(Continued)

OTHER PUBLICATIONS

Xiaojiang S. Chen et al., "Structure of Small Virus-like Particles Assembled from the L1 Protein of Human Papillomavirus 16", Molecular Cell, vol. 5, Mar. 2000, pp. 557-567.
Jeffrey I. Cohen, "Epstein-barr virus vaccines", Clinical & Transitional Immunology, vol. 4, No. 4, 2015, pp. 1-6.
Christopher P. Fox et al., "A novel latent membrane 2 transcript expressed in Epstein-Barr virus-positive NK- and T-cell lymphoproliferative disease encodes a target for cellular immunotherapy", Blood Journal, vol. 116, No. 19, Nov. 11, 2010, pp. 3695-3704.
Gregson et al., "Phase I trail of an alhydrogel adjuvanted hepatitis B core virus like particle containing epitopes of Plasmodium falciparum circumsporozoite protein", PLOS One, 3(2), Feb. 6, 2008, p. e1556 (Abstract Submitted).
PCT International Search Report and Written Opinion dated Dec. 12, 2018, International Application No. PCT/US2018/038701, pp. 1-19.

(Continued)

*Primary Examiner* — Barry A Chestnut
(74) *Attorney, Agent, or Firm* — BioPharma Law Group, PLLC

(57) ABSTRACT

Disclosed are virus-inspired compositions and preparation methods thereof, where the compositions comprise mutant papillomavirus L1 proteins that spontaneously form capsid backbones and that are conjugated to a peptide comprising an epitope to form immune redirector capsids (IRCs). The epitopes on the peptides are designed to be recognized by a subject's immune system based on the subject's preexisting immune memory developed from the subject's past exposure to the epitope through infection or vaccination. The mutant papillomavirus L1 proteins possess three mutations including an amino-terminal truncation, a carboxy-terminal truncation, and a truncation at helix four. These mutations in the L1 protein yield capsomeres that are form non-canonical T=1 geometry capsid backbones. Disclosed are uses and methods of using the compositions in treating and/or preventing cancers in subjects in need thereof.

26 Claims, 48 Drawing Sheets

Specification includes a Sequence Listing.

(56) References Cited

U.S. PATENT DOCUMENTS

| | | |
|---|---|---|
| 2016/0058852 A1 | 3/2016 | Ter Meulen et al. |
| 2017/0152316 A1 | 6/2017 | Cobbold |
| 2017/0274099 A1 | 9/2017 | De Los Pinos et al. |
| 2017/0327543 A1 | 11/2017 | Viscidi et al. |
| 2018/0078655 A1 | 3/2018 | Dziadek et al. |
| 2018/0104320 A1 | 4/2018 | Gravekamp |
| 2018/0110883 A1 | 4/2018 | De Los Pinos et al. |
| 2018/0193382 A1 | 7/2018 | Barrat |
| 2018/0311269 A1 | 11/2018 | Lobb et al. |
| 2018/0311374 A1 | 11/2018 | Lobb et al. |
| 2018/0325952 A1 | 11/2018 | Masopust, Jr. et al. |
| 2019/0022206 A1 | 1/2019 | Pedersen et al. |
| 2019/0117760 A1 | 4/2019 | Graham et al. |
| 2020/0113996 A1 | 4/2020 | Weiyuan et al. |
| 2020/0121779 A1 | 4/2020 | Garcea et al. |
| 2020/0164054 A1 | 5/2020 | Snyder et al. |
| 2020/0291072 A1 | 9/2020 | Weiyuan et al. |

FOREIGN PATENT DOCUMENTS

| | | |
|---|---|---|
| WO | 2010/001409 A2 | 1/2010 |
| WO | 2010/118424 A2 | 10/2010 |
| WO | 2012/033911 A2 | 3/2012 |
| WO | 2012/123755 A1 | 9/2012 |
| WO | 2013080187 A1 | 6/2013 |
| WO | 2014043523 A1 | 3/2014 |
| WO | 2014145932 A1 | 9/2014 |
| WO | 2016176164 A1 | 11/2016 |
| WO | 201720570 A1 | 2/2017 |
| WO | 2017/075615 A1 | 5/2017 |
| WO | 2017/079747 A1 | 5/2017 |
| WO | 2017087789 A1 | 5/2017 |
| WO | 2017/112830 A1 | 6/2017 |
| WO | 2017/177204 A1 | 10/2017 |
| WO | 2018/106972 A1 | 6/2018 |
| WO | 2019/028406 A1 | 2/2019 |
| WO | 2019/090304 A1 | 5/2019 |
| WO | 2020017962 A1 | 1/2020 |
| WO | 2020198344 A1 | 10/2020 |

OTHER PUBLICATIONS

Wen Jun Liu et al., "Papillomavirus Virus-like Particles for the Delivery of Multiple Cytotoxic T Cell Epitopes", Virology, vol. 273, 2000, pp. 374-382.

Slavica Matic et al., "Efficient production of chimeric Human papillomavirus 16 L1 protein bearing the M2e influenza epitope in Nicotiana benthamiana plants", BMC Biotechnology, 11:106, 2011, pp. 1-12.

Cuburu Nicolas et al., "Harnessing pre-existing anti-viral immunity for tumor therapy", SITC 2019, Retrieved from the Internet on Nov. 11, 2019: www.sitcancer.org, pp. 920-921.

Sharmila Pejawar-Gaddy et al., "All in one: VLP-MUC1 vaccine for prevention and treatment of epithelial tumors", The FASEB Journal, vol. 22, No. 1_supplement, Mar. 2008, pp. 1077-7 (Abstract Submitted).

John T. Schiller et al., "Papillomavirus-like particle based vaccines: cervical cancer and beyond", Expert Opinion on Biological Therapy, vol. 1, No. 4, Aug. 2001, pp. 571-581.

Julian P. Sefrin et al., "Sensitization of Tumors for Attack by Virus-Specific CD8+ T-Cells Through Antibody-Mediated Delivery of Immunogenic T-Cell Epitopes", Frontiers in Immunology, vol. 10, Article 1962, Aug. 2019, pp. 1-14.

Katharina Slupetzky et al., "Chimeric papillomavirus-like particles expressing a foreign epitope on capsid surface loops", Journal of General Virology, vol. 82, Issue 11, Nov. 2001, pp. 2799-2804.

Susan Thrane et al., "A Novel Virus-like Particle Based Vaccine Platform Displaying the Placental Malaria Antigen VAR2CSA", Plos One, 10(11), Nov. 23, 2015, pp. 1-16.

S. Kirk Wright et al., "Evaluation of methods for the quantitation of cysteines in proteins", Analytical Biochemistry, vol. 265, Issue 1, Dec. 1, 1998, pp. 8-14 (Abstract Submitted).

David G. Millar et al., "Anti-body mediated delivery of viral epitopes to tumors harnesses CMV-specific T cells for cancer therapy", Nature Biotechnology, 2020, pp. 1-6.

Andreas M. Kaufmann et al., "Vaccination trial with HPV16 L1E7 chimeric virus-like particles in women suffering from high grade cervical intraepithelial neoplasia (CIN 2/3)", International Journal of Cancer, 121(12), Dec. 2007, pp. 2794-2800.

PCT International Search Report and Written Opinion dated Mar. 10, 2020, International Application No. PCT/US2019/068619, pp. 1-24.

Deepali G. Vartak et al., "Matrix metalloproteases: Underutilized targets for drug delivery," Journal of Drug Targeting, Jan. 2007, 15(1), pp. 1-20.

Marion Braun et al., "Virus-like particles induce robust human T-helper cell responses," European Journal of Immunology, 2012, 42: pp. 330-340.

Extended European Search Report dated Mar. 18, 2021, European Application No. 18820136.2, pp. 1-7.

Stefania Bellone et al., "Human Papillomavirus Type 16 (HPV-16) Virus-Like Particle L1-Specific CD8+ Cytotoxic T Lymphocytes (CTLs) Are Equally Effective as E7-Specific CD8+ CTLs in Killing Autologous HPV-16-Positive Tumor Cells in Cervical Cancer Patients: Implications for L1 Dendritic Cell-Based Therapeutic Vaccines," Journal of Virology, vol. 83, No. 13, Jul. 2009, pp. 6779-6789.

R. Kirnbauer et al., "Virus-like Particles of Bovine Papillomavirus Type 4 in Prophylactic and Therapeutic Immunization," Virology, vol. 219, Article 0220, 1996, pp. 37-44.

PCT International Search Report and Written Opinion dated Mar. 8, 2022, International Application No. PCT/US21/55676, pp. 1-12.

```
HPV16-L1   MSLWLPSEATVYLPPV-PVSKVVSTDEYVARTNIYYHAGTSRLLAVGHPYFPIKKPNNK   59
MusPV1-L1  MAMWTPQTGKLYLPPTTPVAKVQSTDEYVYFTSLFIHARTDRLLTVGHPFFSVID--NDK  58
           *;;* *,. ,,;****, **;** ******  *,;; ** *,***;****;* ;   *;*

HPV16-L1   ILVPKVSGLQYRVFRIHLPDPNKFGFPDTSFYNPDTQRLVWACVGVEVGRGQPLGVGISG  119
MusPV1-L1  VTVPKVSGHQYRVFRLKFPDPNKFALPQKDFYDPEKERLVWRLRGLEIGRGGPLGIGTTG  118
           ;;******;******;;;******,;*,..**;*;,;**** *;*;*** ***;* ;*

HPV16-L1   HPLLNKLDDTENASAYAANAGVDNRECISMDYKQTQLCLIGCKPPIGEHWGKGSPCTNVA  179
MusPV1-L1  HPLFNKLGDTENPNKYQQSS-KDNRQNTSMDPKQTQLFIVGCEPPTGEHWDVAKCGA--  175
           ***;***,**** , ,  ,  ;*** ; *** *****;;**;** ****, ,, **

HPV16-L1   VNPGDCPPLELINTVIQDGDMVDTGFGAMDFTTLQANKSEVPLDICTSICKYPDYIKMVS  239
MusPV1-L1  LEKGECPPIQLVNSVIELGDCDDIGFGNMNFKELQQDRSGVPLDIVSTPCKWPDFLKMTN  235
           ;; *****;;*;*;**;**** * *** *;*, ** ;;* ***** ;; **;**;;**,,

HPV16-L1   EPYGDSLFFYLRREQMFVRHLFNRAGTVGENVP-------DDLYIKGSGS---TANLASSNYF  292
MusPV1-L1  EAYGDKMFFFGRREQVYARHFFTRNGSVGEPIPNSVSPSDFYYAPLSTQDQKTLAPSVYF  295
           * ***,;**; ****; ;**;; **,*,* *;***  ;*    ,,*;*   ,,;   ,** * **

HPV16-L1   PTPSGSMVTSDAQIFNKPYWLQRAQGHNNGICWGNQLFVTVVDTTRSTNMSICAAISTSE  352
MusPV1-L1  GTFSGSLVSSDGQLFNPPFWLQRAQGNNNGVCWHNELFVTVVDNTENTNFTISQQTNTPN  355
           *****;;*,**,**;*;**;*******;***,** ;******* **,**,*;;;,  ,* ;

HPV16-L1   --TTYKNTNFKEYLRHGEEYDLQFIFQLCKITLTADVMTYIHSMNSTILEDWNFGLQPPP  411
MusPV1-L1  PDTYDSTNFKNYLRHVEQFELSLIAQLCKVPLDPGVLARINTMNPTILENWNLGFVPPPG  415
           **,,*****;****  *;; ,;* ****; *  *  ,* ;;** ****;***;  *  ***

HPV16-L1   GTLEDTYRFVTSQAIACQKHTPPAPKEDPLKKYTFWEVNLKEKFSADLDQFPLGRKFLLQ  471
MusPV1-L1  QRASRERTVVTSAANTHSRKPPKPEDPYKGLIFWEVDLTERFSQDLDQFALGRKFLYQ   475
           ;;;* **;;**,*  *   *, ,*  *;** * * ****;*,;** ***** ****** *

HPV16-L1   AGLKAKPKFTLGKRKATPTTSSTSTTAKRKKRKL   505
MusPV1-L1  AGIRTAVTGRGVKRAASTTSASSRPVVKRKRGSK   509
```

FIG. 2

Cloning & Transformation
- Gene Synthesis into expression vector
- Transform into host cell → Protein expression of mutated MusPV L1 (MPV.10.34.d) as an inclusion body

Fermentation
- Shake Flask/Fermenter
- Product Fermentation

Recovery & Refolding
- Cell Harvest & Wash
- Cell homogenization
- IB wash & recovery
- IB Solubilization
- Refold into T=1 ViP → Removal of impurities, isolate inclusion body and resolubilize L1 protein and assembly into T=1 capsid backbone

Purification
- Capture Step (IEX)
- Polishing Step (HIC)
- UF/DF
- Purified Intermediate ViP → Two-step purification using chromatographic steps to obtain >95% pure T=1 capsid backbone

Conjugation
- TFF
- Peptide Conjugation
- UF/TFF
- Bulk Drug Substance

→ Conjugation of peptides onto surface of capsid backbone to form Immune Redirecting Capsids (IRCs)

FIG. 3 hCMV peptide/HLA-A*0201 complex hCMV peptide/HLA-A*0201 complex

| Sample (Amount of OVA-conjugated MPV.10.34.d IRC, µg/mL) | Geometric MFI (OVA-conjugated MPV.10.34.d IRC binding level, mean of three replicates) | Mean % Cytotoxicity (6 replicates) | | |
|---|---|---|---|---|
| | | E:T Ratio 18:1 | E:T Ratio 9:1 | E:T Ratio 4.5:1 |
| No sample added | 1964 | 13.7 | 9.3 | 1.7 |
| 0.000625 | 2127 | 25.7 | 19.9 | 11.0 |
| 0.0025 | 2743 | 47.4 | 38.7 | 22.3 |
| 0.01 | 4437 | 68.7 | 56.5 | 34.0 |
| 0.039 | 9892 | 79.0 | 66.9 | 44.1 |
| 0.156 | 19600 | 82.0 | 68.3 | 48.2 |
| 0.625 | 42281 | 81.0 | 68.5 | 46.2 |
| 2.500 | 139024 | 80.2 | 64.4 | 37.6 |

FIG. 28

VIRUS-INSPIRED COMPOSITIONS AND METHODS OF REDIRECTING PREEXISTING IMMUNE RESPONSES USING THE SAME FOR TREATMENT OF CANCER

CROSS REFERENCE TO RELATED APPLICATIONS

This application claims priority to U.S. provisional patent application Ser. No. 63/093,525, filed on Oct. 19, 2020, and U.S. provisional patent application Ser. No. 63/220,485, filed on Jul. 10, 2021, the entire contents of each of which are hereby incorporated by reference.

FIELD OF THE INVENTION

Disclosed are compositions comprising mutated papillomavirus proteins, especially the L1 major capsid protein, that form capsid backbones and are attached to one or more peptides comprising one or more antigens recognized by a subject's preexisting immune system response memory, and their methods of use in treatment, prevention, and/or reduction in the incidence of cancer in a subject.

INCORPORATION OF SEQUENCE LISTING

This application contains a sequence listing submitted in Computer Readable Form (CRF). The paper copy of the sequence listing and the CRF are identical and are incorporated herein by reference. The sequence listing contains one filed named "2021-10-19 8005US_ST25.txt" that was created on Oct. 19, 2021, and is 64 KB in size.

BACKGROUND

Typical cancer treatment includes chemotherapy, radiation, and surgery. However, surgery is highly invasive and often fails, especially after metastasis. Chemotherapy and radiation can be effective, but often yield harsh side-effects that can drastically reduce quality of life for subjects. Despite these treatments, many cancers remain refractory to treatment and the treatments can be ineffective in combating metastatic cancers even when successful in reducing or eliminating the primary tumor. Targeted delivery has become one of the most promising opportunities for improving the treatment of cancer but this approach also presents the most challenges. Immunotherapies such as cancer vaccines have emerged as an attractive option due to the ability to stimulate the immune system and then use this response to specifically target over-expressed proteins preferentially present on the surface of cancer cells, resulting in targeted elimination of the cancer cells. Such therapies are attractive in that they are target specific and potentially less toxic without nonspecific autoimmunity. These targeted therapies are also considered less invasive or traumatic compared to surgery, radiation, or chemotherapy. However, cancer vaccines based on cancer-associated antigens can have limited success due to poor clinical immunogenicity, immune tolerance, and off target effects, for example. Moreover, such methods typically require identifying a cancer-associated antigen specific to a given patient's cancer to achieve effective targeting of the cancer. Hence, this approach has failed on multiple occasions because most cancer-associated antigens are self-antigens that are tolerated by the immune system, resulting in poor immune responses.

Other approaches to the treatment and prevention of cancer are based on adoptive transfer of chimeric antigen receptor (CAR)-transduced T cells (CAR-T) or infusion of monoclonal antibodies that require the laborious identification of cancer-specific antigens and are applicable to only a subset of cancer types or subtypes. Finally, adoptive transfer of tumor-specific lymphocytes expanded ex vivo is a methodology that aims to take advantage of naturally-occurring antitumor responses. All these approaches are similarly highly personalized and require the identification cancer epitopes of the subject's specific cancer and/or expansion of patient autologous cells ex vivo. Importantly, successes demonstrated by these specific cancer antigen approaches in gold standard animal models have not been always translatable to humans. Last, but not least, not all the patients suffering from cancer will express the same antigens on tumors, thus there are some significant limitations to the broad applicability of these approaches.

A solution to the problem of individualized targeted treatment and elimination of cancer presents itself in the form of viral infection history. In these approaches, a subject's infection history is used to re-initiate a past viral infection immune response through cytotoxic memory T-cells. Such therapies based on past viral infections are finely tune-able to target specific cancers by depositing on the cancer cells an epitope recognized by the subject's own immunological memory. Virus L1 proteins provide key functionality for delivering the epitope label onto the cancer cell target, thereby recruiting and activating the subject's own preexisting immune system components to target and eliminate the labeled cancer cells.

Mouse papillomavirus L1 proteins are good candidates for addressing this continuing need for better, more personalized cancer treatments. It has been fortuitously discovered that specific mutations in the mouse papillomavirus L1 protein lead to formation of smaller-sized T=1 virus capsids, called capsid backbones, comprised of twelve (12) capsomeres, that are smaller than the normal T=7 capsids typically formed by virus L1 proteins, for instance as formed with human papillomavirus (HPV). These smaller-sized capsid backbones are very stable, allowing for higher conjugation efficiency, and owing to their smaller size, present less steric hindrance in infiltrating solid tumors or the tumor microenvironment.

SUMMARY

In various embodiments, compositions comprising a plurality of mutant mouse papillomavirus L1 proteins are disclosed. The compositions further comprise one or more peptides that each comprise one or more epitopes from one or more pathogens other than a Papillomaviridae antigenic peptide. The mutated amino acid sequence of the Papillomaviridae L1 protein comprises at least the following mutations with respect to the wild type L1 protein sequence: (a) a deletion of at least five amino acid residues from an amino-terminus, and (b) a deletion of at least ten amino acid residues from the helix four region. The one or more peptides are attached to the plurality of virus proteins. The plurality of virus proteins spontaneously assemble to form an icosahedron or dodecahedron capsid backbone having a triangulation number T equal to 1 that binds to proteoglycan expressed on tumor cells. Thus, the compositions comprise a plurality of mutant Papillomaviridae proteins and one or more such peptides. Said differently, the compositions comprise one or more peptides attached to a plurality of mutant Papillomaviridae L1 proteins.

In some embodiments the mutant L1 proteins further comprise a deletion of at least thirty amino acid residues from the carboxy terminus of the L1 proteins. In some embodiments the peptides are conjugated to the L1 proteins via disulphide, maleimide, or amide bond between the mutant Papillomaviridae L1 protein and a residue of the peptide.

In some embodiments from about 25% to about 85% (w/w) of the L1 proteins are attached to at least one of the peptides. In some embodiments the peptides also comprise a protease cleavage sequence, optionally selected from a furin cleavage sequence, a matrix metalloprotease cleavage sequence, or a disintegrin and metalloprotease (ADAM) cleavage sequence.

The epitopes are not particularly limited other than that they should be from an antigen that the subject to be treated has been previously exposed to and to which the subject has developed an immune reactivity towards, or has an immune memory of the previous exposure such that upon re-exposure the subject's immune system will recognize and attack the cells bearing the epitopes. For instance, the epitope may be from a childhood vaccine. In other instances, the epitope may be from a past pathogenic infection the subject recovered from.

The compositions comprising the Immune Redirector Capsid (IRC) molecules bind to heparin sulfate proteoglycan located on cell surfaces. The IRC molecules do not form T=7 capsids. In some embodiments, the mutant L1 proteins are from mouse L1 proteins.

Contemplated herein are methods of treating, preventing, and/or reducing the occurrence of cancer in a subject in need thereof, which comprises administering to the subject a pharmaceutically effective amount of the compositions described herein. Also provided are methods of inhibiting cancer tumor growth, progression, and/or metastasis in a subject in need thereof, which comprises administering to the subject a pharmaceutically effective amount of the compositions described herein. Uses of the described compositions in the described methods are also contemplated herein.

Such methods further comprise in some embodiments obtaining from the subject a tumor tissue sample and identifying in the tumor tissue a sequence of one or more MHC molecules expressed by one or more tumor cells in the tumor tissue sample.

In certain embodiments, the one or more epitopes are capable of complexing with one or more MHC molecules expressed by a tumor cell in a tumor tissue sample obtained from the subject. Secondary uses of the described compositions are also contemplated, as in the use for manufacture of a medicament useful for such methods.

Further provided herein are processes for producing the described compositions. The processes include various steps, such as: (a) transforming a prokaryotic cell with an expression vector encoding the L1 protein's nuclei acid sequence; (b) culturing the transformed prokaryotic cell under conditions that promote expression of the L1 protein; (c) lysing the transformed prokaryotic cells to release expressed L1 protein; (d) separating cell debris from the expressed L1 protein and recovering the L1 protein as inclusion bodies; (e) optionally washing the L1 protein inclusion bodies; (f) solubilizing the L1 protein inclusion bodies; (g) refolding the L1 protein in refolding buffer in the presence of reducing agent; and (h) forming the icosahedron or dodecahedron capsid having a triangulation number T equal to 1 in the same refolding buffer. Such processes, in some embodiments, further include conjugating in a conjugation buffer the one or more peptides to the assembled L1 protein by incubating the assembled L1 protein under reducing conditions in the presence of one or more peptides and/or removing denaturant from the assembly buffer but maintaining reducing agent when forming the icosahedron or dodecahedron capsid having a triangulation number T equal to 1.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become readily apparent from the Detailed Description, particularly when taken together with the figures

BRIEF DESCRIPTION OF THE DRAWINGS

FIG. 2 is an amino sequence alignment of MusPV L1 protein sequence (SEQ ID NO: 127) aligned with the corresponding human HPV16 L1 protein sequence (SEQ ID NO: 128).

FIG. 3 is a flow chart of process steps leading to the manufacture of MPV.10.34.d capsid backbones, which upon formation subsequently are conjugated to peptides to form immune regulatory capsids (IRCs).

specific murine T-cells similar to OVA-conjugated HPV16 IRC in murine tumor cell lines B16-Luc.

Figure 24A:
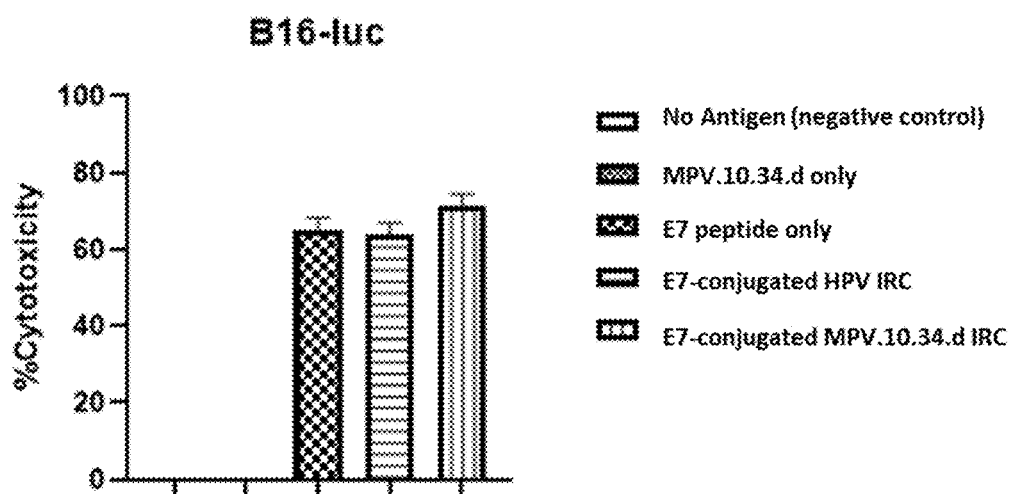

FIG. 24A is a bar graph showing that E7-conjugated HPV16 IRCs elicit an immune redirection of OVA-specific murine T-cells similar to OVA-conjugated HPV16 IRC in murine tumor cell line ID8-Luc.

Figure 24B:
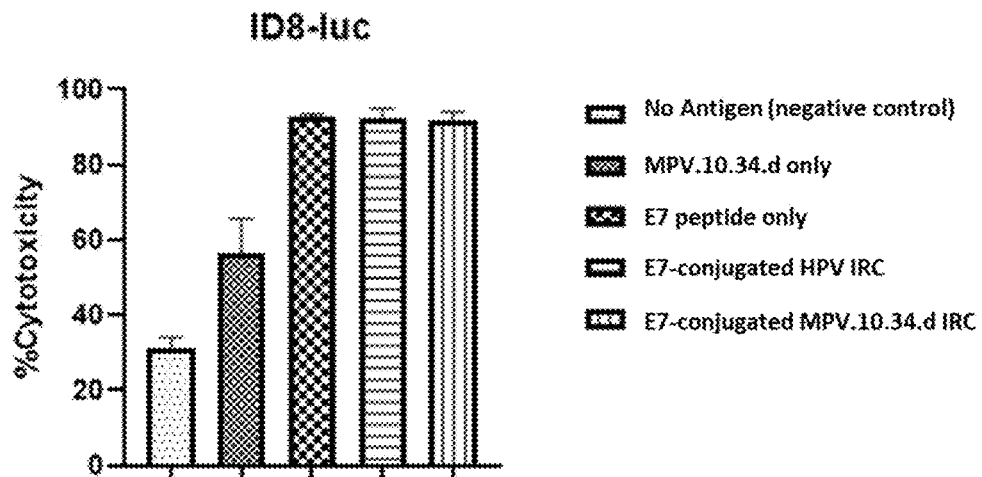

FIG. 24B is a bar graph showing that E7-conjugated HPV16 IRCs elicit an immune redirection of OVA-specific murine T-cells similar to OVA-conjugated HPV16 IRC in murine tumor cell lines B16-Luc.

Figure 25A:
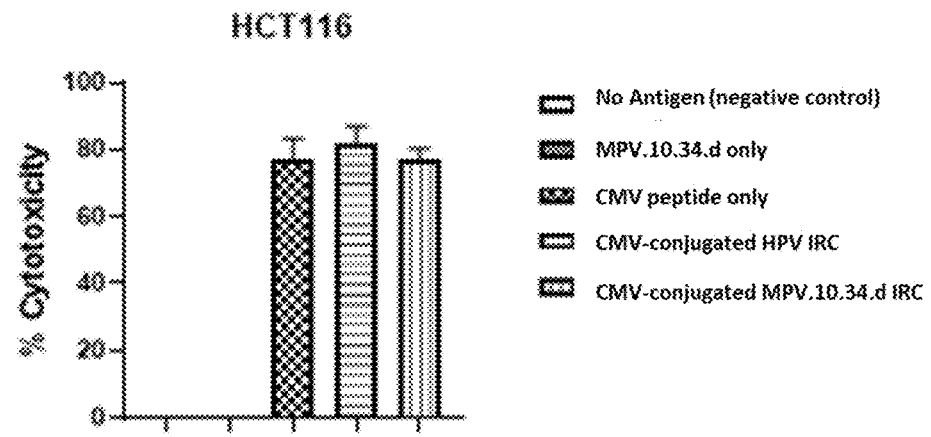

FIG. 25A is a bar graph showing that human CMV-conjugated MPV.10.34.d IRCs elicit an immune redirection of CMV-specific CD8 T-cells similar to CMV-conjugated HPV16 IRCs in human tumor cell line HCT-116.

Figure 25B:
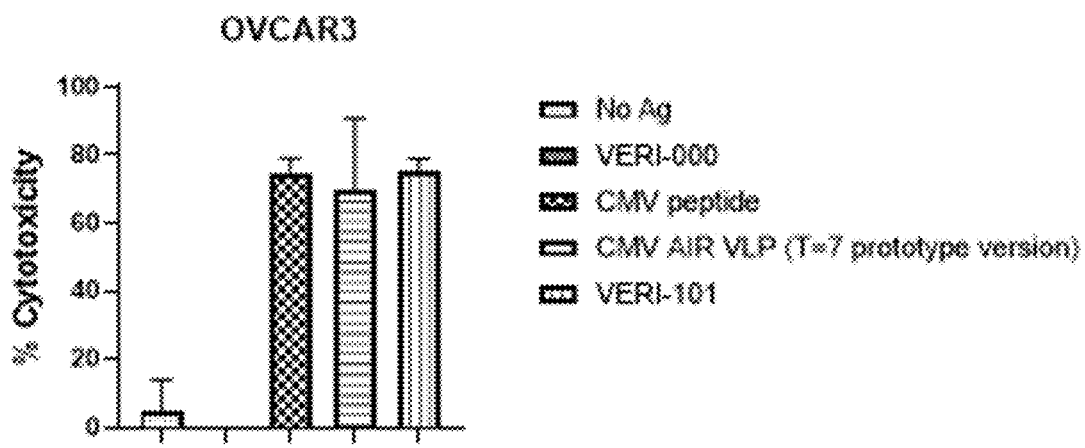

FIG. 25B is a bar graph showing that human CMV-conjugated MPV.10.34.d IRCs elicit an immune redirection of CMV-specific CD8 T-cells similar to CMV-conjugated HPV16 IRCs in human tumor cell line Ovarcar3.

Figure 25C:
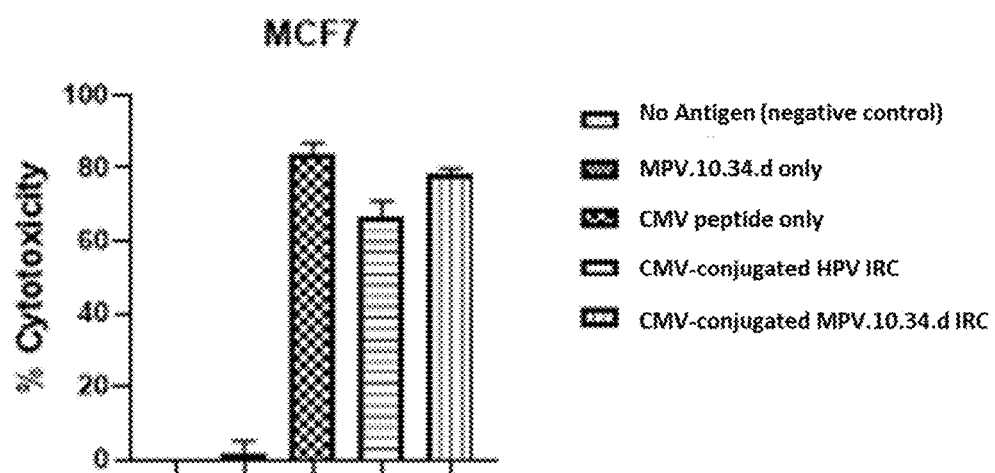

FIG. 25C is a bar graph showing that human CMV-conjugated MPV.10.34.d IRCs elicit an immune redirection of CMV-specific CD8 T-cells similar to CMV-conjugated HPV16 IRCs in human tumor cell line MCF7.

Figure 26:
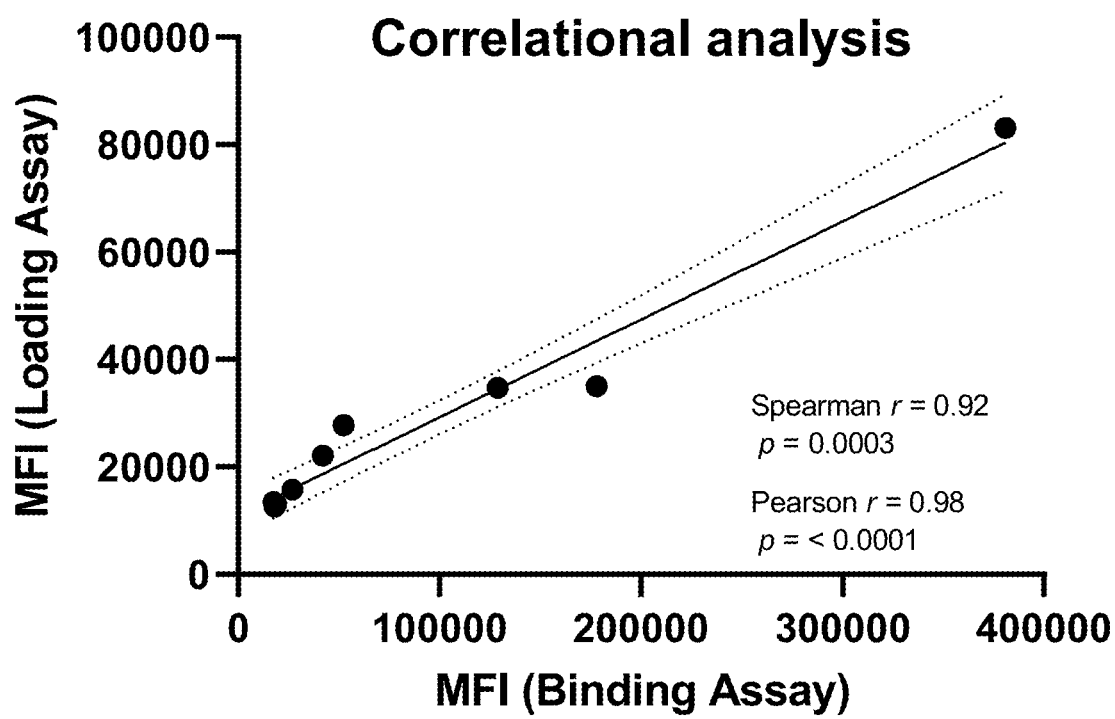

FIG. 26 is a graph demonstrating high statistical correlation of binding of OVA-conjugated MPV.10.34.d IRCs to tumor cells and peptide loading of OVA (SIINFEKL, SEQ ID NO: 95) onto tumor cell surface MHC-I molecules via OVA-conjugated MPV.10.34.d IRCs.

Figure 27A:
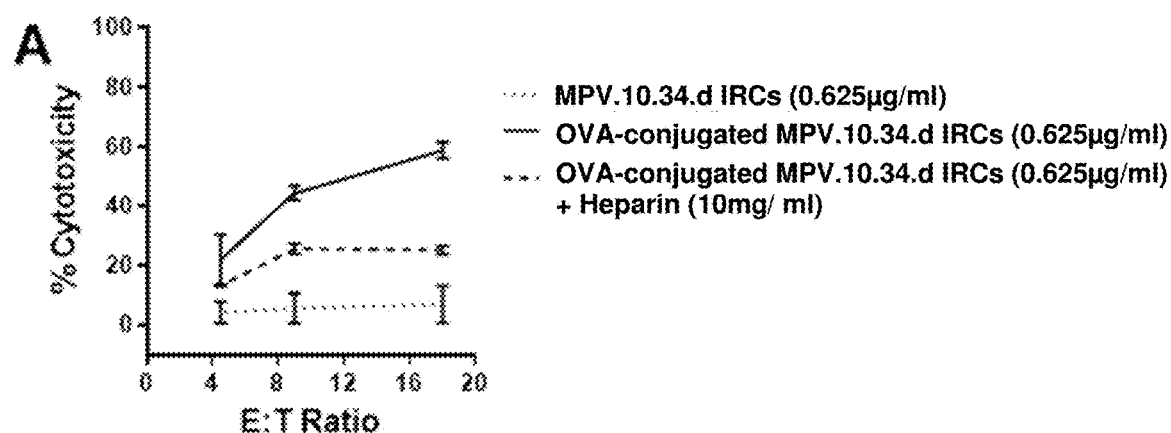

FIG. 27A is a graph of percent cytotoxicity vs. E:T ratio showing blocking of binding of 0.625 μg/mL OVA-conjugated MPV.10.34.d IRCs by incubation with heparin at concentration of 10 mg/mL, an immune redirection response of OVA-specific murine T-cells was not elicited (dashed line). The dotted line represents a negative control of MPV.10.34.d capsid backbones. The solid line represents the positive control sample with no heparin.

Figure 27B:
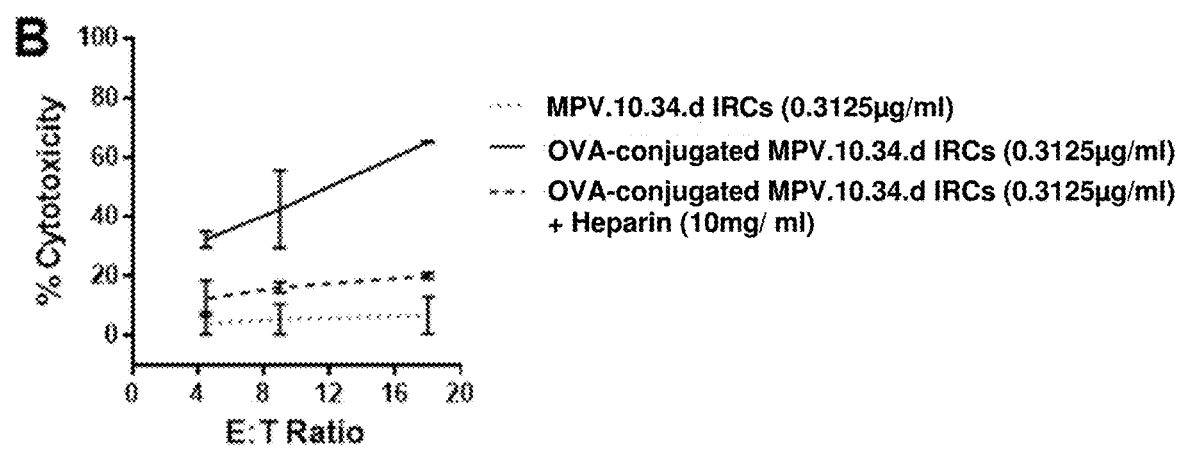

FIG. 27B is a graph of percent cytotoxicity vs. E:T ratio showing blocking of binding of 0.3125 μg/mL OVA-conjugated MPV.10.34.d IRCs by incubation with heparin at concentration of 10 mg/mL, an immune redirection response of OVA-specific murine T-cells was not elicited (dashed line). The dotted line represents a negative control of MPV.10.34.d capsid backbones. The solid line represents the positive control sample with no heparin.

Figure 27C:
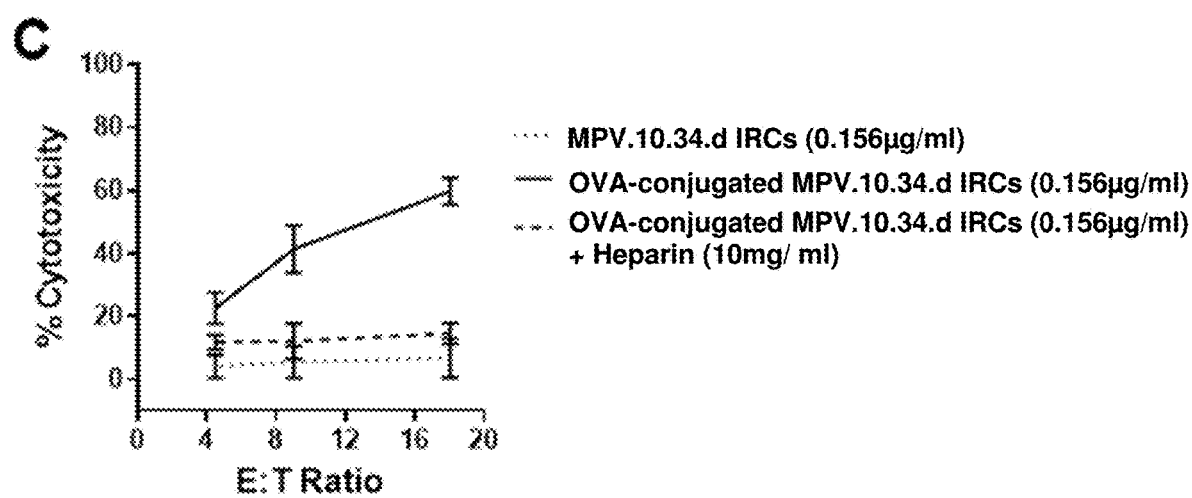

FIG. 27C is a graph of percent cytotoxicity vs. E:T ratio showing blocking of binding of 0.156 μg/mL OVA-conjugated MPV.10.34.d IRCs by incubation with heparin at concentration of 10 mg/mL, an immune redirection response of OVA-specific murine T-cells was not elicited (dashed line). The dotted line represents a negative control of MPV.10.34.d capsid backbones. The solid line represents the positive control sample with no heparin.

FIG. 28 is a table of data obtained from a dose titration of the cell-binding assays and cytotoxicity assays. The study was repeated twice (with at least 3 replicates each). The mean values of geometric mean fluorescent intensity (MFI) are reported from the two experiments. These data were used to assess the statistical correlation of OVA-conjugated MPV.10.34.d IRC binding and cytotoxicity.

Figure 29:
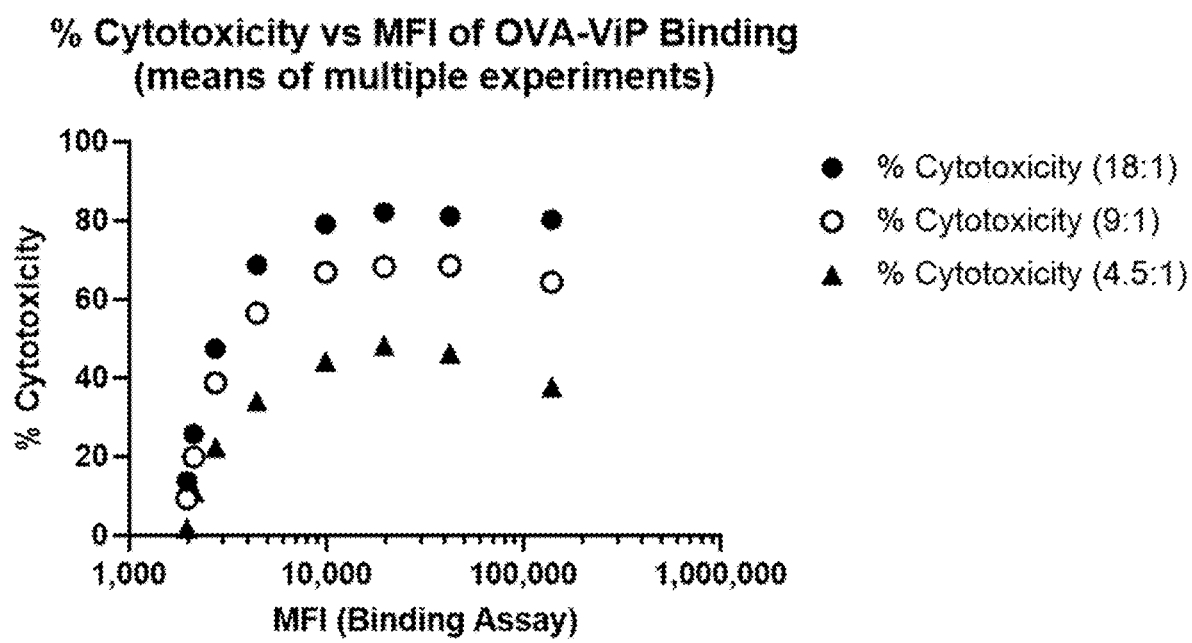

FIG. 29 is a graph of percent cytotoxicity vs. MFI demonstrating high statistical correlation of OVA-conjugated MPV.10.34.d IRC binding and cytotoxicity.

Figure 30A:
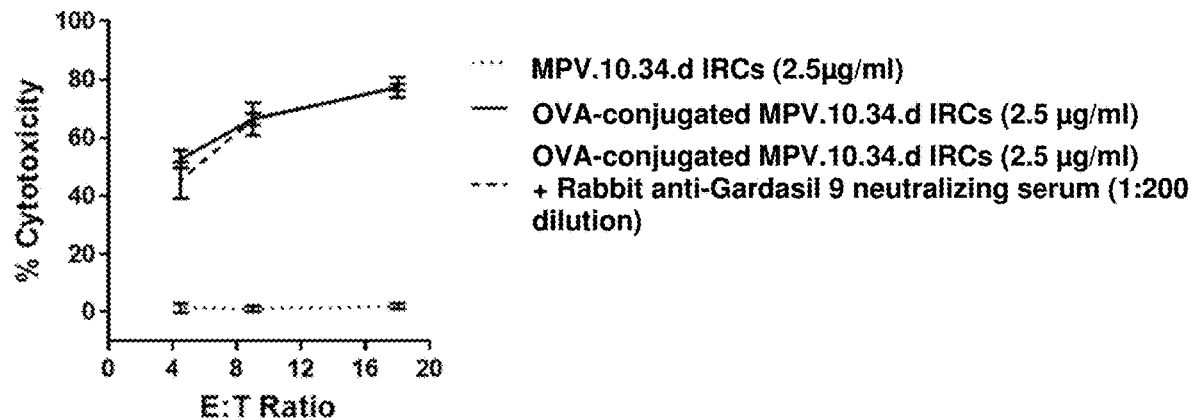

FIG. 30A is a graph of percent cytotoxicity vs. E:T ratio showing that co-incubation of GARDASIL®9-vaccinated sera (1:200) with OVA-conjugated MPV.10.34.d IRCs at 2.5 μg/mL did not inhibit immune redirection of OVA-specific murine T-cells.

FIG. 30B is a graph of percent cytotoxicity vs. E:T ratio showing that co-incubation of GARDASIL®9-vaccinated sera (1:200) with OVA-conjugated MPV.10.34.d IRCs at 0.625 μg/mL did not inhibit immune redirection of OVA-specific murine T-cells.

FIG. 30C is a graph of percent cytotoxicity vs. E:T ratio showing that co-incubation of GARDASIL®9-vaccinated sera (1:200) with OVA-conjugated MPV.10.34.d IRCs at 0.156 μg/mL did not inhibit immune redirection of OVA-specific murine T-cells.

FIG. 31A is a graph of absorbance at 450 nm vs. dilution factor of data obtained from two ELISA assays testing the effect of incubation of anti-MPV.10.34.d sera with MPV.10.34.d on binding to target tumor cells.

Figure 30B:
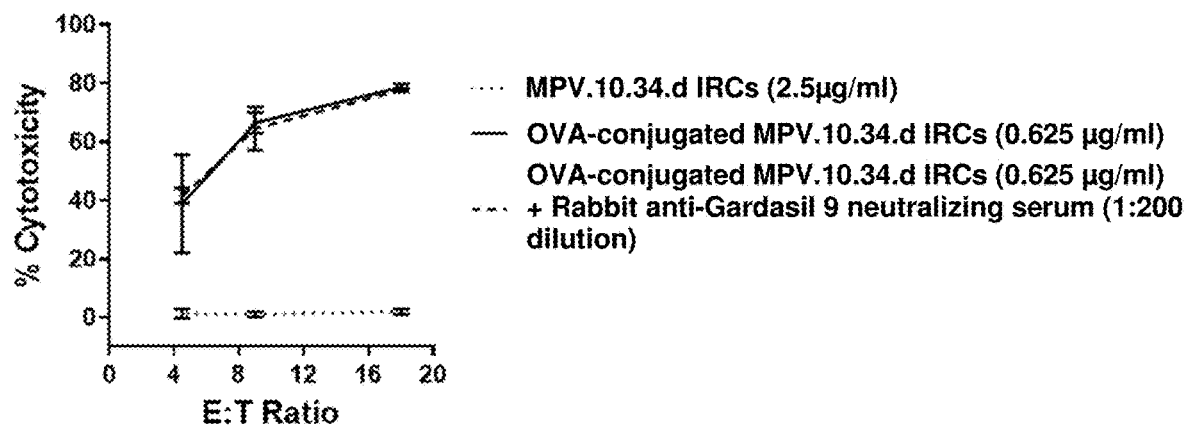

FIG. 31B is a graph of absorbance at 450 nm vs. dilution factor of data obtained from two ELISA assays testing the effect of incubation of anti-MPV.10.34.d sera with MPV.10.34.d IRC. Results show that the sera specifically recognize and bind to MPV.10.34.d capsid backbones.

FIG. 32A is a graph of percent cytotoxicity vs. E:T ratio showing that co-incubation of MPV-specific sera (1:200) with OVA-conjugated MPV.10.34.d IRC at 2.5 μg/mL did not inhibit immune redirection of OVA-specific murine T-cells.

FIG. 32B is a graph of percent cytotoxicity vs. E:T ratio showing that co-incubation of MPV-specific sera (1:200) with OVA-conjugated MPV.10.34.d IRC at 0.625 μg/mL did not inhibit immune redirection of OVA-specific murine T-cells.

FIG. 32C is a graph of percent cytotoxicity vs. E:T ratio showing that co-incubation of MPV-specific sera (1:200) with OVA-conjugated MPV.10.34.d IRC at 0.156 μg/mL did not inhibit immune redirection of OVA-specific murine T-cells.

FIG. 32D is a graph of percent cytotoxicity vs. E:T ratio showing that co-incubation of anti-MPV.10.34.d sera (1:200) with OVA-conjugated MPV.10.34.d IRC at 2.5 μg/mL did not inhibit immune redirection of OVA-specific murine T-cells, despite the fact that the sera specifically bound to OVA-conjugated MPV.10.34.d IRC.

FIG. 32E is a graph of percent cytotoxicity vs. E:T ratio showing that co-incubation of anti-MPV.10.34.d sera (1:200) with OVA-conjugated MPV.10.34.d IRC at 0.625 μg/mL did not inhibit immune redirection of OVA-specific murine T-cells, despite the fact that the sera specifically bound to OVA-conjugated MPV.10.34.d IRC.

FIG. 32F is a graph of percent cytotoxicity vs. E:T ratio showing that co-incubation of anti-MPV.10.34.d sera (1:200) with OVA-conjugated MPV.10.34.d IRC at 0.156 μg/mL did not inhibit immune redirection of OVA-specific murine T-cells, despite the fact that the sera specifically bound to OVA-conjugated MPV.10.34.d IRC.

FIG. 33A is a table of data corresponding to data graphed in FIGS. 32A, 32B, and 32C, showing detection of the binding of OVA-conjugated MPV.10.34.d IRC to tumor cells under different sample concentrations in the presence of MPV serum (1:200) dilution. The results show binding of OVA-conjugated MPV.10.34.d IRC despite the fact that MPV sera also specifically binds to OVA-conjugated MPV.10.34.d IRC.

FIG. 33B is a table of data corresponding to data graphed in FIGS. 32D, 32E, and 32F, showing detection of the binding of OVA-conjugated MPV.10.34.d IRC to tumor cells under different sample concentrations in the presence of anti-MPV.10.34.d IRC serum (1:200) dilution. The results show binding of OVA-conjugated MPV.10.34.d IRC to tumor cells despite the fact that MPV.10.34.d IRC serum sera was shown to also specifically bind to OVA-conjugated MPV.10.34.d IRC.

Figure 34:
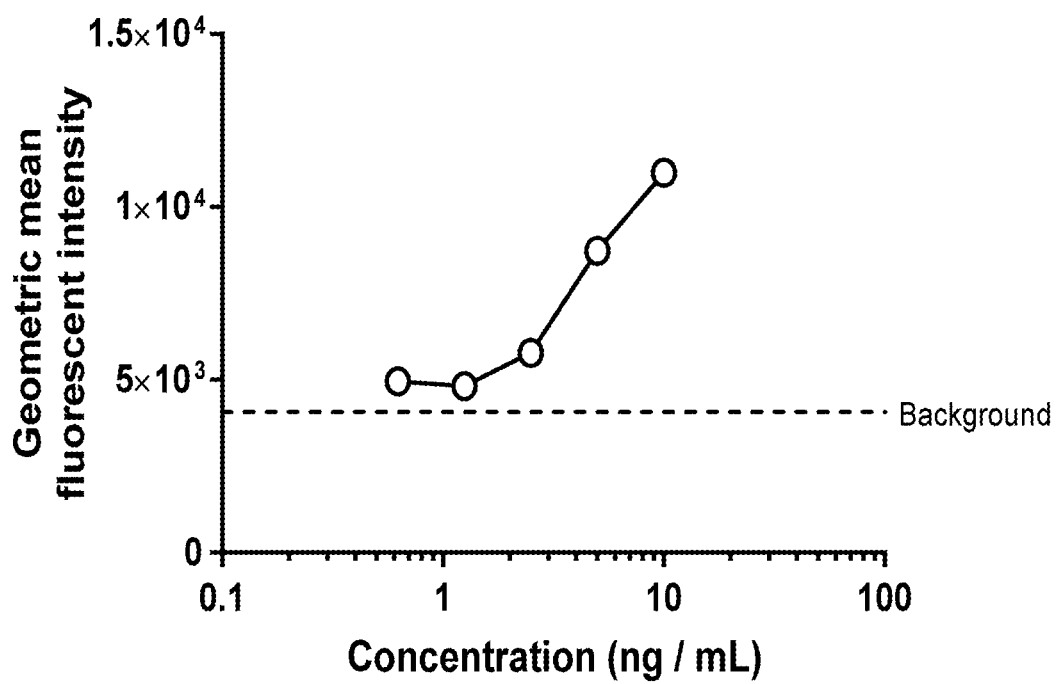

FIG. 34 is a graph of geometric mean fluorescence intensity vs. concentration of OVA-conjugated MPV.10.34.d IRCs (ng/mL) detecting tumor cell surface display of OVA (SIINFEKL, SEQ ID NO: 95)/Kb (MHC-I) complex. The results show that OVA-conjugated MPV.10.34.d IRCs extracellularly load OVA peptides onto MHC receptors on the surface of tumor cells that are deficient in the MHC intracellular processing pathway.

DETAILED DESCRIPTION

Definitions

This specification describes exemplary embodiments and applications of the disclosure. This disclosure, however, is not limited to these exemplary embodiments and applications or to the manner in which the exemplary embodiments and applications operate or are described herein. Various embodiments, features, objects, and advantages of the present teachings will be apparent from the description and accompanying drawings, and from the claims. As used herein, the terms “comprise,” “comprises,” “comprising,” “contain,” “contains,” “containing,” “have,” “having,” “include,” “includes,” and “including,” and their variants, are not intended to be limiting, are inclusive or open-ended, and do not exclude additional, unrecited additives, components, integers, elements, or method steps. For example, a process, method, system, composition, kit, or apparatus that comprises a list of features is not necessarily limited only to those features but may include other features not expressly listed or inherent to such process, method, system, composition, kit, or apparatus.

“About” is used to indicate that a value includes the standard deviation of error for the device or method being employed to determine the value.

“Immune redirector capsid” or “IRC” as used herein is a capsid backbone that also comprises a peptide bound, attached, or conjugated, to the capsid backbone.

“Cleavage sequence” as used herein includes, for example, specific peptide sequences, or more often, peptide motifs at which site-specific proteases cleave or cut the protein. Cleavage sites are used, for example, to cleave off an affinity tag, thereby restoring the natural protein sequence, or to inactivate a protein, or to activate proteins. In the present disclosure “cleavage” refers to proteolytic cleavage. In various embodiments, proteolytic cleavage is catalyzed by peptidases, proteases, or proteolytic cleavage enzymes before the final maturation of the protein. Proteins are also known to be cleaved as a result of intracellular processing of, for example, misfolded proteins. Another example of proteolytic processing of proteins is secretory proteins or proteins targeted to organelles, which have their signal peptide removed by specific signal peptidases before release to the extracellular environment or specific organelle. In one embodiment of the present disclosure, the cleavage sequence is specifically recognized by furin which cleaves and releases the peptides from the IRC, making the peptide available for loading onto or binding by the tumor cell surface receptors. In various embodiments, the cleavage sequence is comprised of cysteine, lysine, and/or arginine residues, that not only allow the peptide to be cleaved from the capsid backbone, but also serve as anchors to conjugate the peptide to the capsid protein until release by the cleavage protein, such as furin, which are in some instances enriched in, or selectively present at, the site of the tumor, i.e., in the tumor microenvironment.

“Epitope” or “antigen” or “antigenic epitope” is a set of amino acid residues that create recognition by or are recognized by a particular immunoglobulin or, in the context of T cells, those residues necessary for recognition by T cell receptor proteins and/or major histocompatibility (MHC) receptors. The amino acid residues of an epitope need not be contiguous/consecutive. In an immune system setting, in vivo or in vitro, an epitope are in some instances a composite of the collective features of a molecule, such as primary, secondary, and tertiary peptide structure, and charge, that together form a three-dimensional structure recognized by an immunoglobulin, T cell receptor, and/or human leukocyte (HLA) molecule.

“HPV” and “human papillomavirus” refer to the members of the family Papillomaviridae that are capable of infecting humans. There are two major groups of HPVs defined by their tropism (genital/mucosal and cutaneous groups), each of which contains multiple virus “types” or “strains/genotypes,” e.g., HPV 16, HPV 18, HPV 31, HPV 32, etc.

“MusPV,” “MMuPV1,” “MPV,” and “mouse papillomavirus,” all alternatively and interchangeably refer to the known members of the family Papillomaviridae that are capable of infecting mice (*Mus musculus*).

“Human vaccine” as used herein means a biological preparation that improves immunity to a particular disease in a human. A vaccine typically contains an antigenic agent(s) that resembles a disease-causing agent (pathogen), and is often made from weakened or killed forms of the microbe, its toxins, or one or multiple immunogenic surface proteins of the disease-causing agent. The antigenic agent stimulates the body’s immune system to recognize the disease-causing agent as foreign, destroy it, and “remember” it, so that the immune system can more easily recognize and destroy any of these pathogens should an actual future infection/exposure occur. Human vaccines include vaccines against viral diseases and bacterial diseases. In various embodiments, vaccines against viral diseases include hepatitis A, B, E virus, human papillomavirus, influenza virus, Japanese encephalitis virus, measles virus, mumps virus, polio virus, rabies virus, rotavirus, rubella virus, tick-borne encephalitis virus, varicella zoster virus, variola virus, and yellow fever virus. Human vaccines against viral diseases that are under development include, for example, dengue vaccine, eastern equine encephalitis virus, HTLV-1 T lymphocyte leukemia vaccine, and respiratory syncytial virus vaccine. Such a vaccine includes, in some embodiments, current vaccines in development or currently United States Food and Drug Administration (FDA)-approved vaccinations. A non-limiting list of examples of vaccines that are compatible with the compositions and methods described herein is provided in Table 2. The embodiments described herein, however, are not limited to these listed vaccines, and are contemplated to apply to any vaccine developed to provide immunity in a human subject.

“Inhibiting,” “reducing,” “prevention,” or “reducing the occurrence of,” and similar terms, when used herein, includes any measurable decrease or complete inhibition/reduction or elimination to achieve a desired result, such as inhibiting, reducing, or preventing, or reducing the occurrence of, or reducing tumor mass, progression, and/or metastasis.

“MHC” or “major histocompatibility complex” is a group of genes that encode proteins found on the surfaces of cells that help the immune system recognize foreign substances.

MHC proteins (receptors, or molecules) are expressed by all higher vertebrates. There are two main types of MHC molecules, MHC class I and MHC class II. In humans there are three different genetic loci that encode MHC class I molecules (the MHC-molecules of the human are also designated human leukocyte antigens (HLA)): HLA-A, HLA-B, and HLA-C. HLA-A*01, HLA-A *02, and HLA-A*11 are examples of different MHC class I alleles that can be expressed from these loci.

"Papillomavirus" (PV) refers to all members of the papillomavirus family (Papillomaviridae). An extensive list of papillomavirus types and the ability to make the respective capsid backbones can be referenced using this publication: "Classification of papillomaviruses (PVs) based on 189 PV types and proposal of taxonomic amendments," de Villers et al., 401(1):70-79, 2010, PMID: 20206957 (all the tables specifically incorporated herein by reference for all purposes).

"Preferentially cleaved protein" as used herein means that the peptide is preferentially cleaved from the capsid or capsomere or L1 protein at the site of a tumor or tumor microenvironment. Without wishing to be bound by any particular theory, the preferential tumor-site cleavage is in some instances due to: (1) the unique cleavage sequence on the peptide, and/or (2) the unique tumor microenvironment. For example, in one embodiment, the peptide comprises a cleavage sequence that is preferentially cleaved by the enzyme furin, which is known to be expressed in relatively higher concentrations around tumor cells as compared with elsewhere in an organism.

"Protein," "polypeptide," and "peptide," as used herein, are not restricted to any particular number of amino acids; these terms are sometimes used interchangeably herein. The properties and amino acid sequences of the proteins described herein, and of the nucleic acids encoding them, are well-known and are determined routinely, as well as downloaded from various known databases. (See, e.g., the NCBI GenBank databases). Some peptide sequences are provided herein. However, some peptide sequence information is routinely updated, e.g., to correct mistakes in the previous entries, so updated (corrected) information about the proteins and nucleic acids encoding them is included in this application. Information provided in the sequence databases discussed herein is incorporated by reference.

An immune "response" is a humoral and/or cellular response of the subject's immune system in which, in a cellular response, an antigen-primed cytotoxic T cell, Th1 T cell, Th2 T cell, and/or B cells primed by a vaccine or other pathogen present in the subject, or that the subject was previously exposed to, binds the epitope or antigen.

The term "preexisting immune response" as used herein means an immune response that is present in an individual prior to initiation of the inventive cancer treatment methods described herein. Thus, an individual having a preexisting immune response has an immune response capacity stored within their memory T cells or other immune system components against an antigen, prior to the initiation of a method of treatment as described herein with the antigen to treat cancer. A preexisting immune response is in some instances a naturally-occurring immune response. In other instances, the preexisting immune response is an induced immune response. As used herein, a naturally-occurring preexisting immune response is an immune response in an individual that was elicited in response to an antigen, such as a bacterial, fungal, parasitic, or viral antigen, with which the individual unintentionally contacted or contracted. That is, an individual having a preexisting immune response was, in some instances, not exposed to an antigen with the intent to generate an immune response to the antigen. An induced preexisting immune response is an immune response resulting from an intentional exposure to an antigen, such as when receiving a vaccine. The preexisting immune response is in some instances a naturally-occurring immune response, or in other instances the preexisting immune response is an induced immune response.

A "subject," or "subject in need thereof," as used herein, includes any animal that has a tumor/cancer or has had a tumor/cancer or has a precancerous medical condition or cell or has a genetic or other susceptibility, predisposition, or occupational risk of developing cancer or a tumor. Suitable subjects (patients) include laboratory animals, such as mouse, rat, rabbit, guinea pig, or pig, farm animals, such as cattle, sporting animals, such as dogs or horses, domesticated animals or pets, such as a horse, dog, or cat, nonhuman primates, and humans.

"T cell response" as used herein refers to the immune response elicited by T cells as they encounter antigens. Naïve mature T cells are activated upon encountering antigen presented by B cells, macrophages, and dendritic cells, and then thereby produce armed effector T cells. Effector T cells are, in some instances, either CD8+ T cells that differentiate into cytotoxic T cells, or CD4+ T cells that primarily induce the humoral immune response. The T cell immune response further generates immunological memory that gives protection from the subsequent challenge of the subject by the same or a similar pathogen comprising the same or similar epitopes. In various embodiments, the T cell response is at a threshold of at least 2-fold above the baseline of total CD8+ T cells. In various embodiments, the CD8+ T cells are CD69+ as well.

"Therapeutic compositions" are compositions that are designed and administered to patients for the use of treatment of a disease, such as cancer. Therapeutic compositions, e.g., therapeutic IRC-containing compositions, are used to treat benign or malignant tumors or patients/subjects at risk for such tumors, as well as non-solid cancers. In some embodiments, the IRCs are administered to a subject who previously had a tumor and is currently apparently tumor/cancer free, in an effort to enhance the inhibition or the recurrence of the tumor/cancer.

"Capsid backbone" refers to a multi-protein structure comprised of viral structural proteins, such as envelop or capsid proteins, such as an L1 protein, that in some instances self-assemble into a capsomere that resembles a virus but lack viral genetic material. Capsid backbones are non-infectious and non-replicating, yet morphologically similar to viruses. The capsid backbones disclosed herein bind to, or possess an inherent tropism for, tumor cells.

Capsid Structure

Viruses exist in many different morphologies and are generally smaller in size than bacteria, with a diameter between 20 nm and 300 nm, although some filoviruses possess filament lengths of up to 1400 nm. Visualization of viruses or virus capsid backbones requires transmission electron microscopes (TEM) that are more powerful than optical microscopes. Viruses are particle in shape and exist as virions having a nucleic acid surrounded by a protective coat of proteins called the capsid. These capsids are also in turn in some instances surrounded by a protective lipid bilayer that may include surface proteins, receptors, and the like.

Capsids are formed from a plurality of identical capsomeres. Capsids generally fall into helical or icosahedral structures, with the exception of bacteriophages that possess more complex structures. The most common icosahedral shape is composed of 20 equilateral triangular faces and resembles a three-dimensional sphere in overall shape. Helical capsids resemble a common spring shape in the form of a three-dimensional cylinder. Each face of the capsid is comprised of anywhere from one to three different proteins or monomer units (protomers). Capsids, when not surrounding papillomavirus genomes, are commonly referred to in the art as virus-like particles, or herein referred to as capsid backbones. That is, an empty capsid with no viral genomic material is referred to herein at times as a capsid backbone. Capsid backbones are excellent delivery molecules for treatment and/or prevention of various diseases, especially in the human body, because they are non-infectious and are optionally re-engineered to specifically target or bind to tumor cells, although most capsid backbone, as described above, possess an inherent tissue tropism without further engineering.

Capsomeres are formed from individual subunits or protomers. Native L1 protomers self-assemble through intermolecular disulfide bonds to form pentamers (capsomeres). As noted above, the capsid is comprised of many capsomeres. As used herein, the term "capsomere" is intended to mean a pentameric assembly of papillomavirus L1 polypeptides, including full-length L1 protein, or fragments and mutants thereof. A standard icosahedral capsid is comprised of twenty faces and is a polyhedron including twelve vertices. The vertices are comprised of pentagonal capsomeres and the faces of the capsid are comprised of hexagonal capsomeres. There are always twelve pentagons (pentons) and a varying number of hexagons (hexons) in any given capsid depending on the virus type. Capsids that do not have an exogenous peptide attached thereto are termed "capsid backbones" herein.

The icosahedral structure found in most viruses is very common and consists of twenty triangular faces and twelve fivefold vertexes as noted above. The number of capsomeres included in a capsid follows well-known mathematical principles, such as found in the Goldberg polyhedron first described by Michael Goldberg in 1937. The structures can be indexed by two integers h and k, with h being greater than or equal to one and k being greater than or equal to zero, the structure is visualized by taking h steps from the edge of a pentamer, turning 60 degrees counter-clockwise, then taking k steps to get to the next pentamer. The triangulation number "T" for this type of capsid is therefore defined as $T=h^2+h \cdot k+k^2$. In this scheme, icosahedral capsids contain twelve pentamers plus $10(T-1)$ hexamers. (See, Carrillo-Tripp, et al., *Nuc. Acids Res.*, 37(Database issue):D436-D442, 2009). Thus, it can be seen that the "T" number, or triangulation number, is representative of the size and complexity of a given capsid. However, there are many known exceptions to this general "rule of thumb" found in, for instance, the Papillomaviridae family of viruses that can at times possess pentamers instead of hexamers in hexavalent positions, for instance in a quasi T=7 lattice. Outside of the canonical T=7 capsid structure, other structures such as T=1, T=2, and T=3, are known. A T=1 triangulation value indicates that the capsid is either only an icosahedron or a dodecahedron.

Some viruses are enveloped and further comprise a lipid membrane coating surrounding the capsid structure. The envelope is acquired from the host intracellular membrane. The nucleic acid material is either DNA or RNA and can be either single stranded or double stranded.

The Papillomaviridae family of viruses is a non-enveloped double-stranded DNA virus. There are several hundred family members within the Papillomaviridae family, each of which is referred to as a "type" that infect most known mammals and other vertebrates such as birds, snakes, turtles, and fish. The Papillomaviridae family members are considered to be relatively highly host- and tissue-tropic, meaning that its members usually possess a specific tissue tropism (preference for infection target) and a preference for host type, and are rarely transmitted between species. For example, it is known that the Papillomaviridae family member human papillomavirus (HPV) type 1 exhibits tropism for the soles of the feet, whereas HPV type 2 prefers tissues in the palms of the hands. Papillomaviruses replicate exclusively in keratinocytes.

There are over 170 known human papillomavirus types that have been sequenced and are divided into five genera, including: Alphapapillomavirus, Betapapillomavirus, Gammapapillomavirus, Mupapillomavirus, and Nupapillomavirus. Many more human papillomaviruses have been identified but not yet sequenced.

The papillomavirus has but a single protomer called L1 protein, or major capsid protein L1, that is both necessary and sufficient to form its capsid which is comprised of 72 star-shaped capsomers. The papillomavirus family member capsids are non-enveloped and icosahedral. The papillomavirus genome also includes a second structural protein called L2 that is less abundantly expressed than L1. The presence of L2 in the capsid is optional and not necessary for virus function or for formation of the capsid. All of the capsomeres of the Papillomaviridae family are made of pentamer interactions between proteins.

As described herein, when describing mutant L1 proteins and the like, such mutants, and capsomers, and capsids made therefrom, are meant to include all Papillomaviridae family members and not just human or mouse family members. Thus, mutant L1 proteins as described herein are meant to encompass all L1 proteins in general, and in some instances specifically Papillomaviridae family L1 proteins in particular.

The amino acid domains and sequences of the human papillomavirus L1 protein and its mouse counterpart are presented in FIGS. 1 and 2. A fairly high level of sequence conservation is generally observed across all such L1 proteins of the Papillomaviridae family and is also reflected in this alignment. Further shown in FIG. 2 are sites of possible mutation of the L1 sequence. Some of these mutations are known historically, such as the deletion of ten amino acids from the amino- or N-terminus of the L1 protein. (See, for instance, Conway et al., *J. Dent. Res.*, 88(4):307-317, 2009). Other structural mutations of the peptide sequence of the L1 protein in Papillomaviridae family members are known, such as the removal of the carboxy- or C-terminal residues in a truncation mutation.

The study of an N-terminal truncation mutant of L1 was begun partly in order to obtain stable crystal structures of the protein for high resolution structural analysis of the capsid. Thus, it was found that full length HPV16 L1 were unable to be crystallized under most tested conditions, but upon removal of the ten N-terminal residues, a crystal was able to be formed for further studies. (Conway et al., 2009). Surprisingly, it was found that upon removal of these ten N-terminal residues, the capsomers formed a T=1 capsid structure comprising icosahedral lattices made from twelve L1 pentamers (for a total of 60 protomers). As noted above, the natural structure of the Papillomaviridae family member capsid is that of 72 L1 pentamers to form a T=7 structure. The T=1 structure of the N-terminal truncation mutant of HPV16 lacks certain disulfide bonds normally formed during capsid formation in wild type HPV16 capsids. Studies have shown that serine to cysteine mutation of C428 or deletion of the helix 4 region on human papillomavirus L1 capsid protein results in disrupting both the T=1 or the T=7 capsid backbone formation. (See, Varsani et al., *Virus Res.*, 122(1-2):154-163, 2006, and Schadlich et al., ibid.).

Figure 1A:
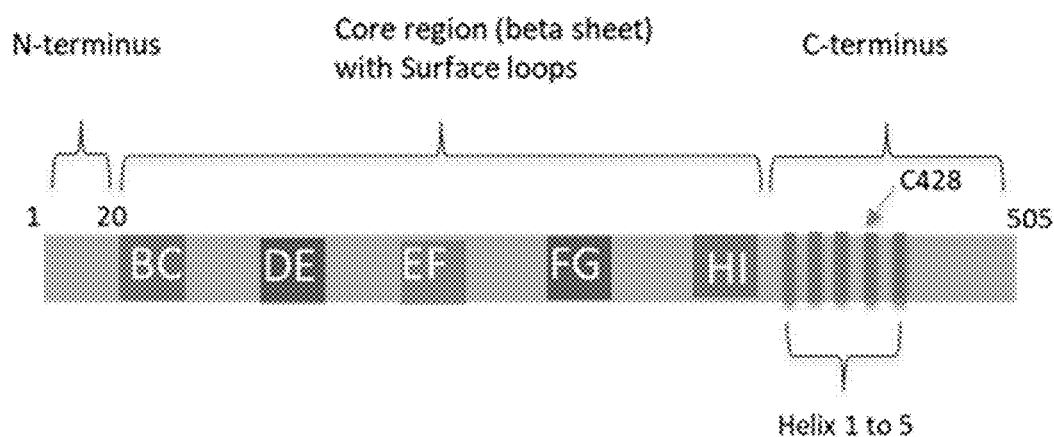
FIG. 1A is a schematic gene map of wildtype mouse papillomavirus L1 (MPV L1) and associated regions.
Figure 1B:
FIG. 1B is a schematic gene map of triple truncated mouse papillomavirus L1 protein (MPV.10.34.d), multiple copies of which combine together to form the T=1 icosahedral papillomavirus capsid backbone.

The overall structure of the papillomavirus L1 protein is presented in FIG. 1A and FIG. 1B and has a tertiary structure consisting generally of various secondary structures including a core of β-strands that form a classic "jelly roll" β-sandwich and five C-terminal α-helices that support five surface-exposed loop regions generally designated in the art as loops BC, DE, EF, FG, and HI. (See, Chen et al., *Mol. Cell*, 5:557-567, 2000, and Bissett et al., *Scientific Reports*, 6:39730, 2016). Three of the α-helices, commonly referred to as h2, h3, and h4, form the surface of contact with other monomers and pentamers (FIG. 1B). (See, Chen et al., FIG. 4, page 561). The five α-helices generally reside at the carboxy-terminus of the L1 sequence.

Design and Production of Mutant L1 Proteins

Deletions of the MPV L1 sequence were made to facilitating the formation of 10 nm to 15 nm capsomeres made from five L1 proteins. It was previously shown that truncation of the amino-, helix-four, and carboxy-terminus residues of the HPV16 L1 protein results in capsomere formation. (See, Bishop et al., *Virol. J.,* 4:3, 2007, and Schadlich et al., *J. Virol.,* 83(15):7690-7705, 2009). On the other hand, it was shown in HPV11 and HPV16 that truncation of the amino-terminal ten residues of L1, alone, would yield T=1 icosahedral capsid backbones. These T=1 icosahedral capsid backbones are approximately 20 nm to 30 nm in diameter and consist of 60 L1 proteins (or 12 capsomers). Deletion of up to 34 amino acids at the carboxy-terminus did not inhibit T=1 formation. However, if deletions in the helix-four region of L1 occurred (amino acids 411 to 436), the formation of T=1 would be ablated, even in the presence of N-terminal or C-terminal truncations. In all permutations, capsomers would be observed. (Chen et al., *Mol. Cell,* 5(3):557-567, 2000, and WO 2000054730). These results were consistent with papillomavirus type 16 L1 produced in *E. coli* or in insect cells. (See, Schadlich et al., *J. Virol.,* 83(15):7690-7705, 2009). Taken together, the authors of this study concluded that the helix-4 structure was needed for the assembly of capsomers into both higher ordered T=1 and T=7 icosahedral structures. (See, Bishop et al., *Virol.,* 4:3, 2007).

Various deletions of the MPV L1 sequence were generated, resulting in the construct called "MPV.10.34.d" shown schematically in FIG. 1B. This construct was designed to create an MPV capsomere as a therapeutic platform. MPV L1 proteins were selected as the carrier vehicle construct instead of HPV L1 because humans have for the most part not been exposed to MPV and therefore it was postulated that virion-derived capsids from MPV would not be sensitive to innate immune response as is seen with HPV L1 proteins.

Recently a ΔN10 deletion of HPV16 L1, in which the amino-terminal ten residues of the HPV L1 sequence are removed, was crystallized and found to conform to the shape of a T=1 capsid backbone. (See, Chen et al., 2000). The structure revealed that the carboxy terminal segment from residue 384 to 446 of L1 folds into three helices with connecting loops and turns. These helices are the primary inter-pentamer bonding contacts in the assembled T=1 capsid backbone. To test whether these helices also affect capsid backbone assembly, L1 proteins comprising the ΔN10 deletion were generated with a specific deletion of helix 4 for both HPV16 (residues 408 to 431) and HPV11 (residues 409 to 429). The pentamers were purified by FPLC and were shown to possess a "donut" shape as observed by electron microscopy (EM). No assembly of capsid backbones from these pentamers was found under any condition tested, suggesting that this carboxy-terminal helical domain is essential for T=1 or T=7 capsid backbone assembly. Crystallographic analysis of the T=1 capsid backbone revealed that inter-pentameric contacts are established by hydrophobic interactions between the α-helices 2 and 3 of one capsomere and α-helix 4 of a neighboring capsomere. (Chen et al., 2000). Consequently, a mutant L1 with helix 4 deleted formed homogenous capsomeres but failed to form T=1 and T=7 capsid backbones. (See, Bishop et al., 2006). The constructs with helix 4 deleted did not exhibit any ability to self-assemble, consistent with previous reports. (See, Schadlich et al., *J. Virol.,* 83(15):7690-7705, 2009).

For the purposes of this description, the term mutant L1 protein means an L1 protein or protomer comprising one or more non-wild type sequences. Such non-wild type sequences include truncations or deletions (internal or at the ends of the sequences), single residue substitutions, and the like. For instance, a mutant L1 protein includes an L1 protein in which any of the following are true: 1) a certain number of the N-terminal residues are deleted, a certain number of the C-terminal residues are deleted, and/or 3) a certain number of internal residues are deleted, in some instances in more than one location internally within the sequence.

The mutant L1 protein is in some embodiments derived from a wild type papillomavirus L1 protein. Any papillomavirus L1 protein is useful in the presently described compositions. L1 protein sequences are relatively conserved. Thus, description of mouse papillomavirus mutant L1 proteins, below, are exemplary and it is contemplated that the same mutations made in other L1 proteins of the papillomavirus family is expected to yield similar results. In various embodiments, a capsid backbone is provided comprising a papillomavirus L1 protein and/or a papillomavirus L2 protein. Thus, the capsid backbone in some embodiments comprises both papilloma L1 and L2 proteins. In other embodiments, the capsid backbone is comprised of only L1 proteins. In some embodiments the L1 protein is a hybrid or chimeric protein comprised of L1 sequences from more than one source merged together into a single L1 sequence.

The L1 protein sequences are known for substantially all papillomavirus genotypes identified to date, and any of these L1 sequences or fragments are contemplated as being included in the present compositions. Examples of L1 polypeptides include, without limitation, full-length L1 polypeptides, e.g., HPV16 L1 polypeptide, SEQ ID NO: 128, L1 truncations that lack any one or more residues of the native C-terminus, L1 truncations that lack any one or more residues of the native N-terminus, and L1 truncations that lack any one or more internal domain residues in any one or more internal locations. The L1 protein is in some instances exemplified as a modified L1 protein, e.g., a modified HPV16 or MPV16 L1 protein, wherein the HPV16 L2 amino acids 17 to 36 (the RG1 epitope) are inserted within the DE-surface loop of HPV16 L1. (See, Schellenbacher et al., *J. Invest. Dermatol.,* 133(12):2706-2713, 2013; Slupetzky et al., *Vaccine,* 25:2001-2010, 2007; Kondo et al., *J. Med. Virol.,* 80:841-6, 2008; Schellenbacher et al., *J. Virol.,* 83:10085-10095, 2009; and Caldeira et al., *Vaccine,* 28:4384-93, 2010).

The L2 polypeptide is in some embodiments full-length L2 protein or an L2 polypeptide fragment. The L2 sequences are known for substantially all papillomavirus genotypes identified to date, and any of these L2 sequences or fragments can be employed in the present disclosure. Examples of L2 polypeptides include, without limitation, full-length L2 polypeptides, e.g., HPV16 L2 polypeptide (SEQ ID NO: 1), or mouse papillomavirus L2 (SEQ ID NO: 2), L2 truncations that lack any one or more of the native C-terminus, L2 truncations that lack any one or more of the native N-terminus, and L2 truncations that lack any one or more internal domain residues in any one or more locations.

The papillomavirus capsid backbone is in some embodiments formed using the L1 and optionally L2 polypeptides from any animal papillomavirus, or derivatives or fragments thereof. Thus, any known (or hereafter identified) L1 and optionally L2 sequences of human, bovine, equine, ovine, porcine, deer, canine, feline, rodent, rabbit, etc., papillomaviruses are employed to prepare the capsid backbones described herein. (See, de Villiers et al., *Virology*, 324:17-27, 2004, for a current description of papillomavirus genotypes and their relatedness, incorporated herein by reference for all purposes).

In certain embodiments, the L1 and optionally L2 polypeptides that are used to form the capsid backbones are from a non-human papillomavirus or a human papillomavirus genotype other than HPV6, HPV11, HPV16, and HPV18. For example, the L1 and/or L2 proteins are in some embodiments from HPV 1, 2, 3, 4, 5, 6, 8, 9, 15, 17, 23, 27, 31, 33, 35, 38, 39, 45, 51, 52, 58, 66, 68, 70, 76, or 92.

As described above, in human papillomavirus HPV16, several different mutations of L1 protein have been characterized. (See, for instance, Chen et al., 2000). Some of these mutations include the following in Table 1. (Chen et al., 2000, Table 1, page 558):

| Deletion | Trypsin Sensitivity | Apparent Diameter of Assembled Particle (Å)$^a$ |
| --- | --- | --- |
| ΔN = 0 | No | 600 |
| ΔN = 8 | No | 600 |
| ΔN = 9 | No | 600 |
| ΔN = 10 | No | 300 |
| ΔN = 15 | Yes$^b$ | NA |
| ΔN = 20 | Yes | NA |
| ΔC = 16 | No | 600 |
| ΔC = 30 | No | 600 |
| ΔC = 46 | Yes | NA |
| ΔC = 86 | Yes | NA |

In Table 1, the delta symbol (Δ) designates deletion and the "N" or "C" designated whether the deletion is located at the N-terminus or C-terminus, respectively. The number following these two symbols indicates the number of residues of the L1 sequence that were deleted. It is noted that Chen et al. does not report any double, triple, or higher number of mutations within a single L1 protein.

Thus, the L1 mutant proteins described herein include N-terminal truncation L1 mutant proteins. The N terminus is truncated by at least 5, 6, 7, 8, 9, 10, 11, 12, 13, 14, or 15 amino acids. In some embodiments the N-terminal truncation is 5 amino acids. In some embodiments the N-truncation is 10 amino acids. In some embodiments the N-terminal truncation is 37, 38, 39, or even 40 amino acids.

The L1 mutant proteins described herein further include C-terminal truncation L1 mutant proteins. The C terminus is truncated by at least 5, 6, 7, 8, 9, 10, 11, 12, 13, 14, or 15 amino acids. In some embodiments the C-terminal truncation is 5 amino acids. In some embodiments the C-truncation is 10 amino acids.

The L1 mutant proteins described herein further include L1 mutants in which any number of internal residues are deleted. Surprisingly, the retention of the helix-4 region is in some embodiments needed for the formation of capsid backbones having a T=1 geometry, whereas in the literature it is reported, as discussed above, that its deletion is not supposed to yield any capsid backbone assembly. Generally, the internal residues deleted in the described mutant L1 proteins are those shown in FIGS. 1 and 2. Contemplated also are deletions of 34 residues in the helix 4 (H4) region. In some instances, the truncation of internal residues of L1 proteins is 25, 26, 27, 28, 29, 30, 31, 32, 33, 34, 35, 36, 37, 38, 39, or even 40 residues in length.

Also described herein are L1 mutant proteins in which any one or more of the C-terminus and/or N-terminus and/or internal residues are deleted simultaneously. For instance, in some embodiments the mutant L1 protein has both C- and N-terminal truncation mutations of similar or varying length. In other embodiments, the mutant L1 protein has a C-terminal truncation and an internal residue truncation. In some embodiments, the mutant L1 protein has an N-terminal truncation and an internal truncation. In certain embodiments, the mutant L1 protein has truncations simultaneously in all three locations, C-terminus, N-terminals, and internal truncations.

The mutant L1 proteins described herein are generally produced recombinantly but are also produced by any known protein expression methodology. For instance, the mutant L1 proteins are generated by first designing DNA primers complimentary to the wild type L1 sequence and then performing PCR amplification of the sequence in the presence of the primers designed to truncate or otherwise mutate the wild type L1 sequence, as further explained in detail below, in the Examples section. (See also, Touze et al., *J. Clin. Microbiol.,* 36(7):2046-2051, 1998). The design and implementation of proper primer sequences and PCR protocols are known and such methods are used to ultimately generate the desired mutant L1 protein nucleic acid sequence, from which the mutant L1 proteins are expressed.

The mutant L1 protein nucleic acid sequence is then in some embodiments codon-optimized for better protein expression and production depending on the organism in which the expression is conducted. Utilization of different codon optimization methods for certain expression vectors and host expression systems are known in the art. (See, Mauro and Chappell, *Trends in Molecular Medicine,* 20(11): 604-613, 2014, for instance).

The mutant L1 protein nucleic acid sequence is then ligated into an acceptably prepared and commercially-available expression vector designed for protein expression. Expression vectors of various types possessing functionality for certain expression hosts are widely commercially available. Recombinant mutant L1 proteins described herein are expressed in bacterial as well as eukaryotic cells and in certain embodiments are expressible in vitro.

Often expression of recombinant proteins in bacterial hosts results in the formation of inclusion bodies (IBs). Thus, in some instances, recombinant mutant L1 protein expressed as IBs are solubilized using known procedures. In a particular embodiment, the solubilization of IBs of expressed mutant L1 proteins described herein includes the steps set forth, for instance, in FIG. 3, and Example 3. The processes include various steps, such as: (a) transforming a prokaryotic cell with an expression vector encoding the L1 protein; (b) culturing the transformed prokaryotic cell under conditions that promote expression of the L1 protein; (c) lysing the transformed prokaryotic cells to release expressed L1 protein; (d) separating cell debris from the expressed L1 protein and recovering the L1 protein in the form of IBs; (e) optionally washing the L1 protein IBs; (f) solubilizing the L1 protein IBs; (g) refolding the L1 protein optionally in the presence of one or more denaturants, reducing agents, and the like; and (h) forming the icosahedron or dodecahedron capsid having a triangulation number T equal to 1 by incubating the refolded L1 protein in assembly buffer. Such processes, in some embodiments, further include conjugating in a conjugation buffer the one or more peptides to the assembled L1 protein by incubating the assembled L1 protein under reducing conditions in the presence of one or more peptides and/or removing denaturant from the conjugation buffer but maintaining reducing agent when forming the icosahedron or dodecahedron capsid having a triangulation number T equal to 1.

The described methods and processes for creating and purifying the described mutant L1 proteins is different in many aspects from such processes described in the art for assembly of papillomavirus capsids. Indeed, it is known in the art that assembly into higher ordered papillomavirus capsids requires that the L1 protein must first be subjected to a disassembly buffer that includes a reducing agent. This step is then often followed by subjecting the L1 protein to an assembly buffer that then removes the reducing agent. This legacy methodology results in stable capsids with improved properties. (See, McCarthy et al., 10.1128/JVI.72.1.32-41, 1998, Zhao et al., *Virol. J.*, 9:52, 2012, Mach et al., *J. Pharm. Sci.*, 95:2195-2206, 2006, and U.S. Pat. No. 6,436,402).

Remarkable Properties of Capsid Backbones Formed From Mutant L1 Proteins

It was serendipitously discovered during the studies described herein that certain mutant L1 proteins possess beneficial and unexpected properties. For instance, certain mutant L1 proteins led primarily to the formation of a T=1 capsid backbone possessing helpful and unexpected conjugation properties. The formation of a T=1 capsid backbone instead of a T=7 capsid backbone leads to higher stability under reducing conditions and therefore higher conjugation efficiency as compared with wild type sequences that form T=7 capsid backbone.

For instance, the efficiency with which the mutant capsid backbone, e.g., the MPV.10.34.d backbone, is able to be conjugated with peptide is from 25 to 85% (w/w). In some embodiments, the conjugation efficiency is about 25%. In other embodiments, the conjugation efficiency is about 25, about 35, about 45, about 55, about 65, about 75, or even about 85% (w/w).

In contrast, wild type T=7 capsid backbones have generally a lower efficiency of conjugation that is less than about 25%. See, for instance, WO 2020/139978. The ability to achieve a higher amount of peptide conjugated to the T=1 capsid backbone compared to T=7 capsid backbone allows for delivery of a higher number of peptides to the target tumor or cancer at an overall lower IRC dose amount compared with IRC forms from T=7 capsid backbones.

Additionally, T=1 capsid backbones having a smaller geometric shape or size as compared to T=7 capsid backbones allows for less stearic hindrance with the IRC made from T=1 capsid backbones is injected into a subject and the IRC infiltrate tumor microenvironments. This beneficial and unexpected effect then leads to a lower IRC dose needed to achieve the same effect as an equivalent T=7, or higher order, capsid backbone-based IRC.

These and other additional beneficial features of the T=1 capsid backbone geometry are described in further detail hereinbelow.

Mutant L1 Protein IRC and Mechanism of Action

In some embodiments, the mutant L1 protein is conjugated to another peptide. To add further beneficial functionality to capsids or capsid backbones comprised of the mutant L1 proteins, additional peptides are conjugated to the surface of such capsids. These peptides add beneficial functionality to the capsid and result in added functionality such as treatment of cancer in subjects in need thereof.

In an embodiment, the conjugated papillomavirus capsid backbone comprises an L1 capsid protein and a peptide. In other embodiments, the IRC comprises an (at least one) L1 capsid protein, an (at least one) L2 capsid protein, and at least one peptide. The L1 polypeptide is in some embodiments a full length L1 protein or in other embodiments is an L1 polypeptide fragment. In specific embodiments, the full-length L1 protein or L1 polypeptide fragment is capsid backbone assembly-competent; that is, the L1 polypeptide will self-assemble to form capsomeres under proper conditions that are competent for self-assembly into higher-order structural geometries, thereby forming a capsid backbone. In more specific embodiments, the capsid backbones comprise a T=1 particle, a structure of about 20 nm to 30 nm in diameter, and composed of 12 capsomeres or 60 copies of L1 protein. In other embodiments, the capsid backbones comprise a fully assembled papillomavirus capsid, a structure of about 50 nm and composed of 72 capsomeres or 360 copies of L1 protein.

In various embodiments, the IRC presented herein bind to, specifically or non-specifically, or otherwise contact, one or more cancer cells. This is in part due to the capsid backbone's selectivity (tropism) for proteins and/or molecules that are in some instances specific to, or expressed in higher abundance by, tumor cells. In various embodiments, the IRC binds to a certain sub-family type of heparin sulfate proteoglycan (HSPG), which is preferentially expressed on tumor cells. As used herein, "binding to a cancer cell" refers to the formation of non-covalent interactions between the capsid protein of the IRC and the tumor cell such that the IRC comes into close proximity to the tumor cell and the peptide is cleaved from the capsid backbone, and then the peptide binds to, or is bound by, or otherwise interacts with, the MHC receptor present on the tumor cell surface.

In various embodiments, the peptide is an epitope that is recognized by a T cell or T cell population that already exists in the subject. In various embodiments, this existing T cell or T cell population exists because of a prior infection or vaccination. In various embodiments, the peptide is an epitope that is capable of being bound by a T cell. In various embodiments, the peptide is an epitope capable of being bound by a T cell already present in a subject. In this context, "capable of being bound" means that an "epitope" is presented on the surface of a cell, where it is bound to MHC molecules. T cell epitopes presentable by MHC class I receptors are bound by the T cell receptor of cytotoxic CD8 T lymphocytes (CD8 T cells or CTLs). T cell epitopes presentable by MHC class I molecules are typically peptides of about 9 to about 12 amino acids in length. In various embodiments, an IRC is provided that releases a T cell response-eliciting peptide that upon release is directly bound by and consequently appropriately presentable by one or more MHC molecules expressed on the surface of one or more cancer or tumor cells. As the released peptide does not require processing by the antigen processing machinery in the cytosol, the T cell response-eliciting peptides are presented on the surface of the target cell in a short amount of time. The process of release of such peptides from the IRC and subsequent binding of the peptides by the MHC molecules of target cells is akin to labelling, tagging, or otherwise "marking" these tumor or cancer cells. This tagging or marking leads to ready identification by other components of the subject's immune system, thereby recruiting these components of the subject's immune system to remove the cancer or tumor cells via the various known cell destruction pathways.

Hence, in one embodiment of the described methods, uses, and compositions described herein, in less than about 8.5 hours after administration of the IRC dose to the subject, the IRC will naturally migrate to the target cell after which the T cell response-eliciting peptide released from the IRC, is bound by the MHC molecule on the cancer cell, and then the peptide is presented on the surface of the target cell via an MHC class I molecule to other components of the subject's immune system for recognition thereby. In another embodiment of the invention, in less than 23.5 hours after introduction of the IRC to the target cell the T cell response eliciting peptide is presented on the surface of the target cell via an MHC class I molecule. In another embodiment of the invention, the IRC is capable of mediating T cell cytotoxicity against the target cell within less than 6 hours after administration of the IRC to the target cell.

In various embodiments, the peptide comprises one epitope or comprises at least two epitopes. The peptide epitopes are in some instances derived from different proteins, or in other embodiments they are epitopes from the same protein (or antigen). In various embodiments, the pathogen is a virus, a bacterium, a fungus, a parasite, or a combination thereof.

In various embodiments, the subject's preexisting T cells are specific to a vaccine epitope. In various embodiments the epitope is derived from a childhood, early childhood, adolescent, or elderly (geriatric), vaccine. In various embodiments the subject's preexisting immunity is the result of prior administration of a human vaccine. Antigens described herein that comprise epitopes incorporated into the peptides described herein are found in any of the known infectious agents, such as viruses, bacteria, parasites, fungi, and the like. In various embodiments, the peptide is selected from the list provided by Table 2.

For instance, non-limiting examples of a viruses from which antigens bearing epitopes that are incorporated in some embodiments into the described peptides include, for instance, a vaccinia virus, a varicella zoster virus, a herpesvirus, e.g., herpes zoster virus or cytomegalovirus or Epstein-Barr virus, rubella, a hepatitis virus, e.g., hepatitis A virus or hepatitis B virus or hepatitis C virus, influenza, e.g., type A or type B, a measles virus, a mumps virus, a polio virus, a variola (smallpox) virus, a rabies virus, a coronavirus, Dengue virus, an Ebola virus, a West Nile virus, a yellow fever virus, or a zika virus.

For instance, non-limiting examples of a bacteria from which antigens bearing epitopes that are incorporated in some embodiments into the described peptides include, for example, a *Bordetella pertussis, chlamydia, trachomatis, Clostridium tetani, diphtheria, Hemophilus influenza, Meningococcus, pneumococcus, Vibrio cholera, Mycobacterium tuberculosis*, BCG, typhoid, *E. coli, salmonella, Legionella pneumophila, rickettsia, Treponema pallidum, Streptococcus* group A or group B, *Streptococcus pneumonia, Bacillus anthracis, Clostridium botulinum*, or a *Yersinia* sp bacteria.

For instance, non-limiting examples of a parasite from which antigens bearing epitopes that are incorporated in some embodiments into the described peptides include, *Entamoeba histolytica, Toxoplasma gondii*, a *Trichinella* sp., e.g., *Trichinella spiralis*, a *Trichomonas* sp., e.g., *Trichomonas vaginalis*, a *Trypanosoma* sp., e.g., *Trypanosoma brucei gambiense, Trypanosoma brucei rhodesiense*, or a *Trypanosoma cruzi*, or a *plasmodium*, e.g., *Plasmodium falciparum, Plasmodium vivax*, or *Plasmodium malariae*.

TABLE 2

Epitope Peptide Sequences

| Epitope Sequence | SEQ ID NO | Virus Type | MHC allele | Viral Protein |
|---|---|---|---|---|
| SLPRSRTPI | 4 | Chicken Pox (VZV) | A*02:01 | IE62 |
| SAPLPSNRV | 5 | Chicken Pox (VZV) | A*02:01 | IE62 |
| GSAPLPSNRV | 6 | Chicken Pox (VZV) | A*02:01 | IE62 |
| ALWALPHAA | 7 | Chicken Pox (VZV) | A*02:01 | IE62 |
| SLSGLYVFV | 8 | Shingles vaccines | A*02:01 | Glycoprotein E |
| YLGVYIWNM | 9 | Shingles vaccines | A*02:01 | Glycoprotein E |
| KIHEAPFDL | 10 | Shingles vaccines | A*02:01 | Glycoprotein E |
| LLCLVIFLI | 11 | Shingles vaccines | A*02:01 | Glycoprotein E |
| DLLLEWLYV | 12 | Shingles vaccines | A*02:01 | Glycoprotein E |

TABLE 2-continued

Epitope Peptide Sequences

| Epitope Sequence | SEQ ID NO | Virus Type | MHC allele | Viral Protein |
|---|---|---|---|---|
| SMYYAGLPV | 13 | Shingles vaccines | A*02:01 | Glycoprotein E |
| ILHDGGTTL | 14 | Shingles vaccines | A*02:01 | Glycoprotein E |
| WLYVPIDPT | 15 | Shingles vaccines | A*02:01 | Glycoprotein E |
| VLMGFGIIT | 16 | Shingles vaccines | A*02:01 | Glycoprotein E |
| CLVIFLICT | 17 | Shingles vaccines | A*02:01 | Glycoprotein E |
| KEADQPWIV | 18 | Shingles vaccines | A*02:01 | Glycoprotein E |
| VVSTVDHFV | 19 | Shingles vaccines | A*02:01 | Glycoprotein E |
| FLICTAKRM | 20 | Shingles vaccines | A*02:01 | Glycoprotein E |
| VLRTEKQYL | 21 | Shingles vaccines | A*02:01 | Glycoprotein E |
| HMWNYHSHV | 22 | Shingles vaccines | A*02:01 | Glycoprotein E |
| TVNKPVVGV | 23 | Shingles vaccines | A*02:01 | Glycoprotein E |
| FVVYFNGHV | 24 | Shingles vaccines | A*02:01 | Glycoprotein E |
| WIVVNTSTL | 25 | Shingles vaccines | A*02:01 | Glycoprotein E |
| VAYTVVSTV | 26 | Shingles vaccines | A*02:01 | Glycoprotein E |
| FMYMSLLGV | 27 | measles | A*02:01 | m50 |
| SLWGSLLML | 28 | measles | A*02:01 | C protein |
| LLAVIFVMFL | 29 | measles | A*02:01 | H38 |
| SMYRVFEVGV | 30 | measles | A*02:01 | H250-259 |
| ILPGQDLQYV | 31 | measles | A*02:01 | H516-525 |
| KLWCRHFCV | 32 | measles | A*02:01 | H576 |
| KLWCRHFCVL | 33 | measles | A*02:01 | H576 |
| RLSDNGYYTV | 34 | measles | A*02:01 | M164 |
| KLLRYYTEI | 35 | measles | A*02:01 | F205 |
| KLWESPQEI | 36 | measles | A*02:01 | C 84 |
| RLLDRLVRL | 37 | measles | A*02:01 | N50 |
| KLMPNITLL | 38 | measles | A*02:01 | F57 |
| TLLNNCTRV | 39 | measles | A*02:01 | F64 |
| EMLTLATWV | 40 | Hep B | A*02:01 | C64-72 |
| FLPSDFFPSV | 41 | Hep B | A*02:01 | Core 18 |
| FLPADFFPSV | 42 | Hep B | A*02:01 | Core 19 |

TABLE 2-continued

Epitope Peptide Sequences

| Epitope Sequence | SEQ ID NO | Virus Type | MHC allele | Viral Protein |
|---|---|---|---|---|
| FLPSDFFPSI | 43 | Hep B | A*02:01 | Core 20 |
| WLSLLVPF | 44 | Hep B | A*02:01 | ENV335 |
| FLLTRILTI or FLLTRILTL | 45 or 46 | Hep B | A*02:01 | ENV183 |
| GLSPTVWLSV | 47 | Hep B | A*02:01 | ENV348 |
| LLDYQGMLPV | 48 | Hep B | A*02:01 | ENV260 |
| LLCLIFLLV | 49 | Hep B | A*02:01 | ENV251 |
| SIVSPFIPLL | 50 | Hep B | A*02:01 | ENV370 |
| FLLTKILTI | 51 | Hep B | A*02:01 | ENV183 |
| ILSPFLPLL | 52 | Hep B | A*02:01 | ENV371 |
| FLLSLGIHL | 53 | Hep B | A*02:01 | POL 575 |
| GLSRYVARL | 54 | Hep B | A*02:01 | POL 455 |
| SLYADSPSV | 55 | Hep B | A*02:01 | POL 816 |
| YMDDVVLGA | 56 | Hep B | A*02:01 | POL 551 |
| ALMPLYACI | 57 | Hep B | A*02:01 | POL 655 |
| VLHKRTLGL | 58 | Hep B | A*02:01 | HBx 92 |
| CLFKDWEEL | 59 | Hep B | A*02:01 | Hbx115 |
| STLPETTVVRR | 60 | Hep B | A*03, A*11 | Core 141 |
| EYLVSFGVW | 61 | Hep B | A*31, A*68 | core 117 |
| FFPSIRDLL | 62 | Hep B | A*24 | Core 23 |
| SWLSLLVPF | 63 | Hep B | A*24 | Env 334 |
| KYTSFPWLL | 64 | Hep B | A*24 | Pol 756 |
| HLSLRGLFV | 65 | Hep B | A*02:01 | HBx 52-60 |
| CLFKDWEEL | 66 | Hep B | A*02:01 | HBx 115-123 |
| LPSDFFPSV | 67 | Hep B | B*51 | Core 19 |
| GILGFVFTL | 68 | Influenza | HLA-A2 | M1 |
| ILGFVFTLTVPSERGLQRRRF | 69 | Influenza | | |
| LIRHENRMVLASTTAKA | 70 | Influenza | | |
| LQAYQKRMGVQMQR | 71 | Influenza | | |
| YVYDHSGEAVK | 72 | Measles | | |
| WLSLLVPFV | 73 | Hep B | | |
| (K)GILGFVFTL(T)(V) | 74 | Influenza | | |
| KLSTRGVQIASNEN | 75 | Influenza | | |
| RGLQRRRFVQNALNGNG | 76 | Influenza | | |
| FMYSDFHFI | 77 | Influenza | | |
| NLVPMVATV | 3 | Cytomegalovirus | HLA-A2 | |
| VAIIEVDNEQPTTRAQKL | 78 | Poliovirus | | |

TABLE 2-continued

Epitope Peptide Sequences

| Epitope Sequence | SEQ ID NO | Virus Type | MHC allele | Viral Protein |
|---|---|---|---|---|
| Any 9-mer sequence of GACV AIIEVDNEQPTTRAQKLF AMWRITYKDTVQLRRKL | 79 | Poliovirus | | |
| SVRDRLARL | 80 | EBV | | |
| LLDRVRFMGV | 81 | EBV | | |
| CLGGLLTMV | 82 | EBV | | |
| GLCTLVAML | 83 | EBV | | |
| SVLGPISGHVLK | 84 | Cytomegalovirus | HLA-A11 | |
| RPHERNGFTVL | 85 | Cytomegalovirus | HLA-B7 | |
| FTSQYRIQGKL | 86 | Cytomegalovirus | HLA-A24 | |
| YSEHPTFTSQY | 87 | Cytomegalovirus | HLA-A1 | |
| EFFWDANDIY | 88 | Cytomegalovirus | HLA-B44 | |
| TTVYPPSSTAK | 90 | Cytomegalovirus | HLA-A3 | |
| FVFPTKDVALR | 91 | Cytomegalovirus | HLA-A68 | |
| QTVTSTPVQGR | 92 | Cytomegalovirus | HLA-A68 | |
| PTFTSQYRIQGKL | 93 | Cytomegalovirus | HLA-B38 | |
| FPTKDVAL | 94 | Cytomegalovirus | HLA-B35 | |
| SIINFEKL | 95 | | | |
| RAHYNIVTF | 96 | | | |
| SSPPMFRV | 97 | | | |
| KLWAQCVQL | 98 | SARS-CoV-2 | A*02:01 | |
| KLPDDFTGCV | 99 | SARS-CoV-2 | A*02:01 | |
| YLQPRTFLL | 100 | SARS-CoV-2 | A*02:01 | |
| LLYDANYFL | 101 | SARS-CoV-2 | A*02:01 | |
| ALWEIQQVV | 102 | SARS-CoV-2 | A*02:01 | |
| LLLDRLNQL | 103 | SARS-CoV-2 | A*02:01 | |
| YLFDESGEFKL | 104 | SARS-CoV-2 | A*02:01 | |
| FTSDYYQLY | 105 | SARS-CoV-2 | A*01:01 | |
| PTDNYITTY | 106 | SARS-CoV-2 | A*01:01 | |
| ATSRTLSYY | 107 | SARS-CoV-2 | A*01:01 | |
| CTDDNALAYY | 108 | SARS-CoV-2 | A*01:01 | |
| NTCDGTTFTY | 109 | SARS-CoV-2 | A*01:01 | |
| DTDFVNEFY | 110 | SARS-CoV-2 | A*01:01 | |
| GTDLEGNFY | 111 | SARS-CoV-2 | A*01:01 | |
| KTFPPTEPK | 112 | SARS-CoV-2 | A*03:01 | |
| KCYGVSPTK | 113 | SARS-CoV-2 | A*03:01 | |
| VTNNTFTLK | 114 | SARS-CoV-2 | A*03:01 | |
| KTIQPRVEK | 115 | SARS-CoV-2 | A*03:01 | |

TABLE 2-continued

Epitope Peptide Sequences

| Epitope Sequence | SEQ ID NO | Virus Type | MHC allele | Viral Protein |
|---|---|---|---|---|
| KTFPPTEPK | 116 | SARS-CoV-2 | A*11:01 | |
| VTDTPKGPK | 117 | SARS-CoV-2 | A*11:01 | |
| ATEGALNTPK | 118 | SARS-CoV-2 SARS-CoV-2 | A*11:01 | |
| ASAFFGMSR | 119 | SARS-CoV-2 | A*11:01 | |
| ATSRTLSYYK | 120 | SARS-CoV-2 | A*11:01 | |
| QYIKWPWYI | 121 | SARS-CoV-2 | A*24:02 | |
| VYFLQSINF | 122 | SARS-CoV-2 | A*24:02 | |
| VYIGDPAQL | 123 | SARS-CoV-2 | A*24:02 | |
| SPRWYFYYL | 124 | SARS-CoV-2 | B*07:02 | |
| RPDTRYVL | 125 | SARS-CoV-2 | B*07:02 | |
| IPRRNVATL | 126 | SARS-CoV-2 | B*07:02 | |

In various embodiments the epitope is found in one or more known human vaccines, such as a childhood vaccine, early childhood, adolescent, or elderly (geriatric), vaccine. In various embodiments the vaccine is an early childhood vaccine. Certain non-limiting examples of suitable vaccines from which such epitopes are found that are compatible with the described peptides are listed in Table 3.

TABLE 3

Human Vaccines Containing Peptide-Compatible Epitopes

| Type | Commercial Name | Form | Source | Responsible National Regulatory Authority |
|---|---|---|---|---|
| Diphtheria-Tetanus-Pertussis (whole cell)-Hepatitis B-Hemophilus influenzae type b | Quinvaxem | Liquid: ready to use | Janssen Vaccines Corp. | Ministry of Food and Drug Safety |
| Diphtheria-Tetanus | Adsorbed DT Vaccine | Liquid: ready to use | PT Bio Farma (Persero) | National Agency of Drug and Food Control Indonesia |
| Diphtheria-Tetanus-Pertussis (whole cell) | DTP Vaccine | Liquid: ready to use | PT Bio Farma (Persero) | National Agency of Drug and Food Control Indonesia |
| Hepatitis B | Hepatitis B Vaccine Recombinant | Liquid: ready to use | PT Bio Farma (Persero) | National Agency of Drug and Food Control Indonesia |
| Polio Vaccine - Oral (OPV) Trivalent | Oral polio | Liquid: ready to use | PT Bio Farma (Persero) | National Agency of Drug and Food Control Indonesia |
| Polio Vaccine - Oral (OPV) Trivalent | Oral polio | Liquid: ready to use | PT Bio Farma (Persero) | National Agency of Drug and Food Control Indonesia |
| Tetanus Toxoid | TT vaccine | Liquid: ready to use | PT Bio Farma (Persero) | National Agency of Drug and Food Control Indonesia |
| Tetanus Toxoid | TT vaccine | Liquid: ready to use | PT Bio Farma (Persero) | National Agency of Drug and Food Control Indonesia |
| Tetanus Toxoid | TT vaccine | Liquid: ready to use | PT Bio Farma (Persero) | National Agency of Drug and Food Control Indonesia |

TABLE 3-continued

Human Vaccines Containing Peptide-Compatible Epitopes

| Type | Commercial Name | Form | Source | Responsible National Regulatory Authority |
|---|---|---|---|---|
| Measles | Measles vaccine | Lyophilized Lyophilized active component to be reconstituted with excipient diluent before use | PT Bio Farma (Persero) | National Agency of Drug and Food Control Indonesia |
| Yellow Fever | Yellow Fever | Lyophilized Lyophilized active component to be reconstituted with excipient diluent before use | Bio-Manguinhos/Fiocruz | Agencia Nacional da Vigilancia Sanitaria |
| Yellow Fever | Yellow Fever | Lyophilized Lyophilized active component to be reconstituted with excipient diluent before use | Bio-Manguinhos/Fiocruz | Agencia Nacional da Vigilancia Sanitaria |
| Yellow Fever | Yellow Fever | Lyophilized Lyophilized active component to be reconstituted with excipient diluent before use | Bio-Manguinhos/Fiocruz | Agencia Nacional da Vigilancia Sanitaria |
| Hepatitis B | Heberbiovac HB | Liquid: ready to use | Centro de Ingenieria Genetica y Biotecnologia | Centro para el Control Estatal de la Calidad de los Medicamentos |
| Hepatitis B | Heberbiovac HB | Liquid: ready to use | Centro de Ingenieria Genetica y Biotecnologia | Centro para el Control Estatal de la Calidad de los Medicamentos |
| Rabies | Rabipur | Lyophilized active component to be reconstituted with excipient diluent before use | Chiron Behring Vaccines Private Ltd. | Central Drugs Standard Control Organization |
| Rabies | Rabipur | Lyophilized active component to be reconstituted with excipient diluent before use | GlaxoSmithKline Vaccines GmbH | Paul-Ehrlich-Institut |
| Haemophilus influenzae type b | Vaxem HIB | Liquid: ready to use | Novartis Vaccines and Diagnostics S.r.l | Agenzia Italiana del Farmaco |

TABLE 3-continued

Human Vaccines Containing Peptide-Compatible Epitopes

| Type | Commercial Name | Form | Source | Responsible National Regulatory Authority |
|---|---|---|---|---|
| Hepatitis B | Engerix | Liquid: ready to use | GlaxoSmithKline Biologicals SA | Federal Agency for Medicines and Health Products |
| Hepatitis B | Engerix | Liquid: ready to use | GlaxoSmithKline Biologicals SA | Federal Agency for Medicines and Health Products |
| Hepatitis B | Engerix | Liquid: ready to use | GlaxoSmithKline Biologicals SA | Federal Agency for Medicines and Health Products |
| Polio Vaccine - Oral (OPV) Trivalent | Polio sabin | Liquid: ready to use | GlaxoSmithKline Biologicals SA | Federal Agency for Medicines and Health Products |
| Polio Vaccine - Oral (OPV) Trivalent | Polio sabin | Liquid: ready to use | GlaxoSmithKline Biologicals SA | Federal Agency for Medicines and Health Products |
| Measles, Mumps and Rubella | Priorix | Lyophilized active component to be reconstituted with excipient diluent before use | GlaxoSmithKline Biologicals SA | Federal Agency for Medicines and Health Products |
| Rotavirus | Rotarix | Liquid: ready to use | GlaxoSmithKline Biologicals SA | Federal Agency for Medicines and Health Products |
| Polio Vaccine - Oral (OPV) Trivalent | Polioviral vaccine | Liquid: ready to use | Haffkine Bio Pharmaceutical Corporation Ltd | Central Drugs Standard Control Organization |
| Yellow Fever | Stabilized Yellow Fever Vaccine | Lyophilized active component to be reconstituted with excipient diluent before use | Institut Pasteur de Dakar | Ministère de la Santé publique |
| Yellow Fever | Stabilized Yellow Fever Vaccine | Lyophilized active component to be reconstituted with excipient diluent before use | Institut Pasteur de Dakar | Ministère de la Santé publique |
| Yellow Fever | Stabilized Yellow Fever Vaccine | Lyophilized active component to be reconstituted with excipient diluent before use | Institut Pasteur de Dakar | Ministère de la Santé publique |
| BCG | BCG Freeze Dried Glutamate vaccine | Lyophilized active component to be reconstituted with excipient diluent before use | Japan BCG Laboratory | Chiba Local Government |

TABLE 3-continued

Human Vaccines Containing Peptide-Compatible Epitopes

| Type | Commercial Name | Form | Source | Responsible National Regulatory Authority |
| --- | --- | --- | --- | --- |
| Hepatitis B | Euvax B | Liquid: ready to use | LG Chem Ltd | Ministry of Food and Drug Safety |
| Hepatitis B | Euvax B | Liquid: ready to use | LG Chem Ltd | Ministry of Food and Drug Safety |
| BCG | BCG Vaccine | Lyophilized active component to be reconstituted with excipient diluent before use | Bul Bio - National Center of Infectious and Parasitic Diseases Ltd. | Bulgarian Drug Agency |
| BCG | BCG Vaccine | Lyophilized active component to be reconstituted with excipient diluent before use | Bul Bio - National Center of Infectious and Parasitic Diseases Ltd. | Bulgarian Drug Agency |
| Tetanus Toxoid | Tetatox | Liquid: ready to use | Bul Bio - National Center of Infectious and Parasitic Diseases Ltd. | Bulgarian Drug Agency |
| Tetanus Toxoid | Tetatox | Liquid: ready to use | Bul Bio - National Center of Infectious and Parasitic Diseases Ltd. | Bulgarian Drug Agency |
| Diphtheria-Tetanus | Diftet | Liquid: ready to use | Bul Bio - National Center of Infectious and Parasitic Diseases Ltd. | Bulgarian Drug Agency |
| Diphtheria-Tetanus | Diftet | Liquid: ready to use | Bul Bio - National Center of Infectious and Parasitic Diseases Ltd. | Bulgarian Drug Agency |
| Diphtheria-Tetanus (reduced antigen content) | Tetadif | Liquid: ready to use | Bul Bio - National Center of Infectious and Parasitic Diseases Ltd. | Bulgarian Drug Agency |
| Diphtheria-Tetanus (reduced antigen content) | Tetadif | Liquid: ready to use | Bul Bio - National Center of Infectious and Parasitic Diseases Ltd. | Bulgarian Drug Agency |

TABLE 3-continued

Human Vaccines Containing Peptide-Compatible Epitopes

| Type | Commercial Name | Form | Source | Responsible National Regulatory Authority |
|---|---|---|---|---|
| Diphtheria-Tetanus-Pertussis (whole cell)-Hepatitis B-Haemophilus influenzae type b | Easyfive-TT | Liquid: ready to use | Panacea Biotec Ltd. | Central Drugs Standard Control Organization |
| Diphtheria-Tetanus (reduced antigen content) | IMOVAX dT adult | Liquid: ready to use | Sanofi Pasteur SA | Agence nationale de sécurité du médicament et des produits de santé |
| Polio Vaccine - Inactivated (IPV) | IMOVAX POLIO | Liquid: ready to use | Sanofi Pasteur SA | Agence nationale de sécurité du médicament et des produits de santé |
| Polio Vaccine - Oral (OPV) Trivalent | OPVERO | Liquid: ready to use | Sanofi Pasteur SA | Agence nationale de sécurité du médicament et des produits de santé |
| Polio Vaccine - Oral (OPV) Trivalent | OPVERO | Liquid: ready to use | Sanofi Pasteur SA | Agence nationale de sécurité du médicament et des produits de santé |
| Polio Vaccine - Oral (OPV) Trivalent | OPVERO | Liquid: ready to use | Sanofi Pasteur SA | Agence nationale de sécurité du médicament et des produits de santé |
| Tetanus Toxoid | TETAVAX | Liquid: ready to use | Sanofi Pasteur SA | Agence nationale de sécurité du médicament et des produits de santé |
| Tetanus Toxoid | TETAVAX | Liquid: ready to use | Sanofi Pasteur SA | Agence nationale de sécurité du médicament et des produits de santé |
| Haemophilus influenzae type b | Act-HIB | Lyophilized active component to be reconstituted with excipient diluent before use | Sanofi Pasteur SA | Agence nationale de sécurité du médicament et des produits de santé |
| Rabies | VERORAB | Lyophilized active component to be reconstituted with excipient diluent before use | Sanofi Pasteur SA | Agence nationale de sécurité du médicament et des produits de santé |
| Yellow Fever | STAMARIL | Lyophilized active component to be reconstituted with excipient diluent before use | Sanofi Pasteur SA | Agence nationale de sécurité du médicament et des produits de santé |
| Meningococcal A + C | POLYSACCHARIDE MENINGOCOCCAL A + C VACCINE | Lyophilized active component to be reconstituted with excipient diluent before use | Sanofi Pasteur SA | Agence nationale de sécurité du médicament et des produits de santé |
| Polio Vaccine - Oral (OPV) Monovalent Type 1 | ORAL MONOVALENT TYPE 1 POLIOMYELITIS VACCINE | Liquid: ready to use | Sanofi Pasteur SA | Agence nationale de sécurité du médicament et des produits de santé |

TABLE 3-continued

Human Vaccines Containing Peptide-Compatible Epitopes

| Type | Commercial Name | Form | Source | Responsible National Regulatory Authority |
|---|---|---|---|---|
| cholera: inactivated oral | Dukoral | Liquid: ready to use | Valneva Sweden AB | Medical Products Agency |
| BCG | BCG Vaccine | Lyophilized active component to be reconstituted with excipient diluent before use | Serum Institute of India Pvt. Ltd. | Central Drugs Standard Control Organization |
| Diphtheria-Tetanus | Diphtheria and Tetanus Vaccine Adsorbed (Paediatric) | Liquid: ready to use | Serum Institute of India Pvt. Ltd. | Central Drugs Standard Control Organization |
| Diphtheria-Tetanus | Diphtheria and Tetanus Vaccine Adsorbed (Pediatric) | Liquid: ready to use | Serum Institute of India Pvt. Ltd. | Central Drugs Standard Control Organization |
| Diphtheria-Tetanus | Diphtheria and Tetanus Vaccine Adsorbed (Pediatric) | Liquid: ready to use | Serum Institute of India Pvt. Ltd. | Central Drugs Standard Control Organization |
| Diphtheria-Tetanus (reduced antigen content) | Diphtheria and Tetanus Vaccine Adsorbed for Adults and Adolescents | Liquid: ready to use | Serum Institute of India Pvt. Ltd. | Central Drugs Standard Control Organization |
| Diphtheria-Tetanus (reduced antigen content) | Diphtheria and Tetanus Vaccine Adsorbed for Adults and Adolescents | Liquid: ready to use | Serum Institute of India Pvt. Ltd. | Central Drugs Standard Control Organization |
| Diphtheria-Tetanus (reduced antigen content) | Diphtheria and Tetanus Vaccine Adsorbed for Adults and Adolescents | Liquid: ready to use | Serum Institute of India Pvt. Ltd. | Central Drugs Standard Control Organization |
| Diphtheria-Tetanus-Pertussis (whole cell) | Diphtheria-Tetanus-Pertussis Vaccine Adsorbed | Liquid: ready to use | Serum Institute of India Pvt. Ltd. | Central Drugs Standard Control Organization |
| Diphtheria-Tetanus-Pertussis (whole cell) | Diphtheria-Tetanus-Pertussis Vaccine Adsorbed | Liquid: ready to use | Serum Institute of India Pvt. Ltd. | Central Drugs Standard Control Organization |
| Diphtheria-Tetanus-Pertussis (whole cell) | Diphtheria-Tetanus-Pertussis Vaccine Adsorbed | Liquid: ready to use | Serum Institute of India Pvt. Ltd. | Central Drugs Standard Control Organization |
| Diphtheria-Tetanus-Pertussis (whole cell)-Hepatitis B | Diphtheria, Tetanus, Pertussis and Hepatitis B Vaccine Adsorbed | Liquid: ready to use | Serum Institute of India Pvt. Ltd. | Central Drugs Standard Control Organization |
| Diphtheria-Tetanus-Pertussis (whole cell)-Hepatitis B | Diphtheria, Tetanus, Pertussis and Hepatitis B Vaccine Adsorbed | Liquid: ready to use | Serum Institute of India Pvt. Ltd. | Central Drugs Standard Control Organization |
| Diphtheria-Tetanus-Pertussis (whole cell)-Hepatitis B | Diphtheria, Tetanus, Pertussis and Hepatitis B Vaccine Adsorbed | Liquid: ready to use | Serum Institute of India Pvt. Ltd. | Central Drugs Standard Control Organization |

TABLE 3-continued

Human Vaccines Containing Peptide-Compatible Epitopes

| Type | Commercial Name | Form | Source | Responsible National Regulatory Authority |
|---|---|---|---|---|
| Hepatitis B | Hepatitis B Vaccine (rDNA) (Adult) | Liquid: ready to use | Serum Institute of India Pvt. Ltd. | Central Drugs Standard Control Organization |
| Hepatitis B | Hepatitis B Vaccine (rDNA) (Adult) | Liquid: ready to use | Serum Institute of India Pvt. Ltd. | Central Drugs Standard Control Organization |
| Hepatitis B | Hepatitis B Vaccine (rDNA) (Paediatric) | Liquid: ready to use | Serum Institute of India Pvt. Ltd. | Central Drugs Standard Control Organization |
| Hepatitis B | Hepatitis B Vaccine (rDNA) (Paedriatic) | Liquid: ready to use | Serum Institute of India Pvt. Ltd. | Central Drugs Standard Control Organization |
| Tetanus Toxoid | Tetanus Toxoid Vaccine Adsorbed | Liquid: ready to use | Serum Institute of India Pvt. Ltd. | Central Drugs Standard Control Organization |
| Tetanus Toxoid | Tetanus Toxoid Vaccine Adsorbed | Liquid: ready to use | Serum Institute of India Pvt. Ltd. | Central Drugs Standard Control Organization |
| Tetanus Toxoid | Tetanus Toxoid Vaccine Adsorbed | Liquid: ready to use | Serum Institute of India Pvt. Ltd. | Central Drugs Standard Control Organization |
| Measles and Rubella | Measles and Rubella Vaccine, Live, Attenuated | Lyophilized active component to be reconstituted with excipient diluent before use | Serum Institute of India Pvt. Ltd. | Central Drugs Standard Control Organization |
| Measles and Rubella | Measles and Rubella Vaccine, Live, Attenuated | Lyophilized active component to be reconstituted with excipient diluent before use | Serum Institute of India Pvt. Ltd. | Central Drugs Standard Control Organization |
| Measles and Rubella | Measles and Rubella Vaccine, Live, Attenuated | Lyophilized active component to be reconstituted with excipient diluent before use | Serum Institute of India Pvt. Ltd. | Central Drugs Standard Control Organization |
| Measles and Rubella | Measles and Rubella Vaccine, Live, Attenuated | Lyophilized active component to be reconstituted with excipient diluent before use | Serum Institute of India Pvt. Ltd. | Central Drugs Standard Control Organization |
| Measles, Mumps and Rubella | Measles, Mumps and Rubella Vaccine, Live, Attenuated | Lyophilized active component to be reconstituted with excipient diluent before use | Serum Institute of India Pvt. Ltd. | Central Drugs Standard Control Organization |

TABLE 3-continued

Human Vaccines Containing Peptide-Compatible Epitopes

| Type | Commercial Name | Form | Source | Responsible National Regulatory Authority |
|---|---|---|---|---|
| Measles, Mumps and Rubella | Measles, Mumps and Rubella Vaccine, Live, Attenuated | Lyophilized active component to be reconstituted with excipient diluent before use | Serum Institute of India Pvt. Ltd. | Central Drugs Standard Control Organization |
| Measles, Mumps and Rubella | Measles, Mumps and Rubella Vaccine, Live, Attenuated | Lyophilized active component to be reconstituted with excipient diluent before use | Serum Institute of India Pvt. Ltd. | Central Drugs Standard Control Organization |
| Measles, Mumps and Rubella | Measles, Mumps and Rubella Vaccine, Live, Attenuated | Lyophilized active component to be reconstituted with excipient diluent before use | Serum Institute of India Pvt. Ltd. | Central Drugs Standard Control Organization |
| Measles | Measles Vaccine, Live, Attenuated | Lyophilized active component to be reconstituted with excipient diluent before use | Serum Institute of India Pvt. Ltd. | Central Drugs Standard Control Organization |
| Measles | Measles Vaccine, Live, Attenuated | Lyophilized active component to be reconstituted with excipient diluent before use | Serum Institute of India Pvt. Ltd. | Central Drugs Standard Control Organization |
| Measles | Measles Vaccine, Live, Attenuated | Lyophilized active component to be reconstituted with excipient diluent before use | Serum Institute of India Pvt. Ltd. | Central Drugs Standard Control Organization |
| Measles | Measles Vaccine, Live, Attenuated | Lyophilized active component to be reconstituted with excipient diluent before use | Serum Institute of India Pvt. Ltd. | Central Drugs Standard Control Organization |
| Rubella | Rubella Vaccine, Live, Attenuated | Lyophilized active component to be reconstituted with excipient diluent before use | Serum Institute of India Pvt. Ltd. | Central Drugs Standard Control Organization |

TABLE 3-continued

Human Vaccines Containing Peptide-Compatible Epitopes

| Type | Commercial Name | Form | Source | Responsible National Regulatory Authority |
|---|---|---|---|---|
| Rubella | Rubella Vaccine, Live, Attenuated | Lyophilized active component to be reconstituted with excipient diluent before use | Serum Institute of India Pvt. Ltd. | Central Drugs Standard Control Organization |
| Rubella | Rubella Vaccine, Live, Attenuated | Lyophilized active component to be reconstituted with excipient diluent before use | Serum Institute of India Pvt. Ltd. | Central Drugs Standard Control Organization |
| Rubella | Rubella Vaccine, Live, Attenuated | Lyophilized active component to be reconstituted with excipient diluent before use | Serum Institute of India Pvt. Ltd. | Central Drugs Standard Control Organization |
| Tetanus Toxoid | ShanTT | Liquid: ready to use | Shantha Biotechnics Private Limited (A Sanofi Company) | Central Drugs Standard Control Organization |
| Tetanus Toxoid | ShanTT | Liquid: ready to use | Shantha Biotechnics Private Limited (A Sanofi Company) | Central Drugs Standard Control Organization |
| Diphtheria-Tetanus-Pertussis (whole cell)-Hepatitis B-Haemophilus influenzae type b | Shan-5 | Liquid: ready to use | Shantha Biotechnics Private Limited (A Sanofi Company) | Central Drugs Standard Control Organization |
| Diphtheria-Tetanus-Pertussis (whole cell)-Hepatitis B-Haemophilus influenzae type b | Shan-5 | Liquid: ready to use | Shantha Biotechnics Private Limited (A Sanofi Company) | Central Drugs Standard Control Organization |
| BCG | BCG Vaccine SSI | Lyophilized active component to be reconstituted with excipient diluent before use | AJ Vaccines A/S | Danish Medicines Agency |
| Rotavirus | Rotateq | Liquid: ready to use | Merck Vaccines | CBER/FDA |
| Measles, Mumps and Rubella | rHA M-M-R II | Lyophilized active component to be reconstituted with excipient diluent before use | Merck Vaccines | European Medicines Agency |

TABLE 3-continued

Human Vaccines Containing Peptide-Compatible Epitopes

| Type | Commercial Name | Form | Source | Responsible National Regulatory Authority |
|---|---|---|---|---|
| Rotavirus | Rotarix | Liquid: ready to use | GlaxoSmithKline Biologicals SA | Federal Agency for Medicines and Health Products |
| Yellow Fever | — | Lyophilized active component to be reconstituted with excipient diluent before use | Federal State Budgetary Scientific Institution «Chumakov Federal Scientific Center for Reserch & Development of Immune- And Biological Products», Russian Academy of Sciences | Federal Service on Surveillance in Healthcare (ROSZDRAVNADZOR) of the Russian Federation |
| Yellow Fever | — | Lyophilized active component to be reconstituted with excipient diluent before use | Federal State Budgetary Scientific Institution «Chumakov Federal Scientific Center for Reserch & Development of Immune- And Biological Products», Russian Academy of Sciences | Federal Service on Surveillance in Healthcare (ROSZDRAVNADZOR) of the Russian Federation |
| Yellow Fever | — | Lyophilized active component to be reconstituted with excipient diluent before use | Federal State Budgetary Scientific Institution «Chumakov Federal Scientific Center for Reserch & Development of Immune- And Biological Products», Russian Academy of Sciences | Federal Service on Surveillance in Healthcare (ROSZDRAVNADZOR) of the Russian Federation |
| Human Papillomavirus (Quadrivalent) | Gardasil | Liquid: ready to use | Merck Vaccines | European Medicines Agency |
| Human Papillomavirus (Bivalent) | Cervarix | Liquid: ready to use | GlaxoSmithKline Biologicals SA | Federal Agency for Medicines and Health Products |
| Human Papillomavirus (Bivalent) | Cervarix | Liquid: ready to use | GlaxoSmithKline Biologicals SA | Federal Agency for Medicines and Health Products |
| Polio Vaccine - Oral (OPV) Monovalent Type 1 | Polio Sabin Mono T1 | Liquid: ready to use | GlaxoSmithKline Biologicals SA | Federal Agency for Medicines and Health Products |
| Polio Vaccine - Oral (OPV) Monovalent Type 1 | Polio Sabin Mono T1 | Liquid: ready to use | GlaxoSmithKline Biologicals SA | Federal Agency for Medicines and Health Products |
| Polio Vaccine - Oral (OPV) Bivalent Types 1 and 3 | Polio Sabin One and Three | Liquid: ready to use | GlaxoSmithKline Biologicals SA | Federal Agency for Medicines and Health Products |

TABLE 3-continued

Human Vaccines Containing Peptide-Compatible Epitopes

| Type | Commercial Name | Form | Source | Responsible National Regulatory Authority |
|---|---|---|---|---|
| Polio Vaccine - Oral (OPV) Bivalent Types 1 and 3 | Polio Sabin One and Three | Liquid: ready to use | GlaxoSmithKline Biologicals SA | Federal Agency for Medicines and Health Products |
| Haemophilus influenzae type b | Haemophilus influenzae type b Conjugate Vaccine | Lyophilized active component to be reconstituted with excipient diluent before use | Serum Institute of India Pvt. Ltd. | Central Drugs Standard Control Organization |
| Polio Vaccine - Oral (OPV) Monovalent Type 1 | Monovalent type 1 Oral Poliomyelitis vaccine, IP (mOPV1) | Liquid: ready to use | Haffkine Bio Pharmaceutical Corporation Ltd | Central Drugs Standard Control Organization |
| Polio Vaccine - Oral (OPV) Monovalent Type 1 | Monovalent Oral Poliomyelitis Vaccine Type 1 (mOPV1) | Liquid: ready to use | PT Bio Farma (Persero) | National Agency of Drug and Food Control Indonesia |
| Tetanus Toxoid | None used on labelling for supply through UN agencies. Also marketed with labelled commercial name BEtt. | Liquid: ready to use | Biological E. Limited | Central Drugs Standard Control Organization |
| Pneumococcal (conjugate) | Synflorix | Liquid: ready to use | GlaxoSmithKline Biologicals SA | European Medicines Agency |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine | Lyophilized active component to be reconstituted with liquid active component before use | Serum Institute of India Pvt. Ltd. | Central Drugs Standard Control Organization |
| Polio Vaccine - Oral (OPV) Bivalent Types 1 and 3 | Bivalent Oral Poliomyelitis Vaccine Type 1&3 (bOPV 1&3) | Liquid: ready to use | PT Bio Farma (Persero) | National Agency of Drug and Food Control Indonesia |
| Meningococcal A Conjugate 10 μg | Meningococcal A Conjugate MenAfriVac | Lyophilized active component to be reconstituted with excipient diluent before use | Serum Institute of India Pvt. Ltd. | Central Drugs Standard Control Organization |
| Haemophilus influenzae type b | Quimi-Hib | Liquid: ready to use | Centro de Ingenieria Genetica y Biotecnologia | Centro para el Control Estatal de la Calidad de los Medicamentos |
| Pneumococcal (conjugate) | Synflorix | Liquid: ready to use | GlaxoSmithKline Biologicals SA | European Medicines Agency |
| Influenza, seasonal | Fluvirin | Liquid: ready to use | Seqirus Vaccines Limited | CBER/FDA |
| Polio Vaccine - Oral (OPV) Bivalent Types 1 and 3 | Bivalent type 1&3 Oral Poliomyelitis vaccine, IP (bOPV1&3) | Liquid: ready to use | Haffkine Bio Pharmaceutical Corporation Ltd | Central Drugs Standard Control Organization |

TABLE 3-continued

Human Vaccines Containing Peptide-Compatible Epitopes

| Type | Commercial Name | Form | Source | Responsible National Regulatory Authority |
|---|---|---|---|---|
| Influenza, seasonal | Fluzone | Liquid: ready to use | Sanofi Pasteur-USA | CBER/FDA |
| Influenza, seasonal | Fluzone | Liquid: ready to use | Sanofi Pasteur-USA | CBER/FDA |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine | Lyophilized active component to be reconstituted with liquid active component before use | Serum Institute of India Pvt. Ltd. | Central Drugs Standard Control Organization |
| Influenza, seasonal | GC FLU Multi inj. | Liquid: ready to use | Green Cross Corporation | Ministry of Food and Drug Safety |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine | Lyophilized active component to be reconstituted with liquid active component before use | Serum Institute of India Pvt. Ltd. | Central Drugs Standard Control Organization |
| Influenza, pandemic H1N1 | Panvax | Liquid: ready to use | Seqirus Limited | Therapeutic Goods Administration |
| Influenza, pandemic H1N1 | Green Flu-S | Liquid: ready to use | Green Cross Corporation | Ministry of Food and Drug Safety |
| Influenza, pandemic H1N1 | Influenza A (H1N1) 2009 monovalent vaccine | Liquid: ready to use | MedImmune | CBER/FDA |
| Influenza, pandemic H1N1 | Celtura | Liquid: ready to use | Seqirus GmbH | Paul-Ehrlich-Institut |
| Influenza, pandemic H1N1 | Focetria | Liquid: ready to use | Seqirus Vaccines Limited | |
| Influenza, pandemic H1N1 | Fluvirin-H1N1 | Liquid: ready to use | Seqirus Vaccines Limited | CBER/FDA |
| Influenza, pandemic H1N1 | Panenza | Liquid: ready to use | Sanofi Pasteur SA | Agence nationale de sécurité du médicament et des produits de santé |
| Influenza, pandemic H1N1 | Influenza A (H1N1) 2009 monovalent vaccine | Liquid: ready to use | Sanofi Pasteur-USA | CBER/FDA |
| Influenza, pandemic H1N1 | Influenza A (H1N1) 2009 monovalent vaccine | Liquid: ready to use | Sanofi Pasteur-USA | CBER/FDA |
| Diphtheria-Tetanus-Pertussis (whole cell)-Haemophilus influenzae type b | Diphtheria, Tetanus, Pertussis and Haemophilus influenzae type b Conjugate Vaccine | Lyophilized active component to be reconstituted with liquid active component before use | Serum Institute of India Pvt. Ltd. | Central Drugs Standard Control Organization |
| Polio Vaccine - Inactivated (IPV) | Poliorix | Liquid: ready to use | GlaxoSmithKline Biologicals SA | Federal Agency for Medicines and Health Products |
| Polio Vaccine - Inactivated (IPV) | Poliorix | Liquid: ready to use | GlaxoSmithKline Biologicals SA | Federal Agency for Medicines and Health Products |
| Pneumococcal (conjugate) | Prevenar 13 | Liquid: ready to use | Pfizer | European Medicines Agency |
| Diphtheria-Tetanus-Pertussis | Diphtheria, Tetanus, | Liquid: ready to use | Serum Institute of | Central Drugs Standard Control |

TABLE 3-continued

Human Vaccines Containing Peptide-Compatible Epitopes

| Type | Commercial Name | Form | Source | Responsible National Regulatory Authority |
|---|---|---|---|---|
| (whole cell)-Hepatitis B-Haemophilus influenzae type b | Pertussis, Hepatitis B and Haemophilus influenzae type b Conjugate Vaccine Adsorbed | | India Pvt. Ltd. | Organization |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine Adsorbed | Liquid: ready to use | Serum Institute of India Pvt. Ltd. | Central Drugs Standard Control Organization |
| Diphtheria-Tetanus-Pertussis (whole cell)-Hepatitis B-Haemophilus influenzae type b | Diphtheria, Tetanus, Pertussis, Hepatitis B and Haemophilus influenzae type b Conjugate Vaccine Adsorbed | Liquid: ready to use | Serum Institute of India Pvt. Ltd. | Central Drugs Standard Control Organization |
| Polio Vaccine - Oral (OPV) Monovalent Type 3 | Polio Sabin Mono Three (oral) | Liquid: ready to use | GlaxoSmithKline Biologicals SA | Federal Agency for Medicines and Health Products |
| Polio Vaccine - Oral (OPV) Monovalent Type 3 | Polio Sabin Mono Three (oral) | Liquid: ready to use | GlaxoSmithKline Biologicals SA | Federal Agency for Medicines and Health Products |
| Polio Vaccine - Inactivated (IPV) | Poliomyelitis vaccine | Liquid: ready to use | Bilthoven Biologicals | Medicines Evaluation Board (MEB) |
| Polio Vaccine - Inactivated (IPV) | IPV Vaccine SSI | Liquid: ready to use | AJ Vaccines A/S | Danish Medicines Agency |
| Influenza, seasonal | GC FLU inj | Liquid: ready to use | Green Cross Corporation | Ministry of Food and Drug Safety |
| Polio Vaccine - Oral (OPV) Monovalent Type 2 | Polio Sabin Mono Two (oral) | Liquid: ready to use | GlaxoSmithKline Biologicals SA | Federal Agency for Medicines and Health Products |
| Polio Vaccine - Oral (OPV) Monovalent Type 2 | Polio Sabin Mono Two (oral) | Liquid: ready to use | GlaxoSmithKline Biologicals SA | Federal Agency for Medicines and Health Products |
| Typhoid (Polysaccharide) | Typhim-Vi | Liquid: ready to use | Sanofi Pasteur SA | Agence nationale de sécurité du médicament et des produits de santé |
| Influenza, seasonal | Vaxigrip | Liquid: ready to use | Sanofi Pasteur SA | Agence nationale de sécurité du médicament et des produits de santé |
| Polio Vaccine - Oral (OPV) Bivalent Types 1 and 3 | BIOPOLIO B1/3 | Liquid: ready to use | Bharat Biotech International Limited | Central Drugs Standard Control Organization |
| Diphtheria-Tetanus (reduced antigen content) | none | Liquid: ready to use | PT Bio Farma (Persero) | National Agency of Drug and Food Control Indonesia |
| Polio Vaccine - Oral (OPV) Bivalent Types 1 and 3 | none | Liquid: ready to use | Sanofi Pasteur SA | Agence nationale de sécurité du médicament et des produits de santé |
| Diphtheria-Tetanus-Pertussis (whole cell)-Hepatitis B-Haemophilus influenzae type b | None used on labelling for supply through UN agencies. Also marketed | Lyophilized active component to be reconstituted with liquid active | Biological E. Limited | Central Drugs Standard Control Organization |

TABLE 3-continued

Human Vaccines Containing Peptide-Compatible Epitopes

| Type | Commercial Name | Form | Source | Responsible National Regulatory Authority |
|---|---|---|---|---|
| | with labelled commercial name ComBE Five (Reconstituted). | component before use | | |
| Diphtheria-Tetanus-Pertussis (whole cell)-Hepatitis B-Haemophilus influenzae type b | None used on labelling for supply through UN agencies. Also marketed with labelled commercial name ComBE Five (Reconstituted). | Lyophilized active component to be reconstituted with liquid active component before use | Biological E. Limited | Central Drugs Standard Control Organization |
| cholera: inactivated oral | Shanchol | Liquid: ready to use | Shantha Biotechnics Private Limited (A Sanofi Company) | Central Drugs Standard Control Organization |
| Measles, Mumps and Rubella | Priorix | Lyophilized active component to be reconstituted with excipient diluent before use | GlaxoSmithKline Biologicals SA | Federal Agency for Medicines and Health Products |
| Measles | Measles vaccine | Lyophilized active component to be reconstituted with excipient diluent before use | PT Bio Farma (Persero) | National Agency of Drug and Food Control Indonesia |
| Polio Vaccine - Oral (OPV) Bivalent Types 1 and 3 | Poliomyelitis Vaccine (Oral), Bivalent types 1 and 3 | Liquid: ready to use | Serum Institute of India Pvt. Ltd. | Central Drugs Standard Control Organization |
| Influenza, pandemic H1N1 | NASOVAC Influenza Vaccine, Live Attenuated (Human) Freeze-Dried | Lyophilized active component to be reconstituted with excipient diluent before use | Serum Institute of India Pvt. Ltd. | Central Drugs Standard Control Organization |
| Influenza, pandemic H1N1 | NASOVAC Influenza Vaccine, Live Attenuated (Human) Freeze-Dried | Lyophilized active component to be reconstituted with excipient diluent before use | Serum Institute of India Pvt. Ltd. | Central Drugs Standard Control Organization |
| Tetanus Toxoid | None used on labelling for supply through UN agencies. Also marketed with labelled commercial name BEtt. | Liquid: ready to use | Biological E. Limited | Central Drugs Standard Control Organization |

TABLE 3-continued

Human Vaccines Containing Peptide-Compatible Epitopes

| Type | Commercial Name | Form | Source | Responsible National Regulatory Authority |
|---|---|---|---|---|
| Tetanus Toxoid | None used on labelling for supply through UN agencies. Also marketed with labelled commercial name BEtt. | Liquid: ready to use | Biological E. Limited | Central Drugs Standard Control Organization |
| Japanese Encephalitis Vaccine (Inactivated) 6 µg | JEEV ® | Liquid: ready to use | Biological E. Limited | Central Drugs Standard Control Organization |
| Hepatitis A (Human Diploid Cell), Inactivated (Adult) | Havrix 1440 Adult | Liquid: ready to use | GlaxoSmithKline Biologicals SA | Federal Agency for Medicines and Health Products |
| Hepatitis A (Human Diploid Cell), Inactivated (Paediatric) | Havrix 720 Junior | Liquid: ready to use | GlaxoSmithKline Biologicals SA | Federal Agency for Medicines and Health Products |
| Diphtheria-Tetanus-Pertussis (acellular) | Boostrix | Liquid: ready to use | GlaxoSmithKline Biologicals SA | Federal Agency for Medicines and Health Products |
| Meningococcal ACYW-135 (conjugate vaccine) | Menveo | Lyophilized active component to be reconstituted with liquid active component before use | GlaxoSmithKline Vaccines S.r.l. | European Medicines Agency |
| Meningococcal ACYW-135 (conjugate vaccine) | Menactra | Liquid: ready to use | Sanofi Pasteur-USA | CBER/FDA |
| Diphtheria-Tetanus-Pertussis (whole cell)-Hepatitis B-Haemophilus influenzae type b | Easyfive-TT | Liquid: ready to use | Panacea Biotec Ltd. | Central Drugs Standard Control Organization |
| Japanese Encephalitis Vaccine (live, attenuated) | Japanese Encephalitis Vaccine Live (SA14-14-2) | Lyophilized active component to be reconstituted with excipient diluent before use | Chengdu Institute of Biological Products Co., Ltd | National Medical Products Administration |
| Japanese Encephalitis Vaccine (live, attenuated) | Japanese Encephalitis Vaccine Live (SA14-14-2) | Lyophilized active component to be reconstituted with excipient diluent before use | Chengdu Institute of Biological Products Co., Ltd | National Medical Products Administration |
| Diphtheria-Tetanus-Pertussis (whole cell)-Hepatitis B-Haemophilus influenzae type b | None used on labelling for supply through UN agencies. Also marketed with labelled commercial name ComBE Five (Liquid). | Liquid: ready to use | Biological E. Limited | Central Drugs Standard Control Organization |

TABLE 3-continued

Human Vaccines Containing Peptide-Compatible Epitopes

| Type | Commercial Name | Form | Source | Responsible National Regulatory Authority |
|---|---|---|---|---|
| Diphtheria-Tetanus-Pertussis (whole cell)-Hepatitis B-Haemophilus influenzae type b | None used on labelling for supply through UN agencies. Also marketed with labelled commercial name ComBE Five (Liquid). | Liquid: ready to use | Biological E. Limited | Central Drugs Standard Control Organization |
| Japanese Encephalitis Vaccine (live, attenuated) | IMOJEV MD | Lyophilized active component to be reconstituted with excipient diluent before use | GPO-MBP Co., Ltd. | Thai Food and Drug Administration |
| Diphtheria-Tetanus-Pertussis (whole cell) | None used on labelling for supply through UN agencies. Also marketed with labelled commercial name TRIPVAC | Liquid: ready to use | Biological E. Limited | Central Drugs Standard Control Organization |
| Diphtheria-Tetanus-Pertussis (whole cell) | None used on labelling for supply through UN agencies. Also marketed with labelled commercial name TRIPVAC | Liquid: ready to use | Biological E. Limited | Central Drugs Standard Control Organization |
| Diphtheria-Tetanus (reduced antigen content) | None used on labelling for supply through UN agencies. Also marketed with labelled commercial name BE Td | Liquid: ready to use | Biological E. Limited | Central Drugs Standard Control Organization |
| Diphtheria-Tetanus (reduced antigen content) | None used on labelling for supply through UN agencies. Also marketed with labelled commercial name BE Td | Liquid: ready to use | Biological E. Limited | Central Drugs Standard Control Organization |
| Polio Vaccine - Oral (OPV) Bivalent Types 1 and 3 | Poliomyelitis Vaccine (Oral), Bivalent types 1 and 3 | Liquid: ready to use | Serum Institute of India Pvt. Ltd. | Central Drugs Standard Control Organization |
| Polio Vaccine - Inactivated (IPV) | Poliomyelitis vaccine multidose, suspension for injection 2.5 mL | Liquid: ready to use | Bilthoven Biologicals | Medicines Evaluation Board (MEB) |

TABLE 3-continued

Human Vaccines Containing Peptide-Compatible Epitopes

| Type | Commercial Name | Form | Source | Responsible National Regulatory Authority |
|---|---|---|---|---|
| Influenza, seasonal | Nasovac-S Influenza Vaccine, Live, Attenuated (Human) | Lyophilized active component to be reconstituted with excipient diluent before use | Serum Institute of India Pvt. Ltd. | Central Drugs Standard Control Organization |
| Diphtheria-Tetanus-Pertussis (acellular)-Hepatitis B-Haemophilus influenzae type b-Polio (Inactivated) | Hexaxim | Liquid: ready to use | Sanofi Pasteur SA | European Medicines Agency |
| Meningococcal A Conjugate 5 µg | Meningococcal A Conjugate 5 micrograms MenAfriVac 5 µg | Lyophilized active component to be reconstituted with excipient diluent before use | Serum Institute of India Pvt. Ltd. | Central Drugs Standard Control Organization |
| Diphtheria-Tetanus-Pertussis (whole cell)-Hepatitis B-Haemophilus influenzae type b | None used on labelling for supply through UN agencies. Also marketed with labelled commercial name ComBE Five (Liquid). | Liquid: ready to use | Biological E. Limited | Central Drugs Standard Control Organization |
| Diphtheria-Tetanus-Pertussis (whole cell)-Hepatitis B-Haemophilus influenzae type b | None used on labelling for supply through UN agencies. Also marketed with labelled commercial name ComBE Five (Liquid). | Liquid: ready to use | Biological E. Limited | Central Drugs Standard Control Organization |
| Polio Vaccine - Inactivated (IPV) | Poliomyelitis Vaccine (Inactivated) | Liquid: ready to use | Serum Institute of India Pvt. Ltd. | Central Drugs Standard Control Organization |
| Polio Vaccine - Oral (OPV) Trivalent | BIOPOLIO | Liquid: ready to use | Bharat Biotech International Limited | Central Drugs Standard Control Organization |
| Polio Vaccine - Oral (OPV) Trivalent | BIOPOLIO | Liquid: ready to use | Bharat Biotech International Limited | Central Drugs Standard Control Organization |
| Influenza, seasonal | Influenza Vaccine (Split virion, inactivated) | Liquid: ready to use | Hualan Biological Bacterin Co., Ltd | National Medical Products Administration |
| Influenza, seasonal | IL-YANG FLU Vaccine INJ. | Liquid: ready to use | IL-YANG PHARMACEUTICAL CO., LTD. | Ministry of Food and Drug Safety |

TABLE 3-continued

Human Vaccines Containing Peptide-Compatible Epitopes

| Type | Commercial Name | Form | Source | Responsible National Regulatory Authority |
|---|---|---|---|---|
| BCG | BCG vaccine (Freeze Dried) - Intradermal | Lyophilized active component to be reconstituted with excipient diluent before use | GreenSignal Bio Pharma Limited | Central Drugs Standard Control Organization |
| Influenza, seasonal Quadrivalent | Fluzone Quadrivalent | Liquid: ready to use | Sanofi Pasteur-USA | CBER/FDA |
| Influenza, seasonal Quadrivalent | Fluzone Quadrivalent | Liquid: ready to use | Sanofi Pasteur-USA | CBER/FDA |
| Polio Vaccine - Oral (OPV) Bivalent Types 1 and 3 | Bivalent Oral Poliomyelitis Vaccine Type 1&3 (bOPV 1&3) | Liquid: ready to use | PT Bio Farma (Persero) | National Agency of Drug and Food Control Indonesia |
| cholera: inactivated oral | Euvichol | Liquid: ready to use | EuBiologics Co., Ltd. | Ministry of Food and Drug Safety |
| Polio Vaccine - Oral (OPV) Monovalent Type 2 | ORAL MONOVALENT TYPE 2 POLIOMYELITIS VACCINE (mOPV2) | Liquid: ready to use | Sanofi Pasteur SA | Agence nationale de sécurité du médicament et des produits de santé |
| Polio Vaccine - Oral (OPV) Monovalent Type 3 | ORAL MONOVALENT TYPE 3 POLIOMYELITIS VACCINE | Liquid: ready to use | Sanofi Pasteur SA | Agence nationale de sécurité du médicament et des produits de santé |
| Meningococcal ACYW-135 (conjugate vaccine) | Nimenrix | Lyophilized active component to be reconstituted with excipient diluent before use | Pfizer | European Medicines Agency |
| Diphtheria-Tetanus-Pertussis (whole cell)-Hepatitis B-Haemophilus influenzae type b | Eupenta | Liquid: ready to use | LG Chem Ltd | Ministry of Food and Drug Safety |
| Diphtheria-Tetanus-Pertussis (whole cell)-Hepatitis B-Haemophilus influenzae type b | Eupenta | Liquid: ready to use | LG Chem Ltd | Ministry of Food and Drug Safety |
| Human Papillomavirus (Ninevalent) | Gardasil 9 | Liquid: ready to use | Merck Vaccines | European Medicines Agency |
| Influenza, seasonal Quadrivalent | GCFLU Quadrivalent inj. | Liquid: ready to use | Green Cross Corporation | Ministry of Food and Drug Safety |
| Diphtheria-Tetanus-Pertussis (whole cell)-Hepatitis B-Haemophilus influenzae type b | Pentabio | Liquid: ready to use | PT Bio Farma (Persero) | National Agency of Drug and Food Control Indonesia |
| Diphtheria-Tetanus-Pertussis (whole cell)-Hepatitis B-Haemophilus influenzae type b | Pentabio | Liquid: ready to use | PT Bio Farma (Persero) | National Agency of Drug and Food Control Indonesia |

TABLE 3-continued

Human Vaccines Containing Peptide-Compatible Epitopes

| Type | Commercial Name | Form | Source | Responsible National Regulatory Authority |
| --- | --- | --- | --- | --- |
| Hepatitis A (Human Diploid Cell), Inactivated (Adult) | HEALIVE | Liquid: ready to use | Sinovac Biotech Co. Ltd | National Medical Products Administration |
| Varicella | Varivax | Lyophilized active component to be reconstituted with excipient diluent before use | Merck Vaccines | CBER/FDA |
| Rotavirus (live, attenuated) | Rotavac | Liquid: ready to use | Bharat Biotech International Limited | Central Drugs Standard Control Organization |
| Diphtheria-Tetanus-Pertussis (acellular) | Adacel | Liquid: ready to use | Sanofi Pasteur Limited | Health Canada - Santé Canada |
| Influenza, seasonal | AGRIFLU | Liquid: ready to use | Seqirus Vaccines Limited | Health Canada - Santé Canada |
| Pneumococcal (conjugate) | Prevenar 13 Multidose Vial | Liquid: ready to use | Pfizer | European Medicines Agency |
| Typhoid (Conjugate) | Typbar-TVC | Liquid: ready to use | Bharat Biotech International Limited | Central Drugs Standard Control Organization |
| Polio Vaccine - Oral (OPV) Bivalent Types 1 and 3 | Poliomyelitis Vaccine (live, oral attenuated, human Diploid Cell), type 1 and 3 | Liquid: ready to use | Beijing Bio-Institute Biological Products Co., Ltd | National Medical Products Administration |
| Japanese Encephalitis Vaccine (Inactivated) (3 μg Pediatric) | JEEV ® | Liquid: ready to use | Biological E. Limited | Central Drugs Standard Control Organization |
| Rotavirus (live, attenuated) | ROTASIIL | Lyophilized active component to be reconstituted with excipient diluent before use | Serum Institute of India Pvt. Ltd. | Central Drugs Standard Control Organization |
| Polio Vaccine - Inactivated (IPV) | Poliomyelitis Vaccine (Inactivated) | Liquid: ready to use | Serum Institute of India Pvt. Ltd. | Central Drugs Standard Control Organization |
| Polio Vaccine - Inactivated (IPV) | Poliomyelitis Vaccine (Inactivated) | Liquid: ready to use | Serum Institute of India Pvt. Ltd. | Central Drugs Standard Control Organization |
| Influenza, seasonal Quadrivalent | GCFLU Quadrivalent Multi inj. | Liquid: ready to use | Green Cross Corporation | Ministry of Food and Drug Safety |
| Influenza, seasonal | Serinflu | Liquid: ready to use | Abbott Biologicals BV | Medicines Evaluation Board (MEB) |
| Polio Vaccine - Inactivated (IPV) | ShanIPV | Liquid: ready to use | Shantha Biotechnics Private Limited (A Sanofi Company) | Central Drugs Standard Control Organization |
| Polio Vaccine - Oral (OPV) Bivalent Types 1 and 3 | Bivalent OPV Type 1 and 3 Poliomyelitis | Liquid: ready to use | Panacea Biotec Ltd. | Central Drugs Standard Control Organization |

TABLE 3-continued

Human Vaccines Containing Peptide-Compatible Epitopes

| Type | Commercial Name | Form | Source | Responsible National Regulatory Authority |
|---|---|---|---|---|
| cholera: inactivated oral | Vaccine, Live (Oral) Euvichol-Plus | Liquid: ready to use | EuBiologics Co., Ltd. | Ministry of Food and Drug Safety |
| Polio Vaccine - Oral (OPV) Bivalent Types 1 and 3 | BIOPOLIO B1/3 | Liquid: ready to use | Bharat Biotech International Limited | Central Drugs Standard Control Organization |
| BCG | BCG Freeze Dried Glutamate vaccine | Lyophilized active component to be reconstituted with excipient diluent before use | Japan BCG Laboratory | Chiba Local Government |
| Pneumococcal (conjugate) | Synflorix | Liquid: ready to use | GlaxoSmithKline Biologicals SA | European Medicines Agency |
| Rotavirus (live, attenuated) | Rotavac | Liquid: ready to use | Bharat Biotech International Limited | Central Drugs Standard Control Organization |
| Hepatitis A (Human Diploid Cell), Inactivated (Paediatric) | HEALIVE | Liquid: ready to use | Sinovac Biotech Co. Ltd | National Medical Products Administration |
| Typhoid (Conjugate) | Typbar-TVC | Liquid: ready to use | Bharat Biotech International Limited | Central Drugs Standard Control Organization |
| Rotavirus (live, attenuated) | ROTASIIL | Lyophilized active component to be reconstituted with excipient diluent before use | Serum Institute of India Pvt. Ltd. | Central Drugs Standard Control Organization |
| Japanese Encephalitis Vaccine (Inactivated) 6 µg | JEEV ® | Liquid: ready to use | Biological E. Limited | Central Drugs Standard Control Organization |
| Japanese Encephalitis Vaccine (Inactivated) (3 µg Pediatric) | JEEV ® | Liquid: ready to use | Biological E. Limited | Central Drugs Standard Control Organization |
| SARS-CoV-2 | PFIZER-BIONTECH COVID-19 VACCINE-bnt162b2 | Liquid: ready to use | Pfizer-BIONTECH | CEBR/FDA |
| SARS-CoV-2 | Moderna COVID-19 | Liquid: ready to use | Moderna Inc | CEBR/FDA |
| SARS-CoV-2 | COVID-19 Vaccine (ChAdOx1-S [recombinant]) | Liquid: ready to use | Astra Zeneca | European Medicines Agency |
| SARS-CoV-2 | Janssen COVID-19 Vaccine | Liquid: ready to use | Johnson & Johnson | CEBR/FDA |
| SARS-CoV-2 | CoronaVac, COVID-19 Vaccine (Vero Cell), Inactivated | Liquid: ready to use | Sinovac | National Medical Products Administration |

In various embodiments, the epitope is released following proteolytic cleavage of the peptide from the IRC. After proteolytic cleavage of the peptide from the IRC, the epitope binds to an MHC, optionally an MHC class I, molecule. The MHC molecule is in some embodiments from the HLA-A, B, and/or HLA C families. The specific epitope that binds to the MHC class I molecule is any of those recited in Table 2 or Table 3 or found elsewhere in the art. The MHC class I molecule itself is, in some embodiments, one or more of the following non-limiting examples: HLA-A*02:01, HLA-A*03:01, HLA-A*11:01, HLA-A*201, HLA-A*020101, HLA-A*0203, HLA-A*0206, HLA-A2, HLA-A2.1, or HLA-A*02.

In an aspect the described methods, uses, and compositions, the epitope is about 8 amino acid to about 50 amino acids in length, or about 8 amino acid to about 45 amino acids in length, or about 8 amino acid to about 40 amino acids in length, about 8 amino acid to about 35 amino acids in length, or about 8 amino acid to about 30 amino acids in length, about 8 amino acid to about 25 amino acids in length, about 8 amino acid to about 20 amino acids in length, or is about 8 amino acid to about 15 amino acids in length. In an aspect of the invention the peptide is about 13 amino acid to about 50 amino acids in length, or about 13 amino acid to about 45 amino acids in length, or about 13 amino acid to about 40 amino acids in length, about 13 amino acid to about 35 amino acids in length, or about 13 amino acid to about 30 amino acids in length, about 13 amino acid to about 25 amino acids in length, about 13 amino acid to about 20 amino acids in length, or is about 13 amino acid to about 15 amino acids in length. In some embodiments, the CD8+ T cell epitope is, e.g., about 8, 9, 10, 11, 12, 13, 14, 15, 16, or about 17 amino acids in length.

Cleavage Sequence. In various embodiments, one or more protease cleavage sequences are incorporated into the IRC that, upon cleavage, allows the peptide to be released from the IRC so that the peptide then is free to bind to the MHC on the tumor or cancer cell surface. In various embodiments, the IRC must escape the endosome, disassemble, and release their therapeutic cargo to the cytosol in a functional form. In various embodiments the IRC and/or peptide of the IRC is susceptible to cleavage by a proteolytic enzyme within the tumor microenvironment, i.e., in the nearby interstitial space surrounding tumors or tumor cells, and the position of the target cleavage sequence in the IRC or peptide is such that the cleavage of the target site releases all or a portion of the peptide comprising the CD8+ T cell epitope from the IRC, which then is free to bind to, and/or form a complex with, an MHC molecule expressed on the surface of the tumor cell in the subject. Pharmaceutically effective, or therapeutic amounts of IRC required to achieve this end goal are determined by the skilled artisan by known clinical methods utilizing in vitro cell culture techniques, animal model studies, and small scale to large scale human clinical trials. It will be appreciated that the amount of IRC administered to the subject in need thereof in the described methods and uses herein will depend on, e.g., the characteristics of the subject, e.g., age, weight, gender, and/or medical condition/history, genetic makeup, and other factors pertinent to the subject or class of subjects, and that the characteristics of the tumor, e.g., type, volume, and developmental status will also be taken into account when designing the dosage range finding clinical studies.

The proteolytic cleavage sequence is in some embodiments recognized by any protease present in, on, around, or nearby a tumor cell. At least about 569 known proteases have been described. (See, Lopez-Otin, et al., Nature Reviews Cancer, 7(10):800-808, 2007). All human proteolytic enzymes identified to date are classifiable into five catalytic classes: metalloproteinases, serine, threonine, cysteine, and aspartic proteases. A non-limiting list of potential proteases is demonstrated in Table 4, which is a table summarizing exemplars of the most well-studied proteases distributed into the five noted classes. (See Choi, Ki Young et al., "Protease-activated drug development," Theranostics, (2)2:156-78, 2012). Several of these proteases have been found to be over-expressed in cancer cells relative to healthy cells.

In various embodiments, the proteolytic cleavage sequence is recognized by the protease furin, a matrix metalloproteinase (MMP), of which several different members are identified, e.g., MMP, 1, 2, 3, 7, 8, 9, 11, 13, 14, or 19, an ADAM (a disintegrin and metalloproteinase), e.g., ADAMS 8, 9, 10, 15, 17, or 28, a cathepsin, e.g., cathepsin D, G, H, or N. Also contemplated herein are the proteases elastase, proteinase-3, azurocidin, and ADAMTS-1. In various embodiments, the cleavage sequence is recognized by any one or more of the aforementioned proteases, and in a certain embodiment the sequence is recognized by a human furin protease. In various embodiments, the cleavage sequence comprises at least about 4 amino acid residues, at least about three of which are arginine residues. In various embodiments, the cleavage sequence comprises at least 4 amino acid residues, at least three of which are arginine residues and one of which is either a lysine residue or an arginine residue. In various embodiments, the cleavage sequence is R—X—R/K—R (SEQ ID NO: 89). In various embodiments, the cleavage sequence comprises additional residues. In various embodiments, the cleavage sequence further comprises about 1, 2, 3, 4, 5, 6, 7, 8, or about 9 additional arginine residues. It is known that arginines are positively charged and it has been discovered that a longer chain of positive charged arginine residues will bring the peptides closer to the surface of the capsid backbone which is more negatively charged.

TABLE 4

Proteases and cancers associated with overexpressed proteases

| Family | Protease | Location | Cancer | Ref. | Other Diseases | Ref. |
| --- | --- | --- | --- | --- | --- | --- |
| Cysteine Cathepsins | General | Intracellular, lysosomes | Most | Table in [121] | | |
| | Cathepsin K | Extracellular, bone | Breast | [178] | Artherosclerosis, osteoporosis | [179-182] |
| | Cathepsin B | Extracellular and pericellular under pathological conditions | Breast, cervix, colon, colorectal, gastric, head and neck, liver, lung, melanoma, ovarian, pancreatic, prostate, thyroid | [31, 38, 81, 183-196] | | |

TABLE 4-continued

Proteases and cancers associated with overexpressed proteases

| Family | Protease | Location | Cancer | Ref. | Other Diseases | Ref. |
|---|---|---|---|---|---|---|
| Aspartic Cathepsins | Cathepsin L | | Breast, colorectal | [28] | AD | [197] |
| | Cathepsin E | Endosomal structures, ER, Golgi | Cervical, gastric, lung, pancreas adenocarcinomas | [51-55] | | |
| | Cathepsin D | Lysosome | Breast, colorectal, ovarian | [47-49, 198-200] | Atherosclerosis | [121] |
| | General | Intracellular, secreted | Most | Table in [15, 58] | | |
| Kallikreins (hK) | hK1 | | | | Hypertension, inflammation | [24] |
| | PSA (hK 3) | | Prostate, ovarian | [201-202] | | |
| | hK10 | | Colon, ovarian, pancreatic, head and neck | [203-206] | | |
| | hK15 | | Ovarian, prostate | [207-208] | | |
| Serine Proteases | uPA, uPAR | Membrane, Pericellular | Cervical, colorectal, gastric, prostate | [86, 116, 209-210] | | |
| Caspases | | Intracellular | | | Neurodegenerative disorders | [82] |
| | General | Extracellular | Most | Table in [211] | | |
| MMPs | MMP-1, -8, -13 | | Breast | [85, 102-104, 211-212] | Artherosclerosis, RA | [213-214] |
| | MMP-2, -9 | | Breast, colorectal, lung, malignant gliomas, ovarian | [91-94] [95-98] | Bronchiectasis, chronic asthma, COPD, cystic fibrosis, HIV associated dementia, hypertension, stroke | [87, 113-117] |
| | MMP-14 | Membrane | Breast | [212] | | |
| ADAM | | Extracellular | | | AD | [105, 107, 112] |

*Abbreviations: AD: Alzheimer's disease; ADAM: a disintegrin and metalloproteinase domain protease; COPD: chronic obstructive pulmonary disease; ER: endoplasmic reticulum; RA: rheumatoid arthritis In various embodiments, the peptide is bound to the capsid backbone, as described in more detail below. There are multiple known means by which the peptide is able to be associated with, or bound to, the capsid backbone. In various embodiments of the present disclosure the cleavage sequence is chemically conjugated by way of a maleimide linkage or an amide linkage (discussed below). The peptide is generally linked to any residue on the capsid backbone; however, disulfide linkages, maleimide linkages, and amide linkages are formed by conjugating the peptide to cysteine, lysine, or arginine residues of the mutant L1 proteins that comprise the capsid backbones.

In various embodiments the peptide comprises at least one protease cleavage sequence. In some embodiments, the protease cleavage sequence is any sequence capable of being preferentially cleaved by or near a tumor cell. The insertion of this cleavage sequence into the peptide allows the protein to remain attached to the capsid backbone carrier until the IRC enters the tumor microenvironment. By taking advantage of the elevated activities of particular proteases in cancer tissues or tumor microenvironments, the peptide is to a large extent not released from the capsid backbone and able to actively coat MHC receptors until the peptide enters the tumor microenvironment. Several proteases are known in the art to be active in the tumor microenvironment. For example, several metallo-, cysteine and serine proteases are known. From the standpoint of cancer therapy, an additional attraction is that because the proteases responsible for prodrug cleavage may come not just from cancer cells but also from the stromal components of tumors, release of the active drug direction into the tumor microenvironment does not depend on a target expressed only by the cancer cells. Instead, it is the entire tumor ecosystem that represents the target.

Methods of Attaching Peptides to the L1 Protein

The capsid backbones described herein are in some embodiments first functionalized to deliver an epitope containing on one or more peptides associated with the capsid backbone to the target cells, thereby labeling the tumor or cancer cells for destruction. In various embodiments, peptides are conjugated to the capsid backbone through cysteine residues on the capsid protein. Such cysteine molecule are presented naturally, or by mutation, on the surface of the capsid backbone. In various embodiments, the capsid backbone is subjected to reducing conditions sufficient to reduce the sulfhydryl groups of cysteine residues on the surface of the capsid backbone while maintaining the capsid-like icosahedron structures of the capsid backbone. Because of its free sulfhydryl group, cysteine will readily and spontaneously form disulfide bonds with other sulfhydryl-containing ligands under oxidative conditions. Alternatively, a series of compounds are known to add a maleimide moiety to receptive substrates that readily and irreversibly form thioester linkages with cysteine residues at a pH between about 6.5 and about 7.5. Thus, in one embodiment, the peptide is associated with the capsid backbone via a maleimide linkage.

In various embodiments, the peptide is conjugated to a lysine residue on the capsid backbone. Lysine residues are easily modified because of their primary amine moiety. Using reactions termed n-hydroxysuccinimide (NHS) ester reactions (because NHS is released as prat of the reaction), amide bonds are formed at surface-exposed lysine residues on the capsid backbone. The NHS reaction occurs spontaneously between about pH 7.2 and about pH 9.

In various embodiments, the peptide is conjugated to an aspartate or glutamate residue. Unlike chemical coupling strategies involving cysteine and lysine groups, chemically coupling to aspartate or glutamate residues requires multiple steps. First, the carboxylic acid of the aspartate or glutamate is activated using 1-ethyl-3-(3-dimethylaminopropyl)carbodiimide hydrochloride (EDC), or similar chemical cross-linking reagent. Once activated, this adduct will react with NHS to form an NHS ester. The NHS ester is then reacted with a ligand with an exposed primary amine to from a stable amide bond.

In various embodiments, the capsid backbone comprises a region of negatively charged amino acids on a surface-exposed area that is capable of binding to the peptide comprising a region of positively charged amino acids. In various embodiments, the region of negatively charged amino acids is flanked, on one or on both sides, by one or more cysteine residues, referred to as polyanionic: cysteine or more specifically, polyglutamic acid:cysteine or polyaspartic acid:cysteine. In such cases, the conjugation of the capsid backbone and the peptide would result from non-covalent binding between the complementary amino acid charges of the capsid backbone and the peptide and a disulfide bond between the cysteines. In various embodiments, the cysteine(s) are one or more amino acids away from the region of charged amino acids such that any secondary/tertiary structure would bring the charged amino acid region in close proximity to the cysteine(s). In various embodiments, the peptide comprises at least one peptide and a polyionic:cysteine for attaching the peptide to the capsid backbone comprising a complementary polyionic:cysteine sequence and an enzyme cleavage site positioned between the terminal cysteine and the CD8+ T cell epitope. In various embodiments, the peptide comprises, a terminal cysteine, at least one peptide, and an enzyme cleavage sequence positioned between the terminal cysteine and the peptide(s).

Negatively charged amino acids that are useful in producing the described IRC include, e.g., glutamic acid and aspartic acid. These amino acids are used singly in some embodiments, e.g., polyglutamic acid, or in combination. In a specific embodiment, the negatively charged region comprises glutamic acid. The number of negatively charged amino acids can vary and can include about 4 to about 20 amino acids, about 6 to about 18 amino acids, or about 8 to about 16 amino acids, and the like. In a specific embodiment, the negatively charged region comprises about 8 negatively charged amino acids. In a more specific embodiment, the negatively charged region comprises EEEEEEEEC (E8C, SEQ ID NO: 130). In another embodiment, the negatively charged region comprises CEEEEEEEEC (SEQ ID NO: 131). Methods for conjugating peptides to a capsid backbones via disulfide bonding are known. For instance, the presence of a polyarginine-cysteine moiety on the peptide allows docking of the peptide to the polyanionic site (EEEEEEEEC, E8C, SEQ ID NO: 130) present in the various loops of the capsid backbone. Covalent cross-linking between the two cysteine residues should render this association irreversible under oxidizing conditions. For the conjugation reactions, purified capsid backbones are dialyzed in conjugation buffer (20 mM Tris/HCl, pH 7.5, 150 mM NaCl, 5% glycerol, 0.5 mM $CaCl_2$) and then the peptide and the oxidizing reagents are added, allowing the reaction to proceed for 16 hrs at 4° C. At the end of the incubation, the reaction mixtures are applied to a size-exclusion column (such as SEPHADEX® G-100, Pharmacia, New Jersey, US, volume 20 ml, flow rate 1 ml/min, 10 mM Tris/HCl (pH 7.4), 150 mM NaCl, 0.5 mM $CaCl_2$)) to remove unconjugated peptide and exchange buffer. IRCs that elute in the void volume are identified by the presence of the L1 protein on SDS-PAGE. The conjugated capsid backbones (IRC) are than optionally analyzed by electron microscopy.

In various embodiments, the peptide is genetically fused to the L1 protein. In various embodiments, the peptide is either covalently or non-covalently linked to the capsid backbone. Rather than attaching the peptide to the capsid backbone via, e.g., binding of negatively and positively charged amino acids, or via maleimide based conjugation, a nucleic acid sequence encoding the peptide is inserted in some embodiments into the nucleic acid encoding the L1 protein such that upon expression a peptide is produced that is inserted into a loop of the capsid protein and displayed on the surface of the capsid backbone.

In various embodiments, non-natural amino acids are used to conjugate the peptide to the capsid backbone. Beyond the 20 natural amino acids, many non-natural amino acids have been used for site-specific protein conjugation reactions. For example, an azidohomoalanine (AHA) or a p-amino-phenylalanine (pAF) may be incorporated into the capsid backbone coat protein for conjugation. These amino acids are incorporated into proteins in two ways: global methionine replacement and amber stop codon suppression. Because AHA is very similar to methionine, AHA will be incorporated at each AUG codon if the methionine supply is rate limiting, this is termed global methionine replacement. Bacteria auxotrophic for methionine or cell-free protein synthesis can be used to limit-methionine availability. Amber stop codon suppression will incorporate pAF. Amber stop codon suppression uses nonnative synthetases and tRNAs that do not react with the natural amino acids to incorporate the non-natural amino acid at the amber stop codon UAG. AHA, displaying an azide, will participate in in copper(I)-catalyzed azide-alkyne cycloaddition ("click" reaction) and form covalent triazole rings with alkyne-containing ligands.

In various embodiments, the IRC comprises, at least one-tenth of the L1 proteins display a peptide. In various embodiments, at least one-fifth of the L1 proteins display a peptide. In various embodiments, about half of the L1 proteins display a peptide. In various embodiments, about two-thirds of the L1 proteins display a recall peptide. In various embodiments, nearly all of the L1 proteins display a peptide.

IRCs and Uses Thereof in Clinical Therapies

In various embodiments, the capsid backbone binds preferentially to tumor cells. The capsid backbones' tumor preference originates, in some embodiments, from several sources such as the capsid backbone's charge (positive or negative), shape and size (different aspect ratio filaments and diameter spheres), shielding (self-proteins/peptides and polymers of various sizes and densities), and targeting (ligands for receptors or environmental factors displayed on different linkers at various densities).

In terms of charge, in various embodiments, the capsid backbone contains a positive surface charge. Positively charged capsid backbones have been shown in some studies to remain longer in circulation when injected into a subject. Due to the abundant presence of proteoglycan in cell membranes that confer a negative charge to cell membranes, and collagen within the tumor interstitial space conferring a positive charge, positively charged IRCs are more likely to possess enhanced binding to mammalian cells as compared with non-charged or negatively charged IRCs, and therefor are better able to avoid aggregation and as a result, are able to better penetrate tumor tissue. Some examples demonstrating these charge-based effects include polyarginine-decorated cowpea mosaic virus (CPMV) found to be taken up eight times more efficiently than native CPMV in a human cervical cancer. (Wen et al. *Chem. Soc. Rev.,* 45(15):4074-4126, 2016).

With regards to shape, the shape and flexibility of the capsid backbone in some instances plays an additional functional role in the ability of capsid backbones to diffuse throughout a tumor. A comparison between the diffusion profiles of a spherical and rod-shaped particle was performed with CPMV and TMV using a spheroid model. It was shown in this study that the CPMV (spherical) experienced a steady diffusion profile, but the TMV (rod shaped) exhibited a two-phase diffusion behavior that entailed an extremely rapid early loading phase that could be attributed to its movement axially, like a needle. (Wen et al., *Chem. Soc. Rev.,* 45(15):4074-41:26, 2016). Some other advantageous properties that are conferred by elongated particles include better margination toward the vessel wall and stronger adherence due to greater surface area for interaction, which not only have implications for tumor homing but also for enhanced targeting of cardiovascular disease.

Besides passive tumor homing properties, natural interactions of viruses with certain cells can also be exploited. CPMV in particular exhibits unique specificity in interacting with surface vimentin, which is found on endothelial, cancer, and inflammatory cells. (Wen et al., *Chem. Soc. Rev.,* 45(15):4074-4126, 2016). The native affinity of CPMV for surface vimentin allows for high-resolution imaging of microvasculature up to 500 μm in depth, which cannot be achieved through the use of other nanoparticles, as they tend to aggregate and block the vasculature. This interaction can be utilized for a range of applications, such as delivery to a panel of cancer cells including cervical, breast, and colon cancer cell lines, delineation of atherosclerotic lesions, and intravital imaging of tumor vasculature and angiogenesis. Another example of an existing endogenous association is canine parvovirus (CPV) with transferrin receptor (TfR), an important receptor for iron transport into cells and highly upregulated by numerous cancer cell lines. Even after dye labelling, CPV retains its specificity for TfR and was shown to bind to receptors found on HeLa cervical cancer cells, HT-29 colon cancer cells, and MDA-MB-231 breast cancer cells. (Wen et al., *Chem. Soc. Rev.,* 45(15):4074-4126, 2016).

In various embodiments, the capsid backbone targets a protein expressed preferentially on the tumor cell surface in the subject. Such proteins are typically overexpressed on the surface of tumor cells, but some if not all, are also found in the blood, i.e., serum. Non-limiting examples of such surface markers include: CEA (carcinoembryonic antigen), E-cadherin, EMA (epithelial membrane antigen; aka MUC-1), vimentin, fibronectin, Her2/neu (human epidermal growth factor receptor type 2, also called Erb b2), $\alpha v \beta 3$ integrin, EpCAM (epithelial cell adhesion molecule), FR-$\alpha$ (folate receptor-alpha), PAR (urokinase-type plasminogen activator receptor), and transferrin receptor (over expressed in tumor cells).

Peptides are often used to label cancerous cells based on recognition of their transmembrane proteins. The most commonly used peptide is arginylglycylaspartic acid (RGD), which is composed of L-arginine, glycine, and L-aspartic acid. RGD was first isolated from the cell-binding domain of fibronectin, a glycoprotein that binds to integrins, and is involved in cell-cell and cell-extracellular matrix (ECM) attachment and signaling by binding collagen, fibrin, and proteoglycans. RGD peptides have the highest affinity for a type of cell surface integrins, $\alpha v \beta$ which are highly expressed in tumoral endothelial cells, but not in normal endothelial cells. In various embodiments such a peptide sequence is incorporated into the IRC.

Methods of treating cancers in a subject in need thereof by administering an IRC to patient in need thereof, and related uses of the described IRC compositions, are described herein. The methods described herein comprise, for instance, administering the IRCs described herein to a subject in need thereof in an amount sufficient to inhibit tumor growth, progression or metastasis, i.e., a therapeutic amount or dose. In various embodiments, the IRC is administered to a subject in need thereof in amount sufficient to stimulate cytokine production and/or cellular immunity, particularly innate immunity, including stimulation of the cytotoxic activity of macrophages and natural killer cells. In various embodiments described herein, a subject in need thereof is a subject who has been previously treated for a tumor and is currently deemed cancer-free or disease free in accordance with medical standards.

Briefly, various understood aspects of what is believed to be the mechanism of action of the described IRCs are described and supported by the examples, below. The IRC first bind to a tumor cell, in some embodiments the binding is specific. (See, Example 9, FIGS. 18A and 18B). The peptide epitope on the IRC is then proteolytically cleaved by furin, in some embodiments, or by any other resident protease nearby the tumor cell, which is over-expressed in the tumor microenvironment. This in turn leads to release of the peptide from the IRC and the loading, or binding, of the peptide by an MHC molecule expressed on the surface of the tumor cell ("epitope coating"). (See, Examples 10 and 16, and FIGS. 19, 21, 22, and 34). The epitope-coated tumor cell is then recognized as a pathogen-infected cell by one or more T-cells responsive to the specific peptide bound in the MHC molecules, and pre-existing CD8 T cells, yielding a triggered immune redirection response. (See, Examples 11 and 12). That is, this recognition event leads to triggering or activation of the subject's preexisting immune memory against pathogens and childhood vaccines against the tumor, leading to the attacking and destroying of the subject's tumor cells.

Destruction of tumor cells can result in components of the preexisting immune response being exposed to cancer cell antigens. Thus, antigens released from the killed tumor cells will initiate a further immune response to recruit additional tumor-specific CD8 T cells, or a "second wave" of T cells that then proceed to attack additional tumor cells in the area. This can result in elicitation of an endogenous immune response against the cancer cell antigens (referred in some instances to "epitope spreading") and leads to anti-tumor immune memory.

Thus, the methods and uses disclosed herein are methods of treating cancer in an subject in need thereof that occurs through utilizing, or the re-orienting of, the subject's own preexisting adaptive memory immune system to attack cancer cells. The methods and uses described herein make use of the fact that subjects, in some instances, possess preexisting immune responses that were not originally elicited in response to a cancer, but that were elicited instead by routine vaccination or via natural infection by a parasite or pathogen. Because the cancer cells would not normally express such epitopes that elicit preexisting immune responses, it would not be expected that such an immune response would not normally, without exogeneous intervention, be capable of attacking any cancer cell. However, by way of the present methods and uses described herein, such preexisting immune responses are readily recruited to attack, kill, and clear a cancer in a subject. This recruitment or repurposing effect is therefore achieved by way of the present IRC compositions since these IRC, upon injection or other means of delivery into the subject, introduce into or onto the surface of the cancer one or more epitopes known to be recognized by the preexisting immune response in the subject, resulting in cells of the immune response attacking antigen-displaying cancer cells.

Thus, without wishing to be bound by any specific theory, the methods, uses, and compositions described herein act by recruiting a preexisting immune response in a subject to the site of a cancer, such that the preexisting immune response attacks and kills the cancer cells. Thus, there are generally four or five steps involved in the described methods, including: 1) binding IRC to the tumor cells, 2) cleavage of the epitope from the IRC, 3) MHC binding of the epitopes for display on the tumor cell surface, 4) recognition of the loaded MHC by the subject's pre-existing recalled immunity against the epitope, and optionally 5) triggering of a second wave and longer-term anti-tumoral immunity thereafter.

Data obtained from cell culture assays and animal studies are often used in formulating a range of dosages for use in humans. The dosages of such compositions lie preferably within a range of circulating concentrations that include the $ED_{50}$ with little or no toxicity. The dosage varies within this range depending on the dosage form employed and the route of administration utilized. For any composition used in the methods described herein, the therapeutically effective dose is capable of being estimated initially from cell culture assays. A dose is formulated in animal models to achieve a circulating plasma concentration range that includes the $IC_{50}$ (the concentration of the test composition that achieves a half-maximal inhibition of symptoms) as determined in cell culture. Such information is then used to accurately determine useful doses in humans. Levels in plasma are measured, for example, by high performance liquid chromatography.

In many instances, it will be desirable to have multiple administrations of the IRC-containing compositions, usually at most, at least, or not exceeding 1, 2, 3, 4, 5, 6, 7, 8, 9, 10, 11, 12, 13, 14, 15, or more doses including all ranges therebetween. The administrations will normally be at 1, 2, 3, 4, 5, 6, to 5, 6, 7, 8, 9, 10, 11, to 12 week/month/year intervals, including all values and ranges there between, more usually from three- to five-week intervals.

In various embodiments, a method is provided for stimulating the cytotoxic activity of macrophages and natural killer (NK) cells by administering to a subject in need thereof an effective amount of an IRC described herein. The macrophages and natural killer cells are in some instances those that are present in the tumor microenvironment. In one aspect, the IRCs are administered to the subject in an amount effective to stimulate the cytotoxic activity of macrophages and natural killer cells already present in the tumor microenvironment. In various other embodiments, the IRCs are administered to the subject in an amount effective to attract macrophages and natural killer cells to the tumor microenvironment. In various embodiments, the IRCs are administered to the subject in an amount effective to bind sufficient numbers of antibodies to the peptide or IRC capsid itself to attract and stimulate macrophages, neutrophils and natural killer cells.

In various embodiments, methods and uses are provided for redirecting the cytotoxic activity of an existing memory CD8+ T cell to a tumor cell or tumor microenvironment by administering to a subject in need thereof an effective amount of the IRC described herein. Preferably, the T cell epitope of the peptide of the IRC is from a pathogen for which the subject has been vaccinated or from a pathogen that has previously infected the subject and the subject has memory CD8+ T cells that recognize the T cell epitope in complex with an MHC class I molecule on the tumor cells. In an aspect described herein, the effective or therapeutic amount of the IRC compositions described herein is an amount sufficient to attract the memory CD8+ T cell to the tumor microenvironment. In another alternative aspect, the effective amount of the IRC is an amount sufficient to stimulate the memory CD8+ T cell present in the tumor microenvironment.

In various embodiments, the tumor is a small lung cell cancer, hepatocellular carcinoma, liver cancer, hepatocellular carcinoma, melanoma, metastatic melanoma, adrenal cancer, anal cancer, aplastic anemia, bile duct cancer, bladder cancer, bone cancer, brain/CNS cancer, breast cancer, cancer of unknown primary origin, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (gist), gestational trophoblastic disease, Hodgkin disease, Kaposi sarcoma, kidney cancer, laryngeal and hypopharyngeal cancer, leukemia, liver cancer, lung cancer, lymphoma, malignant mesothelioma, multiple myeloma, myelodysplastic syndrome, nasal cavity and paranasal sinus cancer, nasopharyngeal cancer. neuroblastoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma, skin cancer, stomach cancer, testicular cancer, thymus cancer, thyroid cancer, uterine sarcoma, vaginal cancer, vulvar cancer, Waldenstrom macroglobulinemia, Wilms tumor, non-Hodgkin lymphoma, Hodgkin lymphoma, Burkitt's lymphoma, lymphoblastic lymphomas, mantle cell lymphoma (MCL), multiple myeloma (MM), small lymphocytic lymphoma (SLL), splenic marginal zone lymphoma, marginal zone lymphoma (extra-nodal or nodal), mixed cell type diffuse aggressive lymphomas of adults, large cell type diffuse aggressive lymphomas of adults, large cell immunoblastic diffuse aggressive lymphomas of adults, small non-cleaved cell diffuse aggressive lymphomas of adults, or follicular lymphoma, head and neck cancer, endometrial or uterine carcinoma, non-small cell lung cancer, osteosarcoma, glioblastoma, or metastatic cancer. In a preferred embodiment, the cancer is a breast cancer, a cervical cancer, an ovarian cancer, a pancreatic cancer or melanoma.

The term "cancer" as used herein refers to proliferative diseases, such as lymphomas, lymphocytic leukemias, lung cancer, non-small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewing's sarcoma, including refractory versions of any of the above cancers, or a combination of one or more of the above cancers.

An aspect described herein is a method for treating a cancer in a subject in need thereof by administering an IRC described herein to the subject wherein the CD8+ epitope of the peptide is of a failed therapeutic cancer vaccine against a viral-induced cancer, e.g., HPV cervical cancer, HPV+ oral cancer, EBV nasopharyngeal cancer (the "therapeutic vaccine"). The methods and uses described herein therefore comprise determining whether the subject has been actively vaccinated but did not respond with an anti-tumor effect to the treatment. The IRC composition is then administering to the subject an effective amount of an IRC of this invention wherein the CD8+ epitope of the peptide is of the antigenic determinant in the vaccine previously administered to the subject that infected the subject.

Capsid backbones have inherent adjuvant properties. In some embodiments, the immunogenicity of the IRC compositions described herein are further enhanced by the combination with additional nonspecific stimulators of the immune response, known as adjuvants. Suitable adjuvants include all acceptable immunostimulatory compounds, such as, but not limited to, cytokines, toxins, or synthetic compositions such as alum.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, y-interferon, GM-CSF, BCG, aluminum salts, such as aluminum hydroxide or other aluminum compound, methylenedioxyphenyl (MDP) compounds, such as thur-MDP and nor-MOP, CGP (MTP-PE), lipid A, and monophosphoryl lipid A (MPL), or inactivated microbial agents. RIBI, which contains three components extracted from bacteria, MPL, trehalose dimycolate (TOM), and cell wall skeleton (CWS) in a 2% squalene/Tween 80 emulsion. MHC antigens may even be used.

Various methods of achieving adjuvant affect for the IRC compositions includes use of agents such as aluminum hydroxide or phosphate (alum), commonly used as about 0.05 to about 0.1% solution in phosphate buffered saline, admixture with synthetic polymers of sugars (CARBOPOL®) used as an about 0.25% solution, aggregation of a protein in the composition by heat treatment with temperatures ranging between about 70° C. to about 101° C. for a 30-second to 2-minute period, respectively. Aggregation by reactivating with pepsin-treated (Fab) antibodies to albumin; mixture with bacterial cells, e.g., *C. parvum*, endotoxins or lipopolysaccharide components of Gram-negative bacteria; emulsion in physiologically acceptable oil vehicles, e.g., mannide monooleate (Aracel ATM), or emulsion with a 20% solution of a perfluorocarbon (FLUOSOL-DA®) used as a block substitute may also be employed to produce an adjuvant effect. A typical adjuvant is complete Freund's adjuvant (containing killed *Mycobacterium tuberculosis*), incomplete Freund's adjuvants, and aluminum hydroxide.

For administration to humans, a variety of suitable adjuvants will be evident to a skilled worker. These include, e.g., Alum-MPL as adjuvant, or the comparable formulation, ASO4, which is used in the approved HPV vaccine CERVARIX®, AS03, AS02, MF59, montanide, saponin-based adjuvants such as GPI-0100, CpG-based adjuvants, or imiquimod. In embodiments of the invention, an adjuvant is physically coupled to the capsid backbone, or encapsulated by the capsid backbone, rather than simply mixed with them. In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA, US); or low-dose Cyclophosphamide (CYP; 300 mg/ml) (Johnson/Mead, NJ, US) and cytokines such as γ-interferon, IL-2, or IL-12 or genes encoding proteins involved in immune helper functions, such as B-7. In embodiments described herein, these genes are encapsulated by the capsid backbone to facilitate their delivery into a subject.

The preparation of compositions that contain polypeptide or peptide sequence(s) as active ingredients is generally well understood in the art. Typically, such compositions are prepared as injectables either as liquid solutions or suspensions: solid forms suitable for solution in or suspension in liquid prior to injection may also be prepared. The preparation is in some instances emulsified. The active immunogenic ingredient is in some embodiments mixed with excipients that are pharmaceutically acceptable and compatible with the active ingredient. Suitable excipients are, for example, water, saline, dextrose, glycerol, ethanol, or the like and combinations thereof. In addition, if desired, the compositions may contain amounts of auxiliary substances such as wetting or emulsifying agents, pH buffering agents, or adjuvants that enhance the effectiveness of the vaccines. In specific embodiments, vaccines are formulated with a combination of substances.

The compositions comprising the IRCs of the present disclosure are intended to be in a biologically-compatible form that is suitable for administration in vivo to subjects. The pharmaceutical compositions described herein further comprise one or more optional pharmaceutically acceptable carriers. The term "pharmaceutically acceptable" means approved by a regulatory agency of the Federal or a state government, e.g., the FDA, or listed in the U.S. Pharmacopeia or other generally recognized pharmacopeia for use in animals, and more particularly, in humans. The term "carrier" refers to a diluent, adjuvant, excipient, or vehicle with which the capsid backbone is administered. Such pharmaceutical carriers include, for example, sterile liquids, such as water and oils, including those of petroleum, animal, vegetable or synthetic origin, including but not limited to peanut oil, soybean oil, mineral oil, sesame oil and the like. Water is a carrier in some instances when the pharmaceutical composition described herein is administered orally. Saline and aqueous dextrose are carriers, for example, when the pharmaceutical composition is administered intravenously. Saline solutions and aqueous dextrose and glycerol solutions are employed, for instance, as liquid carriers for injectable solutions. Suitable pharmaceutical excipients include, without limitation, starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition in some embodiments optionally contains minor amounts of wetting or emulsifying agents, or pH buffering agents.

The pharmaceutical compositions comprising the IRCs of the present disclosure take the form of, for example, solutions, suspensions, emulsions, tablets, pills, capsules, powders, sustained-release formulations, and the like. Oral formulation includes in some embodiments standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of an IRC of the present disclosure together with a suitable amount of a pharmaceutically acceptable carrier so as to provide the form for proper administration to the subject. The formulation should suit the mode of administration.

The pharmaceutical compositions of the present disclosure are administered by any particular route of administration including, but not limited to, intravenous, intramuscular, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intraos seous, intrapelvic, intrapericardial, intraperitoneal, intrapleural, intraprostatic, intrapulmonary, intrarectal, intrarenal, intraretinal, intraspinal, intrasynovial, intrathoracic, intrauterine, intravesical, bolus, oral, parenteral, subcutaneous, vaginal, rectal, buccal, sublingual, intranasal, iontophoretic means, or transdermal means. Most suitable routes are intravenous injection or oral administration. In particular embodiments, the compositions are administered at or near the target area, e.g., intratumoral injection.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, intratumoral, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion. (See, for example, Remington's Pharmaceutical Sciences, 1990). Some variation in dosage necessarily occurs depending on the condition of the subject. The person responsible for administration will, in any event, determine the appropriate dose for the individual subject.

The IRC-containing compositions described herein, in some embodiments, are administered by inhalation. In certain embodiments a composition is administered as an aerosol. As used herein the term "aerosol" or "aerosolized composition" refers to a suspension of solid or liquid particles in a gas. These terms are used generally to refer to a composition that has been vaporized, nebulized, or otherwise converted from a solid or liquid form to an inhalable form including suspended solid or liquid drug particles. Such aerosols can be used to deliver a composition via the respiratory system. As used herein, "respiratory system" refers to the system of organs in the body responsible for the intake of oxygen and the expiration of carbon dioxide. The system generally includes all the air passages from the nose to the pulmonary alveoli. In mammals it is generally considered to include the lungs, bronchi, bronchioles, trachea, nasal passages, and diaphragm. For purposes of the present disclosure, delivery of a composition to the respiratory system indicates that a drug is delivered to one or more of the air passages of the respiratory system, in particular to the lungs.

Additional formulations that are suitable for other modes of administration include suppositories (for anal or vaginal application) and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders and contain about 10% to about 95% of active ingredient, preferably about 25% to about 70%.

The IRC compositions described herein are, in some instances, formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical compositions of the present disclosure also include, in certain embodiments, an effective amount of an additional adjuvant. As noted herein, papillomavirus capsid backbones have adjuvant properties. Suitable additional adjuvants include, but are not limited to, Freund's complete or incomplete, mineral gels such as aluminum hydroxide, surface active substances such as lysolecithin, pluronic polyols, polyanions, peptides, oil emulsions, dinitrophenol, and potentially useful human adjuvants such as Bacille Calmette-Guerin (BCG), *Corynebacterium parvum*, and non-toxic cholera toxin.

Under ordinary conditions of storage and use, the described IRC compositions in some embodiments also contain a preservative to prevent the growth of microorganisms. In all cases the pharmaceutical form must be sterile and must be fluid to the extent that it may be easily injected. It also should be stable under the conditions of manufacture and storage and must be preserved against the contaminating action of microorganisms, such as bacteria and fungi.

The carrier is in some embodiments a solvent or dispersion medium containing, for example, water, ethanol, polyol (for example, glycerol, propylene glycol, and liquid polyethylene glycol, and the like), suitable mixtures thereof, and vegetable oils. The proper fluidity is maintained, for example, by the use of a coating, such as lecithin, by the maintenance of the required particle size in the case of dispersion, and by the use of surfactants. The prevention of the action of microorganisms is brought about in some instances by incorporation of various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions is achieved by the addition to the compositions of agents delaying absorption, for example, aluminum monostearate and gelatin.

Sterile injectable solutions are prepared by incorporating the IRCs in the required amount in the appropriate solvent with various ingredients enumerated above, as required may be followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Different aspects of the present disclosure involve administering an effective amount of a composition comprising the IRCs to a subject in need thereof. In some embodiments of the present disclosure, an IRC comprising a target peptide comprising a CD8+ T cell epitope is administered to the patient to treat a tumor or prevent the recurrence of such tumor. Such compositions will generally be dissolved or dispersed in a pharmaceutically acceptable carrier or aqueous medium.

Design of IRC for Specific Uses

In various embodiments, a method for providing an IRC to a subject in need thereof is provided comprising: (1) measuring the preexisting immunity in a subject, and (2) selecting the appropriate IRC for administration of a subject in need. The appropriate IRC to administer to the subject will depend upon the patients T cell profile. The appropriate IRC will be one that is capable of eliciting a T cell response that is at least twice the baseline total of CD8+ cells. In various embodiments, the appropriate IRC will be one that is capable of eliciting a T cell response that is twice the baseline total of CD8+ or total CD8+CD69+ T cells. The goal is to choose the appropriate IRC based on the subject's vaccination history or prior exposure to a pathogen. Determining which IRC is appropriate is, for example, achieved through: (1) subject interviews; (2) review of a subject's medical records; and/or (3) assessing the subject's T cell profile.

In various embodiments, more than one peptide is suitable for eliciting an immune response directed at a tumor. In various embodiments, an IRC carrying either peptide or a mixture of both peptides will be appropriate. In various embodiments, more than one peptide is expressed and bound to the capsid backbone. In various embodiments, a single peptide will comprise more than one peptide. In various embodiments, multiple peptides comprising different peptides will be conjugated to the capsid backbone. In various embodiments, the invention comprises a population of IRCs as described herein and a pharmaceutically acceptable excipient. In various embodiments, the IRCs administered to the subject are identical. In various embodiments, IRCs carrying different peptide(s) are administered to a subject.

Selection Based on Prior Vaccination. In various embodiments of the methods and uses described herein, contemplated is also a method of selecting an appropriate IRC to administer to a subject in need thereof. In various embodiments this involves ascertaining if the subject has been actively vaccinated against a given pathogen, e.g., a parasite, a bacterium, or virus, e.g., measles or polio, and then selecting and administering to the subject an IRC as disclosed herein wherein the CD8+ T cell epitope of the peptide is from the pathogen against which the subject has been immunized in the past. In various embodiments, a subject's vaccination history is obtained by reviewing the subject's medical record. In various embodiments, a subject's vaccination history is obtained by interviewing the subject.

Selection Based on Prior Infection. In various embodiments, the method of selecting an appropriate IRC for administration to a subject in need thereof involves ascertaining if a subject has been previously infected with a given pathogen, e.g., a parasite, a bacterium, or virus, e.g., measles or polio, and resolved the infection. In various embodiments, the subject is then administered an IRC comprising a peptide which comprises said pathogen for which the subject has been previously infected.

One may ascertain if a subject has been infected with a particular pathogen by reviewing the subject's medical records or interviewing the subject. Non-limiting examples of CD8+ T cell epitopes that bind to particular MHC class I molecules are set forth in Table 1. The method also comprises, in certain embodiments, determining which MHC class I determinant(s) the subject's cells express and then administering an IRC described herein wherein the CD8+ T cell epitope of the peptide is a CD8+ T cell epitope of the antigenic component of the pathogen in the vaccine or of the pathogen that previously infected the subject that forms a complex with the subject's MHC class I determinant(s).

Measuring T cell Responses. In various embodiments, a subject's T cell profile is also assessed in order to select an appropriate IRC using various techniques known in the art. This profile is then used to guide selection of the appropriate IRC to administer to the subject. Such techniques include, for example, measuring interferon-γ levels, using flow cytometry to isolate Ag-specific CD8+ T cells, and/or cytotoxicity assays. To measure interferon-γ (a marker of T cell activation), intracellular staining of isolated T cells. Alternatively, an enzyme-linked immunosorbent spot (ELISPOT) assay for interferon-γ may be conducted. This technique allows for a high throughput assessment of a patient's T cell profile. This method can potentially detect one in 100,000-300,000 cells. Briefly, a monoclonal antibody for a specific cytokine is pre-coated onto a polyvinylidene difluoride (PVDF)-backed microplate. CD8+ T cells are pipetted into the wells along with dendritic cells and individual peptides and the microplate is placed into a humidified 37° C. $CO_2$ incubator for a period ranging from 24 to 48 h. During incubation, the immobilized antibody binds the cytokine secreted from the cells. After washing a detection antibody specific for the chosen analyte is added to the wells. Following the washes, enzyme conjugated to streptavidin is added and a substrate is added. A colored precipitate forms, according to the substrate utilized and appears as spot at the sites of cytokine secretion, with each individual spot representing a single producing cell.

In various embodiments, provided are methods of determining the appropriate IRC to administer to a subject in need thereof, by assessing the subject's T cell profile, comprising: (1) collecting PBMCs from subject (pre-vaccination sample), (2) preparing enzyme-linked immune absorbent spot (ELISPot) plates by coating with anti-IFN-γ antibody (incubate overnight), (3) incubating PBMCs with one of the pool of peptides of interest, i.e., the peptides expected to elicit a T cell response (incubate for 1-2 days), (4) washing the plates, adding a biotinylated secondary antibody (incubating for a few hours), (5) washing the plates, adding avidin conjugated horseradish peroxidase and incubating, (6) washing plates, adding aminoethyl carbazole (AEC) for a few minutes, (7) stopping the reaction (by adding water), and (8) visualizing on an ELISPot reader. The disclosed methods detect up to one in 100,000 to 300,000 cells. A two-fold increase in the frequency of antigen-specific T cells should be considered as a signal.

In various embodiments T cell proliferation is measured by 3H (tritiated)-thymidine. Such methods are sensitive and can be used for high throughput assays. Such techniques include, for instance, carboxyfluorescein succinimidyl ester (CFSE) and Ki64 intracellular staining.

Selecting Peptides based on Tropism. It is known in the art that some viruses display a tropism for particular type of tissue. For example: viruses that display a tropism for brain tissue include without limitation, JC virus, measles, LCM virus, arbovirus and rabies; viruses that display a tropism for eye tissue include without limitation herpes simplex virus, adenovirus, and cytomegalovirus; viruses that display a tropism for nasal tissue include without limitation, rhinoviruses, parainfluenza viruses, and respiratory syncytial virus; viruses that display a tropism for oral tissue, e.g., oral mucosa, gingiva, salivary glands, pharynx, include without limitation, herpes simplex virus type I and type II, mumps virus, Epstein Barr virus, and cytomegalovirus; viruses that display a tropism for lung tissue include without limitation, influenza virus type A and type B, parainfluenza virus, respiratory syncytial virus, adenovirus, and SARS coronavirus; viruses that display a tropism for nerve tissue, e.g., the spinal cord, include without limitation poliovirus and HTLV-1; viruses that display a tropism for heart tissue, include without limitation, Coxsackie B virus; viruses that display a tropism for liver tissue, include without limitation, hepatitis viruses types A, B, and C; viruses that display a tropism for gastrointestinal tissue, e.g., stomach, and large and small intestine, include without limitation, adenovirus, rotavirus, norovirus, astrovirus, and coronavirus; viruses that display a tropism for pancreatic tissue, include without limitation, coxsackie B virus; viruses that display a tropism for skin tissue, include without limitation, varicella zoster virus, herpes simplex virus 6, smallpox virus, molluscum contagiosum, papilloma viruses, parvovirus B19, rubella, measles and coxsackie A virus; and viruses that display a tropism for genital tissue, include without limitation, herpes simplex type 2, papillomaviruses, human immunodeficiency virus (HIV).

In various embodiments, a method for treating a cancer in a subject in need thereof is provided by administering an IRC described herein to the subject wherein the peptide is a CD8+ epitope of a pathogen that has a tropism for the tissue that is the source of the cancer (the "source tissue"). In various embodiments, the appropriate IRC is selected by first determining the source tissue of the tumor cell and then selecting a peptide: (1) to which the patient already has existing CD8+ T cells, and (2) that has a tropism for the source tissue of the tumor. The selected IRC(s) are then administered to the subject in need thereof.

In various embodiments, provided are methods for treating a lung cancer comprising determining if a subject has been actively vaccinated against a pathogen that infects lung cells, e.g., an influenza virus, e.g., influenza virus type A or type B, then administering an effective amount of an IRC composition described herein, wherein the CD8+ T cell epitope of the peptide is of the antigenic determinants of the pathogen contained in the vaccine and which T cell epitope forms a complex with an MHC molecule class I of the subject. The methods and uses described herein for treating a lung cancer includes, in some embodiments, determining if a subject has been infected with pathogen that infects lung cells, e.g., an influenza virus, e.g., influenza virus type A or type B, then administering an effective amount of an IRC composition described herein wherein the CD8+ T cell epitope of the peptide is of that pathogen and which T cell epitope forms a complex with an MHC class I molecule of the subject.

Provided also are methods for treating an oral cancer, which are part of the group of cancers commonly referred to as head and neck cancers, by administering an IRC compositions described herein, wherein the CD8+ epitope of the peptide is of a pathogen that has a tropism for oral tissue, e.g., a mumps virus, Epstein Barr virus, cytomegalovirus, or a herpes simplex virus type 1. The method comprises determining if a subject in need thereof has been actively vaccinated against, or infected with, e.g., a mumps virus, Epstein Barr virus, cytomegalovirus, or a herpes simplex virus type 1, and if the subject has been vaccinated or infected previously then administering to the subject an IRC composition described herein wherein the CD8+ epitope of the peptide is of a mumps virus or a measles virus or of the antigenic component of the vaccine the subject had received, or of the pathogen, i.e., mumps, measles, Epstein Barr virus, cytomegalovirus, or a herpes simplex virus type 1, that had previously infected the subject.

Combination Therapy

In various embodiments, the IRC compositions described herein are co-administered with other cancer therapeutics. Furthermore, in some embodiments, the IRCs described herein are administered in conjunction with other cancer treatment therapies, e.g., radiotherapy, chemotherapy, surgery, and/or immunotherapy. In some aspects of methods and uses described herein, the IRC compositions described herein are administered in conjunction with checkpoint inhibitors. In various embodiments the capsid backbone is administered in conjunction with an immune agonist. In various embodiments, the IRC is administered in conjunction with treatment with a therapeutic vaccine. In various embodiments, the IRC is administered in conjunction with treatment with a conjugated antigen receptor expressing T cell (CAR-T cell). In various embodiments, the IRC is administered in conjunction with treatment with another immuno-oncology product. The IRCs of the present disclosure and other therapies or therapeutic agents are, in some embodiments, administered simultaneously or sequentially by the same or different routes of administration. The determination of the identity and amount of therapeutic agent(s) for use in the methods of the present disclosure is readily made by ordinarily skilled medical practitioners using standard techniques known in the art.

All of the references cited above, as well as all references cited herein, are incorporated herein by reference in their entireties for all purposes.

While the methods, uses, and compositions described herein have been illustrated and described in detail in above, such illustration and description are to be considered illustrative or exemplary and not restrictive. It will be understood that changes and modifications may be made by those of ordinary skill within the scope and spirit of the following claims. In particular, the present disclosure covers further embodiments with any combination of features from different embodiments described above and below.

The present disclosure is additionally described by way of the following illustrative non-limiting examples that provide a better understanding of the present disclosure and of its many advantages. The following examples are included to demonstrate preferred embodiments of the invention. It should be appreciated by those of skill in the art that the techniques disclosed in the examples which follow represent techniques used in the present disclosure to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

EXAMPLES

Example 1

Production of Truncated Mouse Papillomavirus (MPV1) L1 Protein

The truncated mouse papillomavirus L1 DNA sequence of 1138 base pairs was codon-optimized for *E. coli* expression and synthesized (SEQ ID NOS:135 and 136, two varieties of codon optimization) (GeneScript Biotech, Piscataway, NJ) and subsequently cloned into the T7 expression vector Pet-24a(+) (MilliporeSigma, Burlington, MA). The sequence was based on the wild type mouse (*Mus musculus*) papillomavirus L1 protein sequence except that it contains three deletion mutations at three specific regions: one deletion at the amino-terminus (10 amino acids removed), one at deletion the carboxy-terminus (34 amino acids deleted), and a third deletion in the helix four (H4) region close to the carboxy-terminal region (deletion of amino acids 411 to 436 of the MPV L1 sequence). This mutant MPV L1 protein is hereinafter referred to as "MPV.10.34.d." (See, FIG. 1B).

The wild type mouse (*Mus musculus*) L1 wild type protein sequence is depicted in FIG. 1A and has the following protein sequence (SEQ ID NO: 132, NCBI Reference Sequence: YP_003778198.1, DNA: 9434943):

Met Ala Met Trp Thr Pro Gln Thr Gly Lys Leu Tyr Leu Pro Pro

Thr Thr Pro Val Ala Lys Val Gln Ser Thr Asp Glu Tyr Val Tyr

Pro Thr Ser Leu Phe Cys His Ala His Thr Asp Arg Leu Leu Thr

Val Gly His Pro Phe Phe Ser Val Ile Asp Asn Asp Lys Val Thr

Val Pro Lys Val Ser Gly Asn Gln Tyr Arg Val Phe Arg Leu Lys

Phe Pro Asp Pro Asn Lys Phe Ala Leu Pro Gln Lys Asp Phe Tyr

Asp Pro Glu Lys Glu Arg Leu Val Trp Arg Leu Arg Gly Leu Glu

Ile Gly Arg Gly Gly Pro Leu Gly Ile Gly Thr Thr Gly His Pro

Leu Phe Asn Lys Leu Gly Asp Thr Glu Asn Pro Asn Lys Tyr Gln

Gln Gly Ser Lys Asp Asn Arg Gln Asn Thr Ser Met Asp Pro Lys

Gln Thr Gln Leu Phe Ile Val Gly Cys Glu Pro Pro Thr Gly Glu

His Trp Asp Val Ala Lys Pro Cys Gly Ala Leu Glu Lys Gly Asp

Cys Pro Pro Ile Gln Leu Val Asn Ser Val Ile Glu Asp Gly Asp

Met Cys Asp Ile Gly Phe Gly Asn Met Asn Phe Lys Glu Leu Gln

Gln Asp Arg Ser Gly Val Pro Leu Asp Ile Val Ser Thr Arg Cys

Lys Trp Pro Asp Phe Leu Lys Met Thr Asn Glu Ala Tyr Gly Asp

Lys Met Phe Phe Phe Gly Arg Arg Glu Gln Val Tyr Ala Arg His

Phe Phe Thr Arg Asn Gly Ser Val Gly Glu Pro Ile Pro Asn Ser

Val Ser Pro Ser Asp Phe Tyr Tyr Ala Pro Asp Ser Thr Gln Asp

Gln Lys Thr Leu Ala Pro Ser Val Tyr Phe Gly Thr Pro Ser Gly

Ser Leu Val Ser Ser Asp Gly Gln Leu Phe Asn Arg Pro Phe Trp

Leu Gln Arg Ala Gln Gly Asn Asn Asn Gly Val Cys Trp His Asn

Glu Leu Phe Val Thr Val Val Asp Asn Thr

Arg Asn Thr Asn Phe Thr Ile Ser Gln Gln Thr Asn Thr Pro Asn

Pro Asp Thr Tyr Asp Ser Thr Asn Phe Lys Asn Tyr Leu Arg His

Val Glu Gln Phe Glu Leu Ser Leu Ile Ala Gln Leu Cys Lys Val

Pro Leu Asp Pro Gly Val Leu Ala His Ile Asn Thr Met Asn Pro

Thr Ile Leu Glu Asn Trp Asn Leu Gly Phe Val Pro Pro Pro Gln

Gln Ser Ile Ser Asp Tyr Arg Tyr Ile Thr Ser Ser Ala Thr

Arg Cys Pro Asp Gln Asn Pro Pro Lys

Likewise, the wild type nucleic acid sequence for MPV1 L1 protein (SEQ ID NO: 133) is as follows:

ATGGCAATGTGGACACCCCAGACCGGGAAGCTTTACCTCCCACCTACAACTCCAGTGGCAAA

AGTGCAGAGCACAGACGAATATGTGTACCCTACGTCTCTCTTCTGTCATGCACACACGGACC

GTTTGCTAACAGTGGGCCACCCTTTTTTTCTGTCATTGACAATGACAAGGTCACTGTGCCT

AAAGTGTCTGGCAACCAATATAGGGTTTTCAGACTTAAATTCCCAGATCCAAATAAATTTGC

ATTGCCCCAAAAGGATTTCTATGATCCTGAGAAAGAACGGTTAGTGTGGAGGTTAAGGGGTC

TGGAAATTGGAAGAGGTGGCCCATTAGGGATTGGCACTACCGGGCACCCCCTTTTTAACAAG

CTTGGAGACACGGAAAATCCAAATAAATATCAGCAAGGCTCTAAGGATAATAGGCAGAACAC

TTCCATGGACCCCAAACAAACACAGCTGTTTATTGTTGGCTGTGAACCCCCTACAGGGGAAC

ACTGGGATGTAGCTAAGCCCTGTGGAGCTCTGGAGAAGGGTGACTGCCCTCCTATCCAACTT

GTAAATAGTGTAATTGAGGATGGGGATATGTGTGACATTGGCTTTGGGAATATGAACTTCAA

AGAGCTGCAGCAGGATAGGAGTGGTGTGCCTCTTGATATTGTATCTACCCGGTGCAAATGGC

CCGACTTTCTGAAAATGACCAATGAGGCATATGGGGATAAGATGTTCTTCTTTGGAAGGAGA

GAGCAAGTGTATGCAAGACACTTTTTCACCAGGAATGGCTCTGTGGGGGAGCCCATACCAAA

CTCTGTGAGTCCCAGTGACTTTTACTACGCACCCGACAGCACACAGGACCAGAAGACACTCG

CACCCTCCGTGTACTTTGGAACTCCTAGTGGGTCACTTGTGTCGAGTGATGGTCAGCTGTTT

AACAGGCCATTTTGGCTTCAAAGGGCTCAGGGAAACAATAATGGTGTGTGCTGGCACAATGA

GCTCTTTGTTACTGTTGTCGACAACACAAGGAATACAAACTTTACTATCTCCCAGCAAACCA

ACACACCAAACCCAGATACATATGACTCTACTAATTTTAAAAACTATTTAAGACATGTGGAA

CAATTTGAGCTGTCCCTTATTGCTCAACTGTGTAAGGTTCCACTTGACCCGGGTGTGCTTGC

CCATATAAACACTATGAACCCAACCATCTTGGAGAACTGGAACTTGGGTTTTGTACCTCCCC

CACAGCAGTCCATCTCTGATGACTATAGGTATATAACATCATCGGCAACTCGCTGTCCAGAT

CAGAATCCGCCCAAGGAAAGAGAGGATCCTTACAAGGGTCTTATATTTTGGGAAGTTGATCT

TACTGAGAGGTTTTCTCAGGACCTTGATCAGTTTGCTCTGGGACGAAAGTTTCTGTATCAAG

CTGGTATACGTACTGCTGTTACGGGCCGCGGGGTCAAAAGGGCAGCGTCTACAACCTCTGCG

TCTTCTAGACGAGTTGTAAAACGGAAGAGGGGAAGCAAATAA

In contrast, the mutant MPV sequence selected for the following studies is depicted in FIG. 1B and has the following amino acid sequence (SEQ ID NO:134):

Met Leu Tyr Leu Pro Pro Thr Thr Pro Val Ala Lys Val Gln Ser

Thr Asp Glu Tyr Val Tyr Pro Thr Ser Leu Phe Cys His Ala His

Thr Asp Arg Leu Leu Thr Val Gly His Pro Phe Phe Ser Val Ile

Asp Asn Asp Lys Val Thr Val Pro Lys Val Ser Gly Asn Gln Tyr

Arg Val Phe Arg Leu Lys Phe Pro Asp Pro Asn Lys Phe Ala Leu

Pro Gln Lys Asp Phe

Tyr Asp Pro Glu Lys Glu Arg Leu Val Trp Arg Leu Arg Gly Leu

Glu Ile Gly Arg Gly Gly Pro Leu Gly Ile Gly Thr Thr Gly His

Pro Leu Phe Asn Lys Leu Gly Asp Thr Glu Asn Pro Asn Lys Tyr

Gln Gln Gly Ser Lys Asp Asn Arg Gln Asn Thr Ser Met Asp Pro

Lys Gln Thr Gln Leu Phe Ile Val Gly Cys Glu Pro Pro Thr Gly

-continued

```
Glu His Trp Asp Val Ala Lys Pro Cys Gly Ala Leu Glu Lys Gly

Asp Cys Pro Pro Ile Gln Leu Val Asn Ser Val Ile Glu Asp Gly

Asp Met Cys Asp Ile Gly Phe Gly Asn Met Asn Phe Lys Glu Leu

Gln Gln Asp Arg Ser Gly Val Pro Leu Asp Ile Val Ser Thr Arg

Cys Lys Trp Pro Asp Phe Leu Lys Met Thr Asn Glu Ala Tyr Gly

Asp Lys Met Phe Phe Phe Gly Arg Arg Glu Gln Val Tyr Ala Arg

His Phe Phe Thr Arg Asn Gly Ser Val Gly Glu Pro Ile Pro Asn

Ser Val Ser Pro Ser Asp Phe Tyr Tyr Ala Pro Asp Ser Thr Gln

Asp Gln Lys Thr Leu Ala Pro Ser Val Tyr Phe Gly Thr Pro Ser

Gly Ser Leu Val Ser Ser Asp Gly Gln Leu Phe Asn Arg Pro Phe

Trp Leu Gln Arg Ala Gln Gly Asn Asn Asn Gly Val Cys Trp His

Asn Glu Leu Phe Val Thr Val Val Asp Asn Thr Arg Asn Thr Asn

Phe Thr Ile Ser Gln Gln Thr Asn Thr Pro Asn Pro Asp Thr Tyr

Asp Ser Thr Asn Phe Lys Asn Tyr Leu Arg His Val Glu Gln Phe

Glu Leu Ser Leu Ile Ala Gln Leu Cys Lys Val Pro Leu Asp Pro

Gly Val Leu Ala His Ile Asn Thr Met Asn Pro Thr Ile Leu Glu

Asn Trp Asn Leu Gly Phe Val Pro Pro Lys Glu Arg Glu Asp Pro

Tyr Lys Gly Leu Ile Phe Trp Glu Val Asp Leu Thr Glu Arg Phe

Ser Gln Asp Leu Asp Gln Phe Ala Leu Gly Arg Lys Phe Leu Tyr

Gln
```

Alignment of the wild type sequence with the triple truncation MPV.10.34.d sequence is shown in FIG. 2. Additionally, the nucleic acid sequence (below) of MPV.10.34.d was optimized for expression. The sequence was optimized for codon usage within the target host as well as for expression level to maximize expression efficiency within the host. Below are provided two alternative optimized nucleic acid sequences for MPV.10.34.d used herein (SEQ ID NO: 135):

```
ATGCTGTACCTGCCGCCGACCACCCCGGTGGCGAAAGTTCAGAGCACCGACGAATACGTTTA
TCCGACCAGCCTGTTCTGCCACGCGCACACCGATCGTCTGCTGACCGTGGGTCACCCGTTCT
TTAGCGTTATCGACAACGATAAGGTGACCGTTCCGAAAGTGAGCGGCAACCAGTACCGTGTT
TTTCGTCTGAAGTTCCCGGACCCGAACAAATTTGCGCTGCCGCAAAAGGACTTCTATGATCC
GGAGAAGGAACGTCTGGTGTGGCGTCTGCGTGGTCTGGAAATTGGTCGTGGTGGCCCGCTGG
GTATTGGTACCACCGGTCACCCGCTGTTCAACAAACTGGGCGATACCGAGAACCCGAACAAA
TATCAGCAAGGTAGCAAGGACAACCGTCAGAACACCAGCATGGACCCGAAGCAGACCCAACT
GTTTATTGTTGGTTGCGAGCCGCCGACCGGTGAACACTGGGATGTTGCGAAACCGTGCGGTG
CGCTGGAAAAGGGCGATTGCCCGCCGATCCAACTGGTGAACAGCGTTATTGAGGACGGTGAT
ATGTGCGACATCGGTTTTGGCAACATGAACTTCAAAGAACTGCAGCAAGACCGTAGCGGCGT
GCCGCTGGATATTGTTAGCACCCGTTGCAAATGGCCGGACTTCCTGAAGATGACCAACGAAG
CGTACGGTGATAAGATGTTCTTTTTCGGCCGTCGTGAGCAGGTTTATGCGCGTCACTTTTTC
ACCCGTAACGGTAGCGTGGGCGAGCCGATCCCGAACAGCGTTAGCCCGAGCGACTTCTACTA
```

-continued

TGCGCCGGACAGCACCCAGGATCAAAAAACCCTGGCGCCGAGCGTGTACTTTGGTACCCCGA

GCGGCAGCCTGGTTAGCAGCGATGGTCAACTGTTTAACCGTCCGTTCTGGCTGCAGCGTGCG

CAGGGTAACAACAACGGCGTGTGCTGGCACAACGAACTGTTTGTTACCGTGGTTGACAACAC

CCGTAACACCAACTTCACCATCAGCCAGCAAACCAACACCCCGAACCCGGACACCTACGATA

GCACCAACTTTAAAAACTATCTGCGTCACGTGGAGCAGTTCGAACTGAGCCTGATTGCGCAA

CTGTGCAAAGTGCCGCTGGACCCGGGTGTGCTGGCGCACATCAACACCATGAACCCGACCAT

TCTGGAGAACTGGAACCTGGGTTTCGTTCCGCCGAAAGAGCGTGAAGACCCGTACAAGGGCC

TGATCTTCTGGGAAGTGGATCTGACCGAACGTTTCAGCCAGGACCTGGATCAATTTGCGCTG

GGCCGTAAATTCCTG TATCAGTAA

And (SEQ ID NO: 136):
GAATTGGCGGAAGGCCGTCAAGGCCACGTGTCTTGTCCGCGGTACCCATATGCTGTATCTGC

CTCCAACTACACCGGTTGCAAAAGTTCAGAGCACCGATGAATATGTTTATCCGACCAGCCTG

TTTTGTCATGCACATACCGATCGTCTGCTGACCGTTGGTCATCCGTTTTTTAGCGTTATTGA

TAACGATAAAGTGACCGTTCCGAAAGTTAGCGGTAATCAGTATCGTGTTTTTCGCCTGAAAT

TTCCGGATCCGAACAAATTTGCACTGCCGCAGAAAGATTTTTACGACCCGGAAAAAGAACGT

CTGGTTTGGCGTCTGCGTGGTCTGGAAATTGGTCGTGGTGGTCCGTTAGGTATTGGCACCAC

CGGTCATCCGCTGTTTAACAAACTGGGTGATACCGAAAATCCGAATAAATACCAGCAGGGCA

GCAAAGATAATCGTCAGAATACCAGTATGGATCCGAAACAGACCCAGCTGTTTATTGTTGGT

TGTGAACCGCCTACCGGTGAACATTGGGATGTTGCAAAACCGTGTGGTGCACTGGAAAAAGG

TGATTGTCCGCCTATTCAGCTGGTTAATAGCGTGATTGAAGATGGTGATATGTGCGATATTG

GCTTTGGCAACATGAACTTTAAAGAACTGCAGCAGGATCGTAGCGGTGTTCCGCTGGATATT

GTTAGCACCCGTTGTAAATGGCCTGATTTTCTGAAAATGACCAATGAAGCCTATGGCGACAA

AATGTTTTTTTCGGTCGTCGTGAACAGGTTTATGCCCGTCACTTTTTTACCCGTAATGGTA

GCGTTGGTGAACCGATTCCGAATAGCGTTAGCCCGAGCGATTTCTATTATGCACCGGATAGC

ACCCAGGATCAGAAAACCCTGGCACCGAGCGTTTATTTTGGCACCCCGAGCGGTAGCCTGGT

TAGCAGTGATGGTCAGCTGTTCAATCGTCCGTTTTGGCTGCAGCGTGCACAGGGTAATAACA

ATGGTGTTTGTTGGCATAACGAACTGTTTGTTACCGTTGTTGATAATACCCGCAATACCAAC

TTTACCATTAGCCAGCAGACCAATACACCGAATCCGGATACCTATGATAGCACCAACTTCAA

AAACTATCTGCGTCATGTGGAACAGTTTGAACTGAGCCTGATTGCCCAGCTGTGTAAAGTGC

CGCTGGATCCGGGTGTTCTGGCACATATTAACACCATGAATCCGACCATTCTGGAAAATTGG

AATCTGGGTTTTGTTCCGCCTAAAGAACGTGAAGATCCGTATAAAGGTCTGATTTTTTGGGA

AGTTGATCTGACCGAACGTTTTAGCCAGGATCTGGATCAGTTTGCACTGGGTCGCAAATTTC

TGTATCAGTAACTCGAGGAGCTCGGAGCACAAGACTGGCCTCATGGGCCTTCCGCTCACTGC

C

The general protocol for recombinant expression and purification of the mutant MPV.10.34.d is schematically depicted in FIG. 3.

The MPV.10.34.d nucleic acid sequence was generated from wild type mouse papillomavirus sequence via site-mutagenesis (Genscript Biotech, Piscataway, N.J.) using the following primer sequence (SEQ ID NO: 137):

```
AAGCTTGTCGACGGAGCTCGAATTCGGATCCTTATTACTGATACAGGAATT
TACGGCCCAGC
```

The MPV.10.34.d nucleic acid sequence was then cloned into the multicloning site of expression vector pet24a(+) (MilliporeSigma, Burlington, MA) using restriction endonucleases NdeI and BamH1 according to standard protocols. The correct cloning into the multiple cloning site and construct sequence was confirmed by both restriction endonuclease enzyme digestion using MIu1 and BamH1 as well as Sanger sequencing using both T7 forward and reverse primers.

Expression was achieved by transforming the pet24a(+) plasmid containing MPV.10.34.d into T7 expression competent *Escherichia coli* 2566 cells (New England Biolabs, Ipswich, MA, US), and colony selection on solid media. A single colony was grown according to standard protocols in Lurea broth (LB) media. Briefly, 5 mL sterile LB including 50 µg/mL kanamycin (Quality Biological, Gaithersburg, MD, US) was seeded with a single colony selected from the solid media and grown overnight at 37° C. with shaking. The seed culture was then diluted 1:25 and growth was continued at 37° C. until OD600 reached about 0.6 to 0.8. Then about 1 mM final concentration of isopropyl β-d-1-thiogalactopyranoside (IPTG, Invitrogen, Carlsbad, CA, US) was added to the culture to induce expression from the plasmid. Induction was continued under these conditions for an additional four hours after which cell pellets are collected by centrifugation at 4000×g for 15 minutes at 4° C. The supernatant was discarded and the cell pellets were stored at −20° C. unless immediately used.

MPV.10.34.d was expressed as inclusion bodies (IBs). To recover IB MPV.10.34.d, pellets were first thawed (if frozen) and then resuspended in 20 mL per 1 L pellet lysis buffer (50 mM Tris, pH 8.0, 500 mM NaCl, 1 mM EDTA, 1 mM protease inhibitor phenylmethylsulfonyl fluoride (PMSF). Resuspended material was then homogenized using a high pressured homogenizer (Avestin Emulsiflex C3™, ATA Scientific, Taren Point, Australia) and cells were passed through the homogenizer and lysed 4 times at about 15,000 to 20,000 PSI. The lysed bacterial cells were then centrifuged at 25,000×g at 4° C. for 20 min. Supernatant was then discarded and the inclusion body pellet was stored at −20° C.

Next the IB were solubilized by resuspending the pellet (50 mL per 1 L pellet) in of 6 M urea buffer (8 M Urea, 50 mM Tris, pH 8.0, 500 mM NaCl, 1 mM EDTA, 1 mM PMSF, and 1 mM DTT). Resuspended contents were once more passaged three to four times through the homogenizer (Avestin Emulsiflex C3™, ATA Scientific, Taren Point, Australia) at about 15,000 to 20,000 PSI. The resolubilized samples were centrifuged at 25,000×g at 4° C. for 20 min. The supernatant was collected into a container that is sufficiently large enough to hold the volume of a sample. The pellet was discarded. The supernatant was stored at 4° C. or −20° C.

Following solubilization, the MPV.10.34.d was refolded by removal of the denaturant (6M Urea) in a step-gradient manner. The solubilized samples were inserted into dialysis tubing (snakeskin dialysis tubing, 10,000 Da molecular weight cut off, 35 mm. (ThermoFisher Scientific, Waltham, MA, US). In general, about 100 to about 150 mL of resolubilized sample solution was dispensed into a single dialysis tube. The samples were first dialyzed (sample to buffer ratio 1:12.5) against 4 M urea buffer (50 mM Tris, pH 8.0, 500 mM NaCl, 1 mM EDTA, 1 mM PMSF, 1 mM DTT, and 0.05% Tween®-80) for 3±1 hour in a cold room at about 4° C. on a stir plate. Then, the samples were again dialyzed against a fresh 1 M urea buffer (50 mM Tris, pH 8.0, 500 mM NaCl, 1 mM EDTA, 1 mM PMSF, 1 mM DTT, and 0.05% Tween-80) for 3±1 hour in a cold room on a stir plate. Subsequently, the samples were dialyzed against 0 M urea buffer (50 mM Tris, pH 8.0, 500 mM NaCl, 1 mM EDTA, 1 mM PMSF, 1 mM DTT, and 0.05% Tween-80) overnight (about 16 to 18 hours) in a cold room at about 4° C. on a stir plate. The dialyzed/refolded sample solutions were aliquoted into 50 mL conical tubes and stored in a −20° C. freezer.

To obtain a MPV.10.34.d of greater than 95% purity for subsequent medicinal use, samples were subjected to a two-step chromatography purification which involves a capture step utilizing cation exchange chromatography (CEX) followed by a polishing step using a hydrophobic interaction column (HIC). For the capture step, the refolded MPV.10.34.d samples were removed from the −20 and thawed on ice. Next, the sample was dialyzed into capture buffer A (25 mM $NaPO_4$, 25 mM NaCl, pH 6.0). Following dialysis, samples were centrifuged 4000×g, for about 10 min, at 4° C. and then filtered through a 0.22 µm polyethersulfone (PES) membrane. The refolded MPV.10.34.d protein was then captured by CEX (Fractogel® EMD S03-M, EMD Millipore, Burlington, MA, US) and then step eluted with 30% 25 mM $NaPO_4$, 1.5 M NaCl, pH 6.0. This resulted in purified refolded MPV.10.34.d of purity of at least 80%.

To further remove contaminants and increase purity of the MPV.10.34.d to above 95%, the CEX eluate was diluted with high-salt buffer to achieve loading conditions of 25 mM $NaPO_4$, 3 M NaCl, pH 6.0, and applied to HIC resin (butyl-S-Sepharose® Fast Flow, GE Healthcare Life Sciences/Fisher Scientific, Waltham, MA, US). The bound refolded MPV.10.34.d product was subjected to a pre-elution wash with 30% 25 mM $NaPO_4$, 25 mM NaCl, pH 6.0, and then eluted with a single step gradient of 70% 25 mM $NaPO_4$, 25 mM NaCl, pH 6.0. Greater than 95% purity MPV.10.34.d was stored in a −20° C. freezer in the elution buffer.

Greater than 95% purity MPV.10.34.d was confirmed via SDS-PAGE followed by Coomassie blue gel and silver staining. For Coomassie staining, gels were incubated in water to remove SDS-PAGE running buffer, then incubated for 5 minutes in SimplyBlue SafeStain (Novex, Carlsbad, CA). Gels were de-stained in water. (See photographs of gels in FIG. 4A). Silver staining was performed using a Pierce Silver stain kit (ThermoFisher Scientific, Rockford, IL) according to manufacturer's instructions. (See, FIG. 4B). To estimate purity, the images of the gels were taken using the Bio-Rad Image Lab 6.01 software. Gel images were then uploaded into the software and the entire vertical lane containing the band of interest ("lane profile") was analyzed using the image analysis software. The specific total density of the band of the protein of interest was calculated by drawing a box or freehand shape around the band. Subsequently, the total density of the entire lane was measured in the same manner. After obtaining the measurements, the background density of a suitably matched area on the gel in each case was subtracted. This background-corrected density of the protein band by the background-corrected density of the whole lane was then multiplied by 100 to obtain the percent purity.

Figure 4A:
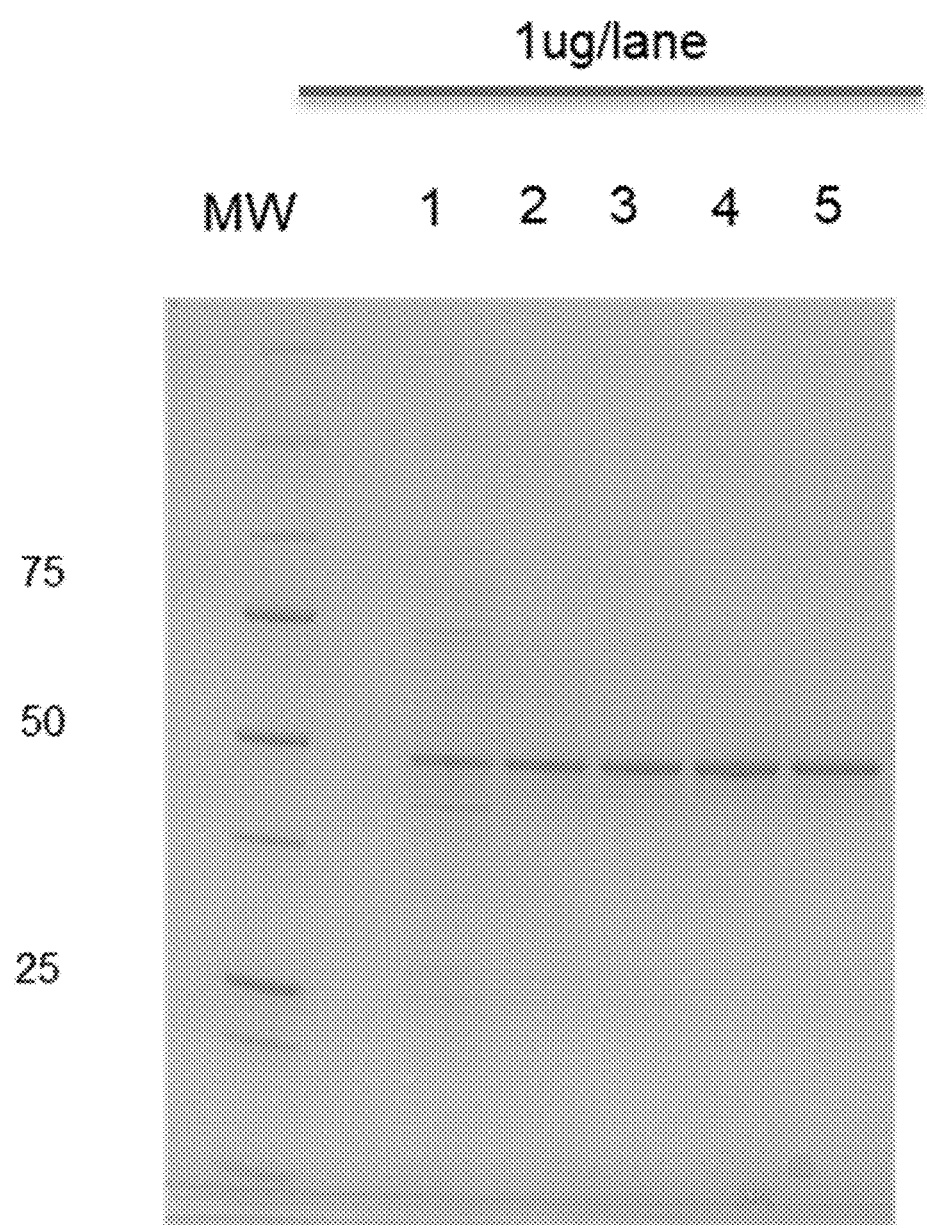
FIG. 4A is a photograph of a stained SDS-PAGE gel showing the incremental purification of the MPV.10.34.d capsid backbone from host cell protein contaminants through the manufacturing process (as described in FIG. 3 and Example 1) demonstrating that host cell protein impurities are significantly reduced throughout the purification process (MW=standard molecular weight bands, numbers on the left-hand side of the gel indicate molecular weight in kiloDaltons (kDa), and top row numbers indicate amount of protein loaded in micrograms).
Figure 4B:
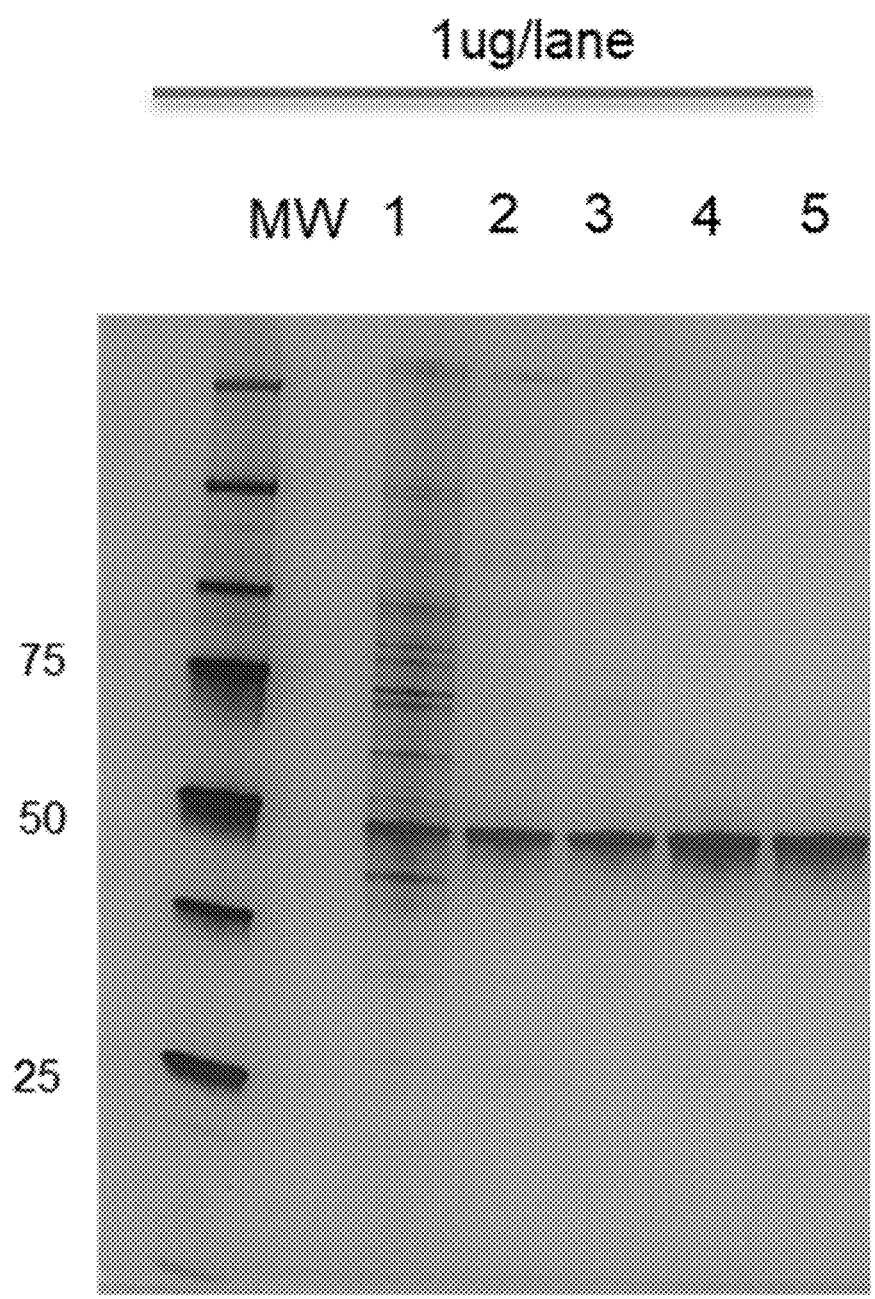
FIG. 4B is a photograph of an SDS-PAGE gel subjected to silver staining, wherein each lane corresponds to a sample of MPV.10.34.d capsid backbone as it is purified from host cell protein contaminants through the manufacturing process (as described in FIG. 3 and Example 1), demonstrating that host cell protein impurities are significantly reduced throughout the purification process (MW=standard molecular weight bands, numbers on the left-hand side of the gel indicate molecular weight in kiloDaltons (kDa), and top row numbers indicate amount of protein loaded in micrograms).

From this analysis and as seen in both FIGS. 4A and 4B, the main process steps described above provided incremental purification of the ~50 kDA MPV.10.34.d protein. Non-specific proteins above and below the 50 kDA band were significantly reduced across each of the purification steps, where lane 1 was a post-cell harvest sample, wash, and homogenization; lane 2 was a post-IB solubilization sample, lane 3 was a post-refolding sample, lane 4 was a post-capture chromatography via CEX sample, and lane 5 was a post-polishing step sample using HIC.

Example 2

Determination of MPV.10.34.d Structure and Size

Figure 5:
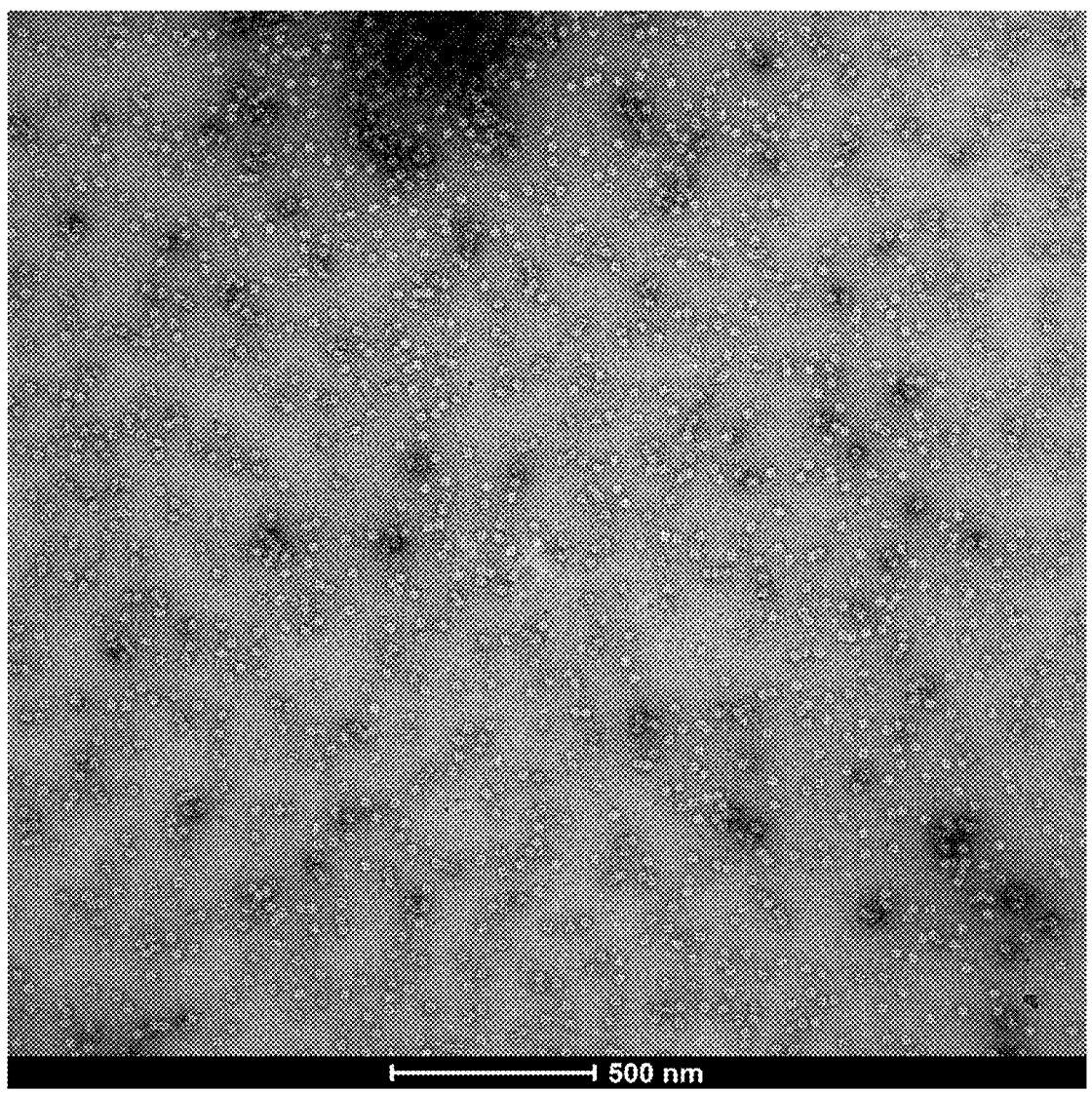
FIG. 5 is a photograph of a transmission electron micrograph (TEM) image with a scale bar of 500 nm of the purified MPV.10.34.d capsid backbone following the production and purification steps as described in FIG. 3 and Example 1. The capsid backbone is approximately between 20 nm to 30 nm in diameter based on this image.
Figure 6A:
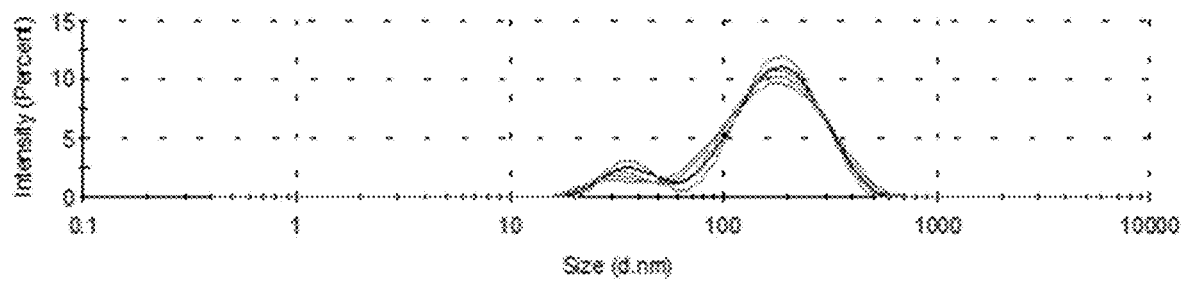
FIG. 6A is a dynamic light scattering (DLS) plot showing the intensity of the particle size distribution of the MPV.10.34.d capsid backbone after the refolding step but before the two-column chromatography purification. The X-axis shows diameter size distribution (nm) and the Y-axis provides percent intensity data.
Figure 6B:
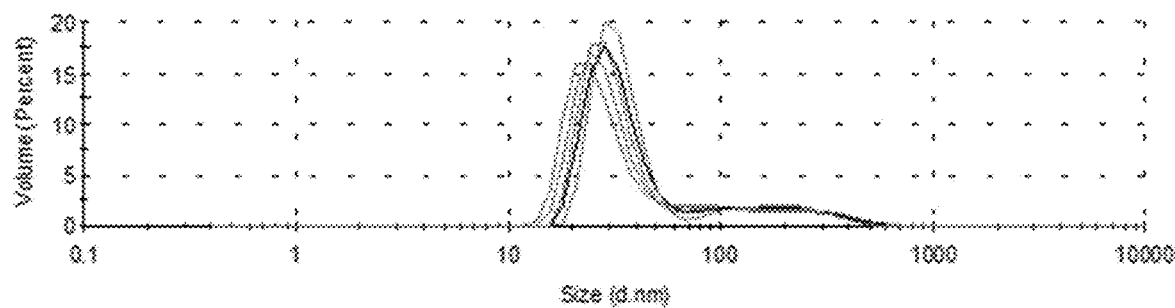
FIG. 6B is a dynamic light scatting plot showing the population size of purified MPV.10.34.d capsid backbone after the refolding step but before two-column chromatography purification. The X-axis shows diameter size distribution (nm) and the Y-axis provides volume percent data.
Figure 7A:
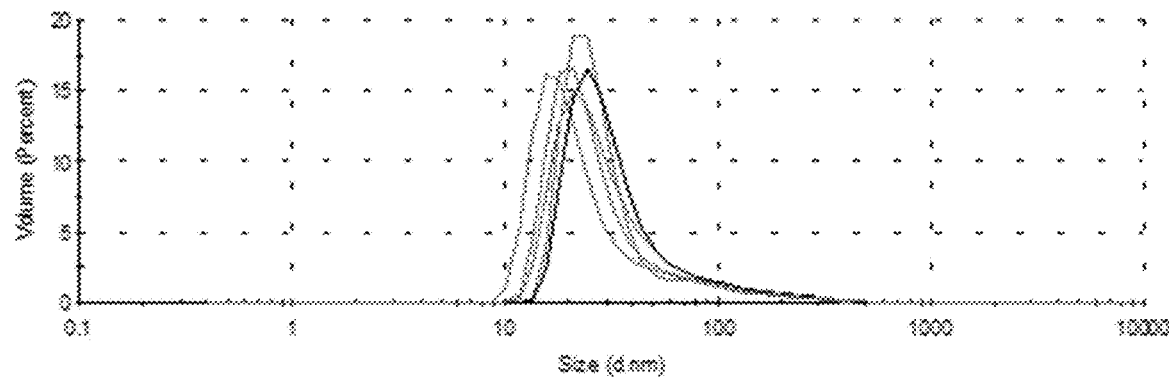
FIG. 7A is a dynamic light scattering plot showing MPV.10.34.d L1 protein refolding in buffer with the following added: 1 mM dithiothreitol (DTT), 1 mM ethylenediamine tetraacetic acid (ETDA), and 1 mM phenylmethylsulfonyl fluoride (PMSF). The X-axis shows diameter size distribution (nm) and the Y-axis provides volume percent data.
Figure 7B:
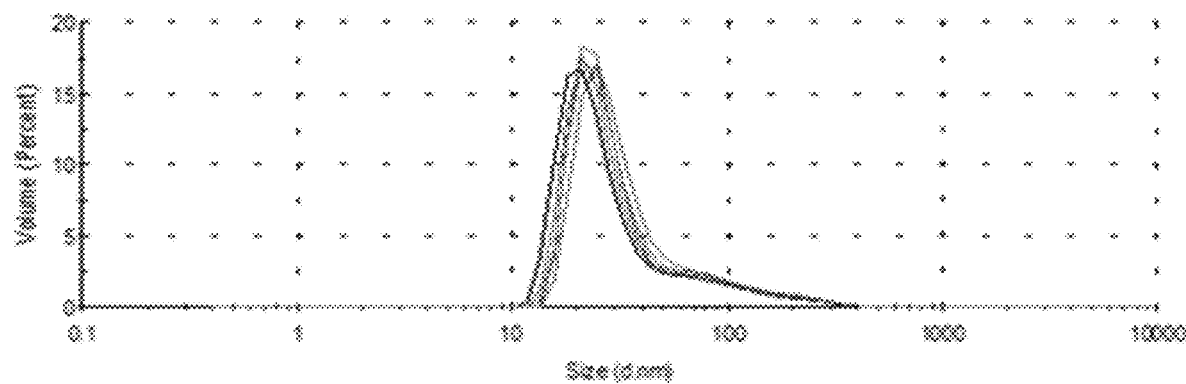
FIG. 7B is a dynamic light scattering plot showing MPV.10.34.d L1 protein refolding in buffer with added 1 mM DTT. The X-axis shows diameter size distribution (nm) and the Y-axis provides volume percent data.
Figure 7C:
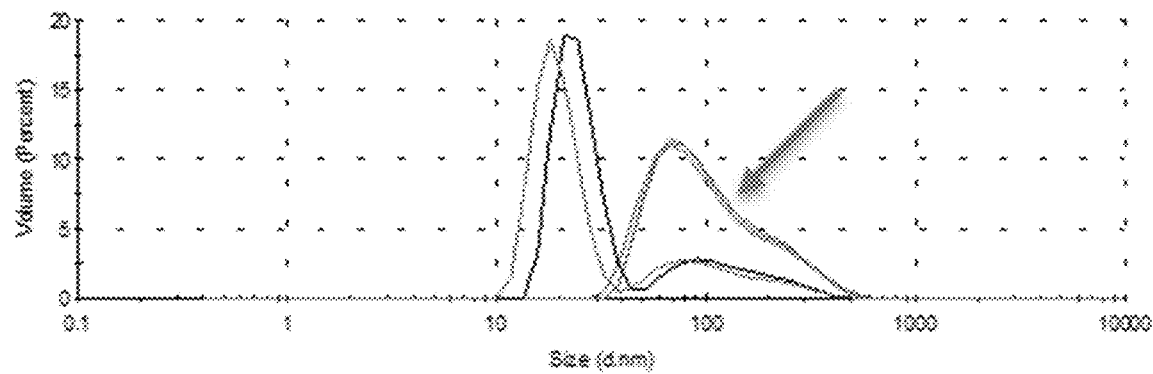
FIG. 7C is a dynamic light scattering plot showing MPV.10.34.d L1 protein refolding in buffer with added 1 mM ETDA. The arrow indicates aggregated protein that is not correctly refolded as detected by the volume intensity plots, which measure population size of the sample as a whole. The X-axis shows diameter size distribution (nm) and the Y-axis provides volume percent data.
Figure 7D:
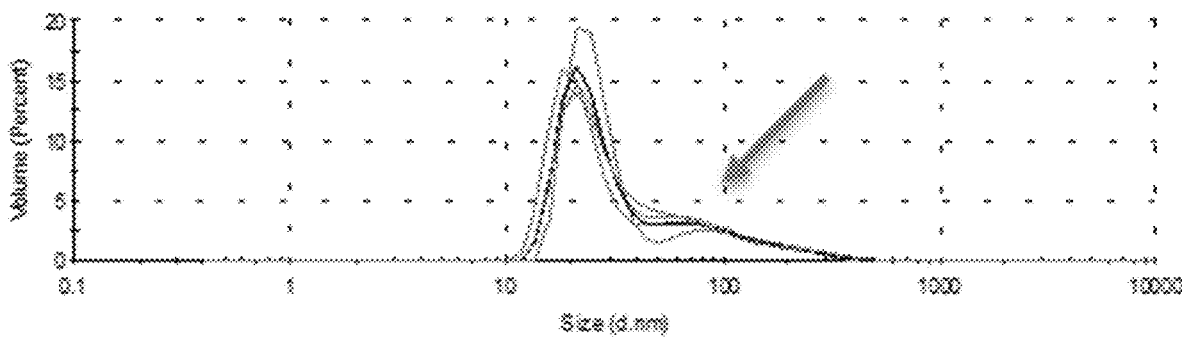
FIG. 7D is a dynamic light scattering plot showing MPV.10.34.d L1 protein refolding in buffer without any added DTT, EDTA, or PMSF. The arrow indicates aggregated protein that is not correctly refolded as detected by the volume intensity plots, which measure population size of the sample as a whole. The X-axis shows diameter size distribution (nm) and the Y-axis provides volume percent data.
Figure 8A:
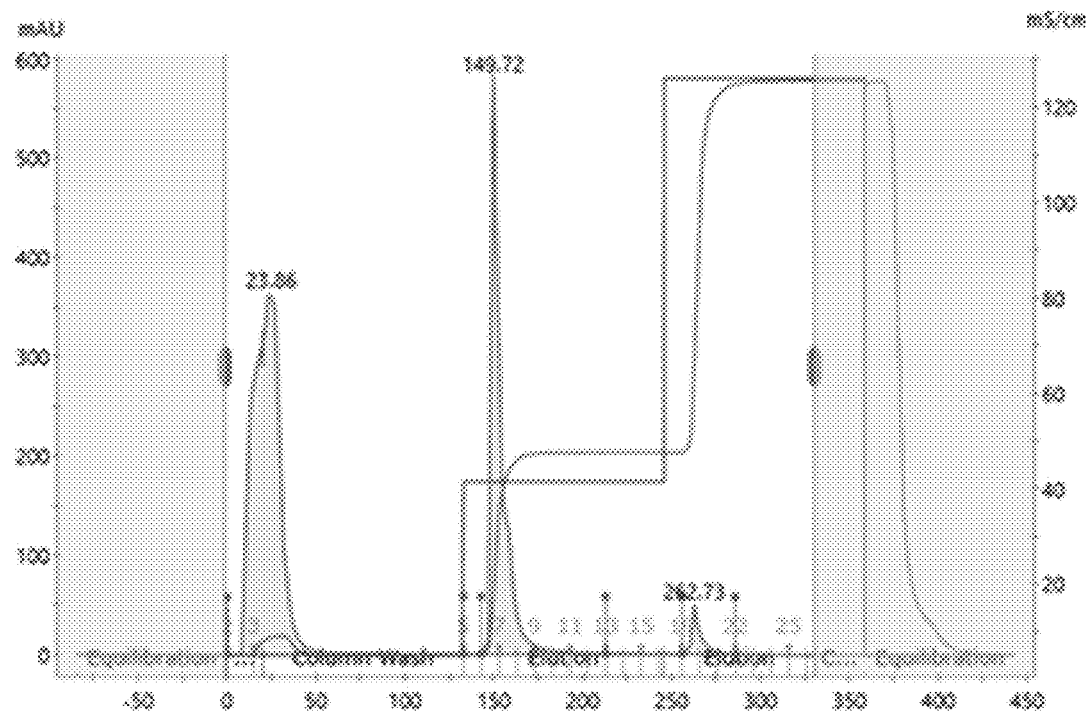
FIG. 8A is a chromatogram showing capture of correctly refolded MPV.10.34.d L1 protein refolded buffer with added 1 mM DTT, 1 mM ETDA, and 1 mM PMSF. The Y-axis provides absorbance units (mAU) on the left and mS/cm on the right, with the X-axis indicating elution volume (mL).
Figure 8B:
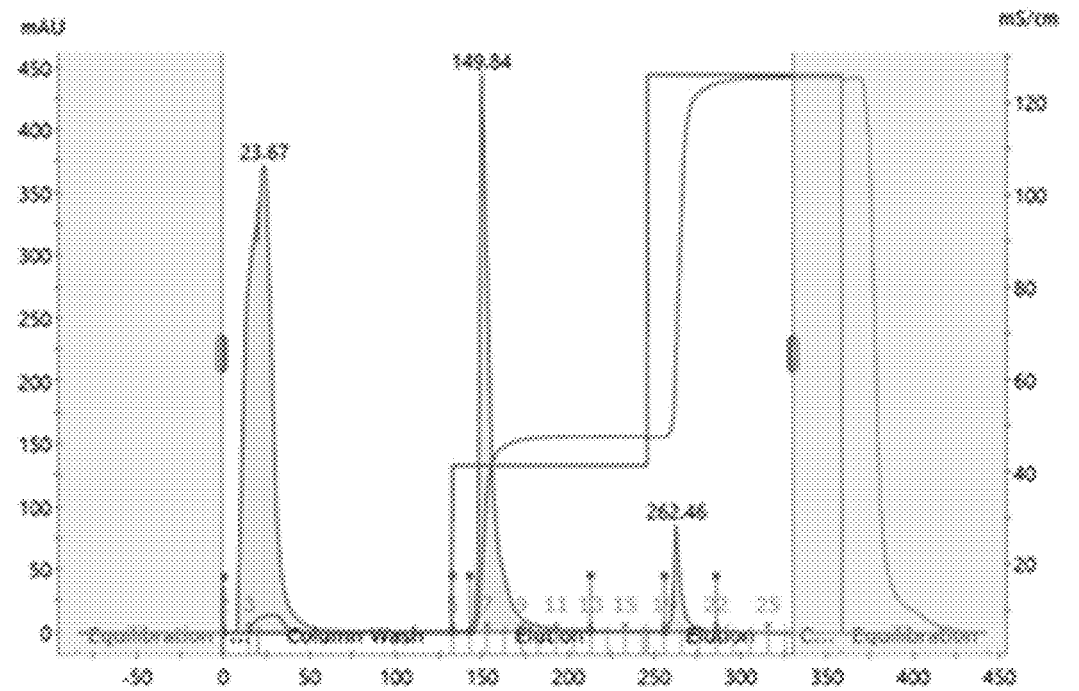
FIG. 8B is a chromatogram showing capture of correctly refolded MPV.10.34.d L1 protein refolded buffer with added 1 mM DTT. The Y-axis provides absorbance units (mAU) on the left and mS/cm on the right, with the X-axis indicating elution volume (mL).
Figure 8C:
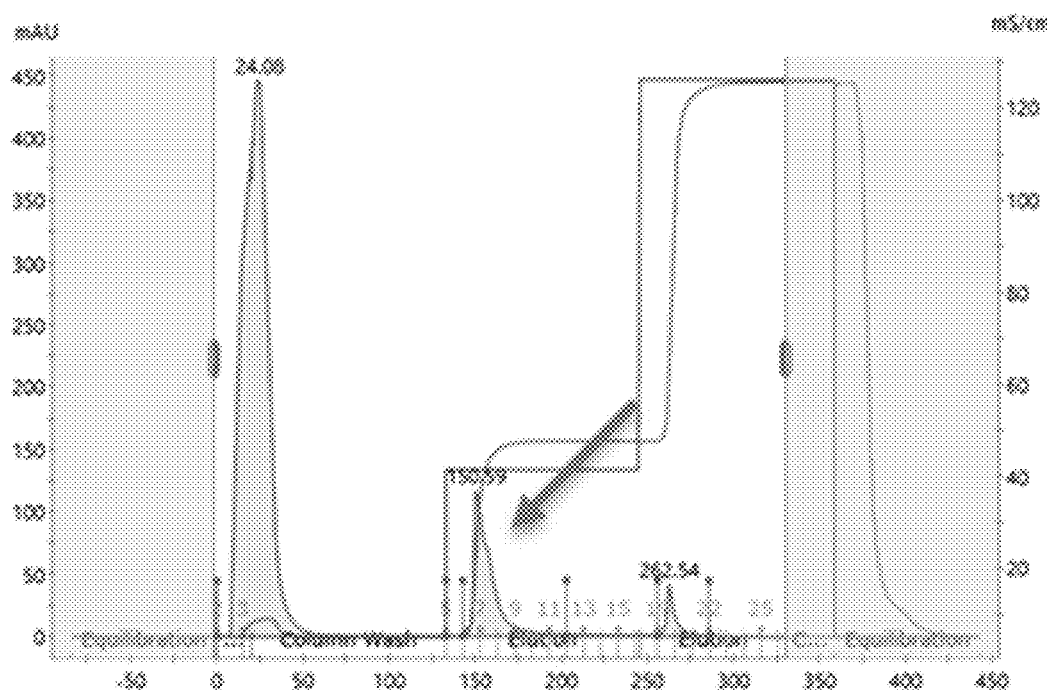
FIG. 8C is a chromatogram showing capture of correctly refolded MPV.10.34.d L1 protein refolded buffer with added 1 mM ETDA. The arrow indicates poor capture and elution, which indicates less correctly refolded MPV.10.34.d capsid backbone was observed under conditions C and D as compared with A and B. The Y-axis provides absorbance units (mAU) on the left and mS/cm on the right, with the X-axis indicating elution volume (mL).
Figure 8D:
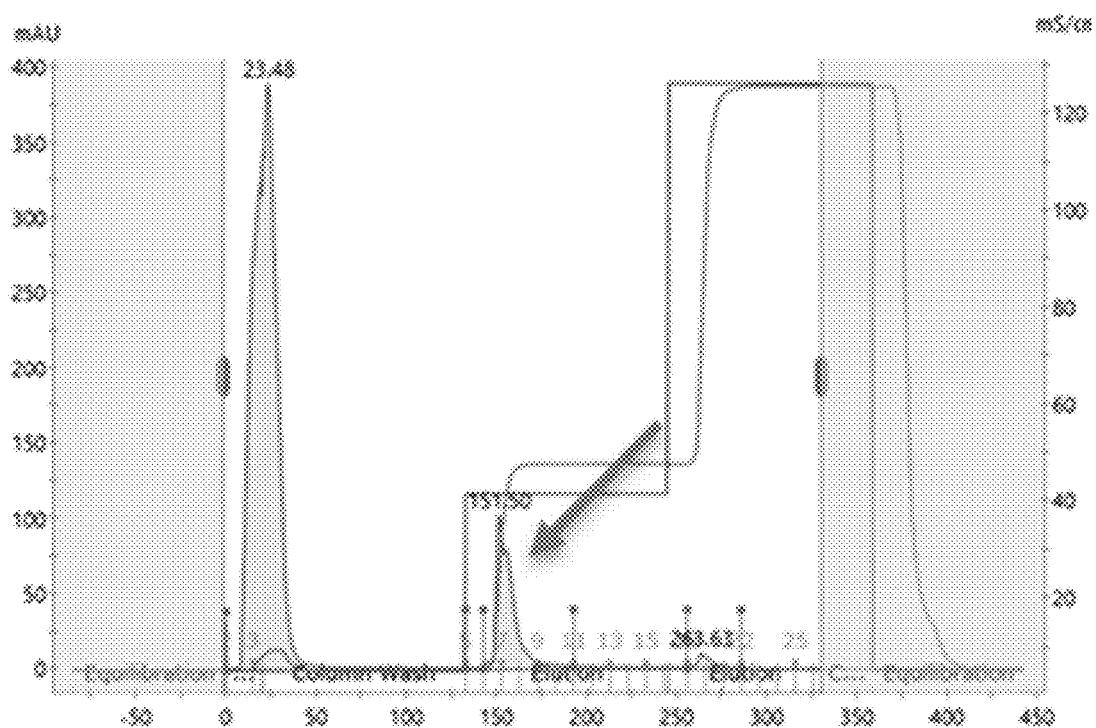
FIG. 8D is a chromatogram showing capture of correctly refolded MPV.10.34.d L1 refolded in the presence of just buffer with no added DTT, EDTA, or PMSF. The arrow indicates poor capture and elution, which indicates less correctly refolded MPV.10.34.d capsid backbone was observed under conditions C and D as compared with A and B. The Y-axis provides absorbance units (mAU) on the left and mS/cm on the right, with the X-axis indicating elution volume (mL).
Figure 9A:
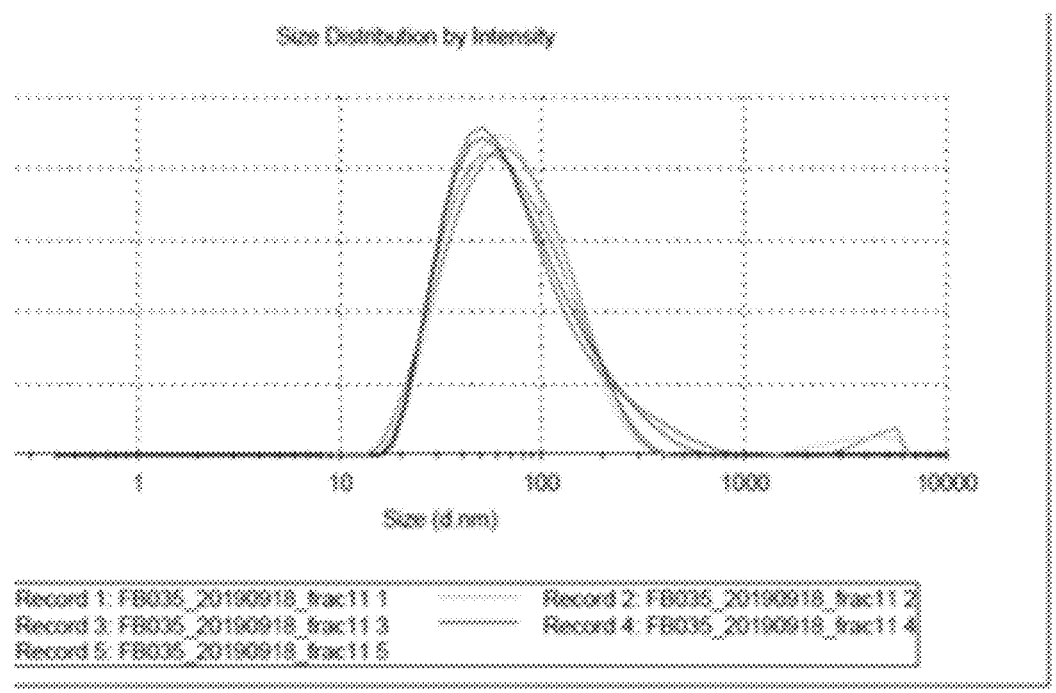
FIG. 9A is a dynamic light scattering plot showing MPV.10.34.d L1 protein showing particle size (diameter, nm) distribution (X-axis) based on intensity (Y-axis) for eluted MPV.10.34d L1 protein, indicating an average particle size of 20 nm to 30 nm.
Figure 9B:
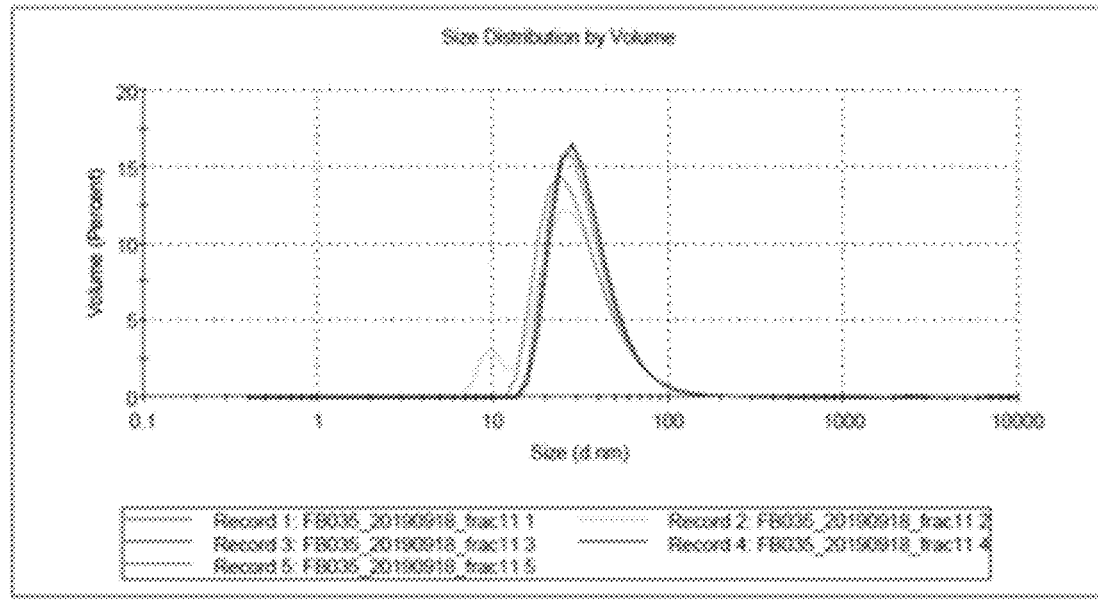
FIG. 9B is a dynamic light scattering plot showing MPV.10.34.d L1 protein showing particle size (diameter, nm) distribution (X-axis) based on volume (the relative proportion of refolded protein with respect to other contaminants, i.e., host bacterial cell proteins, Y-axis) for eluted MPV.10.34d L1 protein, indicating an average particle size of 20 nm to 30 nm.
Figure 9C:
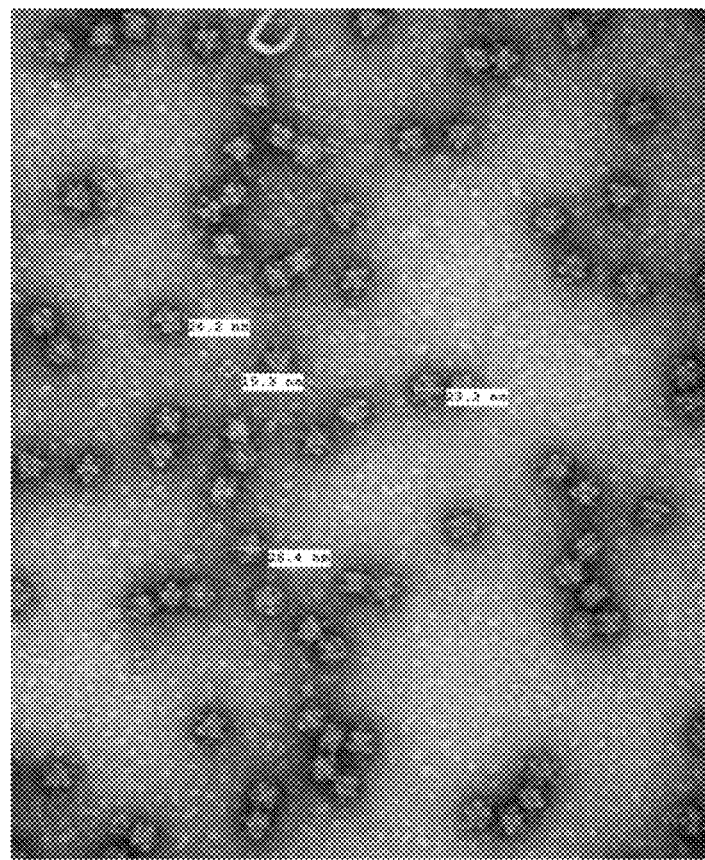
FIG. 9C is a photograph of a transmission electron microscopy (TEM) micrograph including a scale bar of 100 nm showing highly purified soluble expressed MPV.10.34.d capsid backbone.
Figure 10:
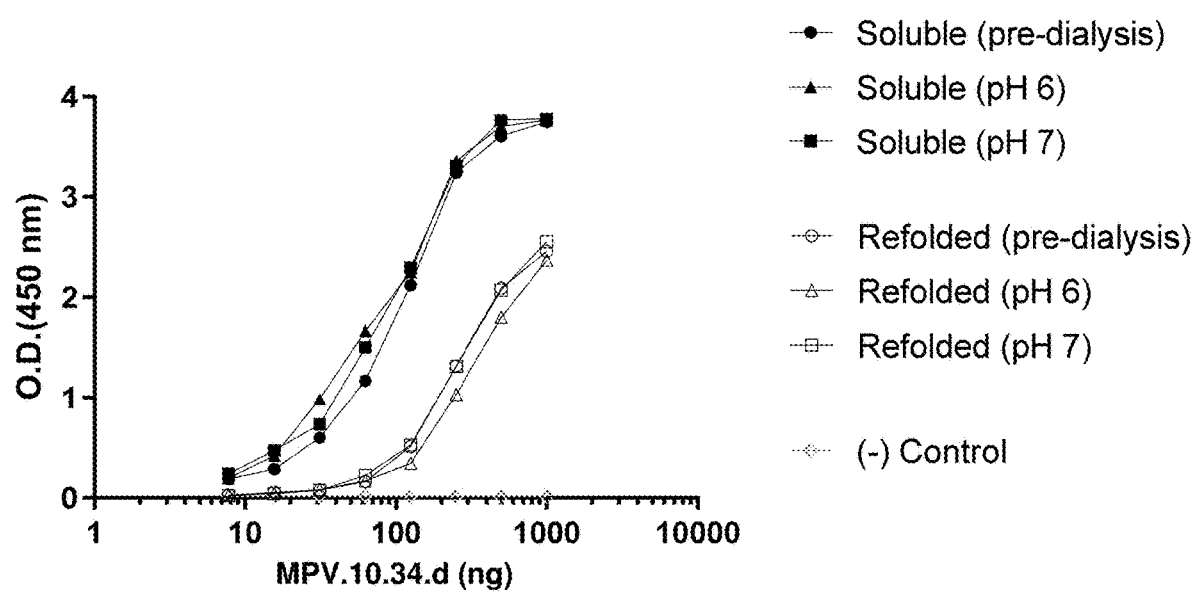
FIG. 10 is a graph of ELISA data obtained by binding a conformational MPV L1-A4 conformation-specific monoclonal antibody to refolded MPV.10.34.d capsid backbone showing that soluble and refolded MPV.10.34.d capsid backbone have the same T=1 conformation under different pH conditions. The Y-axis provides optical density at 450 nm, and the X-axis provides amount of MPV.10.34.d capsid backbone (ng).
Figure 11:
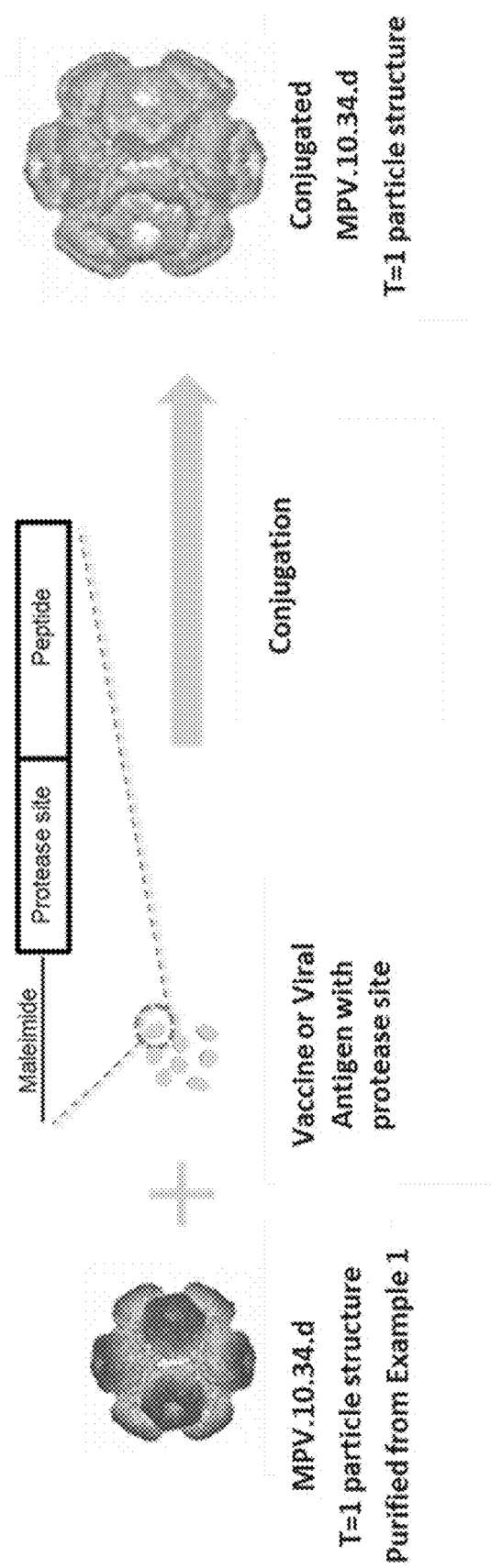
FIG. 11 is a schematic representation of the steps to produce IRCs, i.e., conjugated MPV.10.34.d L1 capsid backbones.
Figure 12:
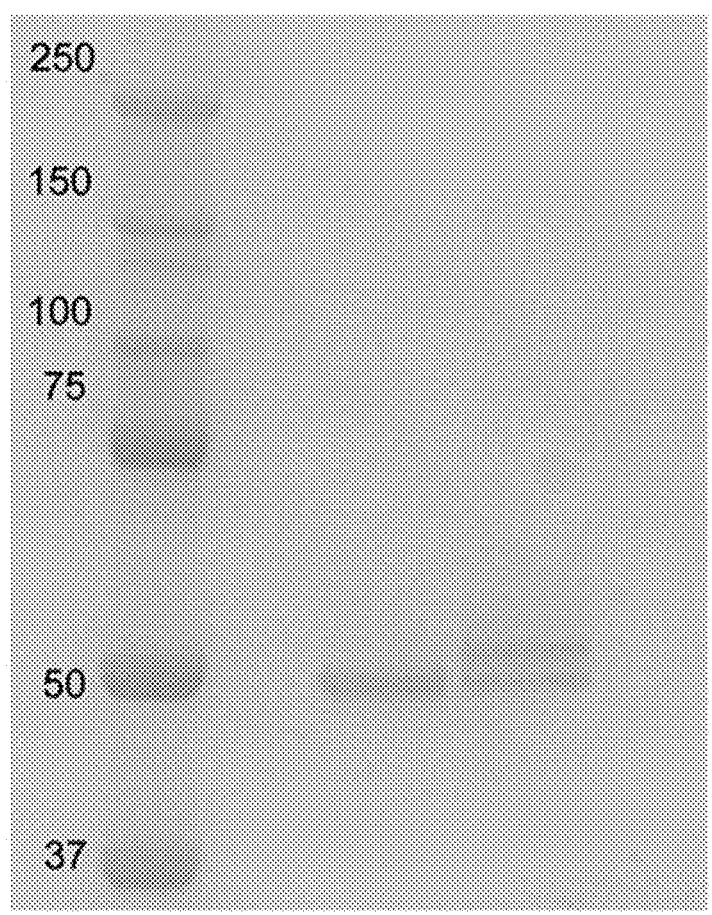
FIG. 12 shows a samples where the reducing agent to L1 ratio was 10:1 (lane 2, 5, and 8) or 20:1 (lanes 3, 6, and 9). Lane 6 is a reference sample containing a ratio of 10:1 reducing agent to L1 protein and 10:1 peptide to L1 concentration. (See, Example 6). This is a condition that has consistently provided approximately 50% peptide conjugation as determined by densitometry. The lane labelled CEX-FB035 (left side) is the MPV.10.34.d capsid backbone control.

DLS (dynamic light scattering) and TEM revealed that upon refolding MPV.10.34.d unexpectedly forms capsid backbones that are about 20 nm to 30 nm in diameter. (See, FIG. 5). To analyze the refolded MPV.10.34.d samples, the purified samples were first analyzed by DLS to obtain determine whether refolding of MPV.10.34.d occurred.

60 μl of sample was placed in a 40 μL solvent-resistant micro-cuvette (ZEN0040, Malvern Panalytical, Waltham, MA) and the cell was subsequently placed into a Zetasizer Nano ZS Dynamic Light scattering instrument (Malvern Panalytical, Waltham, MA). This was a research-grade dynamic light scattering system for measurement of protein size, electrophoretic mobility of proteins, zeta potential of colloids and nanoparticles, and optionally the measurement of protein mobility, and microrheology of protein and polymer solutions. The high performance of the Zetasizer Nano ZS also enables the measurement of the molecular weight and second virial coefficient, $A_2$, of macromolecules and kD, the DLS interaction parameter. The system can also be used in a flow configuration to operate as a size detector for SEC or FFF. Once in the machine, the sample was processed with the companion software (Zetasizer Nano Software, Malvern Panalytical). The program was set to read the sample for a total of 5 runs to generate two plots.

The two plots generated were determine capsid backbone size and structure, intensity (FIG. 6A), and volume (FIG. 6B). The intensity distribution provides the amount of light scattered by the particles in the different sized bins. The volume distribution demonstrates the total volume of particles in various sized bins. In other words, the intensity plot (FIG. 6A) provides an assessment of the overall population sizes of MPV.10.34.d particles including host cell contaminants within the sample, whereas the volume plot (FIG. 6B) determines the relative proportion of refolded protein with respect to other contaminants, i.e., host bacterial cell proteins.

Note that each individual plot line in the graphs of FIGS. 6A and 6B represent individual samples (five samples for each of A and B). If the volume curve was between about 10 to 15 nm (X-axis), the shell was determined to be a capsomer made up of 5 MPV.10.34.d units. For T=1 icosahedral capsid backbones made up of 60 MPV.10.34.d, the volume curve plot is about 20 to 30 nm. For T=7 icosahedral capsid backbones made up of 360 MPV.10.34.d, the volume curve plot was about 50 to 60 nm. As is readily apparent from the intensity graph (FIG. 6A), there are two peaks, one lower at approximately 20 to 30 nm and one at approximately >100 nm, whereas the volume graph (FIG. 6B) shows a single size of about 20 nm to 30 nm. It was postulated that the two peaks on the intensity figure were attributable to the presence of distinct populations of capsid backbones that arose after refolding of the MPV.10.34.d into the capsid backbone since the samples at this stage had not undergone purification. However, the larger of the two peaks shown in the intensity plot constitute only a small portion of the sample, and a majority of the sample falls within the smaller peak. Hence, the DLS results show that a majority of the MPV.10.34.d are structures that are about 20 nm to 30 nm in size.

In DLS, information regarding the motion (diffusion) of submicron particles in a solution is extracted from the rate of scattering intensity fluctuations using a statistical technique called intensity autocorrelation. The mean particle size and distribution are calculated from the distribution of diffusion coefficients using the Stokes Einstein equation. Because the magnitude of the scattering intensity varies roughly with the $6^{th}$ power of the particle size, DLS is highly sensitive to the presence of small amounts of aggregates in a mixture of capsid backbones which is believed to be reflected in the intensity plot shown in FIG. 6A.

TEM analysis was also employed to obtain further visual confirmation of the structure and size of the refolded proteins. Samples (10 μL) were adsorbed to glow discharged (EMS GloQube) carbon coated 400 mesh copper grids (EMS), by floatation for 2 min. Grids were quickly blotted and then rinsed in 3 drops (1 min each) of TBS. Grids were negatively stained in 2 consecutive drops of 1% uranyl acetate with tylose (1% UAT, double filtered, 0.22 μm filter), blotted then quickly aspirated to obtain a thin layer of stain covering the sample. Grids were imaged on a Phillips CM-120 TEM operating at 80 kV with an AMT XR80 CCD (8 megapixel).

TEM results revealed that MPV.10.34.d formed capsid backbones that had a markedly grooved appearance, with pentagonal/capsomer "towers." (See, FIG. 5). Measurements showed that these capsid backbones were approximate 30 nm is size (compare with the 500 nm scale on TEM micrograph, FIG. 5).

These results were unexpected because deletion of residues in the helix four H4 region of L1 has been reported to not lead to T=1 geometry capsid backbone formation. Further, it has been shown that the same deletions result in capsomers of T=7 in HPV11 and HPV16 L1 proteins. (See, Chen et al., *Mol. Cell,* 5:557-567, 2000, WO 2000054730, Bishop et al., *Virol. J.,* 4:3, 2007, and Schädlich et al., *J. Virol.,* 83(15):7690-7705, 2009). In summary, these findings support the conclusion that the MPV.10.34.d constructs form icosahedral capsid backbones of T=1 lattice geometry comprised of 60 monomers, or 12 capsomers.

Example 3

MPV.10.34.d Capsid Backbone Assembly Requires Reductant

HPV particles form T=7 geometry particles that are 50 to 60 nm is diameter. The manufacture and production of such capsid backbones in either eukaryotic or prokaryotic host cell systems involves the expression in suitable host cell system followed by a series of purification step to yield highly purified capsid backbones. These capsid backbones are then subjected to a disassembly and re-assembly (DARA) step. Briefly, this involves the addition of DTT or a similar reducing agent to disassemble the capsid backbones into capsomers/pentamers (made from five L1 monomers) and then removal of the reducing agent for assembly back to T=7 capsid backbones that have been documented as more symmetric and stable.

To further delineate how MPV.10.34.d refolds into a T=1 capsid backbone, the refolding steps in Example 1 were repeated. Briefly, following solubilization of the IB, MPV.10.34.d was subjected to refolding via removal of the denaturant (6M Urea) in a step-gradient manner. The solubilized samples were inserted into dialysis tubing (snakeskin dialysis tubing, 10,000 Da molecular weight cut off 35 mm. (ThermoFisher Scientific, Waltham, MA, US). In general, about 100 mL to about 150 mL of resolubilized sample solution was dispensed into a four dialysis tubes. The samples were then dialyzed against 4 M urea buffer with the general buffer recipe 50 mM Tris, pH 8.0, 500 mM NaCl and 0.05% Tween-80 for 3±1 hour in a cold room at about 4° C. on a stir plate. Then the samples were again dialyzed against a fresh 1 M urea buffer for 3±1 hour in a cold room on a stir plate. Subsequently, the samples were dialyzed against 0 M urea buffer overnight (about 16 to 18 hours) in a cold room at about 4° C. on a stir plate.

The main difference between the four buffer conditions in this experiment were the presence of: (i) 1 mM EDTA, 1 mM PMSF, and 1 mM DTT; (ii) 1 mM EDTA, (iii) 1 mM DTT, and (iv) no added ETDA, PMSF or DTT. The dialyzed/refolded sample solutions under all four conditions were aliquoted into 50 mL conical tubes and analyzed via DLS as described in Example 2 before being stored in a −20° C. freezer. As shown in FIG. 7 using volume plots (and as explained in Example 2), aggregates as marked by the arrow were observed in sample (ii) and sample (iv). (See, FIG. 7C and FIG. 7D, respectively). Little to no aggregates were observed on the DLS volume plots in sample (i) or sample (iii). (See, FIG. 7A and FIG. 7B, respectively).

To further confirm whether MPV.10.34.d successfully refolded into T=1 capsid backbones, all samples were dialyzed into capture buffer A (25 mM $NaPO_4$, 25 mM NaCl, pH 6.0) overnight at 4° C. Following dialysis, samples were centrifuged at 4000×g for 10 min at 4° C. and then filtered through a 0.22 μm PES membrane. The T=1 capsid backbone platform was then captured by CEX (EMD Fractogel S03 (M), EMD Millipore, Darmstadt, Germany) and then step eluted with 30% 25 mM $NaPO_4$, 1.5M NaCl, pH 6.0. Results are shown in FIG. 8. FIG. 8 shows successful capture and elution of correctly refolded T=1 capsid backbones in samples that were either refolded in DTT/ETDA/PMSF (FIG. 8A) or DTT alone (FIG. 8B). In contrast, there was little to no capture and elution of correctly refolded T=1 capsid backbones under refolding conditions that included ETDA alone (FIG. 8C) or no additives (FIG. 8D) as demarcated by the arrows in FIG. 8.

Taken together, the data indicate that the process of producing T=1 capsid backbones favors reducing conditions. This contrasts with the known process of producing HPV T=7 capsid backbones that require the eventual removal of any reducing agents for successful capsid backbone assembly.

Example 4

Production of Soluble MPV.10.34.d

Bacterial expression of MPV.10.34.d at 37° C. for 4 hours in the presence of 1 mM IPTG results in the expression and formation of IBs that must be treated in a series of process steps as described in Example 1 to obtain highly purified 20 nm to 30 nm T=1 capsid backbone structures. To investigate whether soluble MPV.10.34d can be expressed intracellularly in *E. coli* and whether it can assemble into a T=1 capsid backbone as opposed to an IB, a strategy was adopted to lower the induction temperature and IPTG concentrations to slow down expression, and thereby to prevent formation of IBs.

From Example 1, induction temperature was lowered from 37° C. to 16° C. at a concentration of IPTG of 100 μM and 1 mM. Briefly, freshly picked *E. coli* C2566 colonies transformed with the MPV.10.34d DNA were inoculated into LB with 50 μg/mL of kanamycin (henceforth LB+KAN) starter cultures, grown overnight at 37° C. and 250 rpm. The next day the starter culture was used to inoculate a fresh 250 mL LB+KAN culture at 1:25 dilution and grown at 37° C., 250 rpm, for about 1.5 to 2 hours, such that the culture reached an OD600 of about 0.5 to 0.7. At this point, the culture was induced with 1 mM and other tested IPTG concentration(s) and shaken at 16° C. induction temperature overnight. The next day, post-induction samples (1 mL each) were pelleted at 1500×g for 10 min. The supernatant was removed and the remaining bulk samples were pelleted at 4000×g for 10 min at 4° C. These samples were stored at −20° C. until analysis.

To determine soluble material, cell were lysed using a homogenizer (15,000-20,000 psi, 3 cycles). Samples of uninduced, induced, post-lysis soluble, and post-lysis insoluble material were analyzed by SDS-PAGE and Western blot. Results show that lowering the induction temperature to 16° C. resulted in undetectable levels of protein (Data not shown).

Since expression of MPV.10.34.d was low to undetectable at 16° C., induction was attempted at a higher temperature, 25° C. At an induction temperature of 25° C., MPV.10.34d was successfully expressed. A majority of MPV.10.34.d was expressed in the form of IBs (data not shown). A third attempt at 30° C. was attempted under the induction conditions described above. It was discovered that soluble expression improved tremendously at this temperature. There appeared to be a critical transition between 25° C. and 30° C. that allows for MPV.10.34.d to be successfully translated with approximately 50% expressed in a soluble form. In contrast, the concentration of IPTG appeared to have a minor effect in the amount of translated MPV.10.34.d.

To purify these soluble MPV.10.34.d, a single step elution chromatography purification was developed and subsequently employed. Briefly, soluble lysate containing MPV.10.34d was prepared in 50 mM $NaPO_4$, 50 mM NaCl, pH 7.0. A 1 mL prepacked Fractogel SO3 (M) column was equilibrated to 50 mM $NaPO_4$, 50 mM NaCl, pH 7.0 and 500 μL of MPV.10.34d lysate was injected onto the column. A series of step gradient elutions were performed to identify a conductivity window for elution of MPV.10.34d, including 5, 10, 15, 20, 25, and 100% B steps (B=50 mM $NaPO_4$, 1.5M NaCl, pH 7.0; which translates to a theoretical NaCl concentration of 0.075M, 0.15M, 0.225M, 0.3M, 0.375M, and 1.5M). Based on the elution of MPV.10.34d, a single step method was developed and scaled up to a 5 mL prepacked Fractogel SO3 (M) column with injection volumes of up to 5 mL. This single step method used 15% B, where B was 50 mM $NaPO_4$, 500 mM NaCl, pH 7.0. (The lower concentration of NaCl allowed for more consistent control of the conductivity, as relying on small percentage changes of a 1.5M NaCl resulted in conductivity irregularities when using 1 mL columns, likely due to pre-column mixing volumes).

Based on these efforts, a single step gradient elution method was developed to generate milligram-scale amounts of CEX-captured MPV.10.34d. Elution material was subsequently collected and analyzed as described in Example 2. Results revealed that DLS (FIGS. 9A and 9B) and TEM data (FIG. 9C) from eluted MPV.10.34d yielded T=1 capsid backbones of 20 to 30 nm diameter.

Example 5

Soluble and IB MPV.10.34.D Form T=1 Capsid Backbones

The MPV.A4 antibody is a conformational antibody that specifically binds to MPV L1 in the form of T=1 or T=7 capsid backbone structure. This antibody will not bind to denatured or monomeric MPV L1. (Hafenstein et al., 2020, "Atomic Resolution CRYOEM structure of Mouse Papillomavirus," International Papillomavirus Conference, July 20-24, 2020). To determine whether MPV.10.34.d undergoing the steps in Example 1 or Example 4 yields a T=1 capsid backbone, ELISA was performed on these samples with the MPV.A4 monoclonal antibody.

Samples from Example 1 and Example 4 of equal concentrations (starting concentration of 1000 ng/well) were subjected to ELISA. To ensure that both soluble and refolded MPV.10.34.d were equally bound to the ELISA plate (Nunc Maxisorp, ThermoFisher Scientific, Waltham, MA, US), both samples were first buffer exchanged into either 50 mM $NaPO_4$, 450 mM NaCl at pH 6 or pH 7. This resulted in two different pH conditions for both samples. Based on this, a total of four sample conditions were two-fold serially diluted and subjected to ELISA with the MPV.A4 monoclonal antibody.

Briefly, eight different amounts of protein (7.8 ng to 1μg) for each sample under both pH conditions (into either 50 mM $NaPO_4$, 450 mM NaCl at pH 6 or pH 7) were first added to the ELISA plate and the plate was stored at 4° C. Two days later, ELISA was performed by incubating each plate for one hour at room temperature on an orbital shaker (300 rpm) with MPV.A4 mAb diluted 1:1000 using blocking buffer (4% dry milk, 0.2% Tween-20) and the plates incubated for one hour at 4° C. A wash step was then employed using wash buffer (0.35 M NaCl, 1.5 mM $KH_2PO_4$, 6.5 mM $Na_2HPO_4$, 0.05% Tween-20) at room temperature for a total of three washes (200 μL per sample per wash). Following the wash step, a goat anti-mouse IgG-HRP antibody (Millipore Sigma, St. Louis, MO, US) was added at 1:7000 dilution in blocking buffer (4% dry milk, 0.2% Tween-20) to a final concentration of 82.9 ng/mL and the plates incubated for one hour at room temperature on an orbital shaker (300 rpm). After the incubation, the plate was washed and incubated with a peroxidase substrate (3, 3', 5, 5' tetramethyl benzidine, SeraCare Life Sciences, Inc., Milford, MA, US) for 30 minutes, followed by the addition and incubation of stop solution (0.36 N H2504) (J. T. Baker/Avantor, Allentown, PA, US) for 20 minutes. The absorbance of the sample plates were read at 450 nm and 620 nm with a plate reader (BioTek, Winooski, VT, US).

Results (FIG. 10) showed that the undialyzed soluble MPV10.34.d capsid backbone, which are captured using buffer at pH 7 (solid circles), as well as the soluble form dialyzed against buffer at pH 7 (solid squares) and pH 6 (solid triangles) were recognized by the MPV.A4 monoclonal antibody.

In summary, both MPV.10.34.d capsid backbones refolded from IBs (Example 1) and soluble MPV.10.34.d capsid backbones (Example 4) are both recognized by the MPV.A4 conformational monoclonal antibody.

Example 6

IRC Formation: MPV.10.34.d Capsid Backbone Conjugation

To functionalize the MPV.10.34.d capsid backbones such that they are effective in recruiting preexisting immune system to attack cancer cells in the subject, the MPV.10.34.d capsid backbones were conjugated to various peptide epitopes including ovalbumin peptide SIINFEKL (OVA, SEQ ID NO: 95), HPV16 E7 protein (SEQ ID NO: 96), and CMV peptide pp65 (SEQ ID NO: 129) to form IRCs.

Design of Peptides: The peptides are epitopes having a general length of about 8 to 10 amino acids that are preceded upstream by a protease recognition site. (See, FIG. 11). The following experiments incorporate an exemplary protease recognition site, the furin protease cleavage sequence R X R/K R (SEQ ID NO:89) which is designed to be located upstream of the epitope peptide. In addition, the epitope peptide is chemically modified at the N-terminus to contain maleimide. The incorporation of maleimide, a sulfhydryl reactive reagent, to the N-terminus of the peptide antigen allows for conjugation of the protease/peptide to the reduced sulfhydryl groups, i.e., cysteines, on the MPV.10.34.d capsid backbones. The end production of this reaction is a conjugated MPV.10.34.d capsid backbone.

To conjugate purified MPV.10.34.d capsid backbones of about >95% purity, the MPV.10.34.d were further dialyzed in conjugation reaction buffer (50 mM $NaPO_4$, pH 6.5, 500 mM NaCl, 2 mM EDTA, and 0.05% Tween® 80), exchanging the buffer three times (3±1 hours, 3±1 hours, and overnight 16±3 hours, at 2° C. to 8° C.). The next day, the MPV.10.34.d was adjusted to a final concentration of at least 0.6 μg/μL. The MPV.10.34.d were then treated with a mild reducing agent, tris(2-carboxyethyl)phosphine (TCEP), for 1 hour without shaking at room temperature (21° C.) at a TCEP:MPV.10.34.d ratio of 10:1. Subsequently, the peptide was then added to the reaction at a molar ratio of X10 the amount of MPV.10.34.d. The reaction was shaken at room temperature (21° C.), 200 rpm, for 1 hour. Following conjugation, to remove excess free peptide, contents from the reaction were subjected to 10 rounds of Amicon spin filtration (molecular cut-off 100 kDa) at 1000 rcf for 10 mins each round. Following this purification step, samples were analyzed by SDS-PAGE stained with Coomassie Brilliant Blue R-250 dye (Bio-Rad, Hercules, CA, US) to determine percent conjugation (4-20% CRITERION™ TGX Stain-Free™ Precast Gels, 10 Well Comb, 30 μL, 1.0 mm, Bio-Rad, Hercules, CA, US). As seen in FIG. 12, the upper band at about 50 kDa was determined to correspond to IRC. (See, FIG. 12, lane 4). The lower bands represent the MPV.10.34.d lacking epitope peptide. These band identities were further confirmed via the conjugated control. (See, FIG. 12, lane 3).

Importantly, the conjugation of MPV.10.34.d yielded a conjugation efficiency of about 50% as determined by densitometry. (See, FIG. 12, lane 4). Percent conjugation was calculated by densitometry. The gel images were scanned into the computer using manufacturer-recommended software. Subsequently, the total density of the upper band and lower band was calculated by drawing a box or freehand shape around each band. The total density of these regions corresponds to the total amount of protein in each band. Next, only the upper lane was measured in the same way. Background density of a suitably matched area on each gel was collected and subtracted from the band signals. The background-corrected density of the upper protein band was then divided by the entire background-corrected density of the region of interest and then multiplied by 100 to obtain the percent conjugation.

Example 7

Conjugation Efficiency of MPV.10.34.d and HPV16 Capsid Backbones

Conjugation of HPV L1 particles using the same conjugation reaction steps as described in Example 6 has been previously described. (See, for instance, WO 2018/237115 and WO 2020/139978). Conjugation experiments were conducted on HPV16 capsid backbones and MPV.10.34.d capsid backbones in the manner described in Example 6. The peptide epitope conjugated to the capsid backbones was the HLA-A*0201 restricted epitope NLVPMVATV (NLV, SEQ ID NO: 138) from the HLA-A2 supertype derived from the CMV pp65 antigen.

Figure 13:
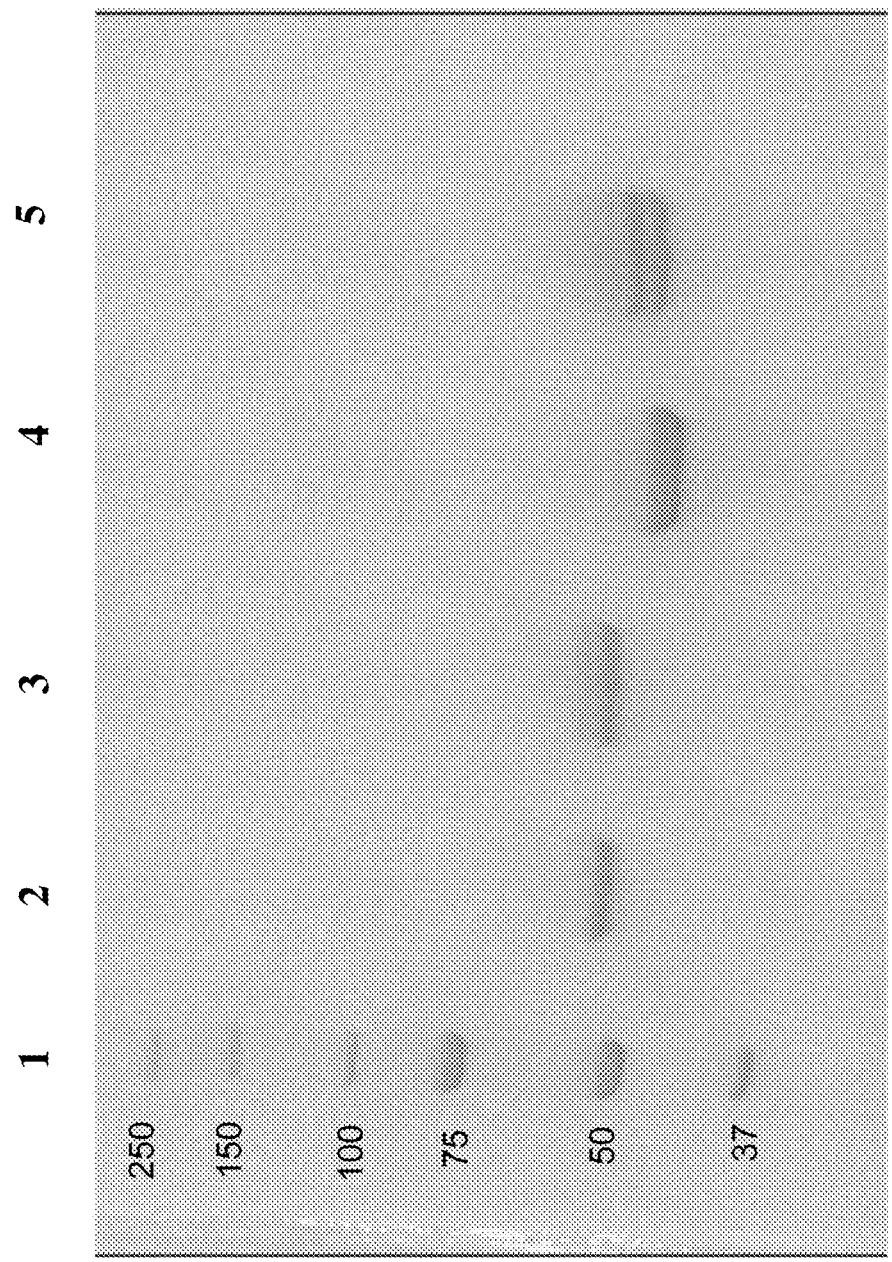

As seen in FIG. 13, under the same conjugation reaction conditions of 10:1 (TCEP:L1) and 10:1 (Peptide:L1) ratios, the MPV.10.34.d capsid backbones exhibited a higher conjugation percentage (50%, FIG. 13, lane 5) as compared to HPV16 (approximately 20%, FIG. 13, lane 3). Percent conjugation was determined by densitometry as described above. Control samples included unconjugated HPV16 (FIG. 13, lane 2) and unconjugated MPV.10.34.d (FIG. 13, lane 4).

The percent peptide conjugation is believed to depend on at least two factors: (1) the ratio of reducing agent to L1 protein, and (2) the amount of free peptide added to the conjugation reaction. For the results shown in FIG. 13, it was determined that a ratio of reducing agent to L1 of 10:1 and peptide to L1 ratio of 10:1 results in at least 50% conjugation for MPV.10.34.d capsid backbone (FIG. 13, lane 5) and at least 20% for WT HPV16 T=7 capsid backbone (FIG. 13, lane 3).

Figure 14:
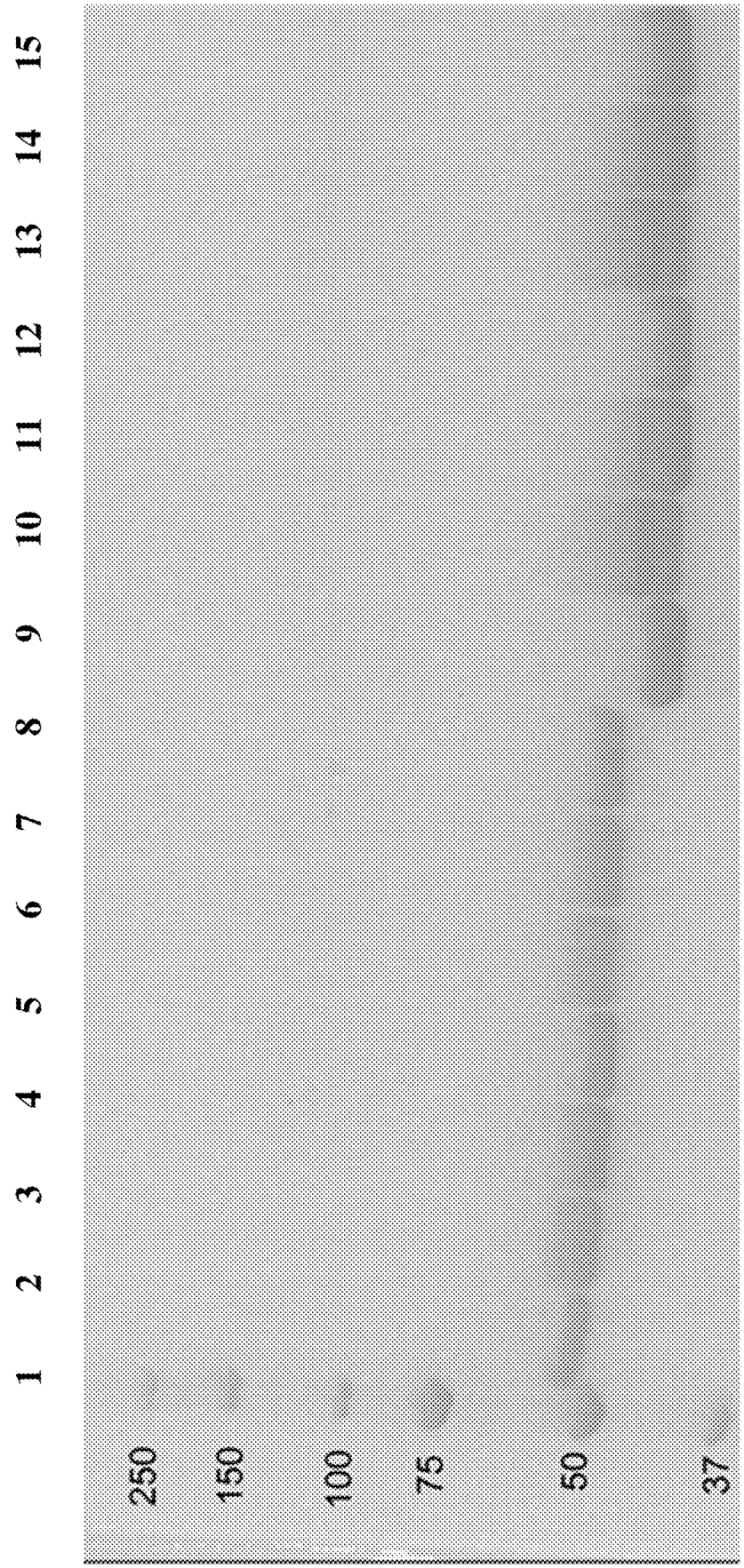

To further assess impact of reducing agent concentration, the conjugation reaction was performed at 10:1 reducing agent to L1 protein (FIG. 14, lane 3 and lane 10 for HPV16 IRC or MPV.10.34.d IRC, respectively), a 100-fold ratio (FIG. 14, lane 4 and lane 11, for HPV16 IRC or MPV.10.34.d IRC, respectively), and a 1000-fold ratio (FIG. 14, lane 5 and lane 12, for HPV16 IRC or MPV.10.34.d IRC, respectively). Surprisingly, a ratio of reducing agent to L1 of 100:1 and 1000:1 yielded a lower percent conjugation, and in some instances even no detectable conjugation, as compared with the standard 10:1 reducing agent to L1 protein ratio. Without wishing to be bound by any specific theory, it is possible that excess reducing agent reacts with the peptides to form an -ylene by-product with approximately the same rate as conjugation of peptides to L1 surface thiols. Such a phenomenon could result in depletion of peptides available for conjugation to L1.

Figure 15A:
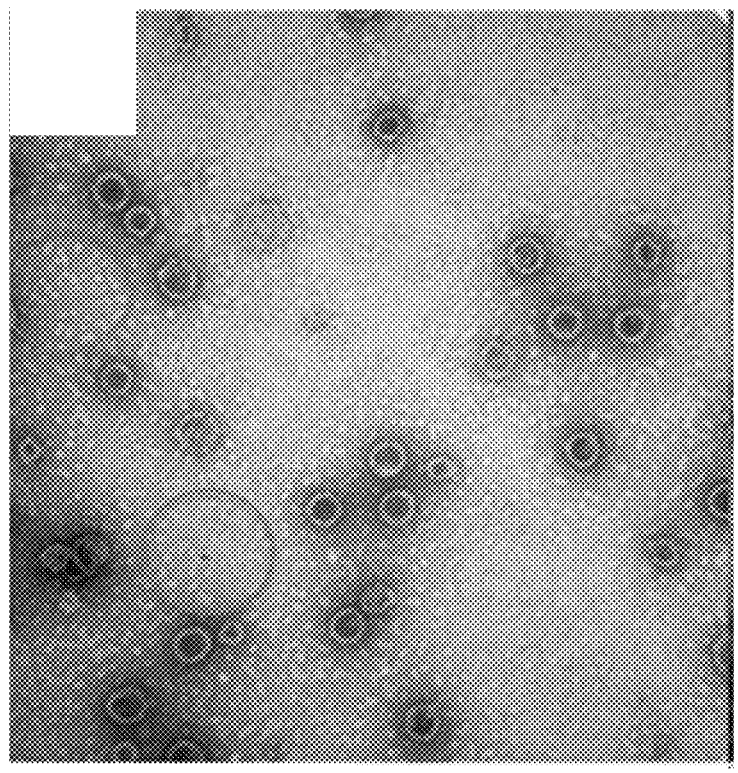
Figure 15B:
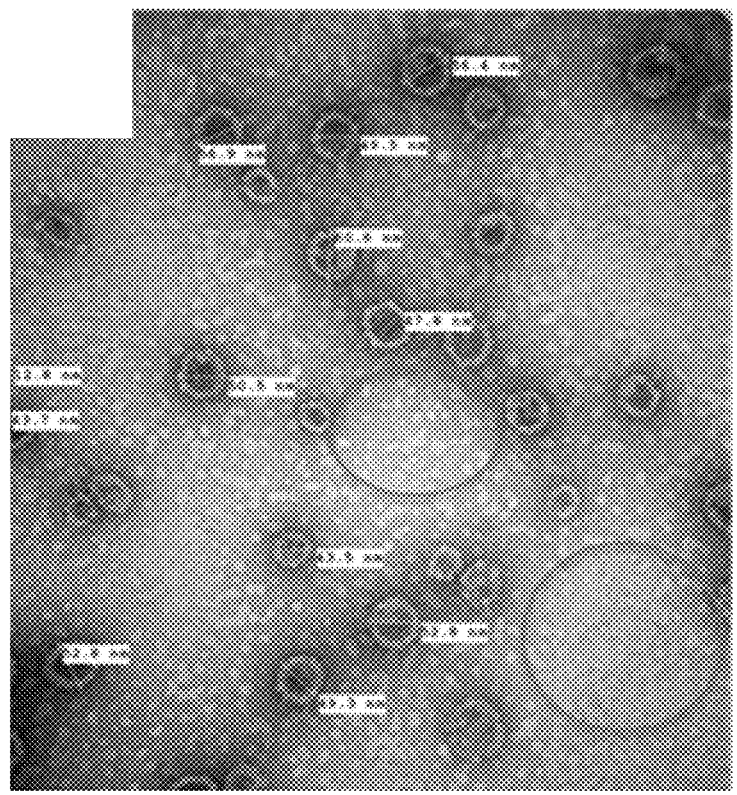
Figure 15C:
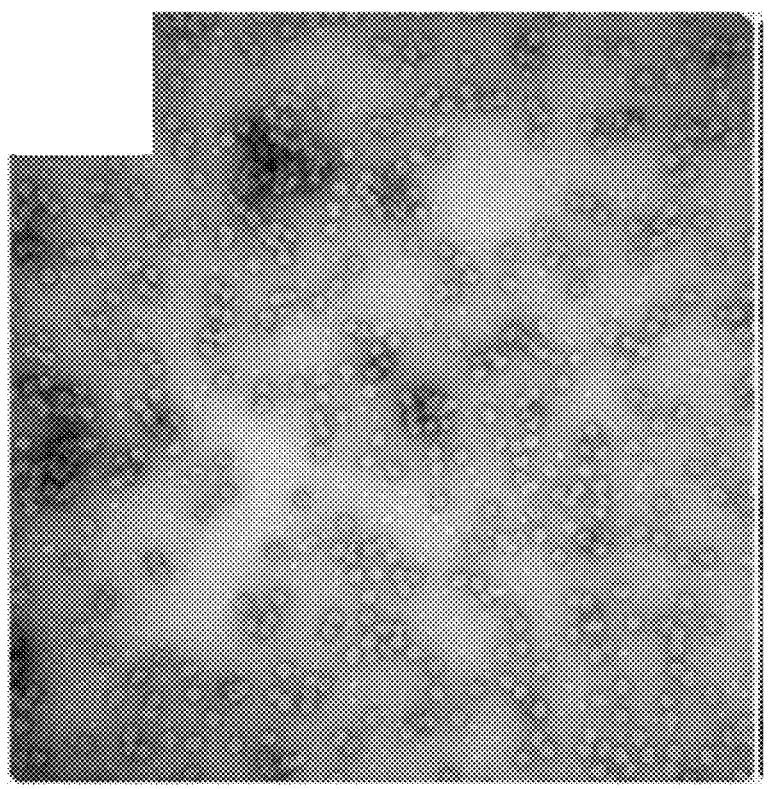
Figure 15D:
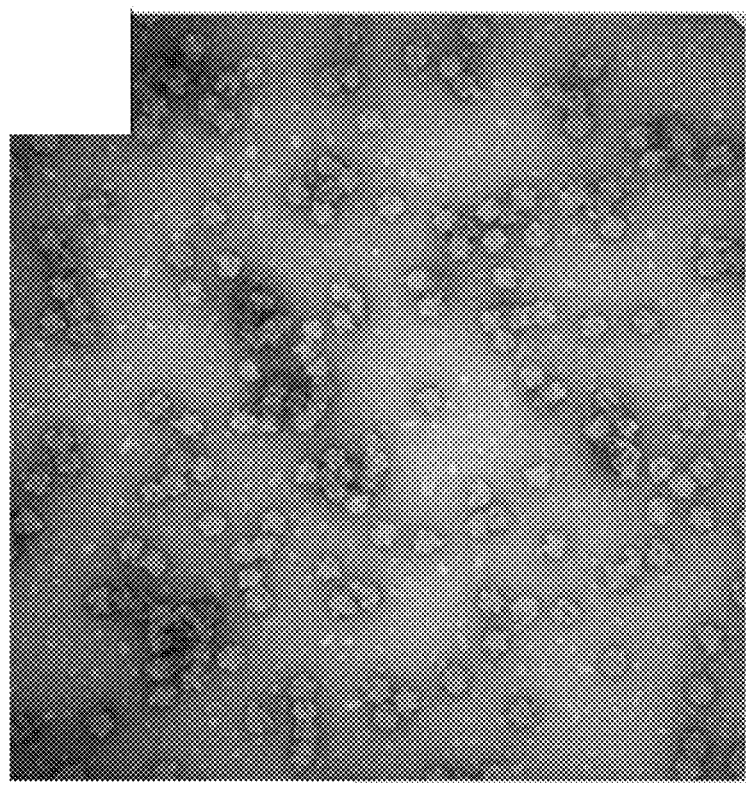

The relative stability of IRC was also assessed. Following conjugation, the IRC samples were filtered with an Amicon 10 kDa filter spin column to remove excess free peptide. Following filtration, the protein concentration of the samples were checked to ensure no protein was lost during filtration. (See, FIG. 14, lanes 6 to 8 and lanes 13 to 15, for HPV16 IRC or MPV.10.34.d IRC, respectively). The samples were then analyzed by TEM as described in Example 2. FIGS. 15A and 15B are exemplary TEM micrographs at 150,000× and 200,000× magnification, respectively, showing the breakdown of the HPV16 IRC after Amicon purification. In contrast, MPV.10.34.d IRC did not exhibit any breakdown, as shown in FIGS. 15C and 15D at 180,000× and 200,000× magnification, respectively.

Without wishing to be bound by any specific theory, it is postulated that perhaps the additional stability of the MPV.10.34.d IRC may be due to the inherent structural stability of the capsid backbone itself, being held together by hydrophobic bonds, as compared to T=7 particles that are held together instead by disulfide bonds. Indeed, the reducing step during the conjugation reaction may in fact destabilize the T=7 structures held together by disulfide bonds via reduction of the necessary thiol groups. As a consequence, the MPV.10.34.d capsid backbone may be comparatively more stable after being treated with up to a ratio of 100:1 or 1000:1 of TCEP to L1.

As a result of these findings it was concluded that MPV.10.34.d capsid backbone would serve well as a stable conjugation platform to recruit preexisting immune system components in a subject for the purpose of treating cancer in subjects.

Although there is no improvement to conjugation (50% as seen by densitometry on SDS-PAGE gel) of MPV.10.34.d capsid backbone at reducing agent ratios above 1:100, reducing agent ratios higher than 1:10 but lower than 1:100 were investigated to determine whether such ranges might increase conjugation efficiency. Thus, the conjugation reactions were repeated as previously described with varying amounts of reducing agent ratios under 1:100, specifically ratios of 5:1, 10:1, and 25:1. Peptide to MPV.10.34.d ratios (5:1, 10:1, and 25:1) were also evaluated.

Figure 16:
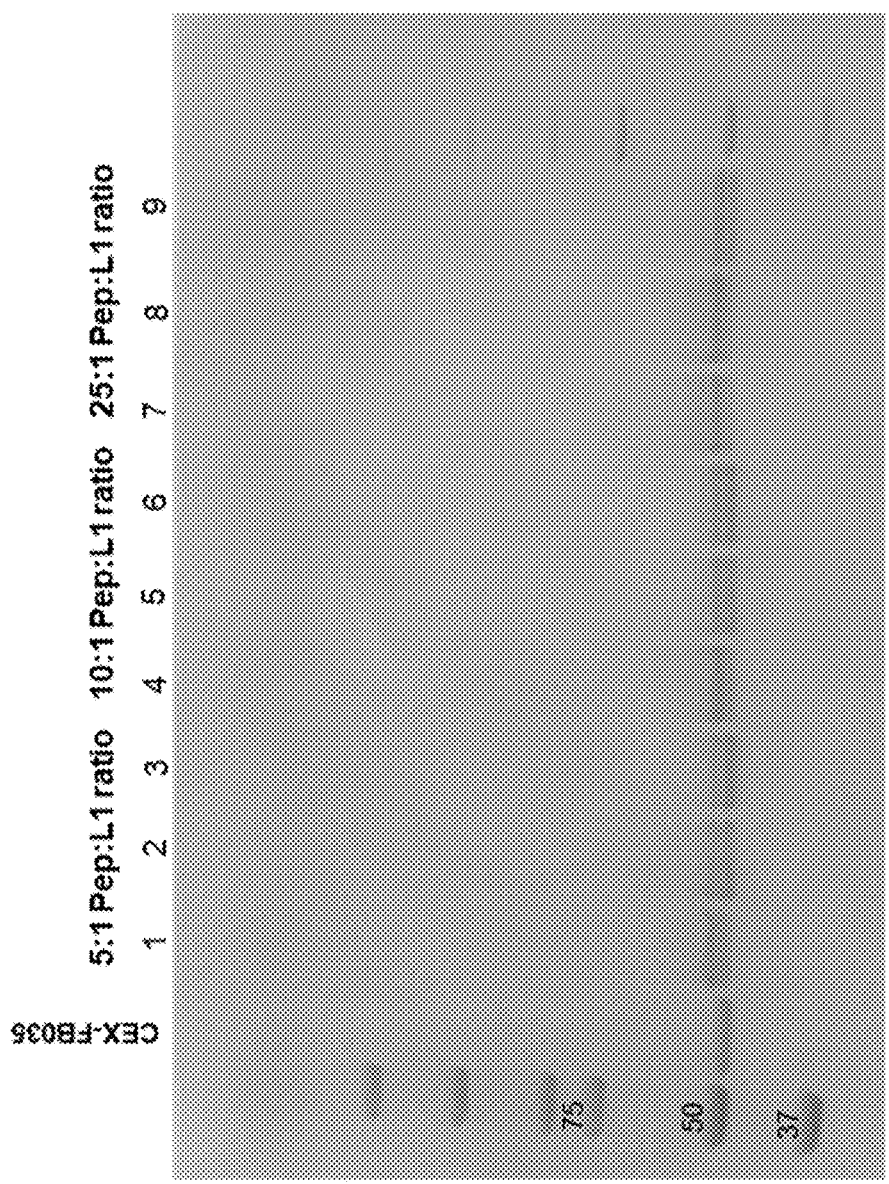

As seen in FIG. 16, a dose-dependent peptide conjugation on MPV.10.34.d capsid backbone using 5:1, 10:1 and 25:1 peptide:L1 ratio when the reducing agent: L1 protein ratio is between 5:1 (lanes 1, 4, and 7) was observed. No peptide dose dependence was seen with reducing agent: L1 protein ratio at 10:1 (lanes 2, 5, and 8) and 20:1 (lanes 3, 6, and 9). Lane 6 is a reference point in which 10:1 reducing agent to L1 ratio and 10:1 peptide to L1 ratio were used, conditions under which an approximately 50% level of peptide conjugation is routinely observed as determined by densitometry. The lane labelled "CEX-FB035" is a control containing only MPV.10.34.d capsid backbones.

Figure 17:
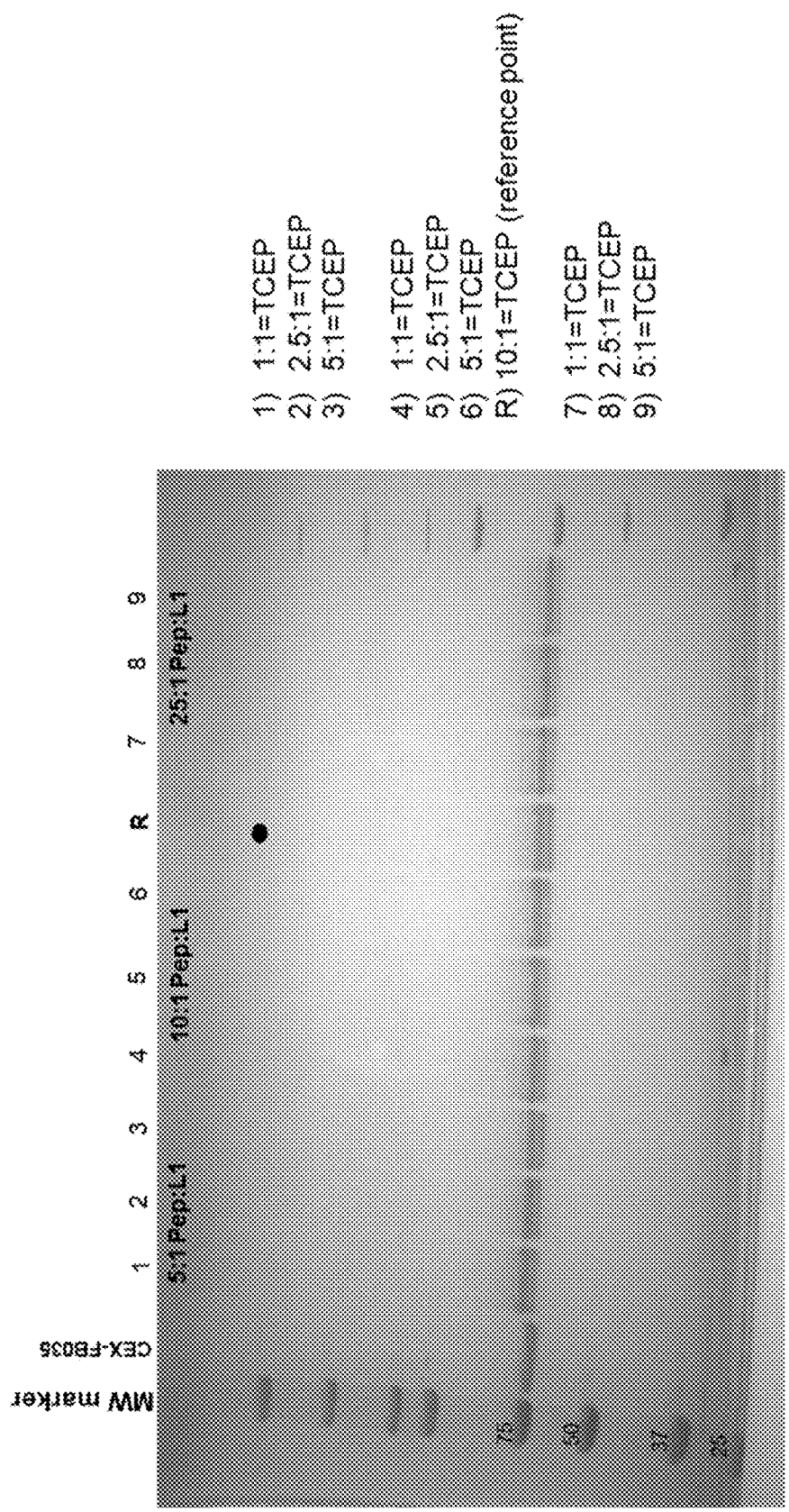
FIG. 17 is a stained SDS-PGE gel showing impact of peptide concentration on peptide conjugation of MPV.10.34.d capsid backbones, where peptide is present during conjugation reactions in ratios of 5:1, 10:1, and 25:1 of peptide:L1 when reducing agent ((tris(2-carboxyethyl) phosphine, TCEP)

It was determined that a 5:1 ratio of reducing agent to L1 along with a 10:1 ratio of peptide to L1 yielded a conjugation efficiency above 50%. (See, FIG. 16, lanes 4 and 7). Conjugation conditions with ratios of 1:1, 2.5:1, and 5:1 reducing agent to L1 protein were also tested. The results obtained at these ratios are reported in FIG. 17. It was determined that lowering the amount of the reducing agent from 5:1 to 1:1 did not improve conjugation efficiency, regardless of the amount of peptide included in the reactions. In FIG. 17, lane R is a reference point sample in which a peptide to L1 ratio of 10:1 was included as well as reducing agent to L1 ratio of 10:1, which typically yields an approximately 50% level of peptide conjugation. The lane labelled "CEX-FB035" is a control containing only MPV.10.34.d capsid backbones. In summary, it was determined that a 5:1 reducing agent to L1 ratio and a 10:1 peptide to L1 ratio achieves conjugation rates above 50%.

Example 8

Binding of IRC to Tumor Cells via HSPG

To assess whether IRC bind to tumor cells, an in vitro cell binding assay was conducted. Specifically, both MPV.10.34.d capsid backbones (unconjugated) as well as different conjugated IRC (human CMV pp65, murine E7, and murine OVA peptide) were examined.

Briefly, $2 \times 10^5$ MC38 cells (murine colon adenocarcinoma, #ENH204-FP Kerafast, Inc., Boston MA) or pgsA- 745 cells (Chinese hamster ovary cell mutant deficient in xylosyltransferase (UDP-D-xylose:serine-1,3-D-xylosyltransferase, ATCC CRL-2242) in which heparin sulfate proteoglycan (HSPG) expression is knocked out, were seeded overnight. The next day, the cells were treated with human CMV pp65, murine HPV16 E7, and murine OVA peptide, as well as the MPV.10.34.d capsid backbone for one hour at 37° C. Cells were then washed twice with 2 to 3 mL of a fluorescence activated cell sorting (FACS) buffer (1% bovine serum albumin in PBS) and then stained with 1 mL of rabbit anti-musPsV serum antibodies for 30 minutes at 4° C. Following this, samples were washed once with 3 mL FACS buffer and stained with 0.5 mL of donkey anti-rabbit IgG-PE antibody (Biolegend, San Diego, CA) for 30 min at 4° C. in the dark. Finally, samples were washed once more with 3 mL FACS buffer and then resuspended in 250 mL of FACS buffer before being analyzed by a CytoFLEX flow cytometer (Beckman Coulter Life Sciences, Brea, CA, US).

Figure 18A:
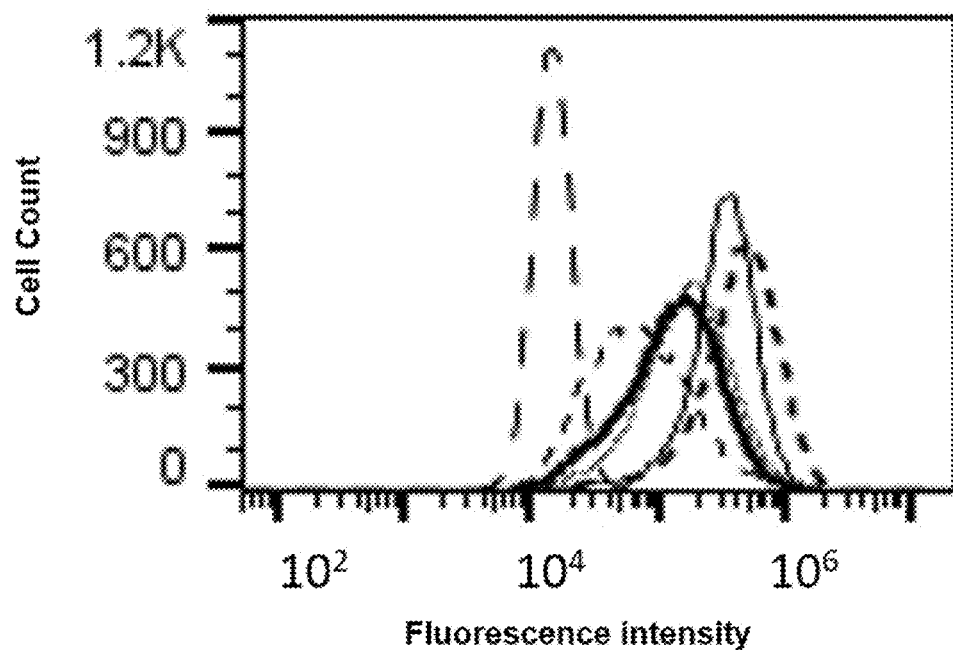
Figure 18B:
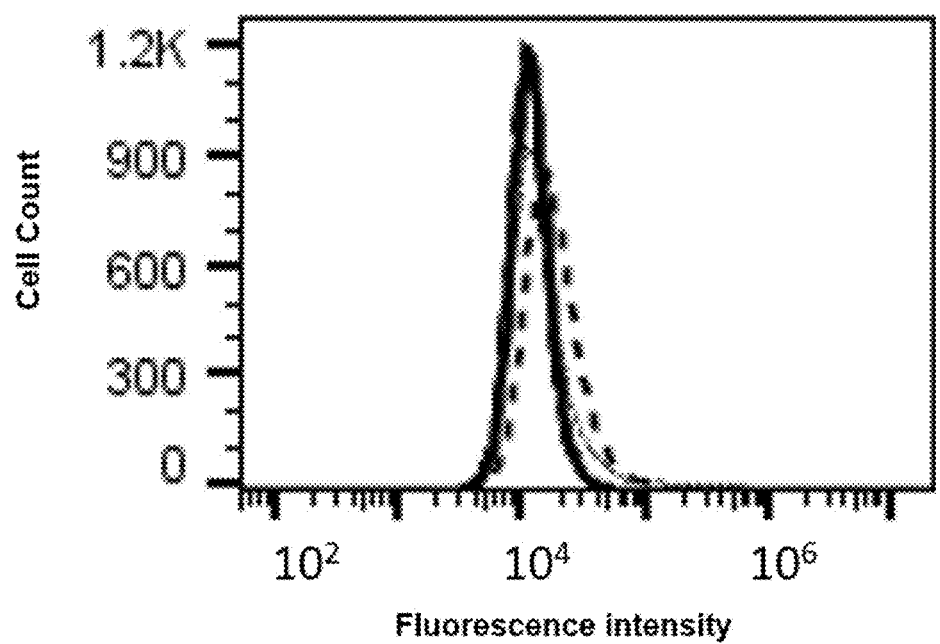

As shown in FIG. 18A and FIG. 18B, all of the constructs, MPV.10.34.d-CMV pp65 IRC (solid line), MPV.10.34.d-E7 IRC (thick solid line), MPV.10.34.d-OVA IRC (thick dashed line), and MPV.10.34.d capsid backbones (dashed-line), exhibited specificity for tumor cells as evidences by the peak shifts to the right. The positive control in these experiments was MPV capsid backbone (wild type, dotted line). The negative control included no IRC or L1 (long-dashed line).

These experiments further show that the IRC exhibited HSPG-specific binding since no binding of MPV.10.34.d capsid backbones was observed in the cell line lacking HSPG expression (pgsA-745 cells, indicated by no shift in the peaks in FIG. 17B). In summary, these results show that binding specificity of MPV.10.34.d capsid backbones for tumor cells is HSPG specific, and importantly, conjugation of epitope peptides to MPV.10.34.d capsid backbone does not reduce or otherwise negatively impact binding of MPV.10.34.d IRC to tumor cells in vitro.

Example 9

Loading of Peptide onto Tumor Cells by MPV.10.34.d IRC

The MPV.10.34.d IRC are designed such that upon entering the tumor microenvironment, the peptide will be cleaved from the IRC, thereby releasing the peptide in the near vicinity of a tumor cell surface. The cleavage event occurs, in some embodiments, upon contact with a tumor-specific protease, i.e., a protease present, in some embodiments at relatively higher concentrations than elsewhere in the subject's system, on or nearby a tumor cell. This cleavage event then is designed to result in the loading, or binding, of the peptide by MHC molecules expressed on the surface of tumor cells. The following experiments are designed to test this mode of operation and whether the designed IRC operate in the manner expected.

For this purpose, an MHC class I molecule loading assay was developed that directly detects peptide loading from IRC onto MHC class I molecules expressed on the surface of tumor cells. This assay involves the use of an antibody that specifically recognizes an OVA peptide (SIINFEKL, SEQ ID NO:95)—MHC class I alloantigen H-2K$^b$ molecule complex but not free peptide, empty MHC class 1 molecules, or peptides conjugated to the IRC. (See, Zhang et al., Proc. Nat'l. Acad. Sci. USA, 89:8403-84-7, 1992).

In this experiment, the OVA conjugated MPV.10.34.d IRC from Example 6 were examined side-by-side with OVA conjugated HPV16 IRC at equivalent molarity based on concentration of conjugated peptide. Briefly, 0.1 to 0.2×10$^6$ MC38 tumor cells (C57BL6 murine colon adenocarcinoma-derived cells, #ENH204-FP, Kerafast, Inc., Boston MA) were incubated with the IRC for one hour at 37° C. A positive control including just free peptide and a negative control including no peptide or IRC were also tested. Cells were then washed twice with 2 to 3 mL FACS buffer and then stained with PE-conjugated-mouse anti-mouse MHC I bounded with OVA (SIINFEKL, SEQ ID NO:95) monoclonal antibody (Biolegend, San Diego, CA) for 30 minutes at 4° C. Following this, samples were washed once with 3 mL FACS buffer then the cells were resuspended in 250 µL of FACS buffer before being analyzed by a CytoFLEX flow cytometer (Beckman Coulter Life Sciences, Brea, CA, US).

Figure 19:
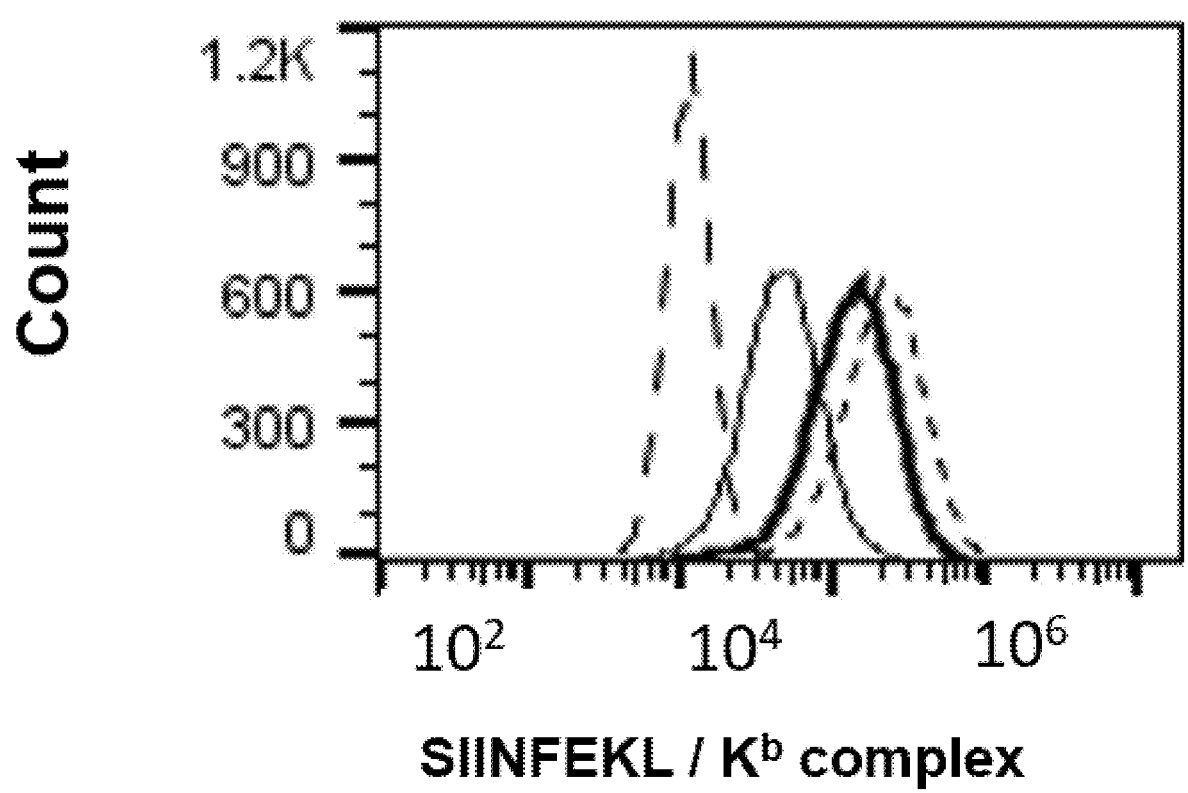

Results of these assays are provided in FIG. 19. The results show that OVA-conjugated MPV.10.34.d IRC (1.4 µg/mL, thick solid line) and OVA-conjugated HPV16 IRC (2.5 µg/mL, solid line) demonstrated loading of epitopes on the surface of MC38 murine tumor cells, with the OVA-conjugated MPV.10.34.d IRC out-performing the OVA-conjugated HPV16 IRC. (See, FIG. 18, negative control—long-dashed line, positive control—thin-dashed line). These results suggest that the MPV.10.34.d IRC is superior to the HPV16 IRC because a smaller amount of MPV.10.34.d IRC achieved the same, or better, "loading" potential of a larger amount of HPV16 IRC.

As OVA is a model antigen utilized for murine MHCs, this experiment was repeated substituting the CMV pp65 peptide for the OVA peptide. The HLA-A*0201 restricted epitope NLVPMVATV (NLV, SEQ ID NO: 138) from the CMV pp65 was used for these studies and the pp65-conjugated MPV.10.34.d IRC were produced as described in Example 6. As there was no commercially available monoclonal antibody that recognizes an MHC class I—NLV complex, a soluble T-cell receptor antibody (2S16) was employed that recognizes this HLA-A2 complex. (See, Wagner et al., J. Biol. Chem., 295(15):5790-5804, 2019). The IRC constructs were analyzed in the same manner as above except that the cell lines HCT116 (human colorectal carcinoma cell line, HCT 116, ATCC, CCL-247) and MCF7 (human breast cancer cell line, MCF7, ATCC, HTB-22) were utilized in this study. These cell lines are HLA-A*0201 restricted and thus are able to present the HLA-A*0201 restricted epitope NLVPMVATV (NLV, SEQ ID NO: 138) from the CMV pp65 peptide.

Figure 20A:
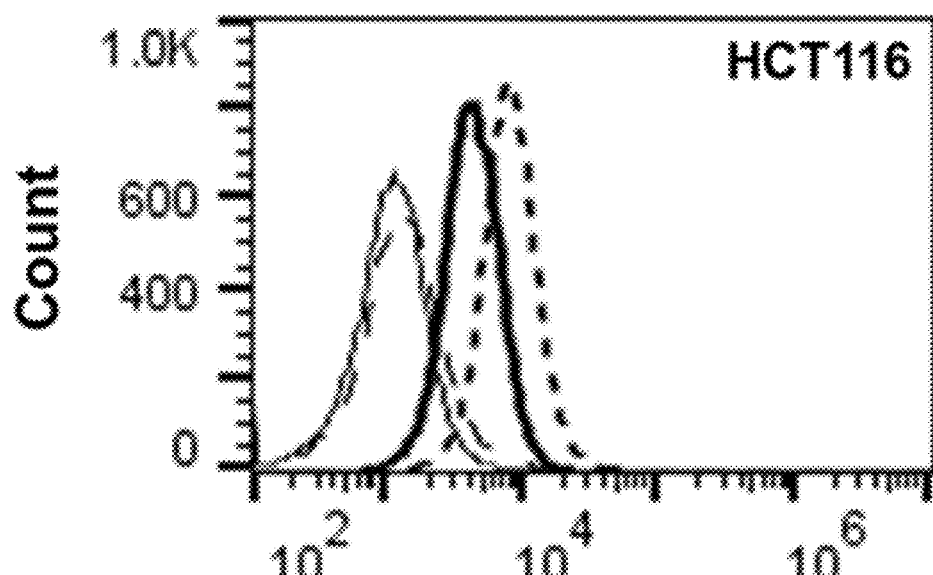
Figure 20B:
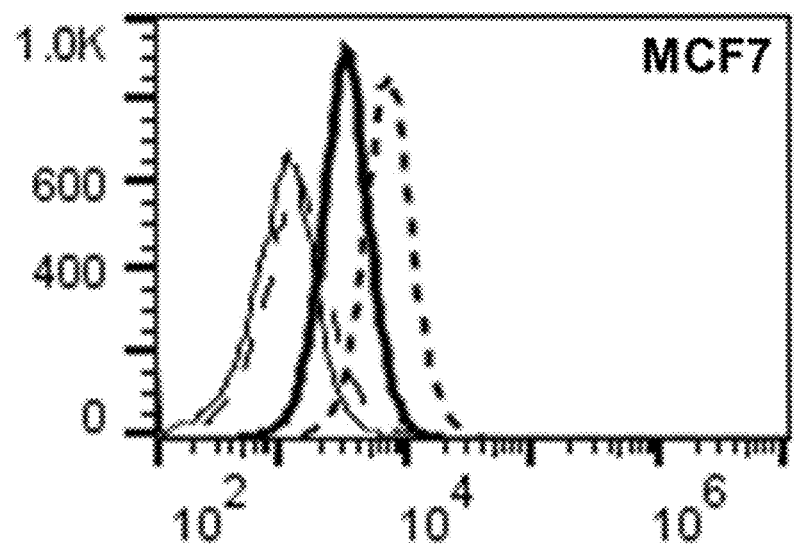

Consistent with the OVA MHC class I loading results, loading of the NLV peptide onto human tumor cells was observed. Results are presented in FIG. 19A (HCT116 cells) and FIG. 19B (MCF7 cells). In FIG. 20A and FIG. 20B, an unrelated hepatitis B peptide was used as a negative control (thin dashed line, 10 µg/mL), unconjugated MPV.10.34.d capsid backbones were used as a further negative control (thin solid line, 100 µg/mL), CMV conjugated MPV.10.34.d IRC is represented as a thick solid line (100 µg/mL, at about 1.7 µg/mL of hCMV peptide conjugated), hCMV free peptide is represented as a thick dashed line (1 µg/mL).

FIGS. 19 and 20 show that incubation of the MPV.10.34.d IRC in vitro with the indicated cell lines leads to release of the peptide and binding to the tumor cell surface MHC Class 1 molecules. To further demonstrate that the mechanism of the IRC first involves the MPV.10.34.d IRC binding to the tumor cell followed by furin cleavage, competitive inhibition experiments were performed that either inhibited tumor cell binding or furin cleavage to show that ablation of either step results in an absence of peptide loading onto the tumor cells. These studies were performed with the OVA-conjugated MPV.10.34.d IRC and conducted under the same conditions as the binding assays described above.

Figure 21A:
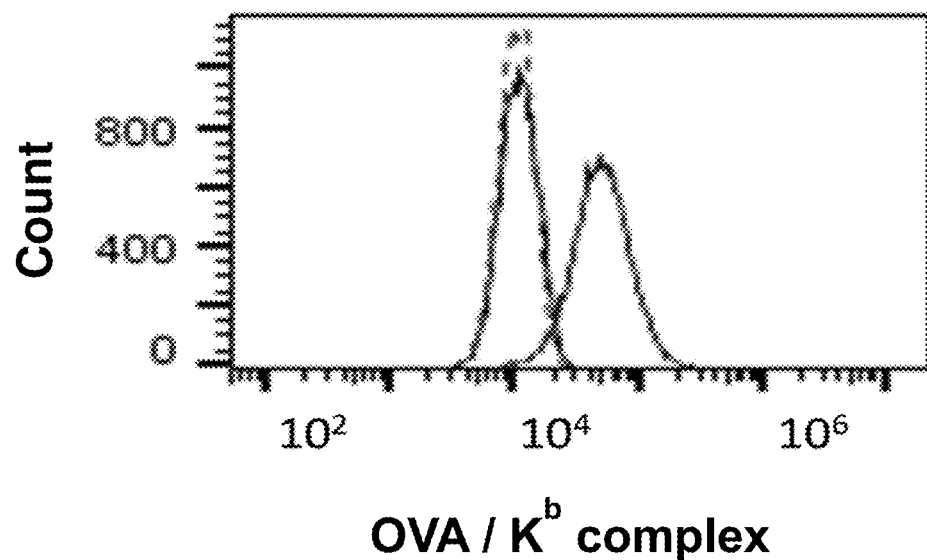
Figure 21B:
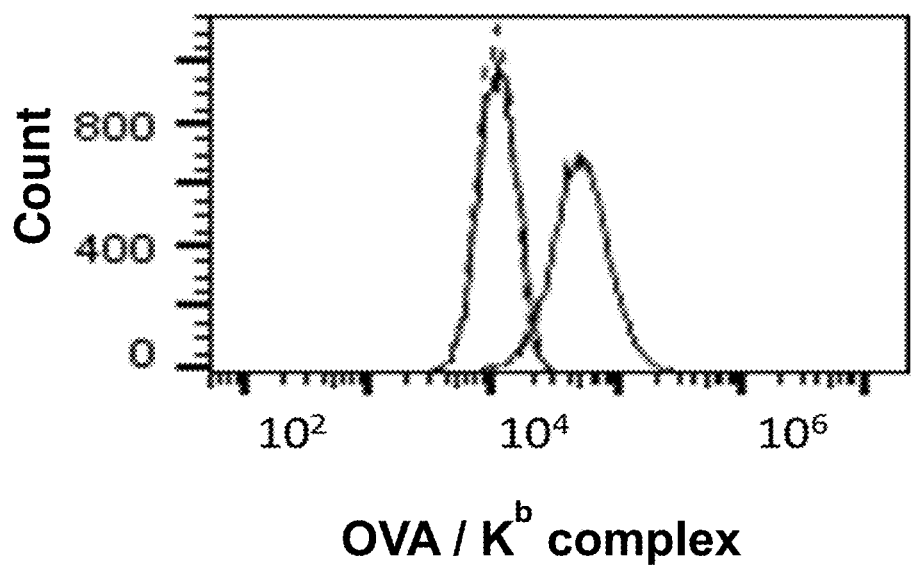
Figure 21C:
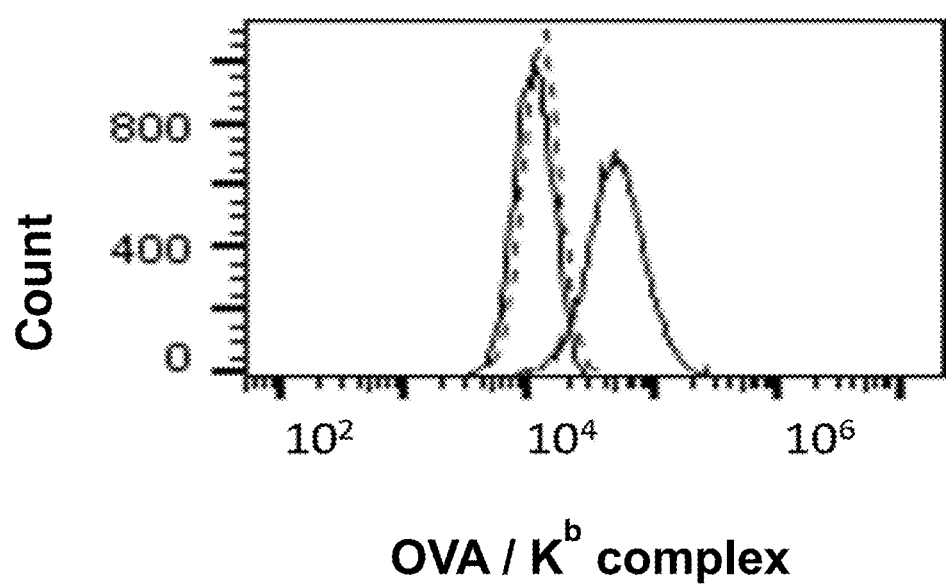

To block tumor binding, soluble heparin (Sigma Aldrich, St. Louis, MO) at 1 mg/mL, 5 mg/mL, or 10 mg/mL was incubated with 2.5 µg/mL of OVA-conjugated MPV.10.34.d IRC for 1 hour at 37° C., 5% $CO_2$ in the presence of $2\times10^5$ MC38 cells in a FACs tube. The final volume of the cells with the sample was 200 µL. A positive control sample was included which contained no soluble heparin as well as a negative control that contained no IRC or heparin. Cells were then washed twice with 2 to 3 mL FACS buffer and then stained with PE-conjugated-mouse anti-mouse MHC I bound to the OVA peptide monoclonal antibody (this monoclonal antibody is able to specifically detect OVA peptide, SIINFEKL, SEQ ID NO: 95, in complex with MHC-I $K^b$) for 30 minutes at 4° C. Following this, samples were washed once with 3 mL FACS buffer, then the cells were resuspended in 250 µL of FACS buffer before being analyzed by a CytoFLEX flow cytometer (Beckman Coulter Life Sciences, Brea, CA, US). As seen in FIGS. 21A, 21B, and 21C, no OVA peptide loading was observed in the negative control (thin black line in FIGS. 21A, 21B, and 21C). No OVA peptide loading was observed in samples including 10 mg/ml (dashed line, FIG. 21A), 5 mg/ml (dashed line, FIG. 20B), or 1 mg/ml (dashed line, FIG. 21C) soluble heparin (these curves overlapped with the negative control data). Loading of OVA peptide was only detected in the samples containing OVA-conjugated MPV.10.34.d IRC with no heparin (thick black line to the right, FIGS. 21A, 21B, and 21C). These results show that OVA-conjugated MPV.10.34.d IRC is HSPG-specific.

To show that loading of peptide from IRC onto tumor cells is dependent on protease cleavage of the epitope peptide form the MPV.10.34.d IRC, the experiments of Example 10 were repeated in the presence of a furin inhibitor, furin inhibitor I—Calbiochem, decanoyl-RVKR-CMKa, peptidyl chloromethylketone. (Millipore-Sigma, St. Louis, MO). This furin inhibitor binds irreversibly to the catalytic site of furin, blocking all furin protease activity.

Briefly, $2\times10^5$ MC38 cells (murine colon adenocarcinoma, #ENH204-FP, Kerafast, Inc., Boston MA) were seeded in a FACs tube and then incubated with either 0.5 µM, 5 µM, or 50 µM furin inhibitor dissolved in DMSO at total final sample volume of 200 µL. Control samples containing no inhibitor were prepared the same way with the same volume equivalent of DMSO. The samples were incubated for fifteen minutes in a tissue culture incubator at 37° C., 5% $CO_2$. Then, 2.5 µg/mL of OVA-conjugated MPV.10.34.d IRC was added to all samples and the samples were incubated in a tissue culture incubator at 37° C., 5% $CO_2$. Samples were then washed twice with 2 to 3 mL FACS buffer and then stained with PE-conjugated-mouse anti-mouse MHC I bounded with OVA (SIINFEKL, SEQ ID NO:95) monoclonal antibody (Biolegend, Cat #141604, San Diego, CA) for 30 minutes at 4° C. Following this, samples were washed once with 3 mL FACS buffer then the cells were resuspended in 250 µL of FACS buffer before being analyzed by a CytoFLEX flow cytometer. (Beckman Coulter Life Sciences, Brea, CA, US).

Figure 22A:
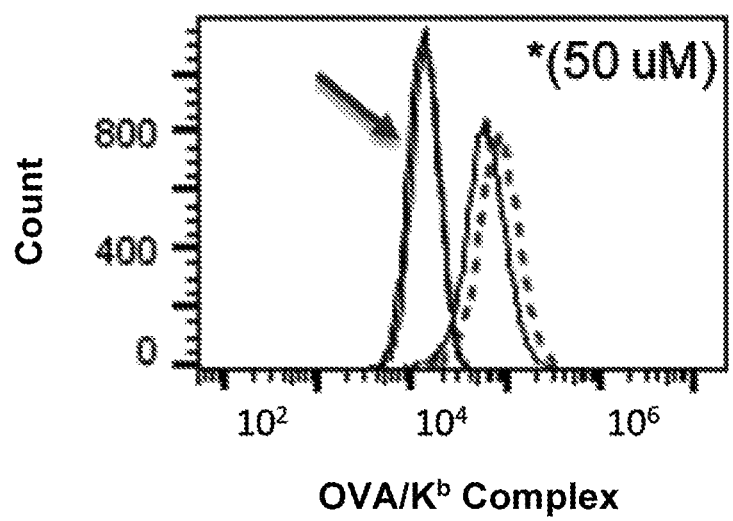
Figure 22B:
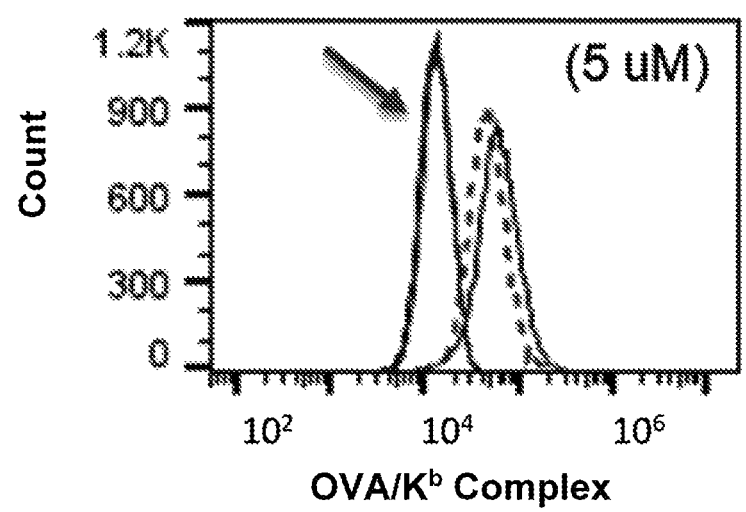
Figure 22C:
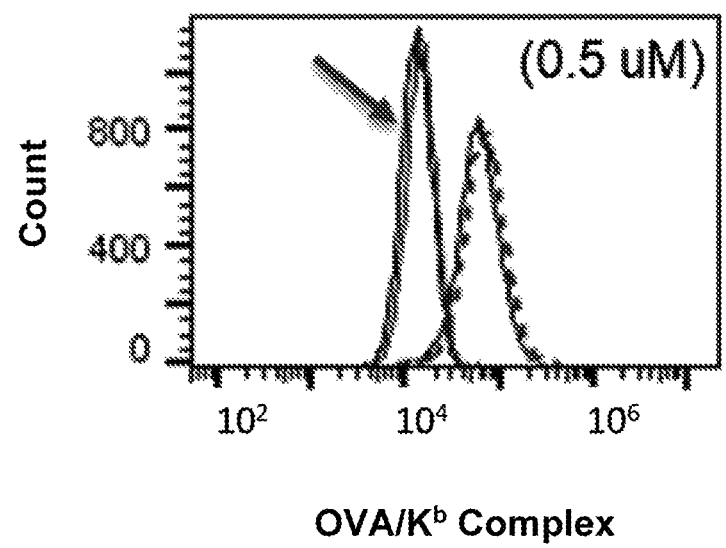

As seen in FIGS. 22A, 22B, and 22C, OVA-conjugated MPV.10.34.d IRC loaded OVA peptide onto tumor cells in the samples that had no inhibitor added (thin black line, FIGS. 22A, 22B, and 22C), and samples treated only with DMSO and no furin inhibitor (dashed black line, FIGS. 22A, 22B, and 22C). In contrast, no OVA peptide loading was observed in the negative control (thin grey line in FIGS. 22A, 22B, and 22C, the control curves overlapped with the experimental data) as well as samples treated with furin inhibitor at 50 µM (arrow pointing to dark thin line, FIG. 22A), 5 µM (arrow pointing to dark thin line, FIG. 22B), and 0.5 µM (arrow pointing to dark thin line, FIG. 22C). Therefore, inhibition of furin cleavage of the epitope peptide from the IRC prevented binding of OVA to the MHC molecules of the target cancer cell, thereby confirming the mechanism of action of the IRC. This mechanism is further confirmed by, and consistent with, the results shown in FIGS. 18 to 22.

Example 10

In Vitro Cytotoxic Killing Assays with MPV.10.34.d IRC

Since it was shown in Example 9, that in vitro MPV.10.34.d IRC were able to deposit peptide epitopes onto murine and human MHC Class I molecules and that this mechanism was dependent on furin activity, additional experiments were designed to determine whether labelling these cancer cells would trigger activation and redirection of cellular immune system components against target tumor cells. Upon activation and redirection, the goal is delivery of a cytotoxic signal to the tumor cells and tumor cell death. For this purpose, three different in vitro cytotoxic T-cell-dependent tumor cell killing assays were designed involving the co-culture of tumor cells and viral antigen-specific CD8+ T cells in the presence or absence of MPV.10.34.d IRC. The three CD8 T-cells were tested, including: (1) murine OVA-specific preclinical CD8+ T cells, (2) murine HPV16 E7-specific CD8+ T cells, and (3) human HLA-A*0201-restricted CMV-specific T cells (Astarte Biologicals, cat #1049-4367JY19). (See, Example 12, for (3)).

Murine B16 (melanoma/skin) (B16-F10 (ATCC® CRL-6475™), and murine ID8 (ovarian) tumor cells (Hung et al., Gene Ther., 14(12):921-020, 2007) overexpressing luciferase gene (B16-luc and ID8-luc) were grown in culture. Under normal circumstances, murine tumor cell lines B16 and ID8 will not be killed by murine OVA-specific CD8+ T cells since these cell lines do not express the murine OVA (SIINFIKEL, SEQ ID NO: 95) antigen.

Approximately $0.01\times10^6$ B16-luciferase mutant (B16-luc) or $0.005\times10^6$ ID8-luciferase mutant (ID8-luc) tumor cells were seeded in 100 µL per well on a 96-well assay plate overnight. The cells were then treated with 100 µL of 2.5 µg/mL of MPV.10.34.d capsid backbones, OVA-conjugated MPV.10.34.d IRC, OVA-conjugated HPV16 IRC, and positive control containing 1 µg/mL of free OVA peptide (SIINFIKEL, SEQ ID NO: 95), for one hour at 37° C. in a final volume of 200 µL per well. Cells not receiving any antigen were included as negative control (No Ag). The cells were then washed twice with 200 µL of Roswell Park Memorial Institute (RPMI) media and co-incubated with OVA-specific CD8+ T-cells (Jackson, stock no. 003831) at an effector (CD8+ T-cell) to target cell (tumor cell) ratio ("E:T Ratio") of 10:1 (B16-luc) or 20:1 (ID8-luc) for 16 hours in a final volume of 200 µL per well in a cell incubator at 37° C., 5% $CO_2$. An E:T ratio of 10:1 means that for every 1 tumor cell, ten CD8+OT-1 T cells will be co-incubated with the tumor cell. These co-incubated cells were then washed with 200 µL of PBS and lysed with 35 µL of 1× cell lysis buffer (Promega, Madison, WI, US) for 15 to 20 minutes before adding 50 µL of luciferase assay substrate and detected on a Promega GloMax Explorer Microplate Reader (Promega, Madison, WI, US).

The number of viable tumor cells after co-incubation with T cells were measured by quantification of concentration of luciferase released from lysed cells. This acts as a surrogate marker for cell viability since the target cells were incubated under conditions in which they over-express luciferase.

Reduced luciferase activity indicated more cell death suggesting greater immune redirection and hence greater cytotoxicity.

Figure 23A:
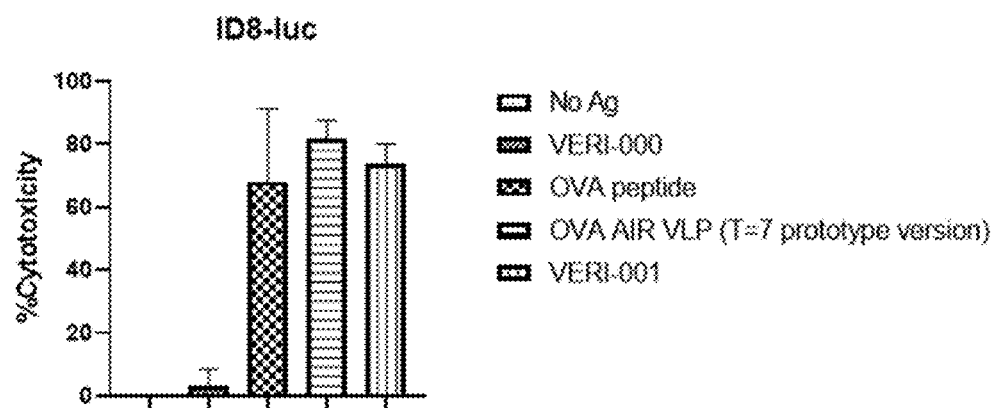
Figure 23B:
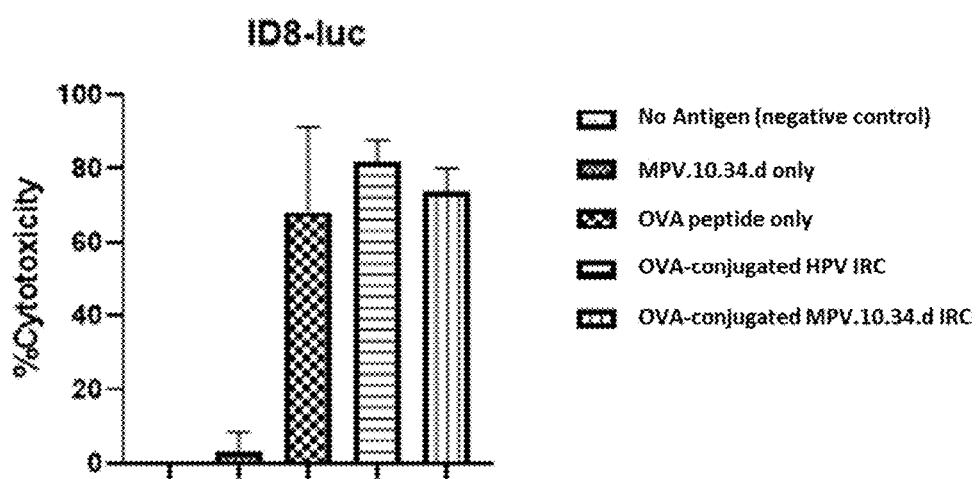

As shown in FIG. 23A and FIG. 23B, the OVA-conjugated MPV.10.34.d IRC, OVA-conjugated HPV16 IRC, and the peptide positive control showed much higher tumor cell cytotoxicity (>70%) than the negative control samples in both B16-luc (FIG. 23A) and ID8-luc (FIG. 23B) tumor killing assays. At the same concentration (2.5 μg/mL), OVA-conjugated MPV.10.34.d IRC also showed similar high cytotoxicity on tumor cells as the OVA-conjugated HPV16 IRC.

Similar to the above experiment, a second experiment was performed in like manner, except with the substitution of the E7 peptide (RAHYNIVTF, SEQ ID NO:96) for the OVA peptide. The same tumor cells and samples were investigated in this experiment using the same protocol.

As shown in FIG. 24A and FIG. 24B, the E7-conjugated MPV.10.34.d IRC, E7-conjugated HPV16 IRC, and the positive control showed much higher tumor cell cytotoxicity (>70%) than the negative control groups in both B16-luc (FIG. 24A) and ID8-luc (FIG. 24B) tumor killing assays. At the same concentration (2.5 μg/mL), OVA-conjugated MPV.10.34.d IRC also showed similar high cytotoxicity on tumor cells as the OVA-conjugated HPV16 IRC.

Example 11

MPV.10.34.d IRC Effectiveness in Human Assays

While the in vitro functional test results of the above experiments were promising, the next desired step in the analysis was to perform similar experiments in human-based assays. To this end, the response of mock human cellular immune system components to tumor cells exposed to MPV.10.34.d IRC was examined in vitro. Human CMV (HCMV) was selected for this study since human CMV is highly prevalent (infecting 50-90% of the human population) and mostly asymptomatic in healthy individuals. (See, Longmate et al., *Immunogenetics*, 52(3-4):165-73, 2001; Pardieck et al., F1000Res, 7, 2018; and van den Berg et al., *Med. Microbiol. Immunol.*, 208(3-4):365-373, 2019). Importantly, HCMV establishes a life-long persistent infection that requires long-lived cellular immunity to prevent disease. Hence, it is rational to hypothesize that a complex adaptive cell-mediated anti-viral immunity developed over many years to strongly control a viral infection in an aging person can be repurposed and harnessed to treat cancer.

In these experiments, CD8+ T cell responses to CMV peptides were tested in three different human tumor cell lines, including HCT116, OVCAR3, and MCF7. All three of these human tumor cell lines are HLA-A*0201 positive.

In vitro cytotoxicity assays. HTC112, human colon cancer cells, MCF7, human breast cancer cells, and OVCAR3, human ovarian cancer cells (all from ATCC, Manassas, VA, US) were seeded overnight at 0.01 to 0.2×10⁶ per well per 100 μL per 96 well plate. The next day (about 20 to 22 hrs later), each cell line was incubated for one hour at 37° C. under the following conditions: (1) CMV peptide at a final concentration of 1 μg/mL (positive control), (2) MPV.10.34.d at a final concentration of 2.5 μg/mL (negative control), (3) CMV-conjugated MPV.10.34.d IRC at a final concentration of 2.5 μg/mL, (4) CMV-conjugated HPV16 IRC at a final concentration of 2.5 μg/mL, and (5) no antigen (negative control). After 1 hour, the cells were washed vigorously with 200 μL of media for three times to remove non-specific binding. Human patient donor CMV T cells (ASTARTE Biologics, Seattle, WA, US) were added at the E:T (effector cell:target cell) ratio of 10:1 and incubated in a tissue culture incubator for 24 hrs at 37 C, 5% $CO_2$. The total final volume of each sample after co-culture was 200 μL. Cell viability was measured after co-culturing. Cell viability was measured with CELLTITER-GLO® (Promega, Madison, WI, US). This assay provides a luciferase-expressing chemical probe that detects and binds to ATP, a marker of cell viability. The amount of ATP generated from tumor cells was quantified according to manufacturer protocols. In these assays, reduced luciferase activity indicates cell death and suggests greater immune redirection and greater cytotoxicity.

The results are provided in FIG. 25. CMV-conjugated MPV.10.34.d IRC ("VERI-101" in FIGS. 25A, 25B, and 25C) was equally effective as CMV-conjugated HPV16 IRC ("CMV AIR-VLP" in FIGS. 25A, 25B, and 25C) in redirecting human healthy donor CMV pp65-specific CD8+ T-cells (Astarte Biologics, Inc., Bothell, WA, US) to kill immortalized HLA.A2 positive human colon cancer cells (HCT116), human ovarian cancer cells (OVCAR3), and human breast cancer cells (MCF7). The control samples ("No Ag" or "VERI-000" in FIGS. 25A, 25B, and 25C) showed no background tumor killing. Together, these data demonstrate that MPV.10.34.d IRC redirects mouse and human immune responses against tumor cells in vitro.

Example 12

Sequential Mechanism of MPV.10.34.d IRC Binding and Peptide Cleavage

Example 9 demonstrates that MPV.10.34.d IRC binding must occur prior to furin-dependent cleavage of the peptide and peptide loading onto target tumor cells. A dose-response curve using different concentrations of OVA-conjugated MPV.10.34.d IRC to detect binding and loading in separate assays was generated. These assays were performed as described in Examples 7 and 8. Based on the geometric MFIs from both assays, a correlation analysis was conducted.

The results shown in FIG. 26 indicate that there is a highly statistically significant correlation between the number of OVA-conjugated MPV.10.34.d IRC binding to tumor cells with the level of the OVA peptide/$K^b$ complex on the tumor cells (Spearman r=0.92, P=0.0003; Pearson r=0.98, p<0.001). This statistical analysis further demonstrates the requirement for the sequential steps of OVA-conjugated MPV.10.34.d IRC to first bind or contact the tumor cell, followed by furin-dependent cleavage of the peptide from the IRC, and MHC loading of the peptide.

Example 13

Sequential Mechanism of MPV.10.34.d IRC Binding and Tumor Cell Death

Example 9 shows that inhibition of OVA-conjugated MPV.10.34.d IRC binding results in inhibition of furin-dependent cleavage of the peptide from the IRC and OVA peptide loading onto tumor cell surfaces. To further show that inhibition of this binding step also inhibits redirection of CD8+ T-cells and tumor cell death, cytotoxicity studies conducted as in Example 10 were performed in the presence and absence of soluble heparin, a competitor of HSPG binding.

A range of OVA-conjugated MPV.10.34.d IRC concentrations (0.156 μg/mL to 0.625 μg/mL) as well as E:T ratios (1:4.5, 1:9 and 1:18) were investigated in the presence and absence of 10 mg/mL of soluble heparin in the assays described in Example 10. This concentration of soluble heparin was previously shown to cause complete inhibition of OVA-conjugated MPV.10.34.d IRC binding, as well as inhibition of peptide loading onto tumor cells. In these assays, 15,000 TC-1 cells overexpressing luciferase were first seeded in a flat-bottom 96-well plate overnight in a cell culture incubator at 37° C., 5% $CO_2$. The next day, cells were washed 3 times with PBS before being incubated with AIM-V media (serum free) with 2% BSA for 1.5 hours in a cell culture incubator at 37° C., 5% $CO_2$. In parallel, OVA-conjugated MPV.10.34.d IRC was diluted in the same AIM-V media+2% BSA into 0.625, 0.3125, 0.156 µg/mL. (See, FIGS. 27A, 27B, and 27C). Each sample was incubated with (thick dash lines) or without (solid line) 10 mg/mL of soluble heparin for 1 hour at 2° C. to 8° C. MPV.10.34.d capsid backbones (thin dash line, "ViP" only) was included as a negative control. After 1 hour, the samples were added to the TC-1 cells and co-incubated for a further 30 minutes in a cell culture incubator at 37° C., 5% $CO_2$. Following this, treated cells were washed 3 times with just AIM-V media before being incubated with OT-1 T-cells at an effector to target (E:T) ratio of 18:1, 9:1, or 4.5:1. This co-culture was then incubated for a further 3 hours at 37° C., 5% $CO_2$. After 3 hours, target cells were analyzed for cytotoxicity using the Promega Luciferase Assay system as per the manufacturer's protocol (Promega, Madison, WI, US). Cytotoxicity was determined by detection of loss of luciferase signal which is used as a surrogate marker of cell viability in this assay. All studies were performed in triplicate.

Results are shown in FIG. 27. The presence of soluble heparin exhibited no OVA-conjugated MPV.10.34.d IRC-mediated cytotoxicity under all concentrations and E:T ratio conditions tested. These results further substantiate the sequential nature of the MPV.10.34.d IRC mechanism of action.

A correlation analysis was conducted on the binding and cytotoxicity activities of OVA-conjugated MPV.10.34.d IRC. Briefly, a dose-response curve using different concentrations of OVA-conjugated MPV.10.34.d IRC to detect binding and cytotoxicity in separate assays was generated. Cytotoxicity assays were conducted as previously described in Example 10 with the following changes: a range of $6.25 \times 10^{-5}$ µg/mL to 2.5 µg/mL of OVA-conjugated MPV.10.34.d IRC was tested at 3 different E:T ratios (18:1, 9:1, and 4.5:1).

Under all 3 E:T ratio conditions tested, a dose dependent killing was observed with OVA-conjugated MPV.10.34.d IRC concentrations below 0.04 µg/mL and higher, whereas concentrations of OVA-conjugated MPV.10.34.d IRC between 0.156 µg/mL to 2.5 µg/mL lead to a maximal level of cytotoxicity. Binding assays were conducted according to the protocols described in Example 7 with the following changes: a concentration range of $6.24 \times 10^{-4}$ to 2.5 µg/mL of OVA-conjugated MPV.10.34.d IRC was investigated.

Results show that a dose-dependent binding was observed and that the limit of binding detection was reached at $2.5 \times 10^{-4}$ µg/mL. Both assays were repeated twice (with at least 3 replicates). The mean values of geometric mean fluorescent intensity (MFI) was reported from the two experiments and is summarized in FIG. 28.

Based on the MFIs from both assays (FIG. 28), a graphical and correlation analysis was conducted using Spearman correlational analysis (FIG. 29). Briefly, the mean of the percentages of two independent OVA-conjugated MPV.10.34.d IRC cytotoxicity assays performed on two different days and the mean of MFIs of OVA-conjugated MPV.10.34.d IRC binding experiments from two different days were calculated (FIG. 28) and plotted (FIG. 29). Spearman correlational analysis was performed on these results reveals a significant relationship ($r=0.83-0.9$) between these two variables at all three E:T ratios. These results show that there is a highly statistically significant correlation (r value between 0.83 to 0.9, depending on E:T ratio) between the OVA-conjugated MPV.10.34.d IRC binding to tumor cells and the level of cytotoxicity that followed.

Example 14

GARDASIL®9-Generated Antibodies do Not Inhibit MPV.10.34.d IRC Effects

Vaccination with GARDASIL®9 results in long term (>10 years) of sustained HPV L1 capsid-specific antibodies that are able to prevent HPV infection and subsequently, prevent HPV-associated cervical cancers. Although GARDASIL®9 has been reported to be only effective against nine types of HPVs, some cross-neutralization against other types of papillomavirus capsids may be expected. As MPV.10.34.d IRC is derived from murine papillomavirus capsids, it was desirable to determine whether vaccine sera elicited from GARDASIL®9 vaccination could inhibit MPV.10.34.d IRC tumor cell killing.

GARDASIL®9 sera was generated as follows: New Zealand white rabbits (n=10) were administered three intramuscular vaccinations of a human dose of GARDASIL®9 (270 µg of VLPs per dose). Rabbits were vaccinated at months 0, 1, and 2. After two weeks post final vaccination, rabbits were bled to obtain the GARDASIL®9 sera. 100 µL aliquots of sera from each rabbit were pooled. As a control, GARDASIL®9 sera were also tested for neutralizing activity against HPV types 6, 11, 16, 18, 31, 45, 52, and 58 and results showed no neutralization activity (data not shown).

Figure 30C:
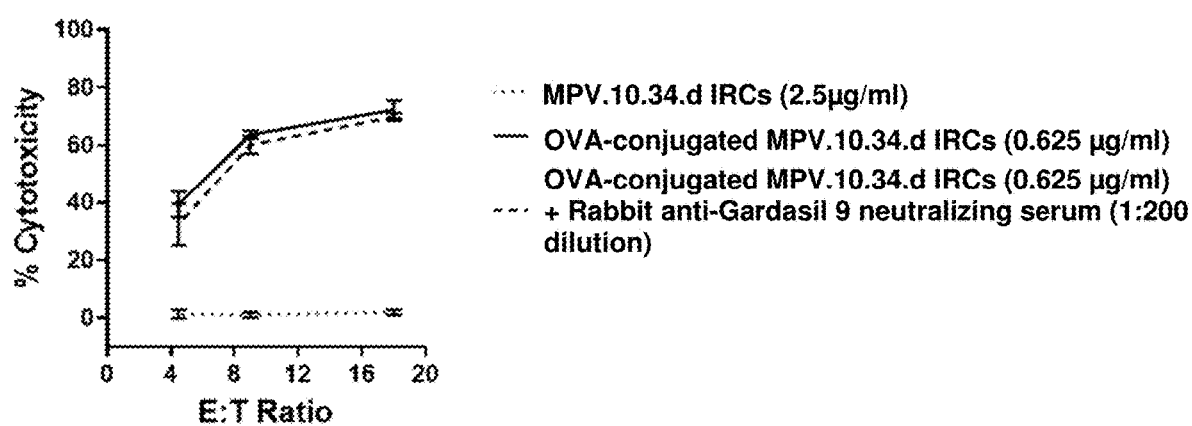
Figure 31A:
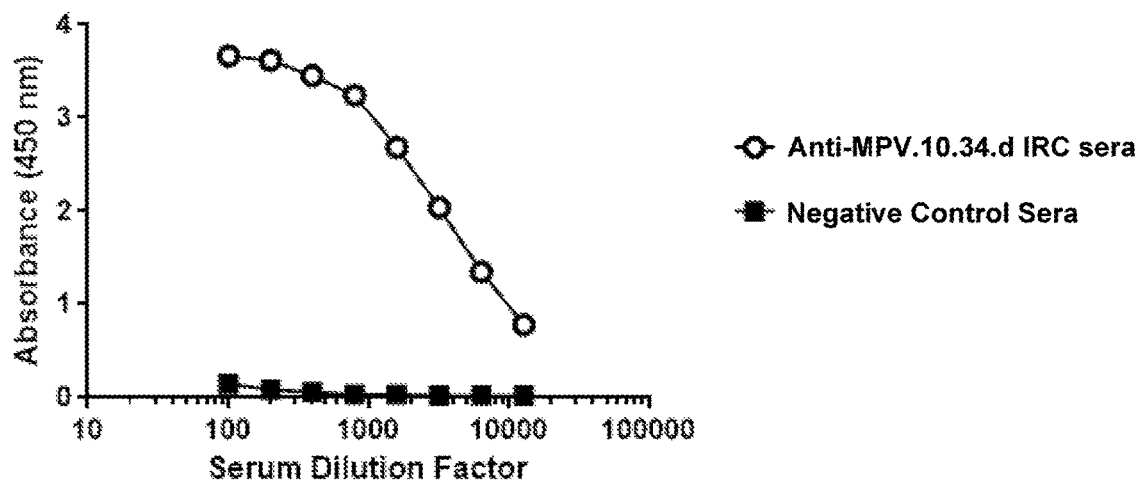
Figure 31B:
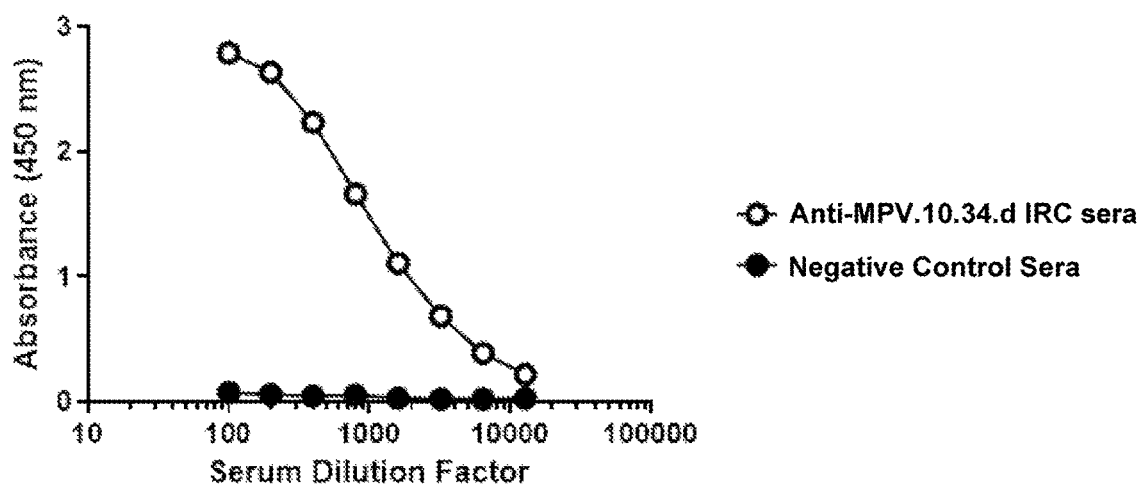
Figure 32A:
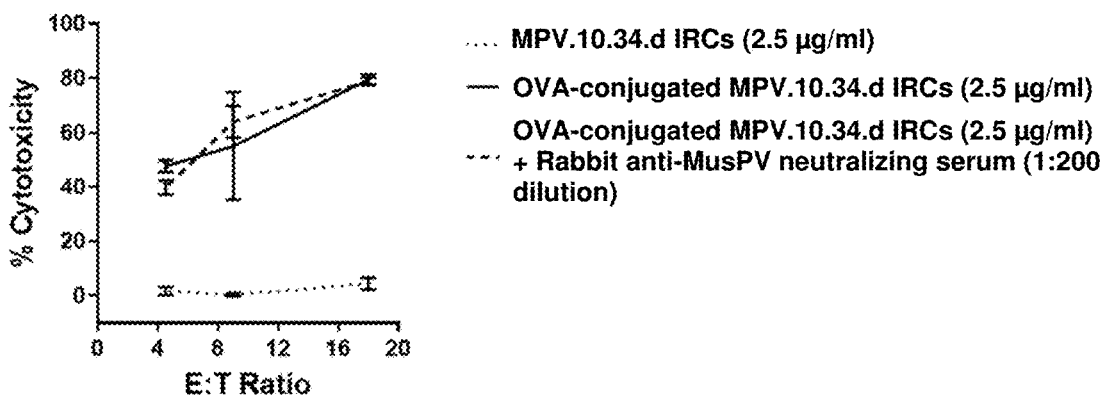
Figure 32B:
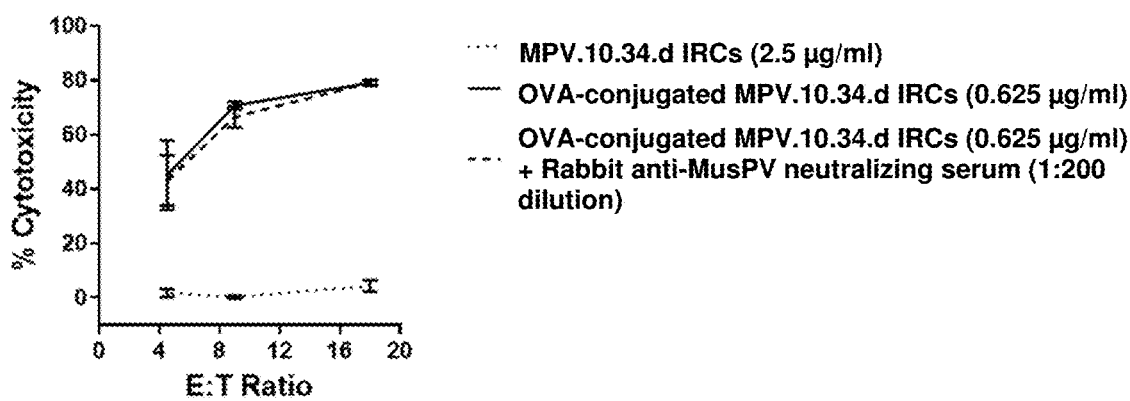
Figure 32C:
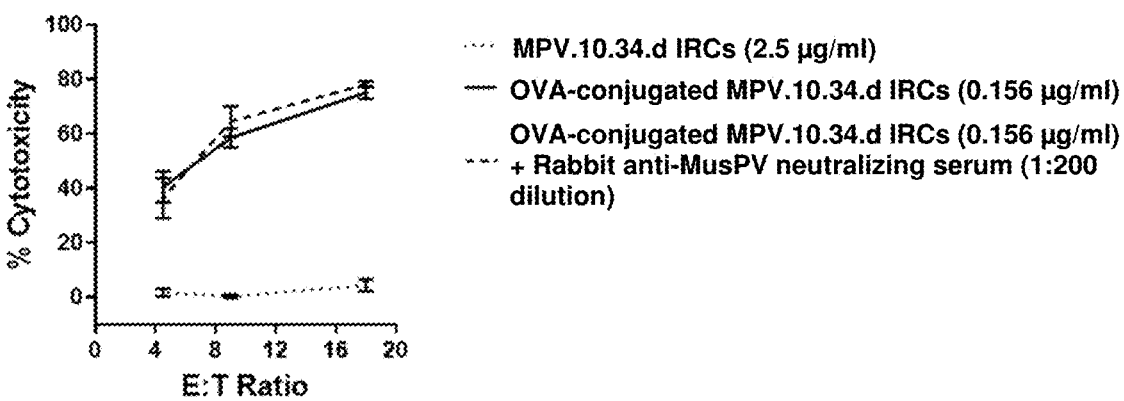
Figure 32D:
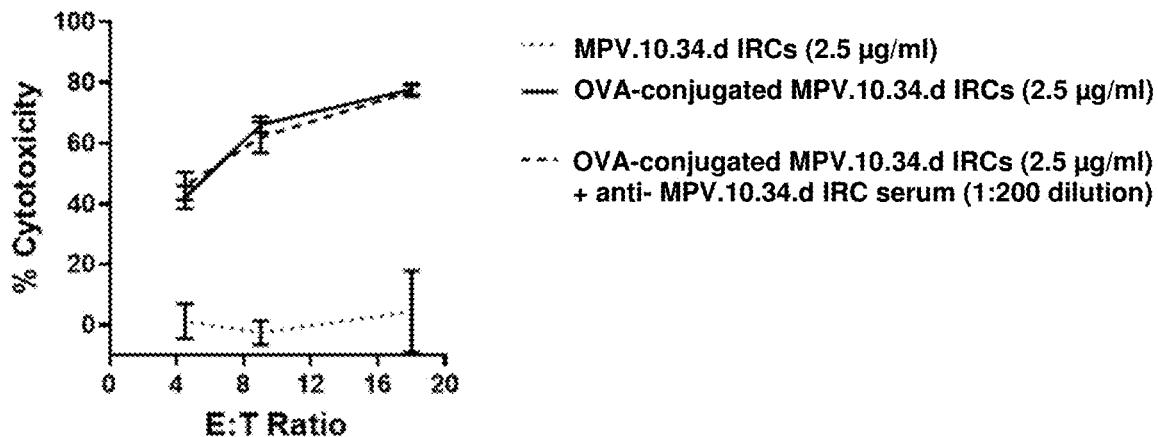
Figure 32E:
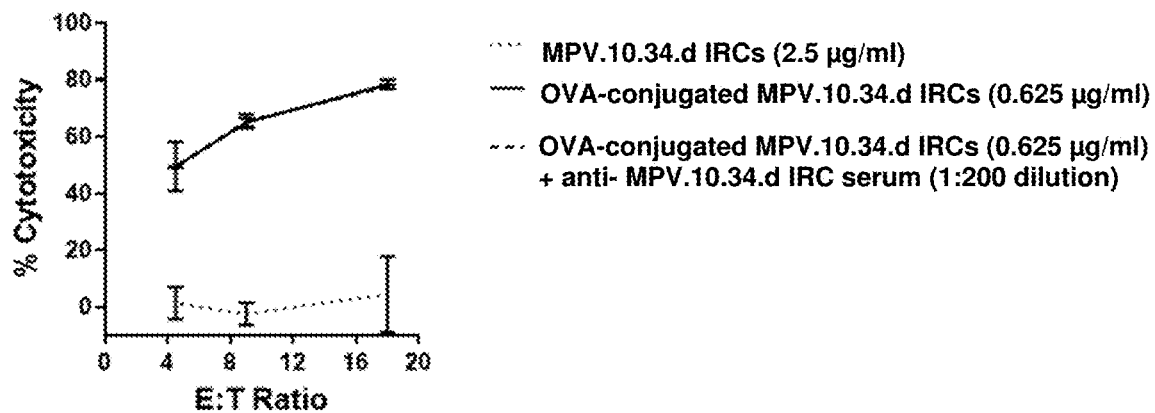
Figure 32F:
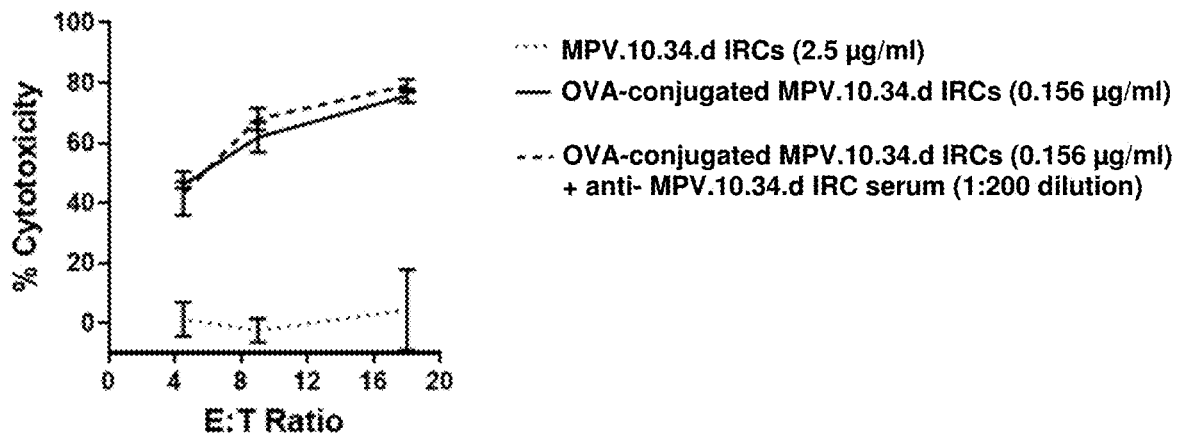
Figure 33A:
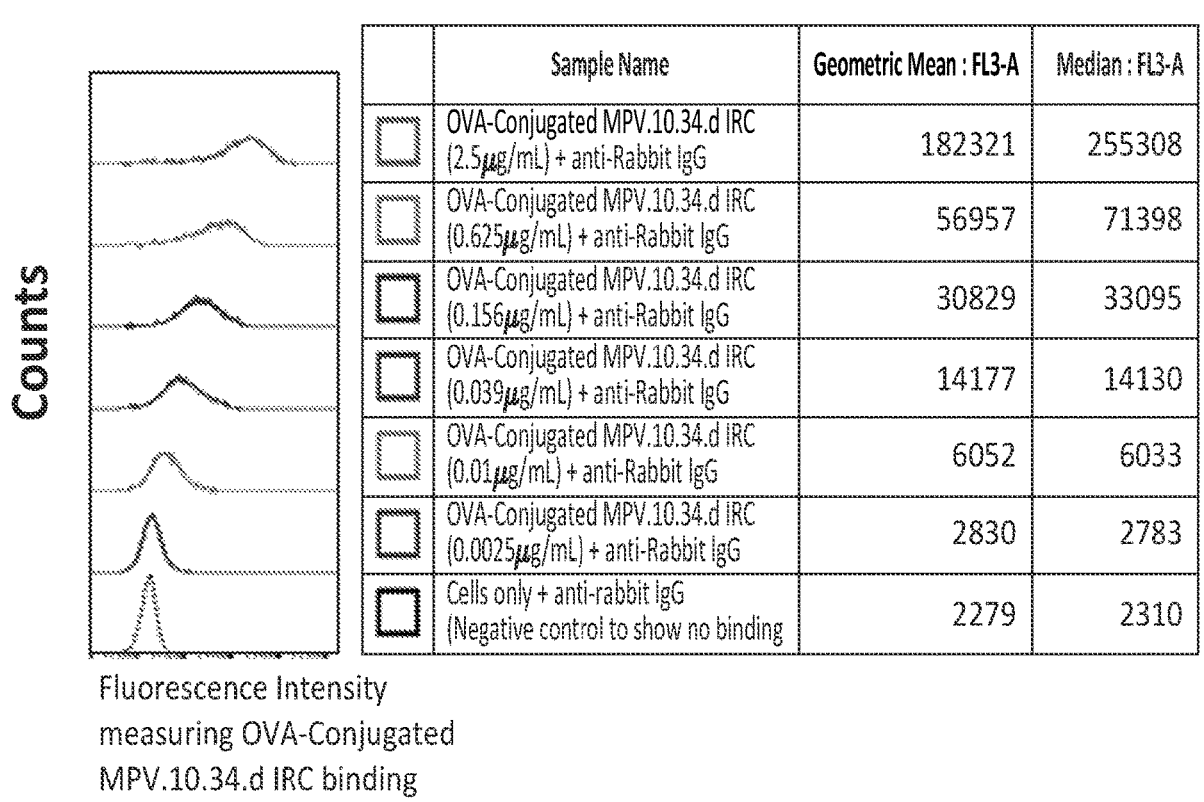
Figure 33B:
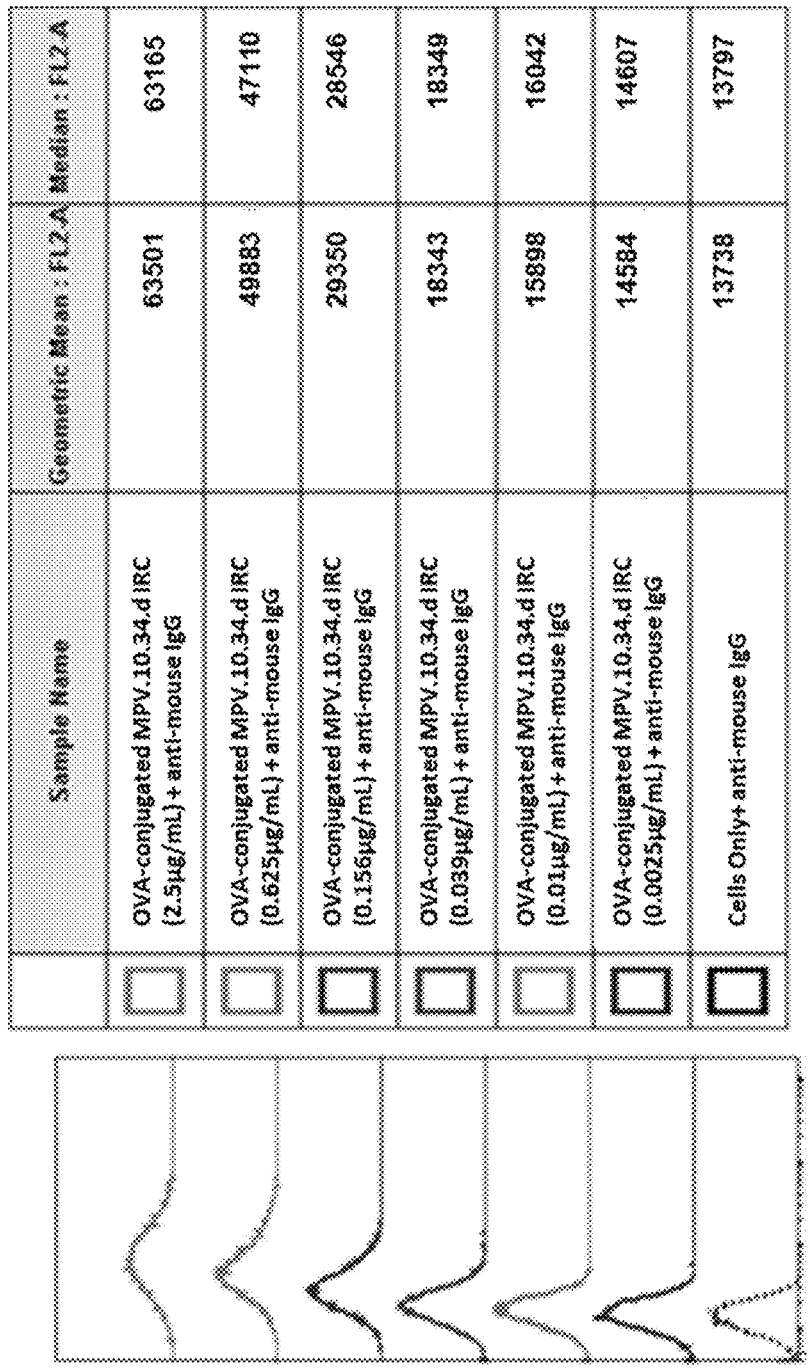

OVA-conjugated MPV.10.34.d IRCs were tested with GARDASIL®9 sera using the protocol described in Examples 11 and 13. Briefly, 15,000 TC-1 cells overexpressing luciferase were first seeded in a flat-bottom 96-well plate overnight in a cell culture incubator at 37° C., 5% $CO_2$. The next day, cells were washed 3 times with PBS before being incubated with AIM-V media (serum free)+2% BSA for 1.5 hours in a cell culture incubator at 37° C., 5% $CO_2$. In parallel, OVA-conjugated MPV.10.34.d IRC was diluted in the same AIM-V media+2% BSA into 0.625 µg/mL, 0.3125 µg/mL, and 0.156 µg/mL, and each sample was incubated with a 1:200 dilution of GARDASIL®9 serum (thick-dashed lines) or without (solid line) for 1 hour at 2° C. to 8° C. MPV.10.34.d alone (thin dashed line) was also included as a negative control. (See, FIGS. 30A, 30B, and 30C). After 1 hour, the samples were added to the TC-1 cells and co-incubated for 30 minutes in a cell culture incubator at 37° C., 5% $CO_2$. Following this, treated cells were washed 3 times with just AIM-V media before being incubated with OT-1 T-cells at an effector to target (E:T) ratio of 18:1, 9:1, or 4.5:1. This co-culture was then incubated for 3 hours at 37° C., 5% $CO_2$. After 3 hours, target cells were analyzed for cytotoxicity using the Promega Luciferase Assay system as per the manufacturer's protocol (Promega, Madison, WI, US). Cytotoxicity was determined by quantitation of the loss of luciferase signal which is used as a surrogate marker of cell viability. All studies were performed in triplicate.

No inhibition of cytotoxicity was observed in the presence of GARDASIL®9 sera. The results in FIG. 30 suggests that MPV.10.34.d IRC would not be negatively impacted in subjects who might possess preexisting HPV vaccine-generated antibodies.

Example 15

Anti-MPV.10.34.d IRC Antibodies do Not Inhibit Tumor Cell Cytotoxicity

Since MPV.10.34.d IRC sequences are based on MPV L1 capsids, it was desirable to test whether antibodies generated against wild type MPV or MPV.10.34.d IRC affect the mechanism of action of MPV.10.34.d IRCs against tumors.

Antibodies against wild type MPV were generated as follows: New Zealand white rabbits (n=3) were administered three intra-muscular vaccinations of 50 μg of wild type mouse papillomavirus particles per dose. Rabbits were vaccinated at months 0, 1, and 2. After two weeks post final vaccination, rabbits were bled to obtain the anti-MPV sera. Antibodies against MPV.10.34.d IRC were obtained as follows: naïve 6 to 8 week old C57/BL6 mice (n=10) were injected systemically with two doses of 150 μg of E7-conjugated MPV.10.34.d over a period of 48 hours. After 48 hours, the mice were bled to obtain the anti-MPV.10.34.d IRC sera.

Specificity of anti-MPV.10.34.d IRC sera and anti-MPV sera to both MPV.10.34.d capsid backbone and MPV.10.34.d IRC was examined by ELISA. The assays were performed as described in Example 5 with the following differences: serum samples were tested at a 1:100 dilution factor and two-fold serial dilutions. Goat anti-mouse IgG-HRP secondary antibody was used in the ELISA (1:7000). Binding of anti-MPV.10.34.d IRC sera (FIG. 31) and anti-MPV serum (data not shown) to both MPV.10.34.d capsid backbone (FIG. 31A) and MPV.10.34.d IRC (FIG. 31B) was observed.

To determine whether binding of either antibody serum to MPV.10.34.d IRCs would affect the subsequent tumor cytotoxicity, binding and cytotoxicity assays were conducted with OVA-conjugated MPV.10.34.d IRC in the presence or absence of either sera. Cytotoxicity assays were conducted as in Example 14 in the presence of anti-MPV serum (FIGS. 32A, 32B, and 32C) or anti-MPV.10.34.d IRC serum (FIGS. 32D, 32E, and 32F). Results reveal that no difference in cytotoxicity when OVA-conjugated MPV.10.34.d IRC was pre-incubated with either anti-MPV sera (FIGS. 32A, 32B, and 32C) or anti-MPV.10.34.d IRC sera (FIGS. 32D, 32E, and 32F) for all concentrations and E:T ratios tested.

The inability of antibodies to MPV.10.34.d IRC or MPV to inhibit cytotoxicity despite these antibodies showing specificity for binding to both MPV.10.34.d capsid backbones and MPV.10.34.d IRCs via ELISA was further investigated by conducting binding assays in the presence of these sera.

Samples were pre-incubated with different OVA-conjugated MPV.10.34.d IRC concentrations (0.0025 μg/mL to 2.5 μg/mL). These samples were tested in the same binding assays described in Example 5. Briefly, 20,000 TC-1 cells overexpressing luciferase were seeded into FACs tubes and incubated in a cell culture incubator at 37° C., 5% $CO_2$, until needed. In parallel, OVA-conjugated MPV.10.34.d IRC was diluted in the same AIM-V media +2% BSA into a range of concentrations 0.0025 to 2.5 μg/mL and each sample was incubated with 1:200 dilution of either anti-MPV serum (A) or anti-MPV.10.34.d IRC serum (B) for 1 hour at 2° C. to 8° C. After 1 hour, the samples were added to the TC-1 cells seeded in the FACs tubes and co-incubated for 1 hour in a cell culture incubator at 37° C., 5% $CO_2$. Samples were then washed twice with FACS buffer (DBPS, pH 7, 0.1% BSA). The samples were then stained with AF647-conjugated donkey anti-rabbit Ig antibody or PE-conjugated goat anti-mouse IgG antibody for 30 minutes in the dark. Samples were then washed with FACS buffer (DBPS, pH 7, 0.1% BSA). After this, samples were resuspending in 250 μL of FACs buffer and binding was detected by flow cytometry at different concentrations of OVA-conjugated MPV.10.34.d IRC pre-treated with MPV sera (FIG. 33A) or anti-MPV.10.34.d IRC sera (FIG. 33B). All studies were performed in triplicate.

Results of these tests reveals that incubation of samples with anti-MPV rabbit IgG serum (FIG. 33A) or anti-MPV.10.34.d IRC mouse IgG serum (FIG. 33B) are still able to bind to target tumor cells. In summary, the results from Example 15 (FIGS. 31, 32, and 33) collectively show that antibodies specific for MPV.10.34.d IRCs elicited in vivo bind specifically to the MPV.10.34.d IRCs. However, these antibodies do not block MPV.10.34.d IRCs from binding to tumor cells (FIG. 33) and thus, also do not inhibit the overall cytotoxic mechanism of the MPV.10.34.d IRCs (FIG. 32). In contrast, these same antibodies were able to inhibit MPV infection as seen in the pseudo-virus neutralization assays (data not shown). As MPV infection requires cell internalization, one possible explanation is that these anti-MPV.10.34.d IRC serum antibodies block cell internalization of MPV.10.34.d IRC but do not inhibit target cell binding of MPV.10.34.d IRC. Since the mechanism of MPV.10.34.d IRCs is extracellular, it is possible that this is why they are not affected by these antibodies.

Example 16

Peptide Loading on Cells Deficient in MHC Class 1 Intracellular Pathway Components Example 9 demonstrates loading of peptide from IRCs onto the tumor cell surface. It was desirable to determine whether the released peptides from the IRC are bound by the tumor cell and then phagocytosed to be processed through the MHC Class 1 antigen presentation pathway. To test this possibility, peptide loading assays were performed with a cell line (RMA-S cells) that is genetically deficient (TAP-deficient) in intracellular MHC Class 1 processing proteins. If peptide loading onto the tumor cell surface still occurs in this context, it must be through extracellular mechanisms.

A range of OVA-conjugated MPV.10.34.d IRC concentrations (0.625 μg/mL to 10 μg/mL) was tested for their ability to load RMA-S cells with peptide. These binding assays were conducted as previously described. Briefly, RMA-S cells at $2\times10^6$ cells/mL were resuspended into a single cell suspension and 100 μL ($0.2\times10^6$ of RMA-S cells) was dispensed into FACS tubes. Varying amounts of OVA-conjugated MPV.10.34.d IRC was added (0.625 μg/mL to 10 μg/mL) to the samples and the samples were then incubated at 37° C., 5% $CO_2$ for one hour. Afterwards, the cells were washed twice in 2 mL of FACS buffer (PBS, pH7.0, 1% BSA). The cells were stained with 1 μL of PE-conjugated anti-SIINFEKL (SEQ ID NO:95)/Kb antibody. The cells were washed twice in 2 mL of FACS buffer (PBS, pH7.0, 1% BSA). The samples were then resuspended in about 250 μL of FACS buffer and peptide binding was analyzed via MFI.

The data reveal that increasing levels of OVA peptide-MHC complex in these cells as higher concentrations of OVA-conjugated MPV.10.34.d IRCs were added. These data appear to establish that the MPV.10.34.d IRCs label target tumor cells by an extracellular mechanism.

What is claimed is:

1. A composition, comprising:
a plurality of virus proteins, wherein each of said plurality of virus proteins comprises a mutated amino acid sequence of a Papillomaviridae L1 protein;
one or more peptides each comprising one or more epitopes from one or more pathogens other than a Papillomaviridae antigenic peptide;
wherein the mutated amino acid sequence of the Papillomaviridae L1 protein comprises at least the following mutations with respect to the wild type L1 protein sequence: (a) a deletion of at least five amino acid residues from an amino-terminus, (b) a deletion of at least ten amino acid residues from the helix four region, and (c) a deletion of at least thirty amino acid residues from a carboxy-terminus,
wherein the one or more peptides are attached to the plurality of virus proteins, and
wherein said plurality of virus proteins spontaneously assemble to form an icosahedron or dodecahedron capsid having a triangulation number T equal to 1 that binds to proteoglycan expressed on tumor cells.

2. The composition of claim 1, wherein the one or more peptides are conjugated to the plurality of mutant Papillomaviridae L1 proteins.

3. The composition of claim 2, wherein the one or more peptides are conjugated to the mutant Papillomaviridae L1 proteins via a cysteine, lysine, or arginine residue of the mutant Papillomaviridae L1 protein.

4. The composition of claim 2, wherein the one or more peptides are conjugated to the mutant Papillomaviridae L1 proteins via disulphide, maleimide, or amide bond between the mutant Papillomaviridae L1 protein and a residue of the peptide.

5. The composition of claim 1, wherein at least 25% of the plurality of mutant Papillomaviridae L1 proteins are conjugated to at least one of the one or more peptides.

6. The composition of claim 1, wherein at least 25 to 85% (w/w) of the plurality of mutant Papillomaviridae L1 proteins are conjugated to at least one of the one or more peptides.

7. The composition of claim 1, wherein each of the one or more peptides further comprise one or more protease cleavage sequences.

8. The composition of claim 7, wherein the one or more protease cleavage sequences comprise a furin cleavage sequence, a matrix metalloprotease cleavage sequence, or a disintegrin and metalloprotease (ADAM) cleavage sequence.

9. The composition of claim 1, wherein the one or more epitopes are viral, bacterial, parasitic, or fungal epitopes.

10. The composition of claim 9, wherein:

the viral epitopes are one or more of coronavirus, vaccinia, Varicella zoster, Herpes zoster, rubella, hepatitis, influenza, measles, mumps, poliovirus, variola, rabies, dengue, Ebola, West Nile, yellow fever, or zika epitopes;

the bacterial epitopes are one or more of *Bordetella pertussis, Clostridium tetani, Chlamydia trachomatis, Corynebacterium diphtheriae, Hemophilus influenza, Neisseria meningitidis, Streptococcus, Vibrio cholera, Mycobacterium tuberculosis, Bacillus* Calmette-Guérin, *Salmonella, Escherichia coli, Legionella pneumophila, Rickettsia, Treponema pallidum pallidum, Bacillus anthracis, Clostridium botulinum*, or *Yersinia* epitopes; or the parasitic epitopes are one or more of *Entamoeba histolytica, Toxoplasma gondii, Trichinella, Trichomonas, Trypanosoma*, or *Plasmodium* epitopes.

11. The composition of claim 1, wherein at least one of the one or more epitopes is a childhood vaccine antigenic epitope.

12. The composition of claim 1, wherein the one or more peptides comprises at least two epitopes from one or more pathogens other than a Papillomaviridae antigenic peptides.

13. The composition of claim 1, wherein the proteoglycan expressed on tumor cells is heparin sulfate proteoglycan (HSPG), perlecan, hyalectan versican, glypican-3, small leucine-rich proteoglycans (SLRP), and/or biglycan.

14. The composition of claim 1, wherein the plurality of mutant Papillomaviridae L1 proteins do not form a T=7 capsid backbone.

15. The composition of claim 1, wherein said plurality of mutant Papillomaviridae L1 proteins are mouse mutant Papillomaviridae L1 proteins.

16. A composition, comprising:

a plurality of virus proteins, wherein each of said plurality of virus proteins comprises a mutated amino acid sequence of a Papillomaviridae L1 protein;

one or more peptides each comprising one or more epitopes from one or more pathogens other than a Papillomaviridae antigenic peptide, wherein an amino acid sequence of each of said plurality of mutant Papillomaviridae L1 proteins is SEQ ID NO:134, and is encoded by nucleic acid sequence SEQ ID NO:135 or 136, wherein the one or more peptides are attached to the plurality of virus proteins, and wherein said plurality of virus proteins spontaneously assemble to form an icosahedron or dodecahedron capsid having a triangulation number T equal to 1 that binds to proteoglycan expressed on tumor cells.

17. A method of treating, reducing the occurrence of, inhibiting the progression and/or metastasis of, a cancer in a subject in need thereof, which comprises administering to the subject a pharmaceutically effective amount of a composition comprising:

a plurality of virus proteins, wherein each of said plurality of virus proteins comprises a mutated amino acid sequence of a Papillomaviridae L1 protein;

one or more peptides each comprising one or more epitopes from one or more pathogens other than a Papillomaviridae antigenic peptide;

wherein the mutated amino acid sequence of the Papillomaviridae L1 protein comprises at least the following mutations with respect to the wild type L1 protein sequence: (a) a deletion of at least five amino acid residues from an amino-terminus, and (b) a deletion of at least ten amino acid residues from the helix four region, wherein the one or more peptides are attached to the plurality of virus proteins, and wherein said plurality of virus proteins spontaneously assemble to form an icosahedron or dodecahedron capsid having a triangulation number T equal to 1 that binds to proteoglycan expressed on tumor cells.

18. The method of claim 17, further comprising:

obtaining from the subject a tumor tissue sample; and identifying in the tumor tissue a sequence of one or more MHC molecules expressed by one or more tumor cells in the tumor tissue sample.

19. The method of claim 17, wherein the subject was previously infected or vaccinated against a pathogen, and wherein the one or more epitopes is an antigenic epitope of the pathogen.

20. The method of claim 17, wherein the one or more epitopes are capable of complexing with one or more MHC molecules expressed by a tumor cell in a tumor tissue sample obtained from the subject.

21. A process for producing the composition of claim 1, which comprises:

(a) transforming a prokaryotic cell with an expression vector encoding the L1 protein;

(b) culturing the transformed prokaryotic cell under conditions that promote expression of the L1 protein;

(c) lysing the transformed prokaryotic cells to release expressed L1 protein;

(d) separating cell debris from the expressed L1 protein and recovering the L1 protein as inclusion bodies;

(e) optionally washing the L1 protein inclusion bodies;

(f) solubilizing the L1 protein inclusion bodies;

(g) refolding the L1 protein; and (h) forming the icosahedron or dodecahedron capsid having a triangulation number T equal to 1 by incubating the refolded L1 protein in refolding buffer.

22. The process of claim 21, further comprising:

(i) conjugating in a conjugation buffer the one or more peptides to the assembled L1 protein by incubating the assembled L1 protein under reducing conditions in the presence of one or more peptides.

23. The process of claim 21, wherein the refolding buffer comprises a denaturant, a reducing agent, 250 to 500 mM of a salt, a non-ionic surfactant, a metal chelating agent, and a buffer of pH 7.5 to 8.5.

24. The process of claim 23, wherein the salt is present from 250 mM to 500 mM.

25. The process of claim 23, wherein the molar ratio of the one or more peptides to the L1 protein is at least 1:5.

26. The process of claim 21, further comprising removing denaturant from the refolding buffer but maintaining reducing agent when forming the icosahedron or dodecahedron capsid having a triangulation number T equal to 1.

* * * * *

SEQUENCE LISTING

<160> NUMBER OF SEQ ID NOS: 140

<210> SEQ ID NO 1
<211> LENGTH: 473
<212> TYPE: PRT
<213> ORGANISM: Human papillomavirus type 16
<220> FEATURE:
<221> NAME/KEY: SITE
<222> LOCATION: (1)..(473)
<223> OTHER INFORMATION: minor capsid protein L2

<400> SEQUENCE: 1

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190

Tyr Glu Glu Ile Pro Met Asp Thr Phe Ile Val Ser Thr Asn Pro Asn
        195                 200                 205

Thr Val Thr Ser Ser Thr Pro Ile Pro Gly Ser Arg Pro Val Ala Arg
210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
290                 295                 300

Arg Ile Gly Asn Lys Gln Thr Leu Arg Thr Arg Ser Gly Lys Ser Ile
305                 310                 315                 320

Gly Ala Lys Val His Tyr Tyr Tyr Asp Leu Ser Thr Ile Asp Pro Ala
                325                 330                 335

Glu Glu Ile Glu Leu Gln Thr Ile Thr Pro Ser Thr Tyr Thr Thr Thr
            340                 345                 350
```

```
Ser His Ala Ala Ser Pro Thr Ser Ile Asn Asn Gly Leu Tyr Asp Ile
        355                 360                 365

Tyr Ala Asp Asp Phe Ile Thr Asp Thr Ser Thr Thr Pro Val Pro Ser
370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
                420                 425                 430

Gly Ser Pro Gln Tyr Thr Ile Ile Ala Asp Ala Gly Asp Phe Tyr Leu
        435                 440                 445

His Pro Ser Tyr Tyr Met Leu Arg Lys Arg Arg Lys Arg Leu Pro Tyr
    450                 455                 460

Phe Phe Ser Asp Val Ser Leu Ala Ala
465                 470

<210> SEQ ID NO 2
<211> LENGTH: 538
<212> TYPE: PRT
<213> ORGANISM: Mus musculus papillomavirus type 1
<220> FEATURE:
<221> NAME/KEY: SITE
<222> LOCATION: (1)..(538)
<223> OTHER INFORMATION: mouse papillomavirus L2

<400> SEQUENCE: 2

Met Val Ser Ala Asp Arg Ser Arg Arg Val Lys Arg Asp Ser Ala Ser
1               5                   10                  15

Asn Leu Tyr Arg Gln Cys Gln Val Thr Gly Asn Cys Pro Pro Asp Val
            20                  25                  30

Val Asn Lys Val Glu Gly Asn Thr Leu Ala Asp Arg Ile Leu Lys Val
        35                  40                  45

Ile Ser Ser Ile Val Tyr Leu Gly Gly Leu Gly Ile Gly Thr Gly Arg
    50                  55                  60

Gly Ser Gly Gly Thr Thr Gly Tyr Gly Pro Ile Asn Ser Ala Gly Gly
65                  70                  75                  80

Arg Val Thr Gly Thr Gly Thr Val Met Arg Pro Gly Val Thr Val Glu
                85                  90                  95

Pro Ile Gly Pro Gly Asp Ile Val Thr Val Asp Ser Val Gly Pro Gly
            100                 105                 110

Asp Ser Ser Leu Ile Pro Leu Leu Glu Val Thr Pro Asp Val Pro Ile
        115                 120                 125

Asn Gly Gly Pro Glu Val Pro Ser Ser Gly Pro Asp Ile Ser Thr Val
    130                 135                 140

Asp Val Thr Ser Ser Ile Asp Pro Ile Ser Asp Leu Ser Val Thr Gly
145                 150                 155                 160

Thr Thr Ile Ser Asn Thr Asp Ser Ala Val Ile Asp Val Gln Pro Ser
                165                 170                 175

Pro Gly Pro Arg Arg Val Ile Ile Thr Arg Ser Asp Phe Asn Asn Pro
            180                 185                 190

Ser Tyr Val Ser Val Val His Pro Thr Gln Gly Leu Gly Glu Ser Gly
        195                 200                 205

Gly Val Ile Ser Gly Glu Ser Gly Gly Ile Ile Ser Ile His Glu
    210                 215                 220
```

```
Leu Asp Asn Thr Thr Val Ile Gly Ala Arg Pro Pro Glu Arg Ile
225                 230                 235                 240

Leu Asp Glu Val Pro Gly Pro Phe Glu Asp Ile Val Leu Asp Thr Phe
            245                 250                 255

Val Glu Ser Ser Gly Leu Ser Glu Phe Asp Ile Glu Gln Pro Leu Thr
            260                 265                 270

Ser Thr Pro Glu Gly Pro Leu Gln Arg Ala Ala Thr Arg Phe Arg Asp
        275                 280                 285

Leu Tyr Asn Arg Arg Val Gln Val Arg Val Ser Asn Pro Glu Ala
        290                 295                 300

Phe Leu Thr Gly Pro Arg Gln Ala Val Val Phe Glu Asn Pro Ala Phe
305                 310                 315                 320

Glu Pro Gly Ser Leu Asp Phe Glu Leu Pro Ala Ser Pro Val Ala
                325                 330                 335

Ala Pro Asp Pro Glu Tyr Thr Asp Val Val His Leu Gly Arg Gln Arg
                340                 345                 350

Phe Ser Glu Val Asn Arg Val Ile Arg Val Ser Arg Leu Gly Gln Arg
            355                 360                 365

Ala Ser Met Lys Thr Arg Ser Gly Leu Ile Ile Gly Gly Lys Val His
370                 375                 380

Phe Tyr Thr Asp Leu Ser Pro Val Ala Thr Asp Ile Glu Met His Thr
385                 390                 395                 400

Leu Gly Glu Ile Ser Gly Thr Glu Leu Ile Asp Gly Leu Gly Ser
                405                 410                 415

Ser Ser Val Ile Glu Phe Pro Arg Gly Val Glu Ser Val Glu Leu Pro
            420                 425                 430

Asp Gly Ser Asp Ser Val Asn Glu Leu Leu Asp Thr Asp Ser Ala Asp
        435                 440                 445

Phe Ser Ser Arg Leu Glu Leu Leu Ile Gly Asn Gly Thr Ser Arg
450                 455                 460

Phe Val Met Pro Asp Leu Val Glu Thr Leu Gly Pro Asp Met Phe Phe
465                 470                 475                 480

Pro Ser Ile Asp Ser Gly Thr Val Ile His His Pro Gln Asp Asn Tyr
            485                 490                 495

Val Pro Ile Ile Leu Pro Ala Ala Asp Leu Phe Pro Ala Ser Thr Val
            500                 505                 510

Ile Ser Val Asp Asp Asp Phe Ala Asp Phe Tyr Leu His Pro Ser Leu
            515                 520                 525

Arg Lys Arg Lys Arg Lys Tyr Arg Ile Tyr
530                 535

<210> SEQ ID NO 3
<211> LENGTH: 9
<212> TYPE: PRT
<213> ORGANISM: Cytomegalovirus sp.
<220> FEATURE:
<221> NAME/KEY: SITE
<222> LOCATION: (1)..(9)
<223> OTHER INFORMATION: Cytomegalovirus

<400> SEQUENCE: 3

Asn Leu Val Pro Met Val Ala Thr Val
1               5

<210> SEQ ID NO 4
<211> LENGTH: 9
<212> TYPE: PRT
```

```
<213> ORGANISM: Cytomegalovirus sp.
<220> FEATURE:
<221> NAME/KEY: SITE
<222> LOCATION: (1)..(9)
<223> OTHER INFORMATION: Chicken Pox (VZV)

<400> SEQUENCE: 4

Ser Leu Pro Arg Ser Arg Thr Pro Ile
1               5

<210> SEQ ID NO 5
<211> LENGTH: 9
<212> TYPE: PRT
<213> ORGANISM: Cytomegalovirus sp.
<220> FEATURE:
<221> NAME/KEY: SITE
<222> LOCATION: (1)..(9)
<223> OTHER INFORMATION: Chicken Pox (VZV)

<400> SEQUENCE: 5

Ser Ala Pro Leu Pro Ser Asn Arg Val
1               5

<210> SEQ ID NO 6
<211> LENGTH: 10
<212> TYPE: PRT
<213> ORGANISM: Cytomegalovirus sp.
<220> FEATURE:
<221> NAME/KEY: SITE
<222> LOCATION: (1)..(10)
<223> OTHER INFORMATION: Chicken Pox (VZV)

<400> SEQUENCE: 6

Gly Ser Ala Pro Leu Pro Ser Asn Arg Val
1               5                   10

<210> SEQ ID NO 7
<211> LENGTH: 9
<212> TYPE: PRT
<213> ORGANISM: Cytomegalovirus sp.
<220> FEATURE:
<221> NAME/KEY: SITE
<222> LOCATION: (1)..(9)
<223> OTHER INFORMATION: Chicken Pox (VZV)

<400> SEQUENCE: 7

Ala Leu Trp Ala Leu Pro His Ala Ala
1               5

<210> SEQ ID NO 8
<211> LENGTH: 9
<212> TYPE: PRT
<213> ORGANISM: Cytomegalovirus sp.
<220> FEATURE:
<221> NAME/KEY: SITE
<222> LOCATION: (1)..(9)
<223> OTHER INFORMATION: Shingles vaccines

<400> SEQUENCE: 8

Ser Leu Ser Gly Leu Tyr Val Phe Val
1               5

<210> SEQ ID NO 9
<211> LENGTH: 9
<212> TYPE: PRT
<213> ORGANISM: Cytomegalovirus sp.
<220> FEATURE:
<221> NAME/KEY: SITE
<222> LOCATION: (1)..(9)
```

-continued

```
<223> OTHER INFORMATION: Shingles vaccines

<400> SEQUENCE: 9

Tyr Leu Gly Val Tyr Ile Trp Asn Met
1               5

<210> SEQ ID NO 10
<211> LENGTH: 9
<212> TYPE: PRT
<213> ORGANISM: Cytomegalovirus sp.
<220> FEATURE:
<221> NAME/KEY: SITE
<222> LOCATION: (1)..(9)
<223> OTHER INFORMATION: Shingles vaccines

<400> SEQUENCE: 10

Lys Ile His Glu Ala Pro Phe Asp Leu
1               5

<210> SEQ ID NO 11
<211> LENGTH: 9
<212> TYPE: PRT
<213> ORGANISM: Cytomegalovirus sp.
<220> FEATURE:
<221> NAME/KEY: SITE
<222> LOCATION: (1)..(9)
<223> OTHER INFORMATION: Shingles vaccines

<400> SEQUENCE: 11

Leu Leu Cys Leu Val Ile Phe Leu Ile
1               5

<210> SEQ ID NO 12
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 12

Asp Leu Leu Leu Glu Trp Leu Tyr Val
1               5

<210> SEQ ID NO 13
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 13

Ser Met Tyr Tyr Ala Gly Leu Pro Val
1               5

<210> SEQ ID NO 14
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 14
```

```
Ile Leu His Asp Gly Gly Thr Thr Leu
1               5

<210> SEQ ID NO 15
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 15

Trp Leu Tyr Val Pro Ile Asp Pro Thr
1               5

<210> SEQ ID NO 16
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 16

Val Leu Met Gly Phe Gly Ile Ile Thr
1               5

<210> SEQ ID NO 17
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 17

Cys Leu Val Ile Phe Leu Ile Cys Thr
1               5

<210> SEQ ID NO 18
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 18

Lys Glu Ala Asp Gln Pro Trp Ile Val
1               5

<210> SEQ ID NO 19
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 19

Val Val Ser Thr Val Asp His Phe Val
1               5
```

```
<210> SEQ ID NO 20
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 20

Phe Leu Ile Cys Thr Ala Lys Arg Met
1               5

<210> SEQ ID NO 21
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 21

Val Leu Arg Thr Glu Lys Gln Tyr Leu
1               5

<210> SEQ ID NO 22
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 22

His Met Trp Asn Tyr His Ser His Val
1               5

<210> SEQ ID NO 23
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 23

Thr Val Asn Lys Pro Val Val Gly Val
1               5

<210> SEQ ID NO 24
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 24

Phe Val Val Tyr Phe Asn Gly His Val
1               5

<210> SEQ ID NO 25
<211> LENGTH: 9
<212> TYPE: PRT
<213> ORGANISM: Herpes zoster
```

```
<220> FEATURE:
<221> NAME/KEY: SITE
<222> LOCATION: (1)..(9)
<223> OTHER INFORMATION: Shingles vaccines

<400> SEQUENCE: 25

Trp Ile Val Val Asn Thr Ser Thr Leu
1               5

<210> SEQ ID NO 26
<211> LENGTH: 9
<212> TYPE: PRT
<213> ORGANISM: Herpes zoster
<220> FEATURE:
<221> NAME/KEY: SITE
<222> LOCATION: (1)..(9)
<223> OTHER INFORMATION: Shingles vaccines

<400> SEQUENCE: 26

Val Ala Tyr Thr Val Val Ser Thr Val
1               5

<210> SEQ ID NO 27
<211> LENGTH: 9
<212> TYPE: PRT
<213> ORGANISM: Measles morbillivirus
<220> FEATURE:
<221> NAME/KEY: SITE
<222> LOCATION: (1)..(9)
<223> OTHER INFORMATION: measles

<400> SEQUENCE: 27

Phe Met Tyr Met Ser Leu Leu Gly Val
1               5

<210> SEQ ID NO 28
<211> LENGTH: 9
<212> TYPE: PRT
<213> ORGANISM: Measles morbillivirus
<220> FEATURE:
<221> NAME/KEY: SITE
<222> LOCATION: (1)..(9)
<223> OTHER INFORMATION: measles

<400> SEQUENCE: 28

Ser Leu Trp Gly Ser Leu Leu Met Leu
1               5

<210> SEQ ID NO 29
<211> LENGTH: 10
<212> TYPE: PRT
<213> ORGANISM: Measles morbillivirus
<220> FEATURE:
<221> NAME/KEY: SITE
<222> LOCATION: (1)..(10)
<223> OTHER INFORMATION: measles

<400> SEQUENCE: 29

Leu Leu Ala Val Ile Phe Val Met Phe Leu
1               5                   10

<210> SEQ ID NO 30
<211> LENGTH: 10
<212> TYPE: PRT
<213> ORGANISM: Measles morbillivirus
<220> FEATURE:
<221> NAME/KEY: SITE
<222> LOCATION: (1)..(10)
<223> OTHER INFORMATION: measles
```

```
<400> SEQUENCE: 30

Ser Met Tyr Arg Val Phe Glu Val Gly Val
1               5                   10

<210> SEQ ID NO 31
<211> LENGTH: 10
<212> TYPE: PRT
<213> ORGANISM: Measles morbillivirus
<220> FEATURE:
<221> NAME/KEY: SITE
<222> LOCATION: (1)..(10)
<223> OTHER INFORMATION: measles

<400> SEQUENCE: 31

Ile Leu Pro Gly Gln Asp Leu Gln Tyr Val
1               5                   10

<210> SEQ ID NO 32
<211> LENGTH: 9
<212> TYPE: PRT
<213> ORGANISM: Measles morbillivirus
<220> FEATURE:
<221> NAME/KEY: SITE
<222> LOCATION: (1)..(9)
<223> OTHER INFORMATION: measles

<400> SEQUENCE: 32

Lys Leu Trp Cys Arg His Phe Cys Val
1               5

<210> SEQ ID NO 33
<211> LENGTH: 10
<212> TYPE: PRT
<213> ORGANISM: Measles morbillivirus
<220> FEATURE:
<221> NAME/KEY: SITE
<222> LOCATION: (1)..(10)
<223> OTHER INFORMATION: measles

<400> SEQUENCE: 33

Lys Leu Trp Cys Arg His Phe Cys Val Leu
1               5                   10

<210> SEQ ID NO 34
<211> LENGTH: 10
<212> TYPE: PRT
<213> ORGANISM: Measles morbillivirus
<220> FEATURE:
<221> NAME/KEY: SITE
<222> LOCATION: (1)..(10)
<223> OTHER INFORMATION: measles

<400> SEQUENCE: 34

Arg Leu Ser Asp Asn Gly Tyr Tyr Thr Val
1               5                   10

<210> SEQ ID NO 35
<211> LENGTH: 9
<212> TYPE: PRT
<213> ORGANISM: Measles morbillivirus
<220> FEATURE:
<221> NAME/KEY: SITE
<222> LOCATION: (1)..(9)
<223> OTHER INFORMATION: measles

<400> SEQUENCE: 35

Lys Leu Leu Arg Tyr Tyr Thr Glu Ile
```

-continued 1 5

<210> SEQ ID NO 36
<211> LENGTH: 9
<212> TYPE: PRT
<213> ORGANISM: Measles morbillivirus
<220> FEATURE:
<221> NAME/KEY: SITE
<222> LOCATION: (1)..(9)
<223> OTHER INFORMATION: measles

<400> SEQUENCE: 36

Lys Leu Trp Glu Ser Pro Gln Glu Ile
1 5

<210> SEQ ID NO 37
<211> LENGTH: 9
<212> TYPE: PRT
<213> ORGANISM: Measles morbillivirus
<220> FEATURE:
<221> NAME/KEY: SITE
<222> LOCATION: (1)..(9)
<223> OTHER INFORMATION: measles

<400> SEQUENCE: 37

Arg Leu Leu Asp Arg Leu Val Arg Leu
1 5

<210> SEQ ID NO 38
<211> LENGTH: 9
<212> TYPE: PRT
<213> ORGANISM: Measles morbillivirus
<220> FEATURE:
<221> NAME/KEY: SITE
<222> LOCATION: (1)..(9)
<223> OTHER INFORMATION: measles

<400> SEQUENCE: 38

Lys Leu Met Pro Asn Ile Thr Leu Leu
1 5

<210> SEQ ID NO 39
<211> LENGTH: 9
<212> TYPE: PRT
<213> ORGANISM: Measles morbillivirus
<220> FEATURE:
<221> NAME/KEY: SITE
<222> LOCATION: (1)..(9)
<223> OTHER INFORMATION: measles

<400> SEQUENCE: 39

Thr Leu Leu Asn Asn Cys Thr Arg Val
1 5

<210> SEQ ID NO 40
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 40

Glu Met Leu Thr Leu Ala Thr Trp Val
1 5

<210> SEQ ID NO 41

```
<211> LENGTH: 10
<212> TYPE: PRT
<213> ORGANISM: Hepatitis B virus
<220> FEATURE:
<221> NAME/KEY: SITE
<222> LOCATION: (1)..(10)
<223> OTHER INFORMATION: Hep B

<400> SEQUENCE: 41

Phe Leu Pro Ser Asp Phe Phe Pro Ser Val
1               5                   10

<210> SEQ ID NO 42
<211> LENGTH: 10
<212> TYPE: PRT
<213> ORGANISM: Hepatitis B virus
<220> FEATURE:
<221> NAME/KEY: SITE
<222> LOCATION: (1)..(10)
<223> OTHER INFORMATION: Hep B

<400> SEQUENCE: 42

Phe Leu Pro Ala Asp Phe Phe Pro Ser Val
1               5                   10

<210> SEQ ID NO 43
<211> LENGTH: 10
<212> TYPE: PRT
<213> ORGANISM: Hepatitis B virus
<220> FEATURE:
<221> NAME/KEY: SITE
<222> LOCATION: (1)..(10)
<223> OTHER INFORMATION: Hep B

<400> SEQUENCE: 43

Phe Leu Pro Ser Asp Phe Phe Pro Ser Ile
1               5                   10

<210> SEQ ID NO 44
<211> LENGTH: 8
<212> TYPE: PRT
<213> ORGANISM: Hepatitis B virus
<220> FEATURE:
<221> NAME/KEY: SITE
<222> LOCATION: (1)..(8)
<223> OTHER INFORMATION: Hep B

<400> SEQUENCE: 44

Trp Leu Ser Leu Leu Val Pro Phe
1               5

<210> SEQ ID NO 45
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 45

Phe Leu Leu Thr Arg Ile Leu Thr Ile
1               5

<210> SEQ ID NO 46
<211> LENGTH: 9
<212> TYPE: PRT
<213> ORGANISM: Hepatitis B virus
<220> FEATURE:
```

```
<221> NAME/KEY: SITE
<222> LOCATION: (1)..(9)
<223> OTHER INFORMATION: Hep B

<400> SEQUENCE: 46

Phe Leu Leu Thr Arg Ile Leu Thr Leu
1               5

<210> SEQ ID NO 47
<211> LENGTH: 10
<212> TYPE: PRT
<213> ORGANISM: Hepatitis B virus
<220> FEATURE:
<221> NAME/KEY: SITE
<222> LOCATION: (1)..(10)
<223> OTHER INFORMATION: Hep B

<400> SEQUENCE: 47

Gly Leu Ser Pro Thr Val Trp Leu Ser Val
1               5                   10

<210> SEQ ID NO 48
<211> LENGTH: 10
<212> TYPE: PRT
<213> ORGANISM: Hepatitis B virus
<220> FEATURE:
<221> NAME/KEY: SITE
<222> LOCATION: (1)..(10)
<223> OTHER INFORMATION: Hep B

<400> SEQUENCE: 48

Leu Leu Asp Tyr Gln Gly Met Leu Pro Val
1               5                   10

<210> SEQ ID NO 49
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 49

Leu Leu Cys Leu Ile Phe Leu Leu Val
1               5

<210> SEQ ID NO 50
<211> LENGTH: 10
<212> TYPE: PRT
<213> ORGANISM: Hepatitis B virus
<220> FEATURE:
<221> NAME/KEY: SITE
<222> LOCATION: (1)..(10)
<223> OTHER INFORMATION: Hep B

<400> SEQUENCE: 50

Ser Ile Val Ser Pro Phe Ile Pro Leu Leu
1               5                   10

<210> SEQ ID NO 51
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B
```

```
<400> SEQUENCE: 51

Phe Leu Leu Thr Lys Ile Leu Thr Ile
1               5

<210> SEQ ID NO 52
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 52

Ile Leu Ser Pro Phe Leu Pro Leu Leu
1               5

<210> SEQ ID NO 53
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 53

Phe Leu Leu Ser Leu Gly Ile His Leu
1               5

<210> SEQ ID NO 54
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 54

Gly Leu Ser Arg Tyr Val Ala Arg Leu
1               5

<210> SEQ ID NO 55
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 55

Ser Leu Tyr Ala Asp Ser Pro Ser Val
1               5

<210> SEQ ID NO 56
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 56

Tyr Met Asp Asp Val Val Leu Gly Ala
1               5
```

<210> SEQ ID NO 57
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 57

Ala Leu Met Pro Leu Tyr Ala Cys Ile
1               5

<210> SEQ ID NO 58
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 58

Val Leu His Lys Arg Thr Leu Gly Leu
1               5

<210> SEQ ID NO 59
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 59

Cys Leu Phe Lys Asp Trp Glu Glu Leu
1               5

<210> SEQ ID NO 60
<211> LENGTH: 11
<212> TYPE: PRT
<213> ORGANISM: Hepatitis B virus
<220> FEATURE:
<221> NAME/KEY: SITE
<222> LOCATION: (1)..(11)
<223> OTHER INFORMATION: Hep B

<400> SEQUENCE: 60

Ser Thr Leu Pro Glu Thr Thr Val Val Arg Arg
1               5                   10

<210> SEQ ID NO 61
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 61

Glu Tyr Leu Val Ser Phe Gly Val Trp
1               5

<210> SEQ ID NO 62
<211> LENGTH: 9

```
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 62

Phe Phe Pro Ser Ile Arg Asp Leu Leu
1               5

<210> SEQ ID NO 63
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 63

Ser Trp Leu Ser Leu Leu Val Pro Phe
1               5

<210> SEQ ID NO 64
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 64

Lys Tyr Thr Ser Phe Pro Trp Leu Leu
1               5

<210> SEQ ID NO 65
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 65

His Leu Ser Leu Arg Gly Leu Phe Val
1               5

<210> SEQ ID NO 66
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 66

Cys Leu Phe Lys Asp Trp Glu Glu Leu
1               5

<210> SEQ ID NO 67
<211> LENGTH: 9
<212> TYPE: PRT
<213> ORGANISM: Hepatitis B virus
<220> FEATURE:
<221> NAME/KEY: SITE
```

```
<222> LOCATION: (1)..(9)
<223> OTHER INFORMATION: Hep B

<400> SEQUENCE: 67

Leu Pro Ser Asp Phe Phe Pro Ser Val
1               5

<210> SEQ ID NO 68
<211> LENGTH: 9
<212> TYPE: PRT
<213> ORGANISM: Influenza virus
<220> FEATURE:
<221> NAME/KEY: SITE
<222> LOCATION: (1)..(9)
<223> OTHER INFORMATION: Influenza

<400> SEQUENCE: 68

Gly Ile Leu Gly Phe Val Phe Thr Leu
1               5

<210> SEQ ID NO 69
<211> LENGTH: 21
<212> TYPE: PRT
<213> ORGANISM: Influenza virus
<220> FEATURE:
<221> NAME/KEY: SITE
<222> LOCATION: (1)..(21)
<223> OTHER INFORMATION: Influenza

<400> SEQUENCE: 69

Ile Leu Gly Phe Val Phe Thr Leu Thr Val Pro Ser Glu Arg Gly Leu
1               5                   10                  15

Gln Arg Arg Arg Phe
            20

<210> SEQ ID NO 70
<211> LENGTH: 17
<212> TYPE: PRT
<213> ORGANISM: Influenza virus
<220> FEATURE:
<221> NAME/KEY: SITE
<222> LOCATION: (1)..(17)
<223> OTHER INFORMATION: Influenza

<400> SEQUENCE: 70

Leu Ile Arg His Glu Asn Arg Met Val Leu Ala Ser Thr Thr Ala Lys
1               5                   10                  15

Ala

<210> SEQ ID NO 71
<211> LENGTH: 14
<212> TYPE: PRT
<213> ORGANISM: Influenza virus
<220> FEATURE:
<221> NAME/KEY: SITE
<222> LOCATION: (1)..(14)
<223> OTHER INFORMATION: Influenza

<400> SEQUENCE: 71

Leu Gln Ala Tyr Gln Lys Arg Met Gly Val Gln Met Gln Arg
1               5                   10

<210> SEQ ID NO 72
<211> LENGTH: 11
<212> TYPE: PRT
<213> ORGANISM: Measles morbillivirus
<220> FEATURE:
```

```
<221> NAME/KEY: SITE
<222> LOCATION: (1)..(11)
<223> OTHER INFORMATION: Measles

<400> SEQUENCE: 72

Tyr Val Tyr Asp His Ser Gly Glu Ala Val Lys
1               5                   10

<210> SEQ ID NO 73
<211> LENGTH: 9
<212> TYPE: PRT
<213> ORGANISM: Hepatitis B virus
<220> FEATURE:
<221> NAME/KEY: SITE
<222> LOCATION: (1)..(9)
<223> OTHER INFORMATION: Hep B

<400> SEQUENCE: 73

Trp Leu Ser Leu Leu Val Pro Phe Val
1               5

<210> SEQ ID NO 74
<211> LENGTH: 12
<212> TYPE: PRT
<213> ORGANISM: Influenza virus
<220> FEATURE:
<221> NAME/KEY: SITE
<222> LOCATION: (1)..(1)
<223> OTHER INFORMATION: Lys may or may not be present
<220> FEATURE:
<221> NAME/KEY: SITE
<222> LOCATION: (1)..(12)
<223> OTHER INFORMATION: Influenza
<220> FEATURE:
<221> NAME/KEY: SITE
<222> LOCATION: (11)..(11)
<223> OTHER INFORMATION: Thr may or may not be present
<220> FEATURE:
<221> NAME/KEY: SITE
<222> LOCATION: (12)..(12)
<223> OTHER INFORMATION: Val may or may not be present

<400> SEQUENCE: 74

Lys Gly Ile Leu Gly Phe Val Phe Thr Leu Thr Val
1               5                   10

<210> SEQ ID NO 75
<211> LENGTH: 14
<212> TYPE: PRT
<213> ORGANISM: Influenza virus
<220> FEATURE:
<221> NAME/KEY: SITE
<222> LOCATION: (1)..(14)
<223> OTHER INFORMATION: Influenza

<400> SEQUENCE: 75

Lys Leu Ser Thr Arg Gly Val Gln Ile Ala Ser Asn Glu Asn
1               5                   10

<210> SEQ ID NO 76
<211> LENGTH: 17
<212> TYPE: PRT
<213> ORGANISM: Influenza virus
<220> FEATURE:
<221> NAME/KEY: SITE
<222> LOCATION: (1)..(17)
<223> OTHER INFORMATION: Influenza

<400> SEQUENCE: 76

Arg Gly Leu Gln Arg Arg Arg Phe Val Gln Asn Ala Leu Asn Gly Asn
```

-continued

```
1               5                   10                  15

Gly

<210> SEQ ID NO 77
<211> LENGTH: 9
<212> TYPE: PRT
<213> ORGANISM: Influenza virus
<220> FEATURE:
<221> NAME/KEY: SITE
<222> LOCATION: (1)..(9)
<223> OTHER INFORMATION: Influenza

<400> SEQUENCE: 77

Phe Met Tyr Ser Asp Phe His Phe Ile
1               5

<210> SEQ ID NO 78
<211> LENGTH: 18
<212> TYPE: PRT
<213> ORGANISM: Enterovirus C
<220> FEATURE:
<221> NAME/KEY: SITE
<222> LOCATION: (1)..(18)
<223> OTHER INFORMATION: Poliovirus

<400> SEQUENCE: 78

Val Ala Ile Ile Glu Val Asp Asn Glu Gln Pro Thr Thr Arg Ala Gln
1               5                   10                  15

Lys Leu

<210> SEQ ID NO 79
<211> LENGTH: 39
<212> TYPE: PRT
<213> ORGANISM: Enterovirus C
<220> FEATURE:
<221> NAME/KEY: SITE
<222> LOCATION: (1)..(39)
<223> OTHER INFORMATION: Poliovirus

<400> SEQUENCE: 79

Gly Ala Cys Val Ala Ile Ile Glu Val Asp Asn Glu Gln Pro Thr Thr
1               5                   10                  15

Arg Ala Gln Lys Leu Phe Ala Met Trp Arg Ile Thr Tyr Lys Asp Thr
            20                  25                  30

Val Gln Leu Arg Arg Lys Leu
        35

<210> SEQ ID NO 80
<211> LENGTH: 9
<212> TYPE: PRT
<213> ORGANISM: Human herpesvirus 4
<220> FEATURE:
<221> NAME/KEY: SITE
<222> LOCATION: (1)..(9)
<223> OTHER INFORMATION: EBV

<400> SEQUENCE: 80

Ser Val Arg Asp Arg Leu Ala Arg Leu
1               5

<210> SEQ ID NO 81
<211> LENGTH: 10
<212> TYPE: PRT
<213> ORGANISM: Human herpesvirus 4
<220> FEATURE:
<221> NAME/KEY: SITE
```

```
<222> LOCATION: (1)..(10)
<223> OTHER INFORMATION: EBV

<400> SEQUENCE: 81

Leu Leu Asp Arg Val Arg Phe Met Gly Val
1               5                   10

<210> SEQ ID NO 82
<211> LENGTH: 9
<212> TYPE: PRT
<213> ORGANISM: Human herpesvirus 4
<220> FEATURE:
<221> NAME/KEY: SITE
<222> LOCATION: (1)..(9)
<223> OTHER INFORMATION: EBV

<400> SEQUENCE: 82

Cys Leu Gly Gly Leu Leu Thr Met Val
1               5

<210> SEQ ID NO 83
<211> LENGTH: 9
<212> TYPE: PRT
<213> ORGANISM: Human herpesvirus 4
<220> FEATURE:
<221> NAME/KEY: SITE
<222> LOCATION: (1)..(9)
<223> OTHER INFORMATION: EBV

<400> SEQUENCE: 83

Gly Leu Cys Thr Leu Val Ala Met Leu
1               5

<210> SEQ ID NO 84
<211> LENGTH: 12
<212> TYPE: PRT
<213> ORGANISM: Cytomegalovirus sp.
<220> FEATURE:
<221> NAME/KEY: SITE
<222> LOCATION: (1)..(12)
<223> OTHER INFORMATION: Cytomegalovirus

<400> SEQUENCE: 84

Ser Val Leu Gly Pro Ile Ser Gly His Val Leu Lys
1               5                   10

<210> SEQ ID NO 85
<211> LENGTH: 11
<212> TYPE: PRT
<213> ORGANISM: Cytomegalovirus sp.
<220> FEATURE:
<221> NAME/KEY: SITE
<222> LOCATION: (1)..(11)
<223> OTHER INFORMATION: Cytomegalovirus

<400> SEQUENCE: 85

Arg Pro His Glu Arg Asn Gly Phe Thr Val Leu
1               5                   10

<210> SEQ ID NO 86
<211> LENGTH: 11
<212> TYPE: PRT
<213> ORGANISM: Cytomegalovirus sp.
<220> FEATURE:
<221> NAME/KEY: SITE
<222> LOCATION: (1)..(11)
<223> OTHER INFORMATION: Cytomegalovirus

<400> SEQUENCE: 86
```

```
Phe Thr Ser Gln Tyr Arg Ile Gln Gly Lys Leu
1               5                   10

<210> SEQ ID NO 87
<211> LENGTH: 11
<212> TYPE: PRT
<213> ORGANISM: Cytomegalovirus sp.
<220> FEATURE:
<221> NAME/KEY: SITE
<222> LOCATION: (1)..(11)
<223> OTHER INFORMATION: Cytomegalovirus

<400> SEQUENCE: 87

Tyr Ser Glu His Pro Thr Phe Thr Ser Gln Tyr
1               5                   10

<210> SEQ ID NO 88
<211> LENGTH: 10
<212> TYPE: PRT
<213> ORGANISM: Cytomegalovirus sp.
<220> FEATURE:
<221> NAME/KEY: SITE
<222> LOCATION: (1)..(10)
<223> OTHER INFORMATION: Cytomegalovirus

<400> SEQUENCE: 88

Glu Phe Phe Trp Asp Ala Asn Asp Ile Tyr
1               5                   10

<210> SEQ ID NO 89
<211> LENGTH: 4
<212> TYPE: PRT
<213> ORGANISM: Artificial Sequence
<220> FEATURE:
<223> OTHER INFORMATION: Synthetic: cleavage sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: SITE
<222> LOCATION: (3)..(3)
<223> OTHER INFORMATION: X is R or K

<400> SEQUENCE: 89

Arg Xaa Xaa Arg
1

<210> SEQ ID NO 90
<211> LENGTH: 11
<212> TYPE: PRT
<213> ORGANISM: Cytomegalovirus sp.
<220> FEATURE:
<221> NAME/KEY: SITE
<222> LOCATION: (1)..(11)
<223> OTHER INFORMATION: Cytomegalovirus

<400> SEQUENCE: 90

Thr Thr Val Tyr Pro Pro Ser Ser Thr Ala Lys
1               5                   10

<210> SEQ ID NO 91
<211> LENGTH: 11
<212> TYPE: PRT
<213> ORGANISM: Cytomegalovirus sp.
<220> FEATURE:
<221> NAME/KEY: SITE
<222> LOCATION: (1)..(11)
<223> OTHER INFORMATION: Cytomegalovirus
```

<400> SEQUENCE: 91

Phe Val Phe Pro Thr Lys Asp Val Ala Leu Arg
1               5                   10

<210> SEQ ID NO 92
<211> LENGTH: 11
<212> TYPE: PRT
<213> ORGANISM: Cytomegalovirus sp.
<220> FEATURE:
<221> NAME/KEY: SITE
<222> LOCATION: (1)..(11)
<223> OTHER INFORMATION: Cytomegalovirus

<400> SEQUENCE: 92

Gln Thr Val Thr Ser Thr Pro Val Gln Gly Arg
1               5                   10

<210> SEQ ID NO 93
<211> LENGTH: 13
<212> TYPE: PRT
<213> ORGANISM: Cytomegalovirus sp.
<220> FEATURE:
<221> NAME/KEY: SITE
<222> LOCATION: (1)..(13)
<223> OTHER INFORMATION: Cytomegalovirus

<400> SEQUENCE: 93

Pro Thr Phe Thr Ser Gln Tyr Arg Ile Gln Gly Lys Leu
1               5                   10

<210> SEQ ID NO 94
<211> LENGTH: 8
<212> TYPE: PRT
<213> ORGANISM: Cytomegalovirus sp.
<220> FEATURE:
<221> NAME/KEY: SITE
<222> LOCATION: (1)..(8)
<223> OTHER INFORMATION: Cytomegalovirus

<400> SEQUENCE: 94

Phe Pro Thr Lys Asp Val Ala Leu
1               5

<210> SEQ ID NO 95
<211> LENGTH: 8
<212> TYPE: PRT
<213> ORGANISM: Mus musculus
<220> FEATURE:
<221> NAME/KEY: SITE
<222> LOCATION: (1)..(8)
<223> OTHER INFORMATION: Mus musculus

<400> SEQUENCE: 95

Ser Ile Ile Asn Phe Glu Lys Leu
1               5

<210> SEQ ID NO 96
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: Mus musculus

<400> SEQUENCE: 96

Arg Ala His Tyr Asn Ile Val Thr Phe

```
1               5

<210> SEQ ID NO 97
<211> LENGTH: 8
<212> TYPE: PRT
<213> ORGANISM: Mus musculus
<220> FEATURE:
<221> NAME/KEY: SITE
<222> LOCATION: (1)..(8)
<223> OTHER INFORMATION: Mus musculus

<400> SEQUENCE: 97

Ser Ser Pro Pro Met Phe Arg Val
1               5

<210> SEQ ID NO 98
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 98

Lys Leu Trp Ala Gln Cys Val Gln Leu
1               5

<210> SEQ ID NO 99
<211> LENGTH: 10
<212> TYPE: PRT
<213> ORGANISM: Severe acute respiratory syndrome coronavirus 2
<220> FEATURE:
<221> NAME/KEY: SITE
<222> LOCATION: (1)..(10)
<223> OTHER INFORMATION: SARS-CoV-2

<400> SEQUENCE: 99

Lys Leu Pro Asp Asp Phe Thr Gly Cys Val
1               5                   10

<210> SEQ ID NO 100
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 100

Tyr Leu Gln Pro Arg Thr Phe Leu Leu
1               5

<210> SEQ ID NO 101
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 101

Leu Leu Tyr Asp Ala Asn Tyr Phe Leu
1               5

<210> SEQ ID NO 102
```

```
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 102

Ala Leu Trp Glu Ile Gln Gln Val Val
1               5

<210> SEQ ID NO 103
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 103

Leu Leu Leu Asp Arg Leu Asn Gln Leu
1               5

<210> SEQ ID NO 104
<211> LENGTH: 11
<212> TYPE: PRT
<213> ORGANISM: Severe acute respiratory syndrome coronavirus 2
<220> FEATURE:
<221> NAME/KEY: SITE
<222> LOCATION: (1)..(11)
<223> OTHER INFORMATION: SARS-CoV-2

<400> SEQUENCE: 104

Tyr Leu Phe Asp Glu Ser Gly Glu Phe Lys Leu
1               5                   10

<210> SEQ ID NO 105
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 105

Phe Thr Ser Asp Tyr Tyr Gln Leu Tyr
1               5

<210> SEQ ID NO 106
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 106

Pro Thr Asp Asn Tyr Ile Thr Thr Tyr
1               5

<210> SEQ ID NO 107
<211> LENGTH: 9
<212> TYPE: PRT
<213> ORGANISM: Severe acute respiratory syndrome coronavirus 2
<220> FEATURE:
```

```
<221> NAME/KEY: SITE
<222> LOCATION: (1)..(9)
<223> OTHER INFORMATION: SARS-CoV-2

<400> SEQUENCE: 107

Ala Thr Ser Arg Thr Leu Ser Tyr Tyr
1               5

<210> SEQ ID NO 108
<211> LENGTH: 10
<212> TYPE: PRT
<213> ORGANISM: Severe acute respiratory syndrome coronavirus 2
<220> FEATURE:
<221> NAME/KEY: SITE
<222> LOCATION: (1)..(10)
<223> OTHER INFORMATION: SARS-CoV-2

<400> SEQUENCE: 108

Cys Thr Asp Asp Asn Ala Leu Ala Tyr Tyr
1               5                   10

<210> SEQ ID NO 109
<211> LENGTH: 10
<212> TYPE: PRT
<213> ORGANISM: Severe acute respiratory syndrome coronavirus 2
<220> FEATURE:
<221> NAME/KEY: SITE
<222> LOCATION: (1)..(10)
<223> OTHER INFORMATION: SARS-CoV-2

<400> SEQUENCE: 109

Asn Thr Cys Asp Gly Thr Thr Phe Thr Tyr
1               5                   10

<210> SEQ ID NO 110
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 110

Asp Thr Asp Phe Val Asn Glu Phe Tyr
1               5

<210> SEQ ID NO 111
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 111

Gly Thr Asp Leu Glu Gly Asn Phe Tyr
1               5

<210> SEQ ID NO 112
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2
```

```
<400> SEQUENCE: 112

Lys Thr Phe Pro Pro Thr Glu Pro Lys
1               5

<210> SEQ ID NO 113
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 113

Lys Cys Tyr Gly Val Ser Pro Thr Lys
1               5

<210> SEQ ID NO 114
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 114

Val Thr Asn Asn Thr Phe Thr Leu Lys
1               5

<210> SEQ ID NO 115
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 115

Lys Thr Ile Gln Pro Arg Val Glu Lys
1               5

<210> SEQ ID NO 116
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 116

Lys Thr Phe Pro Pro Thr Glu Pro Lys
1               5

<210> SEQ ID NO 117
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 117

Val Thr Asp Thr Pro Lys Gly Pro Lys
1               5
```

<210> SEQ ID NO 118
<211> LENGTH: 10
<212> TYPE: PRT
<213> ORGANISM: Severe acute respiratory syndrome coronavirus 2
<220> FEATURE:
<221> NAME/KEY: SITE
<222> LOCATION: (1)..(10)
<223> OTHER INFORMATION: SARS-CoV-2

<400> SEQUENCE: 118

Ala Thr Glu Gly Ala Leu Asn Thr Pro Lys
1               5                   10

<210> SEQ ID NO 119
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 119

Ala Ser Ala Phe Phe Gly Met Ser Arg
1               5

<210> SEQ ID NO 120
<211> LENGTH: 10
<212> TYPE: PRT
<213> ORGANISM: Severe acute respiratory syndrome coronavirus 2
<220> FEATURE:
<221> NAME/KEY: SITE
<222> LOCATION: (1)..(10)
<223> OTHER INFORMATION: SARS-CoV-2

<400> SEQUENCE: 120

Ala Ser Arg Thr Leu Ser Tyr Tyr Lys
1               5                   10

<210> SEQ ID NO 121
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 121

Gln Tyr Ile Lys Trp Pro Trp Tyr Ile
1               5

<210> SEQ ID NO 122
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 122

Val Tyr Phe Leu Gln Ser Ile Asn Phe
1               5

<210> SEQ ID NO 123
<211> LENGTH: 9

<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 123

Val Tyr Ile Gly Asp Pro Ala Gln Leu
1               5

<210> SEQ ID NO 124
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 124

Ser Pro Arg Trp Tyr Phe Tyr Tyr Leu
1               5

<210> SEQ ID NO 125
<211> LENGTH: 8
<212> TYPE: PRT
<213> ORGANISM: Severe acute respiratory syndrome coronavirus 2
<220> FEATURE:
<221> NAME/KEY: SITE
<222> LOCATION: (1)..(8)
<223> OTHER INFORMATION: SARS-CoV-2

<400> SEQUENCE: 125

Arg Pro Asp Thr Arg Tyr Val Leu
1               5

<210> SEQ ID NO 126
<211> LENGTH: 9
<212> TYPE: PRT
<213> ORGANISM: Severe acute respiratory syndrome coronavirus 2
<220> FEATURE:
<221> NAME/KEY: SITE
<222> LOCATION: (1)..(9)
<223> OTHER INFORMATION: SARS-CoV-2

<400> SEQUENCE: 126

Ile Pro Arg Arg Asn Val Ala Thr Leu
1               5

<210> SEQ ID NO 127
<211> LENGTH: 509
<212> TYPE: PRT
<213> ORGANISM: Mus musculus
<220> FEATURE:
<221> NAME/KEY: SITE
<222> LOCATION: (1)..(509)
<223> OTHER INFORMATION: Mus musculus

<400> SEQUENCE: 127

Met Ala Met Trp Thr Pro Gln Thr Gly Lys Leu Tyr Leu Pro Pro Thr
1               5                   10                  15

Thr Pro Val Ala Lys Val Gln Ser Thr Asp Glu Tyr Val Tyr Pro Thr
            20                  25                  30

Ser Leu Phe Cys His Ala His Thr Asp Arg Leu Leu Thr Val Gly His
        35                  40                  45

Pro Phe Phe Ser Val Ile Asp Asn Asp Lys Val Thr Val Pro Lys Val

-continued

```
                50                   55                   60
    Ser Gly Asn Gln Tyr Arg Val Phe Arg Leu Lys Phe Pro Asp Pro Asn
     65                   70                   75                   80

Lys Phe Ala Leu Pro Gln Lys Asp Phe Tyr Asp Pro Glu Lys Glu Arg
                     85                   90                   95

Leu Val Trp Arg Leu Arg Gly Leu Glu Ile Gly Arg Gly Gly Pro Leu
                    100                  105                  110

Gly Ile Gly Thr Thr Gly His Pro Leu Phe Asn Lys Leu Gly Asp Thr
                    115                  120                  125

Glu Asn Pro Asn Lys Tyr Gln Gln Gly Ser Lys Asp Asn Arg Gln Asn
                    130                  135                  140

Thr Ser Met Asp Pro Lys Gln Thr Gln Leu Phe Ile Val Gly Cys Glu
    145                  150                  155                  160

Pro Pro Thr Gly Glu His Trp Asp Val Ala Lys Pro Cys Gly Ala Leu
                    165                  170                  175

Glu Lys Gly Asp Cys Pro Pro Ile Gln Leu Val Asn Ser Val Ile Glu
                    180                  185                  190

Asp Gly Asp Met Cys Asp Ile Gly Phe Gly Asn Met Asn Phe Lys Glu
                    195                  200                  205

Leu Gln Gln Asp Arg Ser Gly Val Pro Leu Asp Ile Val Ser Thr Arg
                    210                  215                  220

Cys Lys Trp Pro Asp Phe Leu Lys Met Thr Asn Glu Ala Tyr Gly Asp
    225                  230                  235                  240

Lys Met Phe Phe Phe Gly Arg Arg Glu Gln Val Tyr Ala Arg His Phe
                    245                  250                  255

Phe Thr Arg Asn Gly Ser Val Gly Glu Pro Ile Pro Asn Ser Val Ser
                    260                  265                  270

Pro Ser Asp Phe Tyr Tyr Ala Pro Asp Ser Thr Gln Asp Gln Lys Thr
                    275                  280                  285

Leu Ala Pro Ser Val Tyr Phe Gly Thr Pro Ser Gly Ser Leu Val Ser
                    290                  295                  300

Ser Asp Gly Gln Leu Phe Asn Arg Pro Phe Trp Leu Gln Arg Ala Gln
    305                  310                  315                  320

Gly Asn Asn Asn Gly Val Cys Trp His Asn Glu Leu Phe Val Thr Val
                    325                  330                  335

Val Asp Asn Thr Arg Asn Thr Asn Phe Thr Ile Ser Gln Gln Thr Asn
                    340                  345                  350

Thr Pro Asn Pro Asp Thr Tyr Asp Ser Thr Asn Phe Lys Asn Tyr Leu
                    355                  360                  365

Arg His Val Glu Gln Phe Glu Leu Ser Leu Ile Ala Gln Leu Cys Lys
                    370                  375                  380

Val Pro Leu Asp Pro Gly Val Leu Ala His Ile Asn Thr Met Asn Pro
    385                  390                  395                  400

Thr Ile Leu Glu Asn Trp Asn Leu Gly Phe Val Pro Pro Gln Gln
                    405                  410                  415

Ser Ile Ser Asp Asp Tyr Arg Tyr Ile Thr Ser Ser Ala Thr Arg Cys
                    420                  425                  430

Pro Asp Gln Asn Pro Lys Glu Arg Glu Asp Pro Tyr Lys Gly Leu
                    435                  440                  445

Ile Phe Trp Glu Val Asp Leu Thr Glu Arg Phe Ser Gln Asp Leu Asp
                    450                  455                  460

Gln Phe Ala Leu Gly Arg Lys Phe Leu Tyr Gln Ala Gly Ile Arg Thr
    465                  470                  475                  480
```

```
Ala Val Thr Gly Arg Gly Val Lys Arg Ala Ser Thr Thr Ser Ala
                485                 490                 495

Ser Ser Arg Arg Val Val Lys Arg Arg Gly Ser Lys
            500                 505

<210> SEQ ID NO 128
<211> LENGTH: 505
<212> TYPE: PRT
<213> ORGANISM: Human papillomavirus type 16
<220> FEATURE:
<221> NAME/KEY: SITE
<222> LOCATION: (1)..(505)
<223> OTHER INFORMATION: Human papillomavirus type 16

<400> SEQUENCE: 128

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320
```

-continued

```
Asn Gly Ile Cys Trp Gly Asn Gln Leu Phe Val Thr Val Val Asp Thr
            325                 330                 335

Thr Arg Ser Thr Asn Met Ser Leu Cys Ala Ala Ile Ser Thr Ser Glu
        340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
        370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
            405                 410                 415

Thr Tyr Arg Phe Val Thr Ser Gln Ala Ile Ala Cys Gln Lys His Thr
        420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
            485                 490                 495

Thr Ala Lys Arg Lys Lys Arg Lys Leu
            500                 505

<210> SEQ ID NO 129
<211> LENGTH: 9
<212> TYPE: PRT
<213> ORGANISM: Cytomegalovirus sp.
<220> FEATURE:
<221> NAME/KEY: SITE
<222> LOCATION: (1)..(9)
<223> OTHER INFORMATION: tumor cell surface cell count of CMV

<400> SEQUENCE: 129

Asn Leu Ala Pro Met Val Ala Thr Val
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic: peptide

<400> SEQUENCE: 130

Glu Glu Glu Glu Glu Glu Glu Glu Cys
1               5

<210> SEQ ID NO 131
<211> LENGTH: 10
<212> TYPE: PRT
<213> ORGANISM: Artificial Sequence
<220> FEATURE:
<223> OTHER INFORMATION: Synthetic: peptide

<400> SEQUENCE: 131

Cys Glu Glu Glu Glu Glu Glu Glu Glu Cys
1               5                   10

<210> SEQ ID NO 132
```

```
<211> LENGTH: 439
<212> TYPE: PRT
<213> ORGANISM: Mus musculus papillomavirus type 1
<220> FEATURE:
<221> NAME/KEY: SITE
<222> LOCATION: (1)..(439)
<223> OTHER INFORMATION: wild type mouse (Mus musculus) L1 wild type
      protein sequence

<400> SEQUENCE: 132
```

| Met | Ala | Met | Trp | Thr | Pro | Gln | Thr | Gly | Lys | Leu | Tyr | Leu | Pro | Pro | Thr |
|---|---|---|---|---|---|---|---|---|---|---|---|---|---|---|---|
| 1 | | | | 5 | | | | | 10 | | | | | 15 | |

Thr Pro Val Ala Lys Val Gln Ser Thr Asp Glu Tyr Val Tyr Pro Thr
            20                  25                  30

Ser Leu Phe Cys His Ala His Thr Asp Arg Leu Leu Thr Val Gly His
        35                  40                  45

Pro Phe Phe Ser Val Ile Asp Asn Asp Lys Val Thr Val Pro Lys Val
    50                  55                  60

Ser Gly Asn Gln Tyr Arg Val Phe Arg Leu Lys Phe Pro Asp Pro Asn
65                  70                  75                  80

Lys Phe Ala Leu Pro Gln Lys Asp Phe Tyr Asp Pro Glu Lys Glu Arg
                85                  90                  95

Leu Val Trp Arg Leu Arg Gly Leu Glu Ile Gly Arg Gly Gly Pro Leu
            100                 105                 110

Gly Ile Gly Thr Thr Gly His Pro Leu Phe Asn Lys Leu Gly Asp Thr
        115                 120                 125

Glu Asn Pro Asn Lys Tyr Gln Gln Gly Ser Lys Asp Asn Arg Gln Asn
    130                 135                 140

Thr Ser Met Asp Pro Lys Gln Thr Gln Leu Phe Ile Val Gly Cys Glu
145                 150                 155                 160

Pro Pro Thr Gly Glu His Trp Asp Val Ala Lys Pro Cys Gly Ala Leu
                165                 170                 175

Glu Lys Gly Asp Cys Pro Pro Ile Gln Leu Val Asn Ser Val Ile Glu
            180                 185                 190

Asp Gly Asp Met Cys Asp Ile Gly Phe Gly Asn Met Asn Phe Lys Glu
        195                 200                 205

Leu Gln Gln Asp Arg Ser Gly Val Pro Leu Asp Ile Val Ser Thr Arg
    210                 215                 220

Cys Lys Trp Pro Asp Phe Leu Lys Met Thr Asn Glu Ala Tyr Gly Asp
225                 230                 235                 240

Lys Met Phe Phe Phe Gly Arg Arg Glu Gln Val Tyr Ala Arg His Phe
                245                 250                 255

Phe Thr Arg Asn Gly Ser Val Gly Glu Pro Ile Pro Asn Ser Val Ser
            260                 265                 270

Pro Ser Asp Phe Tyr Tyr Ala Pro Asp Ser Thr Gln Asp Gln Lys Thr
        275                 280                 285

Leu Ala Pro Ser Val Tyr Phe Gly Thr Pro Ser Gly Ser Leu Val Ser
    290                 295                 300

Ser Asp Gly Gln Leu Phe Asn Arg Pro Phe Trp Leu Gln Arg Ala Gln
305                 310                 315                 320

Gly Asn Asn Asn Gly Val Cys Trp His Asn Glu Leu Phe Val Thr Val
                325                 330                 335

Val Asp Asn Thr Arg Asn Thr Asn Phe Thr Ile Ser Gln Gln Thr Asn
            340                 345                 350

Thr Pro Asn Pro Asp Thr Tyr Asp Ser Thr Asn Phe Lys Asn Tyr Leu
        355                 360                 365

```
Arg His Val Glu Gln Phe Glu Leu Ser Leu Ile Ala Gln Leu Cys Lys
        370                 375                 380

Val Pro Leu Asp Pro Gly Val Leu Ala His Ile Asn Thr Met Asn Pro
385                 390                 395                 400

Thr Ile Leu Glu Asn Trp Asn Leu Gly Phe Val Pro Pro Gln Gln
                405                 410                 415

Ser Ile Ser Asp Asp Tyr Arg Tyr Ile Thr Ser Ala Thr Arg Cys
                420                 425                 430

Pro Asp Gln Asn Pro Pro Lys
        435

<210> SEQ ID NO 133
<211> LENGTH: 1611
<212> TYPE: DNA
<213> ORGANISM: Mus musculus papillomavirus type 1
<220> FEATURE:
<221> NAME/KEY: misc_feature
<222> LOCATION: (1)..(1611)
<223> OTHER INFORMATION: wild type nucleic acid sequence for MPV1 L1
      protein

<400> SEQUENCE: 133
atgatgactt tgctgatttt tatttgcacc ccagtctccg taaacgcaaa cgaaaatatc     60
gtatttattg atatttttca gatggcaatg tggacacccc agaccgggaa gctttacctc    120
ccacctacaa ctccagtggc aaaagtgcag agcacagacg aatatgtgta ccctacgtct    180
ctcttctgtc atgcacacac ggaccgtttg ctaacagtgg ccacccctt tttttctgtc    240 attgacaatg acaaggtcac tgtgcctaaa gtgtctggca accaatatag ggttttcaga    300
cttaaattcc cagatccaaa taaatttgca ttgccccaaa aggatttcta tgatcctgag    360
aaagaacggt tagtgtggag gttaaggggt ctggaaattg aagaggtgg cccattaggg    420 attggcacta ccgggcaccc ccttttaac aagcttggag acacggaaaa tccaaataaa    480
tatcagcaag gctctaagga taataggcag aacacttcca tggaccccaa acaaacacag    540
ctgtttattg ttggctgtga accccctaca ggggaacact gggatgtagc taagccctgt    600
ggagctctgg agaagggtga ctgccctcct atccaacttg taaatagtgt aattgaggat    660
ggggatatgt gtgacattgg cttttgggaat atgaacttca aagagctgca gcaggatagg    720
agtggtgtgc ctcttgatat tgtatctacc cggtgcaaat ggcccgactt ctgtgaaaatg    780 accaatgagg catatgggga taagatgttc ttctttggaa ggagagagca agtgtatgca    840
agacactttt tcaccaggaa tggctctgtg ggggagccca taccaaactc tgtgagtccc    900
agtgactttt actacgcacc cgacagcaca caggaccaga agacactcgc accctccgtg    960
tactttggaa ctcctagtgg gtcacttgtg tcgagtgatg tcagctgtt taacaggcca   1020 ttttggcttc aaagggctca gggaaacaat aatggtgtgt gctggcacaa tgagctcttt   1080
gttactgttg tcgacaacac aaggaatata aactttacta tctcccagca aaccaacaca   1140
ccaaacccag atacatatga ctctactaat tttaaaaact atttaagaca tgtggaacaa   1200
tttgagctgt cccttattgc tcaactgtgt aaggttccac ttgacccggg tgtgcttgcc   1260
catataaaca ctatgaaccc aaccatcttg agaaactgga acttgggttt tgtacctccc   1320
ccacagcagt ccatctctga tgactatagg tatataacat catcggcaac tcgctgtcca   1380
gatcagaatc cgcccaagga aagagaggat ccttacaagg tcttatatt tgggaagtt   1440 gatcttactg agaggttttc tcaggacctt gatcagtttg ctctgggacg aaagtttctg   1500
```

```
tatcaagctg gtatacgtac tgctgttacg ggccgcgggg tcaaaagggc agcgtctaca      1560
acctctgcgt cttctagacg agttgtaaaa cggaagaggg gaagcaaata a               1611
```

<210> SEQ ID NO 134
<211> LENGTH: 441
<212> TYPE: PRT
<213> ORGANISM: Mus musculus papillomavirus type 1
<220> FEATURE:
<221> NAME/KEY: SITE
<222> LOCATION: (1)..(441)
<223> OTHER INFORMATION: mutant MPV sequence

<400> SEQUENCE: 134

```
Met Leu Tyr Leu Pro Pro Thr Thr Pro Val Ala Lys Val Gln Ser Thr
 1               5                  10                  15

Asp Glu Tyr Val Tyr Pro Thr Ser Leu Phe Cys His Ala His Thr Asp
                20                  25                  30

Arg Leu Leu Thr Val Gly His Pro Phe Phe Ser Val Ile Asp Asn Asp
             35                  40                  45

Lys Val Thr Val Pro Lys Val Ser Gly Asn Gln Tyr Arg Val Phe Arg
         50                  55                  60

Leu Lys Phe Pro Asp Pro Asn Lys Phe Ala Leu Pro Gln Lys Asp Phe
65                  70                  75                  80

Tyr Asp Pro Glu Lys Glu Arg Leu Val Trp Arg Leu Arg Gly Leu Glu
                 85                  90                  95

Ile Gly Arg Gly Gly Pro Leu Gly Ile Gly Thr Thr Gly His Pro Leu
            100                 105                 110

Phe Asn Lys Leu Gly Asp Thr Glu Asn Pro Asn Lys Tyr Gln Gln Gly
        115                 120                 125

Ser Lys Asp Asn Arg Gln Asn Thr Ser Met Asp Pro Lys Gln Thr Gln
    130                 135                 140

Leu Phe Ile Val Gly Cys Glu Pro Pro Thr Gly Glu His Trp Asp Val
145                 150                 155                 160

Ala Lys Pro Cys Gly Ala Leu Glu Lys Gly Asp Cys Pro Pro Ile Gln
                165                 170                 175

Leu Val Asn Ser Val Ile Glu Asp Gly Asp Met Cys Asp Ile Gly Phe
            180                 185                 190

Gly Asn Met Asn Phe Lys Glu Leu Gln Gln Asp Arg Ser Gly Val Pro
        195                 200                 205

Leu Asp Ile Val Ser Thr Arg Cys Lys Trp Pro Asp Phe Leu Lys Met
    210                 215                 220

Thr Asn Glu Ala Tyr Gly Asp Lys Met Phe Phe Gly Arg Arg Glu
225                 230                 235                 240

Gln Val Tyr Ala Arg His Phe Phe Thr Arg Asn Gly Ser Val Gly Glu
                245                 250                 255

Pro Ile Pro Asn Ser Val Ser Pro Ser Asp Phe Tyr Tyr Ala Pro Asp
            260                 265                 270

Ser Thr Gln Asp Gln Lys Thr Leu Ala Pro Ser Val Tyr Phe Gly Thr
        275                 280                 285

Pro Ser Gly Ser Leu Val Ser Ser Asp Gly Gln Leu Phe Asn Arg Pro
    290                 295                 300

Phe Trp Leu Gln Arg Ala Gln Gly Asn Asn Asn Gly Val Cys Trp His
305                 310                 315                 320

Asn Glu Leu Phe Val Thr Val Val Asp Asn Thr Arg Asn Thr Asn Phe
                325                 330                 335
```

```
Thr Ile Ser Gln Gln Thr Asn Thr Pro Asn Pro Asp Thr Tyr Asp Ser
                340                 345                 350

Thr Asn Phe Lys Asn Tyr Leu Arg His Val Glu Gln Phe Glu Leu Ser
            355                 360                 365

Leu Ile Ala Gln Leu Cys Lys Val Pro Leu Asp Pro Gly Val Leu Ala
        370                 375                 380

His Ile Asn Thr Met Asn Pro Thr Ile Leu Glu Asn Trp Asn Leu Gly
385                 390                 395                 400

Phe Val Pro Pro Lys Glu Arg Glu Asp Pro Tyr Lys Gly Leu Ile Phe
                405                 410                 415

Trp Glu Val Asp Leu Thr Glu Arg Phe Ser Gln Asp Leu Asp Gln Phe
            420                 425                 430

Ala Leu Gly Arg Lys Phe Leu Tyr Gln
        435                 440
```

<210> SEQ ID NO 135
<211> LENGTH: 1326
<212> TYPE: DNA
<213> ORGANISM: Artificial Sequence
<220> FEATURE:
<223> OTHER INFORMATION: Synthetic: optimized nucleic acid sequence for MPV.10.34.d

<400> SEQUENCE: 135
atgctgtacc tgccgccgac caccccggtg gcgaaagttc agagcaccga cgaatacgtt 60
tatccgacca gcctgttctg ccacgcgcac accgatcgtc tgctgaccgt gggtcacccg 120
ttctttagcg ttatcgacaa cgataaggtg accgttccga aagtgagcgg caaccagtac 180
cgtgtttttc gtctgaagtt cccggacccg aacaaatttg cgctgccgca aaaggacttc 240
tatgatccgg agaaggaacg tctggtgtgg cgtctgcgtg gtctggaaat tggtcgtggt 300
ggcccgctgg gtattggtac caccggtcac ccgctgttca acaaactggg cgataccgag 360
aacccgaaca aatatcagca aggtagcaag gacaaccgtc agaacaccag catggacccg 420
aagcagaccc aactgtttat tgttggttgc gagccgccga ccggtgaaca ctgggatgtt 480
gcgaaaccgt gcggtgcgct ggaaaagggc gattgcccgc cgatccaact ggtgaacagc 540
gttattgagg acggtgatat gtgcgacatc ggttttggca acatgaactt caaagaactg 600
cagcaagacc gtagcggcgt gccgctggat attgttagca cccgttgcaa atggccggac 660
ttcctgaaga tgaccaacga agcgtacggt gataagatgt tctttttcgg ccgtcgtgag 720
caggtttatg cgcgtcactt tttcacccgt aacggtagcg tgggcgagcc gatcccgaac 780
agcgttagcc cgagcgactt ctactatgcg ccggacagca cccaggatca aaaaaccctg 840
gcgccgagcg tgtactttgg taccccgagc ggcagcctgg ttagcagcga tggtcaactg 900
tttaaccgtc cgttctggct gcagcgtgcg cagggtaaca acaacggcgt gtgctggcac 960
aacgaactgt ttgttaccgt ggttgacaac acccgtaaca ccaacttcac catcagccag 1020
caaaccaaca ccccgaaccc ggacacctac gatagcacca actttaaaaa ctatctgcgt 1080
cacgtggagc agttcgaact gagcctgatt gcgcaactgt gcaaagtgcc gctggacccg 1140
ggtgtgctgg cgcacatcaa caccatgaac ccgaccattc tggagaactg gaacctgggt 1200
ttcgttccgc cgaaagagcg tgaagacccg tacaagggcc tgatcttctg ggaagtggat 1260
ctgaccgaac gtttcagcca ggacctggat caatttgcgc tgggccgtaa attcctgtat 1320
cagtaa 1326
<210> SEQ ID NO 136
<211> LENGTH: 1427
<212> TYPE: DNA
<213> ORGANISM: Artificial Sequence
<220> FEATURE:
<223> OTHER INFORMATION: Synthetic: optimized nucleic acid sequence for MPV.10.34.d

<400> SEQUENCE: 136

```
gaattggcgg aaggccgtca aggccacgtg tcttgtccgc ggtacccata tgctgtatct     60
gcctccaact acaccggttg caaaagttca gagcaccgat gaatatgttt atccgaccag    120
cctgttttgt catgcacata ccgatcgtct gctgaccgtt ggtcatccgt tttttagcgt    180
tattgataac gataaagtga ccgttccgaa agttagcggt aatcagtatc gtgtttttcg    240
cctgaaattt ccggatccga acaaatttgc actgccgcag aaagattttt acgacccgga    300
aaaagaacgt ctggtttggc gtctgcgtgg tctggaaatt ggtcgtggtg gtccgttagg    360
tattggcacc accggtcatc cgctgtttaa caaactgggt gataccgaaa atccgaataa    420
ataccagcag ggcagcaaag ataatcgtca gaataccagt atggatccga aacagaccca    480
gctgtttatt gttggttgtg aaccgcctac cggtgaacat tgggatgttg caaaaccgtg    540
tggtgcactg gaaaaaggtg attgtccgcc tattcagctg gttaatagcg tgattgaaga    600
tggtgatatg tgcgatattg gctttggcaa catgaacttt aaagaactgc agcaggatcg    660
tagcggtgtt ccgctggata ttgttagcac ccgttgtaaa tggcctgatt ttctgaaaat    720
gaccaatgaa gcctatggcg acaaaatgtt tttttttcggt cgtcgtgaac aggtttatgc    780
ccgtcacttt tttacccgta atggtagcgt tggtgaaccg attccgaata gcgttagccc    840
gagcgatttc tattatgcac cggatagcac ccaggatcag aaaaccctgg caccgagcgt    900
ttattttggc accccgagcg gtagcctggt tagcagtgat ggtcagctgt tcaatcgtcc    960
gttttggctg cagcgtgcac agggtaataa caatggtgtt tgttggcata acgaactgtt   1020
tgttaccgtt gttgataata cccgcaatac caactttacc attagccagc agaccaatac   1080
accgaatccg gatacctatg atagcaccaa cttcaaaaac tatctgcgtc atgtggaaca   1140
gtttgaactg agcctgattg cccagctgtg taaagtgccg ctggatccgg gtgttctggc   1200
acatattaac accatgaatc cgaccattct ggaaaattgg aatctgggtt ttgttccgcc   1260
taaagaacgt gaagatccgt ataaaggtct gatttttttgg gaagttgatc tgaccgaacg   1320
ttttagccag gatctggatc agtttgcact gggtcgcaaa tttctgtatc agtaactcga   1380
ggagctcgga gcacaagact ggcctcatgg gccttccgct cactgcc                 1427
```

<210> SEQ ID NO 137
<211> LENGTH: 62
<212> TYPE: DNA
<213> ORGANISM: Artificial Sequence
<220> FEATURE:
<223> OTHER INFORMATION: Synthetic: primer

<400> SEQUENCE: 137

```
aagcttgtcg acggagctcg aattcggatc cttattactg atacaggaat ttacggccca     60
gc                                                                    62
```

<210> SEQ ID NO 138
<211> LENGTH: 9
<212> TYPE: PRT
<213> ORGANISM: Artificial Sequence
<220> FEATURE:
<223> OTHER INFORMATION: Synthetic: NLV

```
<400> SEQUENCE: 138

Asn Leu Val Pro Met Val Ala Thr Val
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic: murine OVA

<400> SEQUENCE: 139

Ser Ile Ile Asn Phe Ile Lys Glu Leu
1               5

<210> SEQ ID NO 140
<211> LENGTH: 9
<212> TYPE: PRT
<213> ORGANISM: Artificial Sequence
<220> FEATURE:
<223> OTHER INFORMATION: Synthetic: free OVA peptide

<400> SEQUENCE: 140

Ser Ile Ile Asn Phe Ile Lys Glu Leu
1               5
```